(12) United States Patent
Willingham et al.

(10) Patent No.: US 10,912,776 B2
(45) Date of Patent: Feb. 9, 2021

(54) METHODS OF TREATING CANCER

(71) Applicant: Corvus Pharmaceuticals, Inc., Burlingame, CA (US)

(72) Inventors: Stephen Willingham, Sunnyvale, CA (US); Richard A. Miller, Portola Valley, CA (US); Po Y. Ho, Burlingame, CA (US); Ian McCaffery, Oakland, CA (US); Andrew Hotson, Burlingame, CA (US)

(73) Assignee: CORVUS PHARMACEUTICALS, INC., Burlingame, CA (US)

( * ) Notice: Subject to any disclaimer, the term of this patent is extended or adjusted under 35 U.S.C. 154(b) by 0 days.

(21) Appl. No.: 16/065,012

(22) PCT Filed: Dec. 22, 2016

(86) PCT No.: PCT/US2016/068459
§ 371 (c)(1),
(2) Date: Jun. 21, 2018

(87) PCT Pub. No.: WO2017/112917
PCT Pub. Date: Jun. 29, 2017

(65) Prior Publication Data
US 2019/0076433 A1 Mar. 14, 2019

Related U.S. Application Data

(60) Provisional application No. 62/421,109, filed on Nov. 11, 2016, provisional application No. 62/421,171, filed on Nov. 11, 2016, provisional application No. 62/350,602, filed on Jun. 15, 2016, provisional application No. 62/324,211, filed on Apr. 18, 2016, provisional application No. 62/387,383, filed on Dec. 24, 2015.

(51) Int. Cl.
*A61K 31/519* (2006.01)
*A61K 39/395* (2006.01)
*C07K 16/28* (2006.01)
*A61P 35/00* (2006.01)
*A61K 9/00* (2006.01)

(52) U.S. Cl.
CPC .......... *A61K 31/519* (2013.01); *A61K 9/0019* (2013.01); *A61K 39/3955* (2013.01); *A61P 35/00* (2018.01); *C07K 16/2818* (2013.01); *C07K 16/2827* (2013.01); *C07K 2317/24* (2013.01); *C07K 2317/76* (2013.01)

(58) Field of Classification Search
CPC ................ A61K 31/519; A61K 9/0019; A61K 39/3955; A61P 35/00; C07K 16/2818; C07K 16/2827; C07K 2317/24; C07K 2317/76
See application file for complete search history.

(56) References Cited

U.S. PATENT DOCUMENTS

| | | |
|---|---|---|
| 7,405,219 B2 | 7/2008 | Gillespie et al. |
| 7,589,097 B2 | 9/2009 | Gillespie et al. |
| 8,450,328 B2 | 5/2013 | Bamford et al. |
| 8,987,279 B2 | 3/2015 | Bamford et al. |
| 9,376,443 B2 | 6/2016 | Bamford et al. |
| 9,765,080 B2 | 9/2017 | Bamford et al. |
| 2011/0172252 A1 | 7/2011 | Bamford et al. |

OTHER PUBLICATIONS

Linehan et al. (Non-Clear Cell Renal Cancer: Disease-Based Management and Opportunities for Targeted Therapeutic Approaches, Semin Oncol. Aug. 2013; 40(4): 511-520). (Year: 2013).*
Herbst, Roy S. et al. "Predictive correlates of response to the anti-PD-L1 antibody MPDL3280A in cancer patients", Nature, vol. 515, No. 7528, Nov. 27, 2014 (Nov. 26, 2014), pp. 563-567.
International Search Report and Written Opinion issued in International Application No. PCT/US2016/68459, dated Mar. 16, 2017. 12 pages.
Mahoney et al. "Combination cancer immunotherapy and new immunomodulatory targets", Nature Reviews Drug Discovery, vol. 14, Aug. 2015 (Aug. 2015), pp. 561-585.
Mediavilla-Varela, Melanie et al. "Antagonism of adenosine A2A receptor expressed by lung adenocarcinoma tumor cells and cancer associated fibroblasts inhibits their growth", Cancer Biology & Therapy, vol. 14, No. 9, Sep. 19, 2013 (Sep. 19, 2013), pp. 860-868.
Mittal, D. et al. (Jul. 15, 2014, e-published Jul. 1, 2014). "Antimetastatic Effects of Blocking PD-1 and the Adenosine A2A Receptor", Cancer Research, vol. 74, No. 14, pp. 3652-3658.

(Continued)

*Primary Examiner* — Kortney L. Klinkel
*Assistant Examiner* — William Y Lee
(74) *Attorney, Agent, or Firm* — Mintz, Levin, Cohn, Ferris, Glovsky and Popeo, P.C.

(57) ABSTRACT

Provided herein are, inter alia, methods of treating cancer by administering to a subject a therapeutically effective amount of an adenosine-A2A(A2A) receptor antagonist or a combination of an adenosine-A2A(A2A) receptor antagonist and a programmed cell death protein 1(PD-1) signaling pathway inhibitor. Further provided are pharmaceutical compositions including an A2A receptor antagonist, a PD-1 signaling pathway inhibitor and a pharmaceutically acceptable excipient. Further provided are methods of detecting cellular effects, for example expression of pCREB, before, after or during adenosine receptor antagonist treatment.

12 Claims, 50 Drawing Sheets

(56) References Cited

OTHER PUBLICATIONS

Powles, Thomas et al. "MPDL3280A (anti-PD-L1) treatment leads to clinical activity in metastatic bladder cancer," Nature, vol. 515, No. 7528, Nov. 27, 2014 (Nov. 26, 2014), pp. 558-562.
Beavis, P.A. et al. (2015, e-published Feb. 11, 2015). "Adenosine Receptor 2A Blockade Increases the Efficacy of Anti-PD-1 through Enhanced Antitumor T-cell Responses." *Cancer Immunol Res*; 3(5):506-517.
Leone, R. D. et al. (2015, e-published Apr. 8, 2015). "A2aR antagonists: Next generation checkpoint blockade for cancer immunotherapy." *Computational and Structural Biotechnology Journal*, 13, 265-272.

* cited by examiner

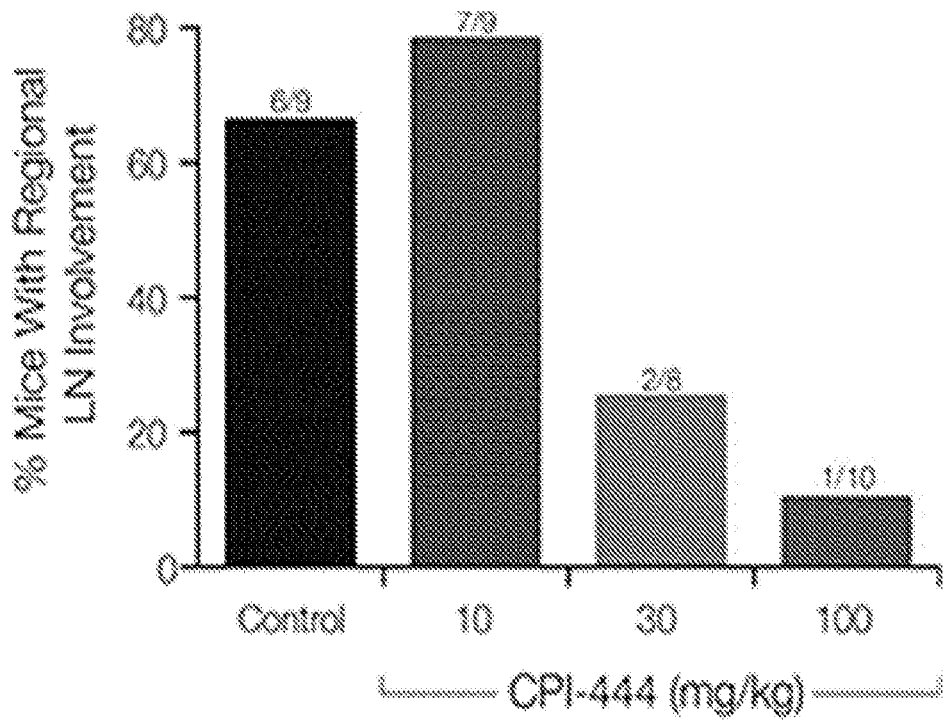
FIG. 11
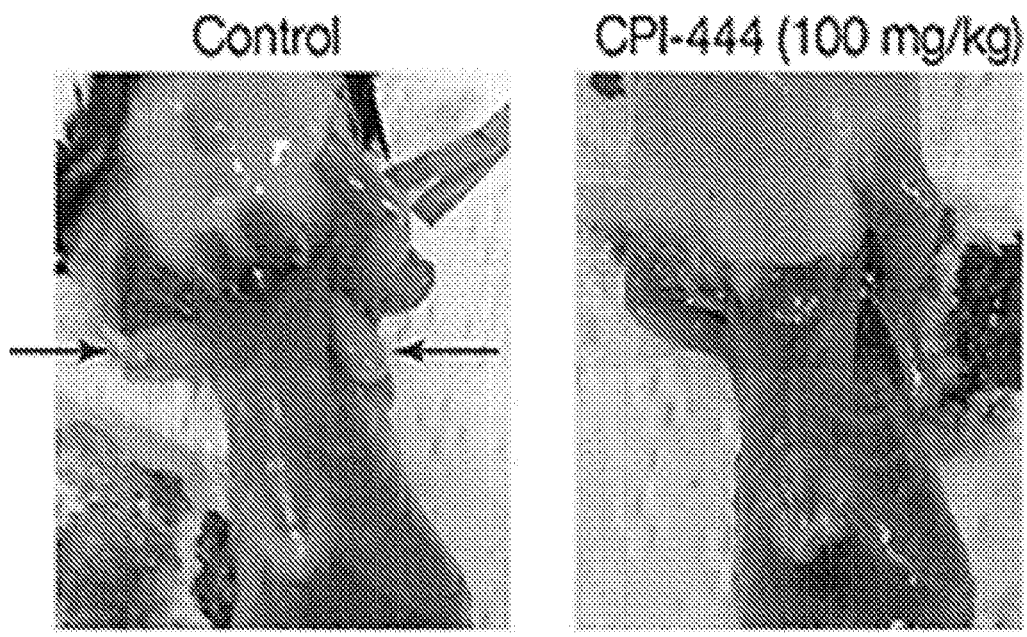

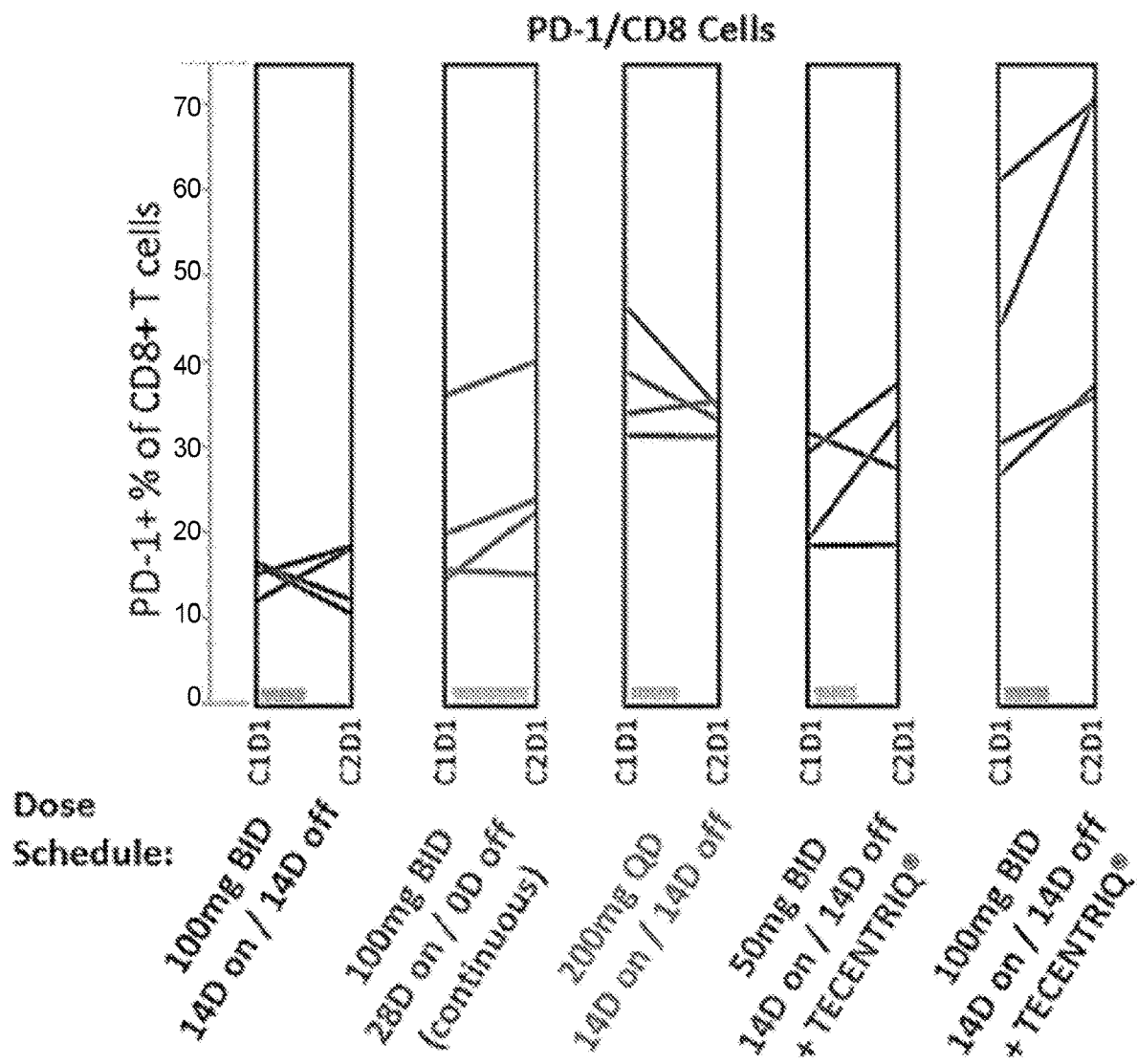

FIG. 21A

Efficacy by PD-L1 Status

| PD-L1 Status | n | Number Evaluable | Number with Stable Disease (%) |
|---|---|---|---|
| Negative | 12 | 7 | 3 (43%) |
| Positive | 4 | 2 | 1 (50%) |

Efficacy by Prior Exposure to anti-PD-1 Therapy

| Prior Response to anti-PD-1 Therapy | n | Number Evaluable | Number with Stable Disease (%) |
|---|---|---|---|
| Naive | 21 | 15 | 6 (40%) |
| Refractory | 25 | 17 | 6 (35%) |

FIG. 27 – cont'd
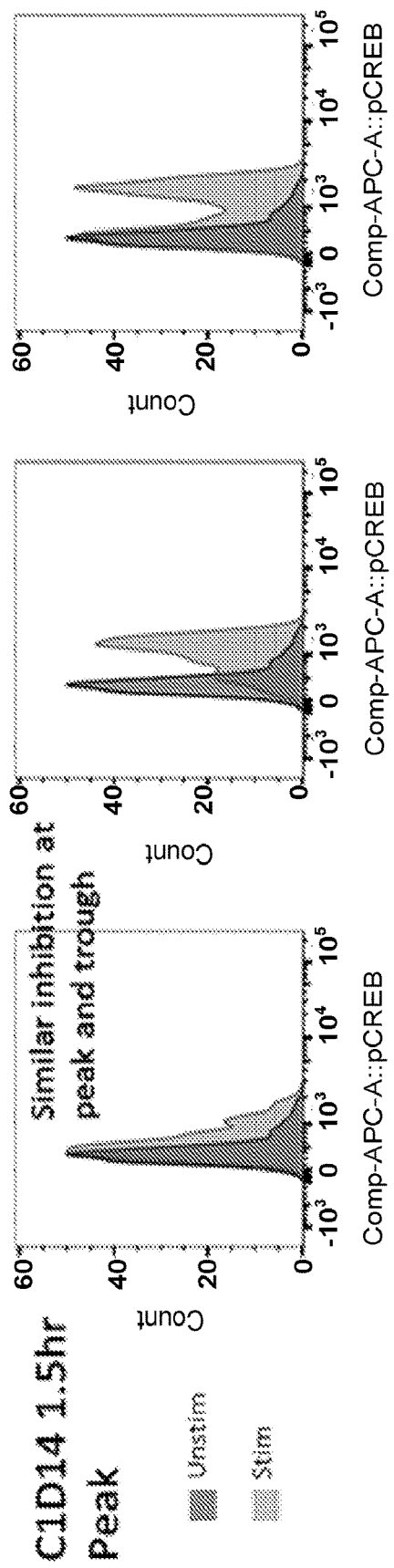

FIG. 28 – cont'd
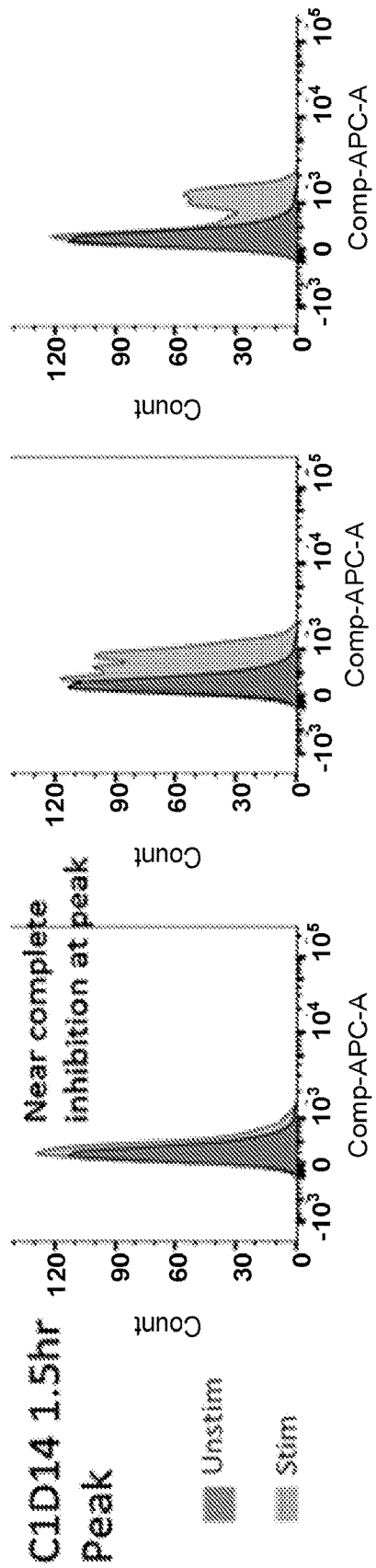

Similar functional inhibition
from trough to peak

Maximal inhibition
maintained

FIG. 29 – cont'd
Subject 100302
50 BID / 14 + Atezo
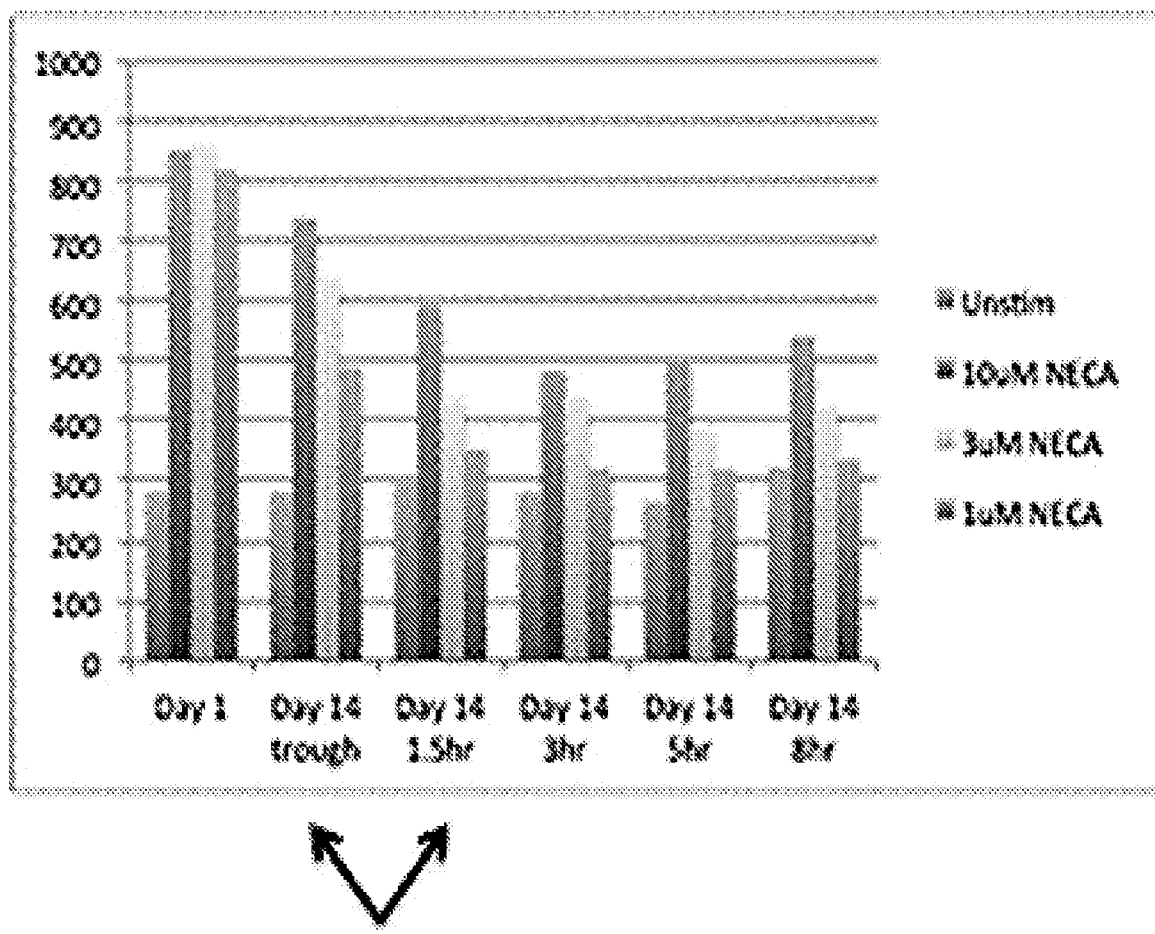
Greater functional inhibition
at peak than trough
Maximal inhibition not
maintained Subject 100302
50 BID / 14 + Atezo
MEL FIG. 30 – cont'd
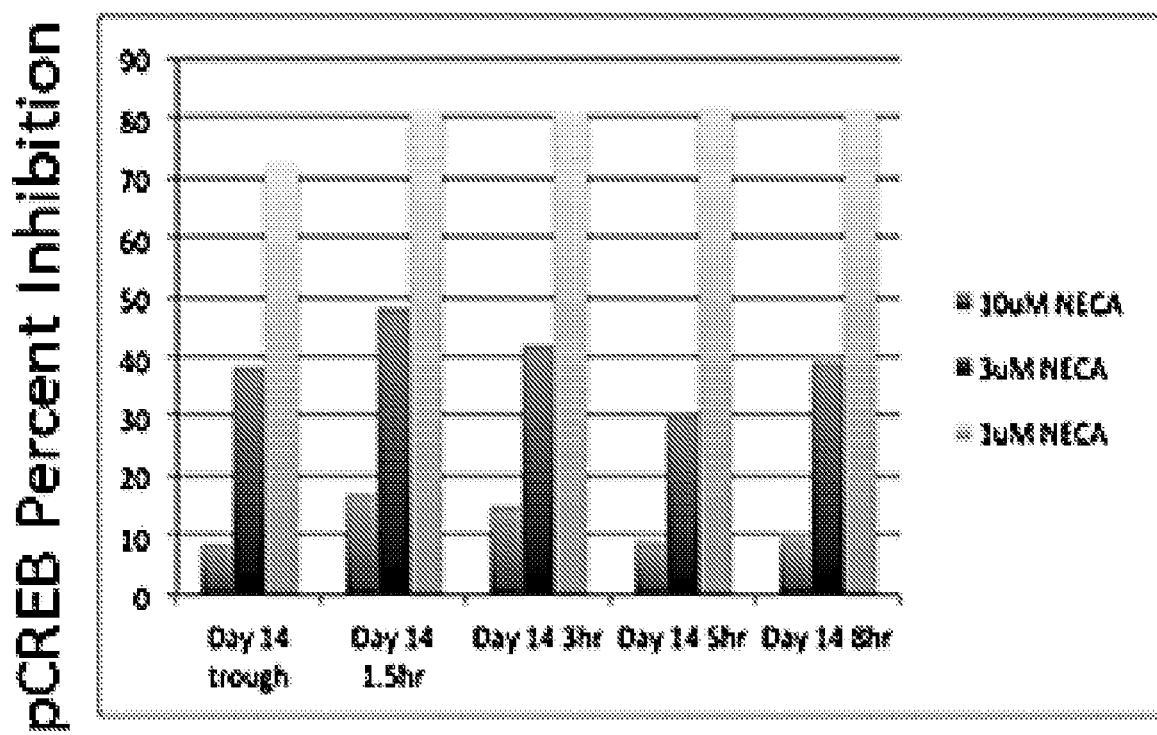
Subject 100301
200 QD / 14
CRC FIG. 30 – cont'd
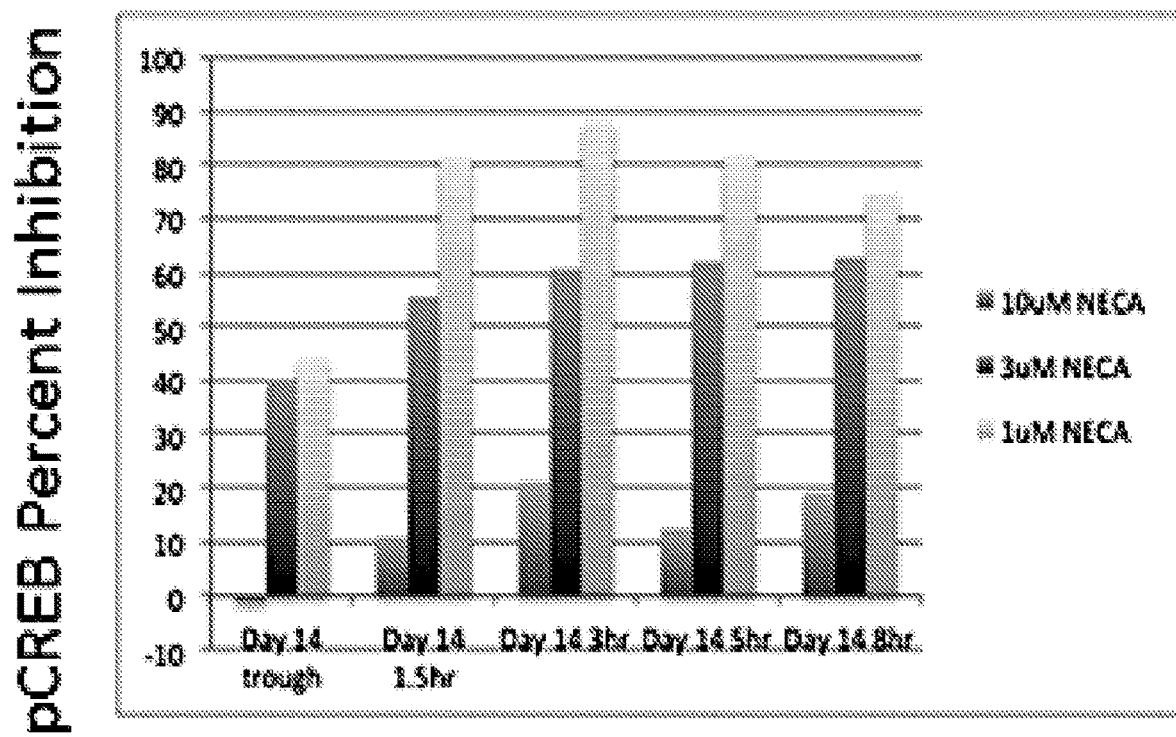
Subject 100402
50 BID / 14 + Atezo
mCRPC FIG. 30 – cont'd
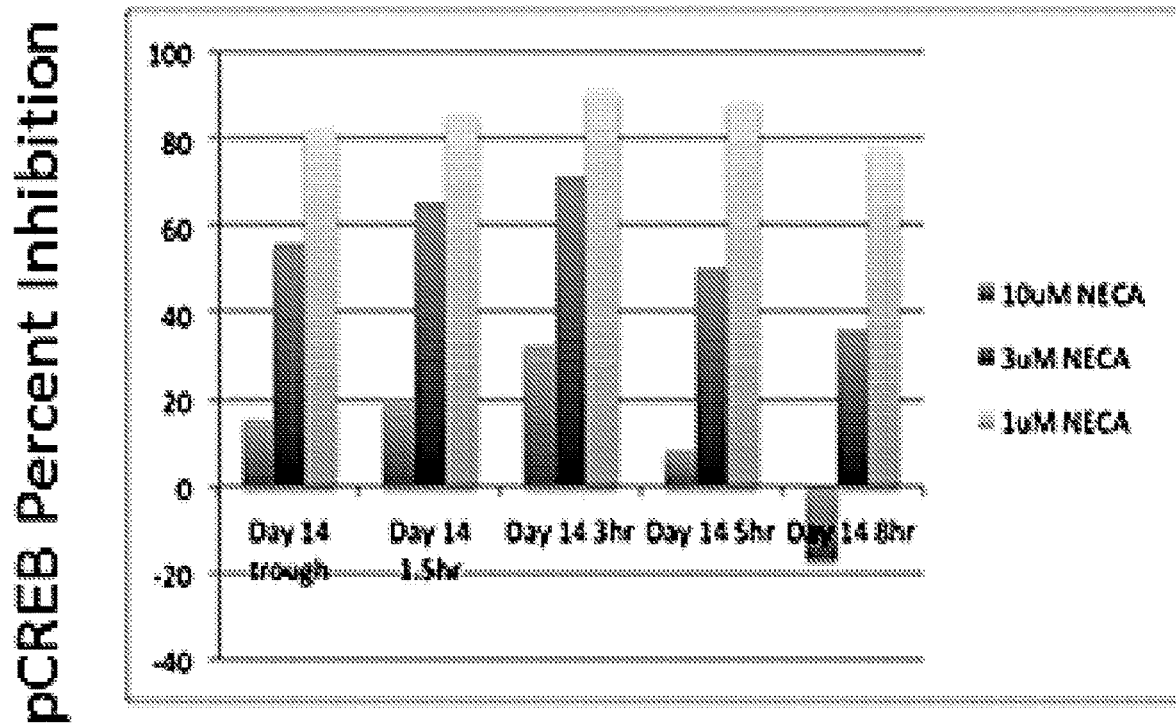
Subject 100303
100 BID / 28
TNBC FIG. 31 – cont'd
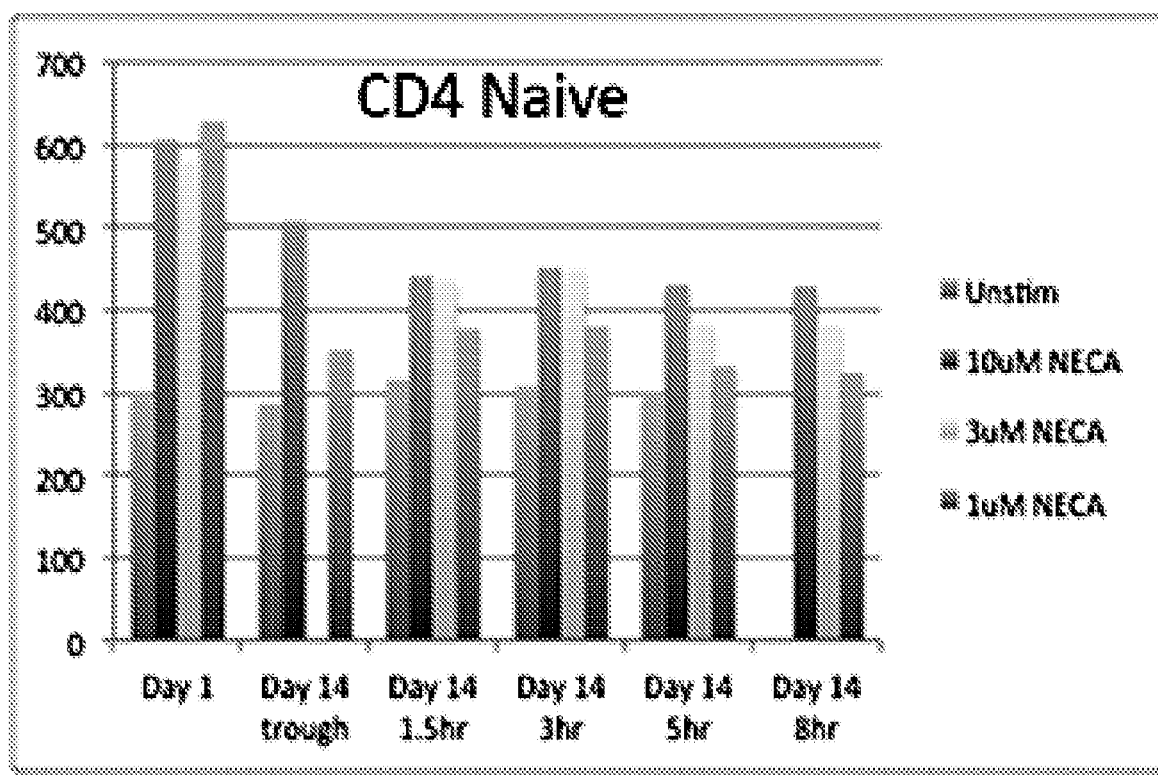

FIG. 31 – cont'd
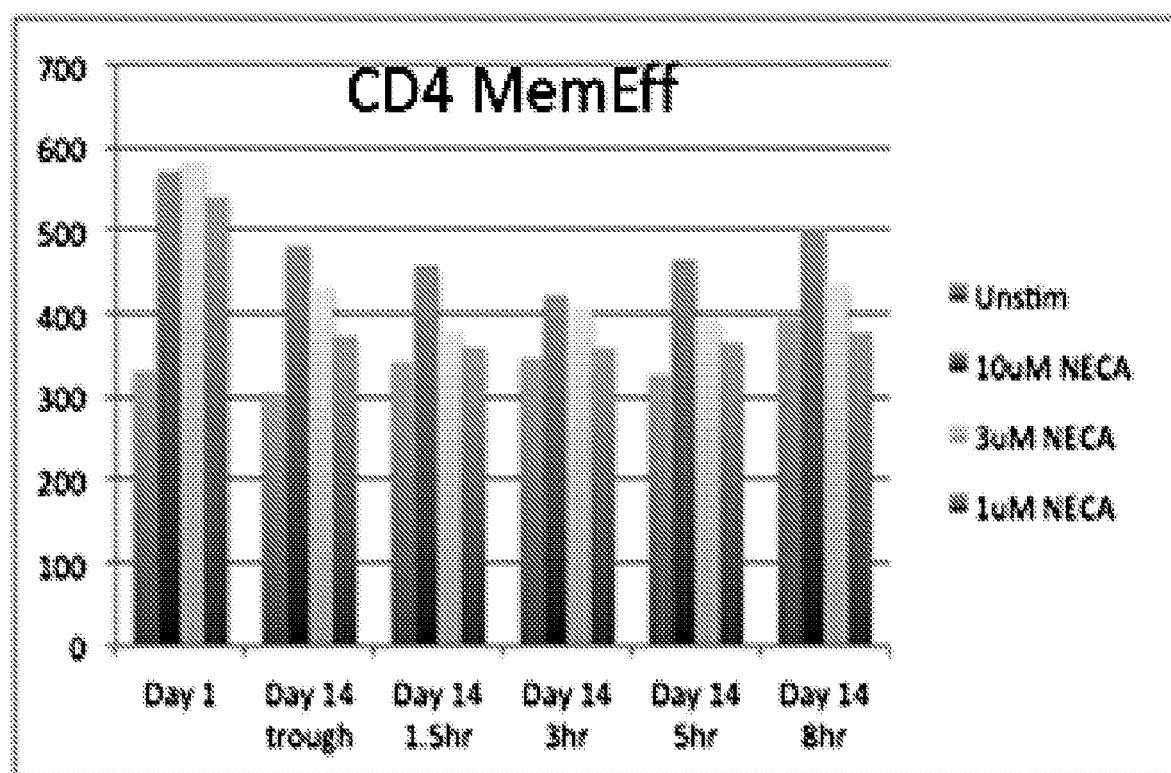

FIG. 31 – cont'd
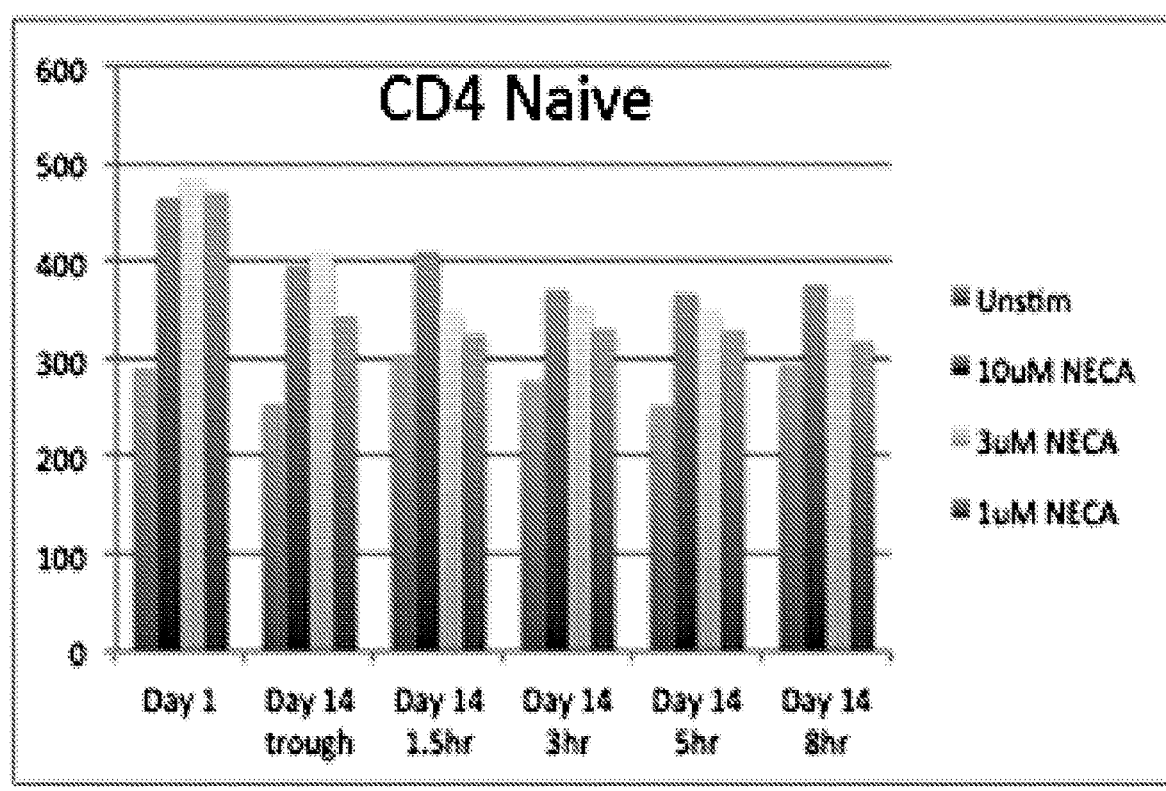

FIG. 32 – cont'd
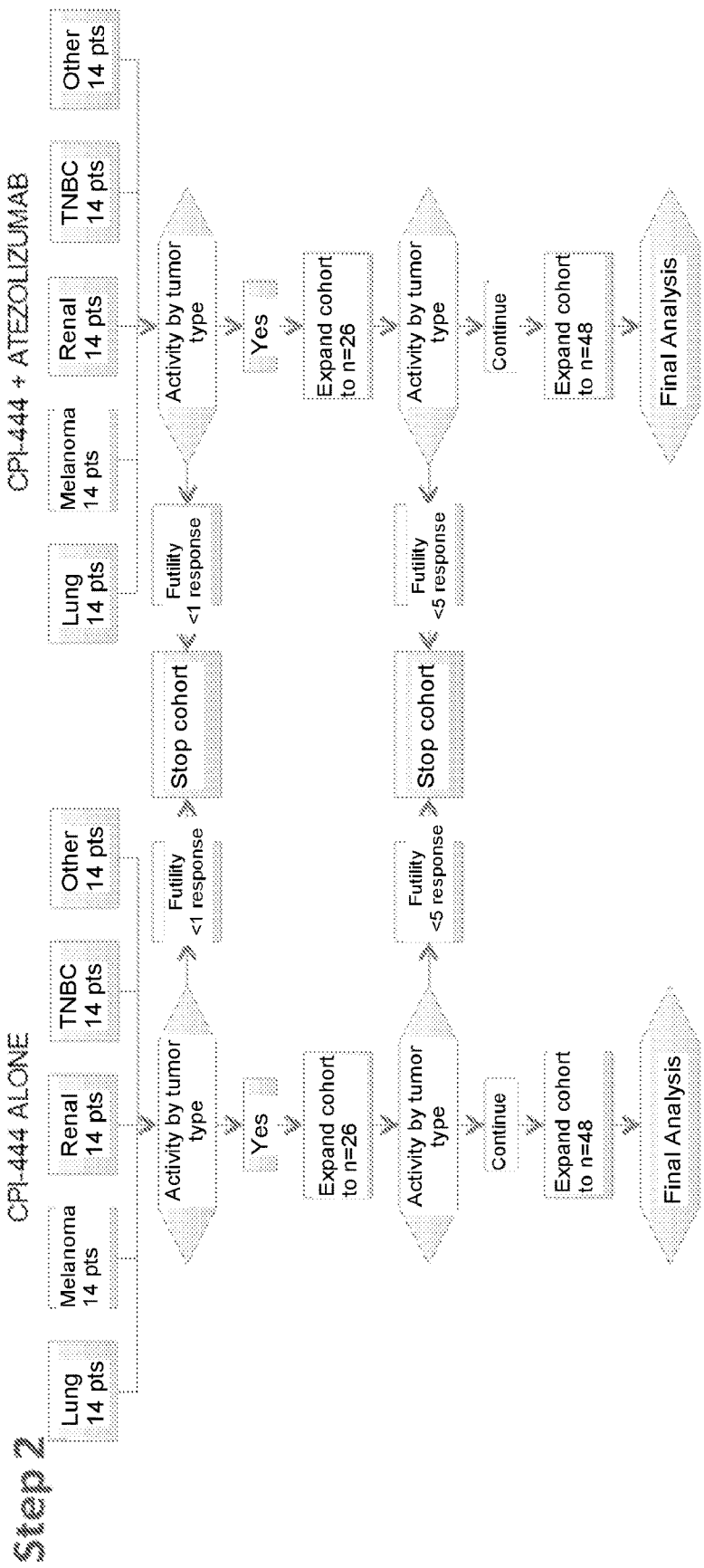

METHODS OF TREATING CANCER

CROSS-REFERENCE TO RELATED APPLICATIONS

This application is a national stage application filed under 35 U.S.C. § 371, of International Patent Application No. PCT/US2016/068459, filed Dec. 22, 2016, which claims priority to U.S. Provisional Application 62/387,383, filed Dec. 24, 2015, U.S. Provisional Application No. 62/324,211, filed Apr. 8, 2016, U.S. Provisional Application No. 62/350,602, filed Jun. 15, 2016, U.S. Provisional Application No. 62/421,109, filed Nov. 11, 2016, and U.S. Provisional Application No. 62/421,171, filed Nov. 11, 2016, which are hereby incorporated by reference in their entirety and for all purposes.

BACKGROUND OF THE INVENTION

The goal of immunotherapy is to drive cytotoxic T-cell responses to eradicate cancer. To prevent reaction to self-antigens, or overreaction, multiple inhibitory checkpoint signals exist including PD½, CTLA4 and adenosine. Extracellular adenosine, a purine nucleoside, is produced during acute, inflammatory processes by conversion from adenosine triphosphate (ATP) through ectonucleotidases CD73 and CD39 expressed on the cell surface of multiple tissue types. Adenosine is normally upregulated to protect a host from over-injury in response to such stimuli as infection or ischemia by binding its extracellular, G-protein coupled receptors on target cells (including MR, A2AR, A2BR, and A3R) and begin healing {Hasko 2008}. However, multiple tumor types can actively sustain extracellular adenosine levels well beyond acute phase reactions to dampen a host's immune response through multiple mechanisms {Antionioli 2013}. Increases in adenosine in the microenvironment by malignant cells recruits regulatory T-cells (Treg), which express substantial CD39, to the area and further drive up adenosine levels {Sica 2010}.

Cancer cells also appear to directly utilize adenosine. As a result, adenosine causes inefficient presentation of tumor antigens to the adaptive system and enhances tumor growth. Thus, there is a need in the art for effective cancer treatments. The methods and compositions provided herein address these and other deficiencies in the art.

BRIEF SUMMARY OF THE INVENTION

In one aspect, a method of treating cancer in a subject in need thereof is provided. The method includes administering to the subject a therapeutically effective amount of an adenosine-A2A (A2A) receptor antagonist and a programmed cell death protein 1 (PD-1) signaling pathway inhibitor.

In another aspect, a method of treating cancer in a subject in need thereof is provided. The method includes administering to the subject a therapeutically effective amount of an adenosine-A2A (A2A) receptor antagonist of formula:

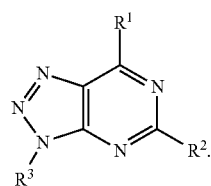

(I)

In formula (I), $R^1$ is independently hydrogen, halogen, $-CX^a{}_3$, $-CN$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$, $-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, $-CX^b{}_3$, $-CN$, $-SO_2Cl$, $-SO_{n2}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-NH-O-R^{11}$, $-C(O)R^{11}$, $-C(O)-OR^{11}$, $-C(O)NR^{11}R^{12}$, $-OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, $-CX^c{}_3$, $-CN$, $-SO_2Cl$, $-SO_{n3}R^{13}$, $-SO_{v3}NR^{13}R^{14}$, $-NHNH_2$, $-ONR^{13}R^{14}$, $-NHC=(O)NHNH_2$, $-NHC=(O)NR^{13}R^{14}$, $-N(O)_{m3}$, $-NR^{13}R^{14}$, $-NH-O-R^{13}$, $-C(O)R^{13}$, $-C(O)-OR^{13}$, $-C(O)NR^{13}R^{14}$, $-OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently $-F$, $-Cl$, $-Br$, or $-I$. The symbols $n_1$, $n_2$ and $n_3$ are independently an integer from 0 to 4. The symbols $m_1$, $m_2$ and $m_3$ are independently an integer from 1 to 2. And the symbols $v_1$, $v_2$ and $v_3$ are independently an integer from 1 to 2.

In one aspect, a method of activating a T cell is provided. The method includes contacting the T cell with an A2A receptor antagonist, wherein the A2A receptor antagonist is a compound of formula:

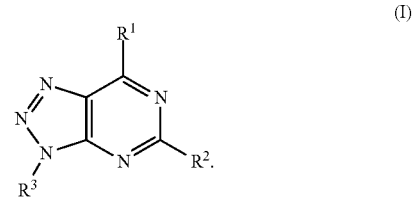

(I)

In formula (I), $R^1$ is independently hydrogen, halogen, $-CX^a{}_3$, $-CN$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$, $-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, $-CX^b{}_3$, $-CN$, $-SO_2Cl$, $-SO_{n2}R^{11}$, $-SO_{v2}NR^{11}R^{12}$, $-NHNH_2$, $-ONR^{11}R^{12}$, —NHC=(O)NHNH$_2$, —NHC=(O)NR$^{11}$R$^{12}$, —N(O)$_{m2}$, —NR$^{11}$R$^{12}$, —NH—O—R$^{11}$, —C(O)R$^{11}$, —C(O)—OR$^{11}$, —C(O)NR$^{11}$R$^{12}$, —OR$^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is independently hydrogen, halogen, —CX$^c_3$, —CN, —SO$_2$Cl, —SO$_{n3}$R$^{13}$, —SO$_{v3}$NR$^{13}$R$^{14}$, —NHNH$_2$, —ONR$^{13}$R$^{14}$, —NHC=(O)NHNH$_2$, —NHC=(O)NR$^{13}$R$^{14}$, —N(O)$_{m3}$, —NR$^{13}$R$^{14}$, —NH—O—R$^{13}$, —C(O)R$^{13}$, —C(O)—OR$^{13}$, —C(O)NR$^{13}$R$^{14}$, —OR$^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^9$, R$^{10}$, R$^{11}$, R$^{12}$, R$^{13}$ and R$^{14}$ are independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X$^a$, X$^b$ and X$^c$ are independently —F, —Cl, —Br, or —I. The symbols $n_1$, $n_2$ and $n_3$ are independently an integer from 0 to 4. The symbols $m_1$, $m_2$ and $m_3$ are independently an integer from 1 to 2. The symbols $v_1$, $v_2$ and $v_3$ are independently an integer from 1 to 2.

In one aspect, a method of inhibiting A2A receptor activity of a cell is provided. The method includes contacting the cell with an A2A receptor antagonist, wherein the A2A receptor antagonist is a compound of formula:

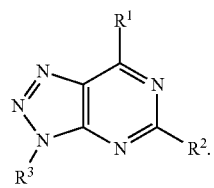

(I)

In formula (I), R$^1$ is independently hydrogen, halogen, —CX$^a_3$, —CN, —SO$_2$Cl, —SO$_{n1}$R$^9$, —SO$_{v1}$NR$^9$R$^{10}$, —NHNH$_2$, —ONR$^9$R$^{10}$, —NHC=(O)NHNH$_2$, —NHC=(O)NR$^9$R$^{10}$, —N(O)$_{m1}$, —NR$^9$R$^{10}$, —NH—O—R$^9$, —C(O)R$^9$, —C(O)—OR$^9$, —C(O)NR$^9$R$^{10}$, —OR$^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ is independently hydrogen, halogen, —CX$^b_3$, —CN, —SO$_2$Cl, —SO$_{n2}$R$^{11}$, —SO$_{v2}$NR$^{11}$R$^{12}$, —NHNH$_2$, —ONR$^{11}$R$^{12}$, —NHC=(O)NHNH$_2$, —NHC=(O)NR$^{11}$R$^{12}$, —N(O)$_{m2}$, —NR$^{11}$R$^{12}$, —NH—O—R$^{11}$, —C(O)R$^{11}$, —C(O)—OR$^{11}$, —C(O)NR$^{11}$R$^{12}$, —OR$^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is independently hydrogen, halogen, —CX$^c_3$, —CN, —SO$_2$Cl, —SO$_{n3}$R$^{13}$, —SO$_{v3}$NR$^{13}$R$^{14}$, —NHNH$_2$, —ONR$^{13}$R$^{14}$, —NHC=(O)NHNH$_2$, —NHC=(O)NR$^{13}$R$^{14}$, —N(O)$_{m3}$, —NR$^{13}$R$^{14}$, —NH—O—R$^{13}$, —C(O)R$^{13}$, —C(O)—OR$^{13}$, —C(O)NR$^{13}$R$^{14}$, —OR$^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^9$, R$^{10}$, R$^{11}$, R$^{12}$, R$^{13}$ and R$^{14}$ are independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X$^a$, X$^b$ and X$^c$ are independently —F, —Cl, —Br, or —I. The symbols $n_1$, $n_2$ and $n_3$ are independently an integer from 0 to 4. The symbols $m_1$, $m_2$ and $m_3$ are independently an integer from 1 to 2. The symbols $v_1$, $v_2$ and $v_3$ are independently an integer from 1 to 2.

In one aspect, a method of increasing an anti-tumor immune response in a subject in need thereof is provided. The method includes administering to the subject a therapeutically effective amount of an adenosine-A2A (A2A) receptor antagonist and a programmed cell death protein 1 (PD-1) signaling pathway inhibitor.

In another aspect, a method of increasing an anti-tumor immune response in a subject in need thereof is provided. The method includes administering to the subject a therapeutically effective amount of an adenosine-A2A (A2A) receptor antagonist, wherein the A2A receptor antagonist is a compound of formula:

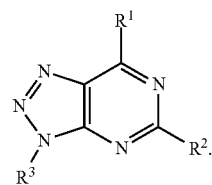

(I)

In formula (I), R$^1$ is independently hydrogen, halogen, —CX$^a_3$, —CN, —SO$_2$Cl, —SO$_{n1}$R$^9$, —SO$_{v1}$NR$^9$R$^{10}$, —NHNH$_2$, —ONR$^9$R$^{10}$, —NHC=(O)NHNH$_2$, —NHC=(O)NR$^9$R$^{10}$, —N(O)$_{m1}$, —NR$^9$R$^{10}$, —NH—O—R$^9$, —C(O)R$^9$, —C(O)—OR$^9$, —C(O)NR$^9$R$^{10}$, —OR$^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ is independently hydrogen, halogen, —CX$^b_3$, —CN, —SO$_2$Cl, —SO$_{n2}$R$^{11}$, —SO$_{v2}$NR$^{11}$R$^{12}$, —NHNH$_2$, —ONR$^{11}$R$^{12}$, —NHC=(O)NHNH$_2$, —NHC=(O)NR$^{11}$R$^{12}$, —N(O)$_{m2}$, —NR$^{11}$R$^{12}$, —NH—O—R$^{11}$, —C(O)R$^{11}$, —C(O)—OR$^{11}$, —C(O)NR$^{11}$R$^{12}$, —OR$^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is independently hydrogen, halogen, —CX$^c_3$, —CN, —SO$_2$Cl, —SO$_{n3}$R$^{13}$, —SO$_{v3}$NR$^{13}$R$^{14}$, —NHNH$_2$, —ONR$^{13}$R$^{14}$, —NHC=(O)NHNH$_2$, —NHC=(O)NR$^{13}$R$^{14}$, —N(O)$_{m3}$, —NR$^{13}$R$^{14}$, —NH—O—R$^{13}$, —C(O)R$^{13}$, —C(O)—OR$^{13}$, —C(O)NR$^{13}$R$^{14}$, —OR$^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently —F, —Cl, —Br, or —I. The symbols $n_1$, $n_2$ and $n_3$ are independently an integer from 0 to 4. The symbols $m_1$, $m_2$ and $m_3$ are independently an integer from 1 to 2. The symbols $v_1$, $v_2$ and $v_3$ are independently an integer from 1 to 2.

In one aspect, a method of increasing the amount of CD8-positive cells relative to the amount of regulatory T cells in a subject in need thereof is provided. The method includes administering to the subject a therapeutically effective amount of an adenosine-A2A (A2A) receptor antagonist and a programmed cell death protein 1 (PD-1) signaling pathway inhibitor.

In one aspect, a method of increasing the amount of CD8-positive cells relative to the amount of regulatory T cells in a subject in need thereof is provided. The method includes administering to the subject a therapeutically effective amount of an adenosine-A2A (A2A) receptor antagonist, wherein the A2A receptor antagonist is a compound of formula:

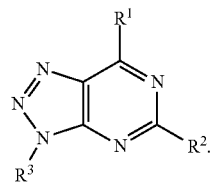

(I)

In formula (I), $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —$N(O)_{m1}$, —$NR^9R^{10}$, —NH—O—$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$NR^{11}R^{12}$, —NH—O—$R^{11}$, —C(O)$R^{11}$, —C(O)—$OR^{11}$, —C(O)$NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —$N(O)_{m3}$, —$NR^{13}R^{14}$, —NH—O—$R^{13}$, —C(O)$R^{13}$, —C(O)—$OR^{13}$, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently —F, —Cl, —Br, or —I. The symbols $n_1$, $n_2$ and $n_3$ are independently an integer from 0 to 4. The symbols $m_1$, $m_2$ and $m_3$ are independently an integer from 1 to 2. The symbols $v_1$, $v_2$ and $v_3$ are independently an integer from 1 to 2.

In one aspect, a method of decreasing tumor volume in a subject in need thereof is provided. The method includes administering to the subject a therapeutically effective amount of an adenosine-A2A (A2A) receptor antagonist and a programmed cell death protein 1 (PD-1) signaling pathway inhibitor.

In one aspect, a method of decreasing tumor volume in a subject in need thereof is provided. The method includes administering to the subject a therapeutically effective amount of an adenosine-A2A (A2A) receptor antagonist, wherein the A2A receptor antagonist is a compound of formula:

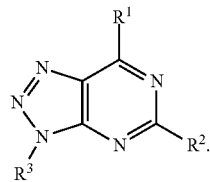

(I)

In formula (I), $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —$N(O)_{m1}$, —$NR^9R^{10}$, —NH—O—$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$NR^{11}R^{12}$, —NH—O—$R^{11}$, —C(O)$R^{11}$, —C(O)—$OR^{11}$, —C(O)$NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —$N(O)_{m3}$, —$NR^{13}R^{14}$, —NH—O—$R^{13}$, —C(O)$R^{13}$, —C(O)—$OR^{13}$, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC═(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X$^a$, X$^b$ and X$^c$ are independently —F, —Cl, —Br, or —I. The symbols n$_1$, n$_2$ and n$_3$ are independently an integer from 0 to 4. The symbols m$_1$, m$_2$ and m$_3$ are independently an integer from 1 to 2. The symbols v$_1$, v$_2$ and v$_3$ are independently an integer from 1 to 2.

In one aspect, a method of enhancing anti-tumor immune memory in a subject in need thereof is provided. The method includes administering to the subject a therapeutically effective amount of an adenosine-A2A (A2A) receptor antagonist and a programmed cell death protein 1 (PD-1) signaling pathway inhibitor.

In one aspect, a method of enhancing anti-tumor immune memory in a subject in need thereof is provided. The method includes administering to the subject a therapeutically effective amount of an adenosine-A2A (A2A) receptor antagonist, wherein the A2A receptor antagonist is a compound of formula:

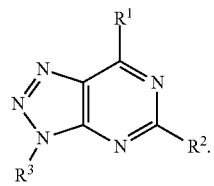

(I)

In formula (I), R$^1$ is independently hydrogen, halogen, —CX$^a{}_3$, —CN, —SO$_2$Cl, —SO$_{n1}$R$^9$, —SO$_{v1}$NR$^9$R$^{10}$, —NHNH$_2$, —ONR$^9$R$^{10}$, —NHC═(O)NHNH$_2$, —NHC═(O)NR$^9$R$^{10}$, —N(O)$_{m1}$, —NR$^9$R$^{10}$, —NH—O—R$^9$, —C(O)R$^9$, —C(O)—OR$^9$, —C(O)NR$^9$R$^{10}$, —OR$^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ is independently hydrogen, halogen, —CX$^b{}_3$, —CN, —SO$_2$Cl, —SO$_{n2}$R$^{11}$, —SO$_{v2}$NR$^{11}$R$^{12}$, —NHNH$_2$, —ONR$^{11}$R$^{12}$, —NHC═(O)NHNH$_2$, —NHC═(O)NR$^{11}$R$^{12}$, —N(O)$_{m2}$, —NR$^{11}$R$^{12}$, —NH—O—R$^{11}$, —C(O)R$^{11}$, —C(O)—OR$^{11}$, —C(O)NR$^{11}$R$^{12}$, —OR$^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is independently hydrogen, halogen, —CX$^c{}_3$, —CN, —SO$_2$Cl, —SO$_{n3}$R$^{13}$, —SO$_{v3}$NR$^{13}$R$^{14}$, —NHNH$_2$, —ONR$^{13}$R$^{14}$, —NHC═(O)NHNH$_2$, —NHC═(O)NR$^{13}$R$^{14}$, —N(O)$_{m3}$, —NR$^{13}$R$^{14}$, —NH—O—R$^{13}$, —C(O)R$^{13}$, —C(O)—OR$^{13}$, —C(O)NR$^{13}$R$^{14}$, —OR$^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^9$, R$^{10}$, R$^{11}$, R$^{12}$, R$^{13}$ and R$^{14}$ are independently hydrogen, halogen, ═O, ═S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC═(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X$^a$, X$^b$ and X$^c$ are independently —F, —Cl, —Br, or —I. The symbols n$_1$, n$_2$ and n$_3$ are independently an integer from 0 to 4. The symbols m$_1$, m$_2$ and m$_3$ are independently an integer from 1 to 2. And the symbols v$_1$, v$_2$ and v$_3$ are independently an integer from 1 to 2.

In one aspect, a method of increasing global immune activation in a subject in need thereof is provided. The method includes administering to the subject a therapeutically effective amount of an adenosine-A2A (A2A) receptor antagonist, wherein the A2A receptor antagonist is a compound of formula:

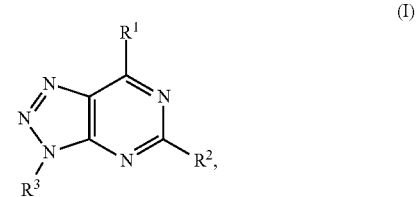

In formula (I), R$^1$ is independently hydrogen, halogen, —CX$^a{}_3$, —CN, —SO$_2$Cl, —SO$_{n1}$R$^9$, —SO$_{v1}$NR$^9$R$^{10}$, —NHNH$_2$, —ONR$^9$R$^{10}$, —NHC═(O)NHNH$_2$, —NHC═(O)NR$^9$R$^{10}$, —N(O)$_{m1}$, —NR$^9$R$^{10}$, —NH—O—R$^9$, —C(O)R$^9$, —C(O)—OR$^9$, —C(O)NR$^9$R$^{10}$, —OR$^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ is independently hydrogen, halogen, —CX$^b{}_3$, —CN, —SO$_2$Cl, —SO$_{n2}$R$^{11}$, —SO$_{v2}$NR$^{11}$R$^{12}$, —NHNH$_2$, —ONR$^{11}$R$^{12}$, —NHC═(O)NHNH$_2$, —NHC═(O)NR$^{11}$R$^{12}$, —N(O)$_{m2}$, —NR$^{11}$R$^{12}$, —NH—O—R$^{11}$, —C(O)R$^{11}$, —C(O)—OR$^{11}$, —C(O)NR$^{11}$R$^{12}$, —OR$^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is independently hydrogen, halogen, —CX$^c{}_3$, —CN, —SO$_2$Cl, —SO$_{n3}$R$^{13}$, —SO$_{v3}$NR$^{13}$R$^{14}$, —NHNH$_2$, —ONR$^{13}$R$^{14}$, —NHC═(O)NHNH$_2$, —NHC═(O)NR$^{13}$R$^{14}$, —N(O)$_{m3}$, —NR$^{13}$R$^{14}$, —NH—O—R$^{13}$, —C(O)R$^{13}$, —C(O)—OR$^{13}$, —C(O)NR$^{13}$R$^{14}$, —OR$^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^9$, R$^{10}$, R$^{11}$, R$^{12}$, R$^{13}$ and R$^{14}$ are independently hydrogen, halogen, ═O, ═S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC═(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X$^a$, X$^b$ and X$^c$ are independently —F, —Cl, —Br, or —I. The symbols n$_1$, n$_2$ and n$_3$ are independently an integer from 0 to 4. The symbols m$_1$, m$_2$ and m$_3$ are independently an integer from 1 to 2. And the symbols v$_1$, v$_2$ and v$_3$ are independently an integer from 1 to 2.

In one aspect, a method of treating cancer in a subject in need thereof is provided. The method includes administering to the subject a therapeutically effective amount of an adenosine-A2A (A2A) receptor antagonist of formula:

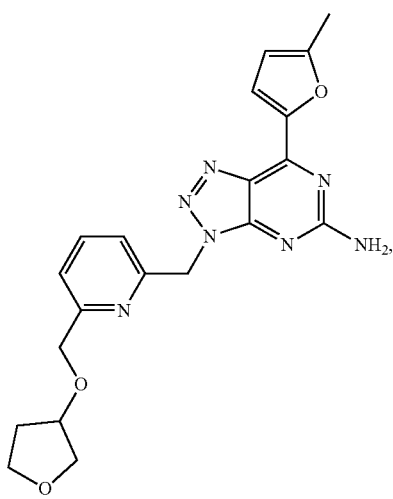 [SMILES: Cc1ccc(-c2nc(N)nc3c2nnn3Cc2cccc(COC3CCOC3)n2)o1]

wherein the adenosine-A2A (A2A) receptor antagonist is administered at 100 mg twice a day (BID).

In one aspect, a method of treating cancer in a subject in need thereof is provided. The method includes administering to the subject a therapeutically effective amount of an adenosine-A2A (A2A) receptor antagonist of formula:

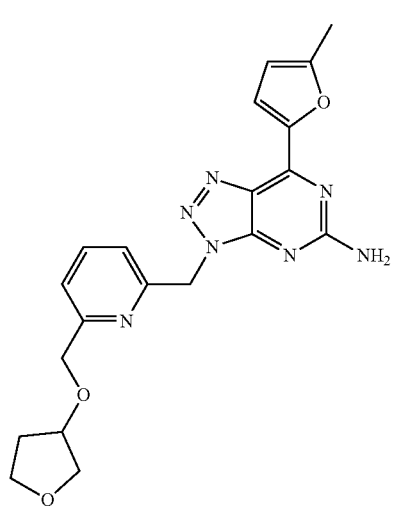 [SMILES: Cc1ccc(-c2nc(N)nc3c2nnn3Cc2cccc(COC3CCOC3)n2)o1]

and a therapeutically effective amount of atezolizumab.

In one aspect, a pharmaceutical composition including an A2A receptor antagonist, a PD-1 signaling pathway inhibitor and a pharmaceutically acceptable excipient is provided.

In one aspect, a pharmaceutical composition including an A2A receptor antagonist of formula:

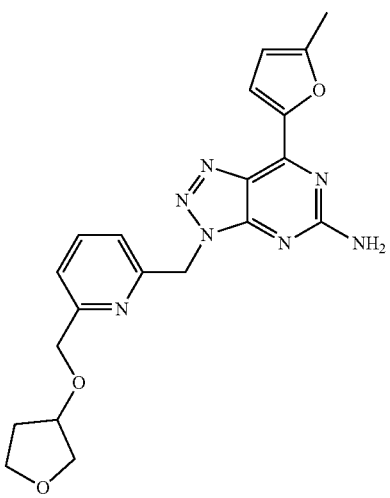 [SMILES: Cc1ccc(-c2nc(N)nc3c2nnn3Cc2cccc(COC3CCOC3)n2)o1]

and a pharmaceutically acceptable excipient is provided, wherein the adenosine-A2A (A2A) receptor antagonist is present at 100 mg.

In one aspect, a pharmaceutical composition including an adenosine-A2A (A2A) receptor antagonist of formula:

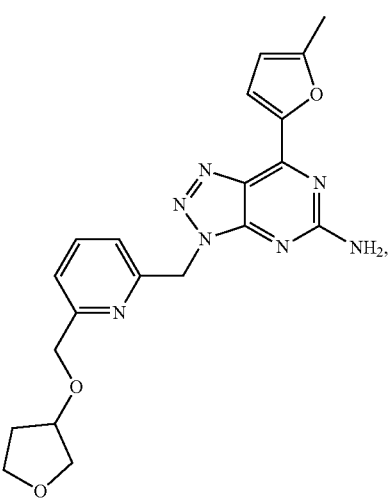

atezolizumab and a pharmaceutically acceptable excipient is provided.

In one aspect, a method of activating a T cell is provided. The method includes contacting the T cell with an A2A receptor antagonist, wherein the adenosine-A2A (A2A) receptor antagonist is a compound of formula:

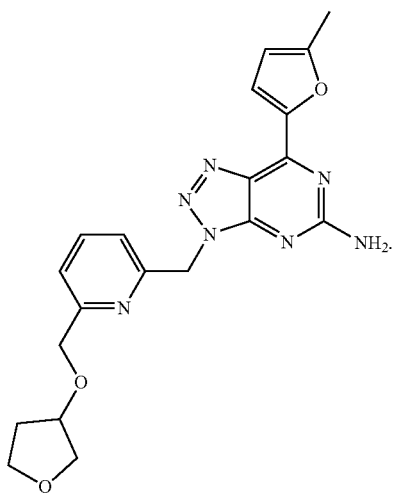

In one aspect, a method of inhibiting A2A receptor activity of a cell is provided. The method includes contacting said cell with an A2A receptor antagonist, wherein the A2A receptor antagonist is a compound of formula:

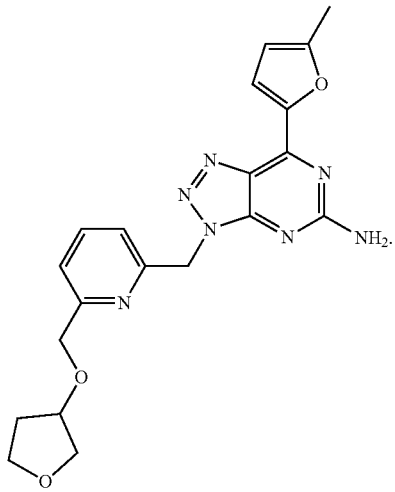 [SMILES: Cc1ccc(-c2nc(N)nc3c2nnn3Cc2cccc(COC3CCOC3)n2)o1]

In one aspect, a method of increasing the amount of CD8-positive cells relative to the amount of regulatory T cells in a subject in need thereof is provided. The method includes administering to the subject a therapeutically effective amount of an adenosine-A2A (A2A) receptor antagonist, wherein the adenosine-A2A (A2A) receptor antagonist is a compound of formula:

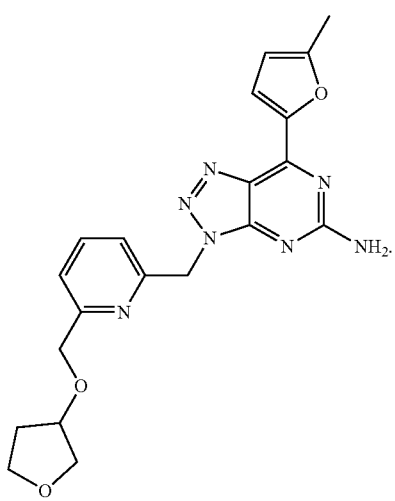 [SMILES: Cc1ccc(-c2nc(N)nc3c2nnn3Cc2cccc(COC3CCOC3)n2)o1]

In one aspect, a method of increasing an anti-tumor immune response in a subject in need thereof is provided. The method includes administering to the subject a therapeutically effective amount of an adenosine-A2A (A2A) receptor antagonist, wherein the adenosine-A2A (A2A) receptor antagonist is a compound of formula:

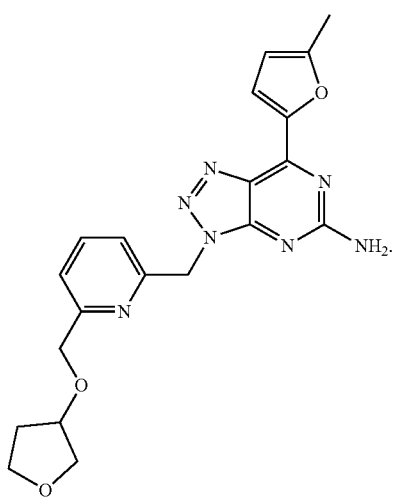

In one aspect, a method of decreasing tumor volume in a subject in need thereof is provided. The method includes administering to said subject a therapeutically effective amount of an adenosine-A2A (A2A) receptor antagonist, wherein the adenosine-A2A (A2A) receptor antagonist is a compound of formula:

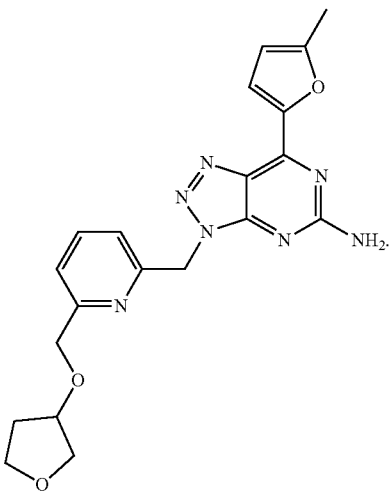

In one aspect, a method of enhancing anti-tumor immune memory in a subject in need thereof is provided. The method includes administering to said subject a therapeutically effective amount of an adenosine-A2A (A2A) receptor antagonist, wherein the adenosine-A2A (A2A) receptor antagonist is a compound of formula:

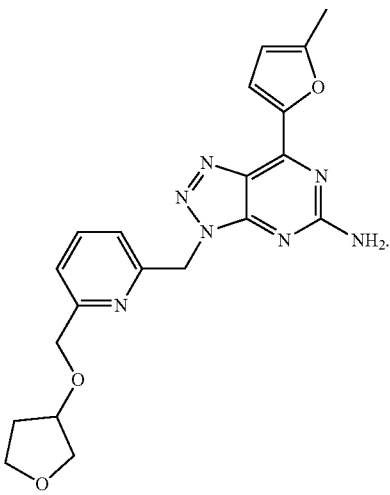

In one aspect, a method of detecting a phosphorylated cAMP response element-binding protein (pCREB) in a B-cell or T-cell of a mammalian subject is provided. The method includes:
(i) obtaining a blood sample from a mammalian subject;
(ii) contacting the blood sample with an adenosine receptor agonist;
(iii) contacting the blood sample with a pCREB detection agent and a blood cell detection agent, wherein the blood cell detection agent includes a B-cell detection agent or T-cell detection agent, thereby forming a T-cell-detection agent complex or a B-cell-detection agent complex; and
(iv) detecting the T-cell detection agent complex or the B-cell detection complex thereby detecting the pCREB in a T-cell or B-cell.

In one aspect, the adenosine receptor agonist includes adenosine, 5'-N-Ethylcarboxamidoadenosine (NECA), or an analog thereof. In one aspect, the pCREB detection agent includes an antibody against pCREB. In one aspect, the B cell detection agent includes an antibody against CD19 and/or an antibody against CD20. In one aspect, the T cell detection agent includes an antibody against CD3, CD4 and/or an antibody against CD8.

In one aspect, the method further includes contacting the blood sample with a fixation agent and cell permeabilizing agent after contacting the blood sample with an adenonsine receptor agonist and prior to contacting the blood sample with a pCREB detection agent. In one aspect, the method further includes contacting the blood sample with an apoptotic cell detection agent. In one aspect, the apoptotic cell detection agent includes an antibody against cPARP. In one aspect, the method further includes, prior to obtaining the blood sample, administering to the mammalian subject an adenosine receptor antagonist.

In one aspect, the adenosine receptor antagonist includes an A2a receptor antagonist or an A2b receptor antagonist. In one aspect, the method further includes, prior to obtaining the blood sample, administering to the mammalian subject an anti-cancer agent. In one aspect, the anti-cancer agent includes a PD-L1 antagonist. In one aspect, the PD-L1 antagonist includes atezolizumab. In one aspect, the method further includes, contacting the blood sample with a cell subset detection agent. In one aspect, the cell subset detection agent includes a naïve cell detection agent, a memory cell detection agent, or an effector cell detection agent. In one aspect, the cell subset detection agent includes an antibody against CD27 or an antibody against CD45RA. In one aspect, the blood sample is collected from circulating blood. In one aspect, the blood sample includes an intratumoral sample.

In one aspect, a method of treating a subject with cancer is provided. The method includes:
(i) obtaining a blood sample from a subject with cancer;
(ii) detecting a level of pCREB induced by an adenosine receptor agonist in the sample;
(iii) administering an effective amount of an adenosine receptor antagonist to the subject.

In one aspect, the detecting of the level of pCREB induced in the sample includes:
(a) contacting the blood sample with an adenosine receptor agonist; and
(b) contacting the blood sample with a pCREB detection agent and a blood cell detection agent, wherein the blood cell detection agent includes a B-cell detection agent or T-cell detection agent.

In one aspect, the pCREB detection agent includes an antibody against pCREB. In one aspect, the B cell detection agent includes an antibody against CD19 and/or against CD20. In one aspect, the T cell detection agent includes an antibody against CD3, CD4 and/or an antibody against CD8. In one aspect, detecting the level of pCREB induced in the subject comprises measuring a level of pCREB in B cells or T cells prior to the administering of the effective amount of an adenosine receptor antagonist to the subject.

In one aspect, the method further includes: (iv) detecting a level of pCREB induced in said sample following said administering of the effective amount of adenosine receptor antagonist to said subject. In one aspect, the detecting of the level of pCREB induce in said sample comprises measuring a level of pCREB induced in B cells or T cells following said administering of the effective amount of adenosine receptor antagonist to said subject.

In one aspect, the method includes increasing a dose of an adenosine receptor antagonist based on the level of pCREB induced in said B cells or T cells.

In one aspect a permeabilized blood cell is provided. The permeabilized blood cell includes a pCREB detection agent and a blood cell detection agent, wherein the blood cell detection agent includes a B-cell detection agent or T-cell detection agent and the permeabilized blood cell includes a permeabilized B-cell or permeabilized T-cell. In one aspect, the permeabilized blood cell further includes an apoptotic cell detection agent. In one aspect, the apoptotic cell detection agent includes an antibody against cPARP. In one aspect the permeabilized blood cell further includes a mature cell detection agent. In one aspect, the mature cell detection agent includes antibody against CD27 or an antibody against CD45RA.

In one aspect, a container including an adenosine receptor agonist in combination with the permeabilized cell as described above is provided.

In one aspect, a flow cytometer including the permeabilized blood cell as described above is provided.

BRIEF DESCRIPTION OF THE DRAWINGS

FIG. 11: CPI-444 Inhibits EL4 Tumor Growth In Regional Lymph Nodes

FIG. 16A: MC38 colon cancer cells were engrafted onto the back of syngeneic C57BL/6 mice. Mice were treated with CPI-444 (100 mg/kg), anti-PD-L1 (10F.9G2, 200 ug), or appropriate controls as indicated. All treatment regimens resulted in an inhibition of tumor growth, however therapeutic efficacy was optimal when CPI-444 was administered prior to or concurrent with anti-PD-L1 (FIG. 16B). The combination of CPI-444 with anti PD-L1 was particularly effective when initiated on established tumors (Day 7) and resulted in full tumor elimination in 8/9 mice.

FIGS. 19A and 19B: T Cell activation in treated subjects. Whole blood was collected on Day 1 of Cycles 1, 2, 4 & 8 for flow analysis. The percentage of CD4 and CD8 T cells that stained PD-1+(FIG. 19A) or CD45RA− (memory/effector cells) (FIG. 19B) is shown. Each line represents a single subject across time. CPI-444 treatment increases PD-1+/CD8+ and memory cell frequencies as a single agent and in combination cohorts, suggesting activation of T cell mediated immunity.

FIGS. 21A-21C: Efficacy by PD-L1 status and prior anti-PD-1 treatment status. The disease is stable in anti-PD-L1 naïve and refractory as well as patient PD-L1+ and PD-L1-tumors (FIG. 21A and FIG. 21B). Tumor regression in a Nivolumab-refractory lung cancer patient (Single agent CPI-444 100 mg po BID×28 days/cycle)(FIG. 21C). In FIG. 21C, Patient's Morisita Index was 0.84 and increased clonality was observed following treatment.

FIG. 22B shows the change in tumor size relative to baseline plotted against the Morisita Index. FIG. 22C shows the change in tumor size relative to baseline plotted against baseline clonality.

FIGS. 23A and 23B show the tumor volume at different time points since engraftment for the dosing cohorts. These results suggest CD8+ T cells are required for the efficacy of CPI-444 alone or in combination with Anti-PD-L1.

FIG. 33A is a graph showing the inhibition of pCREB relative to baseline levels over time. Complete and sustained inhibition was seen in 7 of 7 patients treated with 100 mg BID single agent CPI-444. Variable inhibition was seen in 200 mg QD and 50 mg BID cohorts. FIG. 33B shows the inhibition of pCREB relative to baseline for different concentrations of plasma CPI-444. PK/PD analysis supports 100 mg BID as the optimal dose for Step 2 dose expansion cohorts. The A2AR pathway is completely inhibited at CPI-444 exposures greater than 2000 ng/mL.

FIG. 34A shows pCREB percent inhibition in B cells in patients who received 50 mg BID of CPI-444. FIG. 34B shows pCREB percent inhibition in B cells in patients who received 100 mg BID of CPI-444. FIG. 34C shows pCREB percent inhibition in B cells in patients who received 200 QD of CPI-444. The majority of patients in the 100 mg BID cohort demonstrate high pCREB inhibition at trough and near complete inhibition after taking their morning dose. FIG. 34D is a dot plot showing the change in percent inhibition between trough (0 hr) and peak (3 hr). There is little fluctuation from trough to peak in the 100 mg BID dosing group, making 100 mg BID an appropriate dose for continuous functional inhibition. The 50 mg BID is not high enough for sustained inhibition and the 200 mg QD dose achieves high peak levels but is not maintained at trough since CPI-444 is administered once per day.

FIG. 35B represents a single time point from a single subject. For plasma levels greater than 2,000 ng/mL near complete inhibition was observed in B cells (FIG. 35A) and CD4+ T cells (FIG. 35B).

DETAILED DESCRIPTION OF THE INVENTION

Definitions

Figure 1:
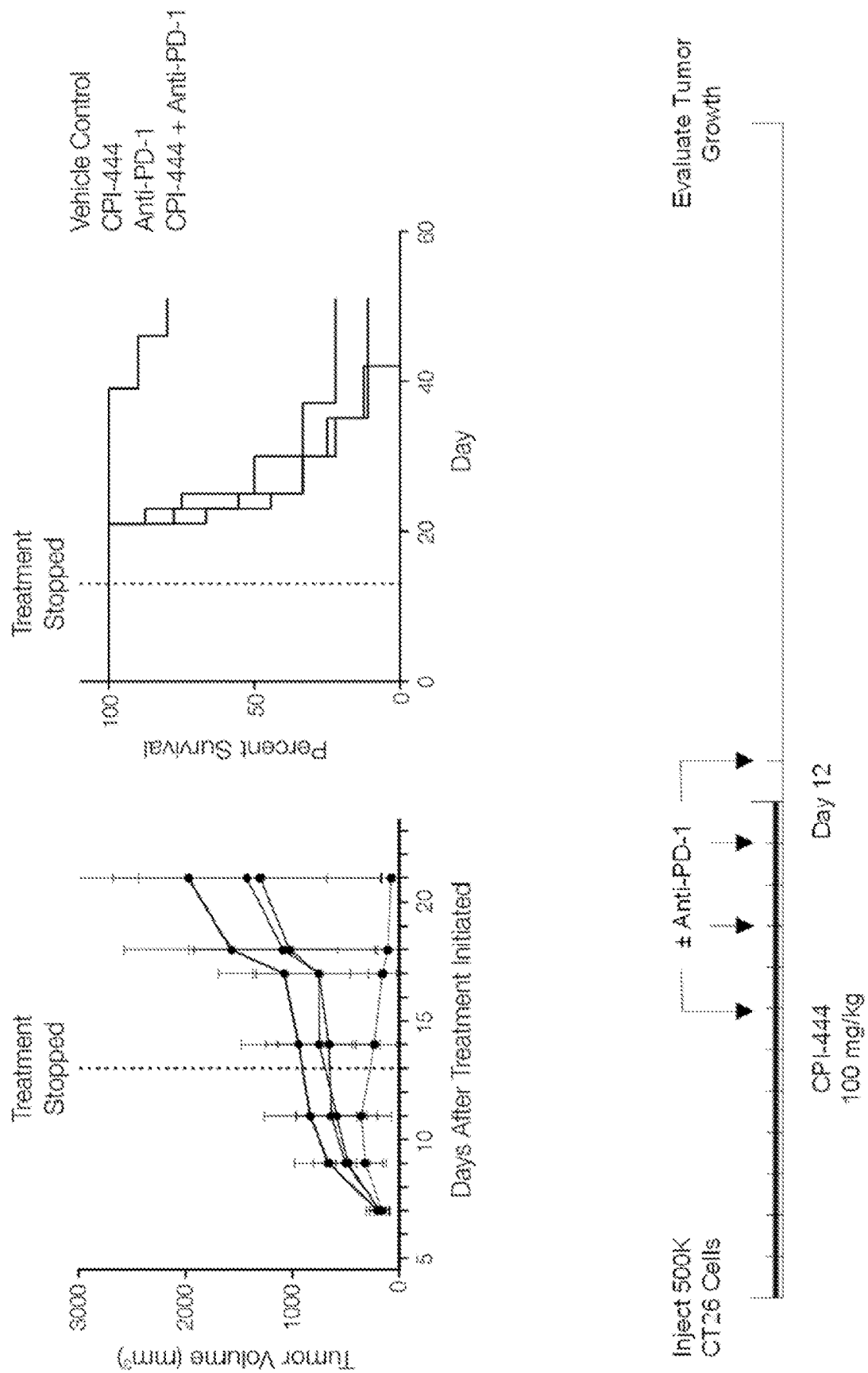
FIG. 1: CPI-444±Anti-PD-1 In Early CT26 Model. Therapeutic synergy in combination with anti-PD-1.
Figure 2:
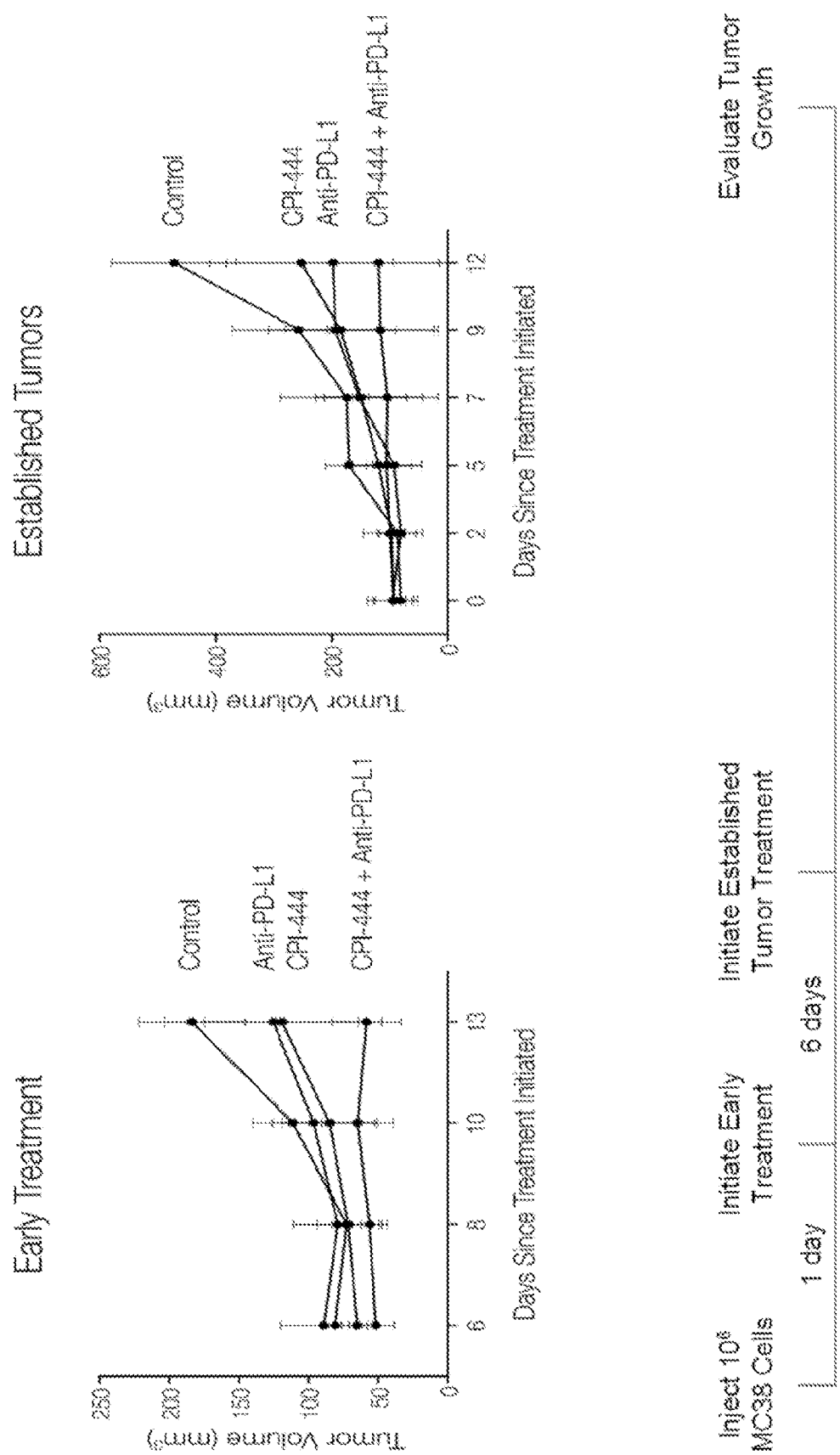
FIG. 2: CPI-444±Anti-PD-L1 In MC38 Model. Combination treatment inhibits tumor growth.
Figure 3:
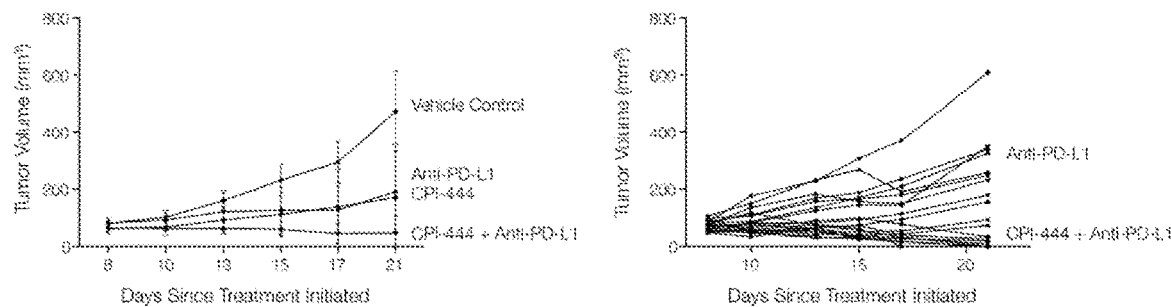
FIG. 3: Efficacy Model: MC38 Colon Cancer. Synergy in combination with anti-PD-L1.
Figure 3:
Figure 4:
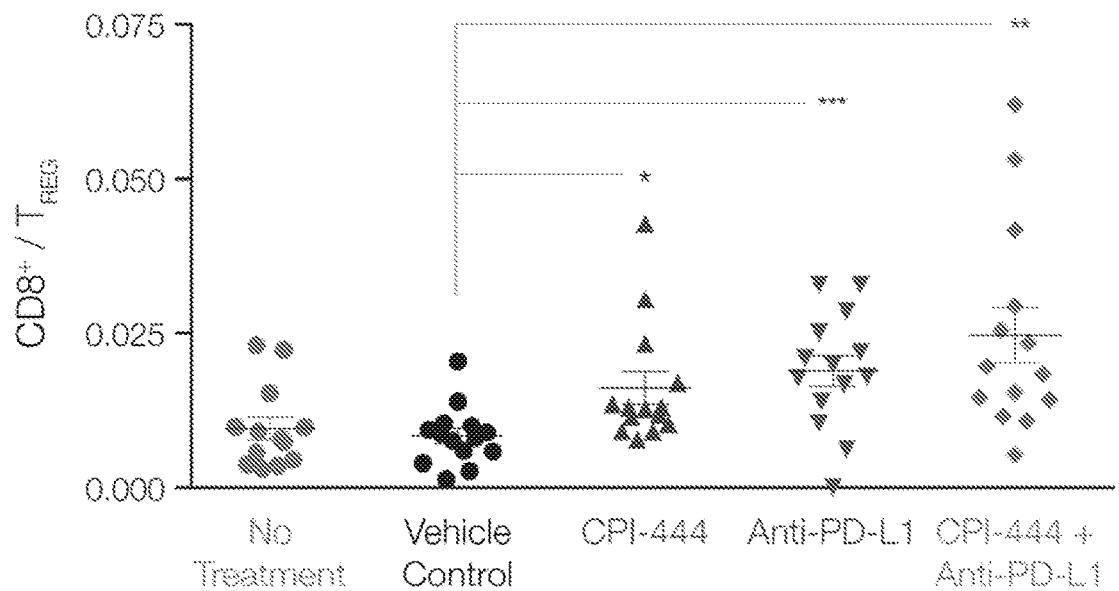
FIG. 4: Efficacy Model: MC38 Colon Cancer. Skewing toward anti-tumor immune response in tumors.
Figure 4:
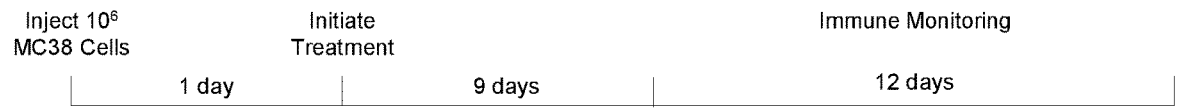
Figure 5:
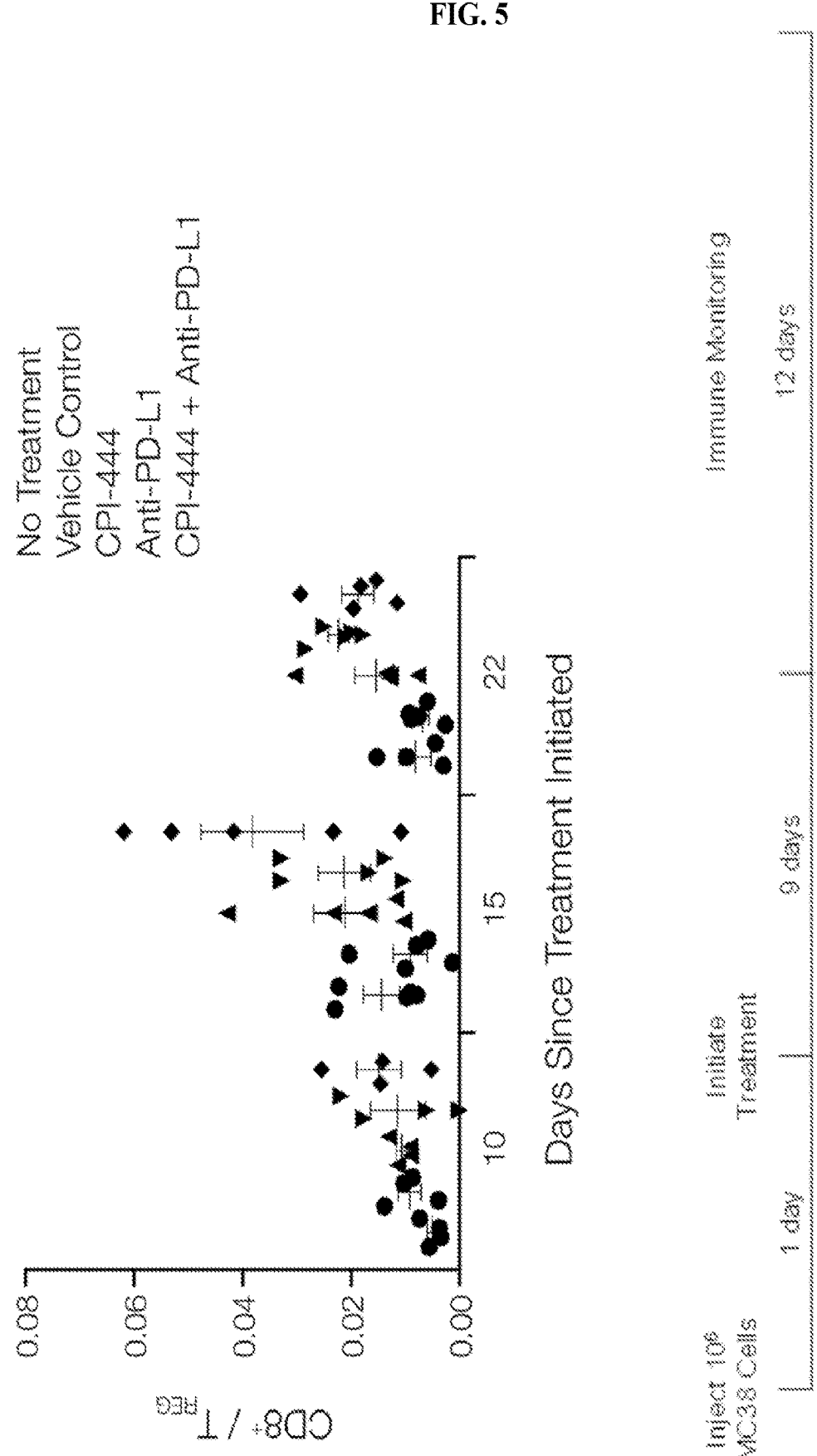
FIG. 5: Efficacy Model: MC38 Colon Cancer. Skewing toward anti-tumor immune response in tumors.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g. O, N, P, Si, and S), and wherein the nitrogen and sulfur atoms may optionally be oxidized, and the nitrogen heteroatom may optionally be quaternized. The heteroatom(s) (e.g. O, N, P, S, and Si) may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

The symbol "〜〜" denotes the point of attachment of a chemical moiety to the remainder of a molecule or chemical formula.

In embodiments, a compound as described herein may include multiple instances of $R^2$ and/or other variables. In such embodiments, each variable may optional be different and be appropriately labeled to distinguish each group for greater clarity. For example, where each $R^2$ is different, they may be referred to, for example, as $R^{2.1}$, $R^{2.2}$, $R^{2.3}$, and/or $R^{2.4}$ respectively, wherein the definition of $R^2$ is assumed by $R^{2.1}$, $R^{2.2}$, $R^{2.3}$, and/or $R^{2.4}$. The variables used within a definition of $R^2$ and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{12}$-substituted or unsubstituted alkyl, a plurality of $R^{12}$ substituents may be attached to the alkyl moiety wherein each $R^{12}$ substituent is optionally different. Where an R-substituted moiety is substituted with a plurality R substituents, each of the R-substituents may be differentiated herein using a prime symbol (') such as R', R", etc. For example, where a moiety is $R^{12}$-substituted or unsubstituted alkyl, and the moiety is substituted with a plurality of $R^{12}$ substituents, the plurality of $R^{12}$ substituents may be differentiated as $R^{12\prime}$, $R^{12\prime\prime}$, $R^{12\prime\prime\prime}$, etc. In embodiments, the plurality of R substituents is 3. In embodiments, the plurality of R substituents is 2.

In embodiments, a compound as described herein may include multiple instances of $R^1$, $R^2$, $R^3$, $R^4$, $R^5$, $R^6$, $R^7$, $R^9$, $R^{10}$, $R^{11}$, $R^{12}$, $R^{13}$, $R^{14}$ and/or other variables. In such embodiments, each variable may optional be different and be appropriately labeled to distinguish each group for greater clarity. For example, where each $R^1$, $R^2$, $R^3$, $R^4$, $R^5$, $R^6$, $R^7$, $R^9$, $R^{10}$, $R^{11}$, $R^{12}$, $R^{13}$, and/or $R^{14}$, is different, they may be referred to, for example, as $R^{1.1}$, $R^{1.2}$, $R^{1.3}$, $R^{1.4}$, $R^{2.1}$, $R^{2.2}$, $R^{2.3}$, $R^{2.4}$, $R^{3.1}$, $R^{3.2}$, $R^{3.3}$, $R^{3.4}$, $R^{4.1}$, $R^{4.2}$, $R^{4.3}$, $R^{4.4}$, $R^{5.1}$, $R^{5.2}$, $R^{5.3}$, $R^{5.4}$, $R^{6.1}$, $R^{6.2}$, $R^{6.3}$, $R^{6.4}$, $R^{7.1}$, $R^{7.2}$, $R^{7.3}$, $R^{7.4}$, $R^{9.1}$, $R^{9.2}$, $R^{9.3}$, $R^{9.4}$, $R^{10.1}$, $R^{10.2}$, $R^{10.3}$, $R^{10.4}$, $R^{11.1}$, $R^{11.2}$, $R^{11.3}$, $R^{11.4}$, $R^{12.1}$, $R^{12.2}$, $R^{12.3}$, $R^{12.4}$, $R^{13.1}$, $R^{13.2}$, $R^{13.3}$, $R^{13.4}$, $R^{14.1}$, $R^{14.2}$, $R^{14.3}$, and/or $R^{14.4}$, respectively, wherein the definition of $R^1$ is assumed by $R^{1.1}$, $R^{1.2}$, $R^{1.3}$, and/or $R^{1.4}$, the definition of $R^2$ is assumed by $R^{2.1}$, $R^{2.2}$, $R^{2.3}$, $R^{2.4}$, the definition of $R^3$ is assumed by $R^{3.1}$, $R^{3.2}$, $R^{3.3}$, and/or $R^{3.4}$, the definition of $R^4$ is assumed by $R^{4.1}$, $R^{4.2}$, $R^{4.3}$, and/or $R^{4.4}$, the definition of $R^5$ is assumed by $R^{5.1}$, $R^{5.2}$, $R^{5.3}$, and/or $R^{5.4}$, the definition of $R^6$ is assumed by $R^{6.1}$, $R^{6.2}$, $R^{6.3}$, and/or $R^{6.4}$, the definition of $R^7$ is assumed by $R^{7.1}$, $R^{7.2}$, $R^{7.3}$, and/or $R^{7.4}$, the definition of $R^9$ is assumed by $R^{9.1}$, $R^{9.2}$, $R^{9.3}$, and/or $R^{9.4}$, the definition of $R^{10}$ is assumed by $R^{10.1}$, $R^{10.2}$, $R^{10.3}$, and/or $R^{10.4}$, the definition of $R^{11}$ is assumed by $R^{11.1}$, $R^{11.2}$, $R^{11.3}$, and/or $R^{11.4}$, the definition of $R^{12}$ is assumed by $R^{12.1}$, $R^{12.2}$, $R^{12.3}$, and/or $R^{12.4}$, the definition of $R^{13}$ is assumed by $R^{13.1}$, $R^{13.2}$, $R^{13.3}$, and/or $R^{13.4}$, the definition of $R^{14}$ is assumed by $R^{14.1}$, $R^{14.2}$, $R^{14.3}$, and/or $R^{14.4}$. The variables used within a definition of $R^1$, $R^2$, $R^3$, $R^4$, $R^5$, $R^6$, $R^7$, $R^9$, $R^{10}$, $R^{11}$, $R^{12}$, $R^{13}$, and/or $R^{14}$, and/or other variables that appear at multiple instances and are different may similarly be appropriately labeled to distinguish each group for greater clarity.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Antibodies are large, complex molecules (molecular weight of 150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

The term "antibody" is used according to its commonly known meaning in the art. As used herein, "antibody" may also refer to the antigen binding fragment thereof. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348: 552-554 (1990); Marks et al., *Biotechnology* 10:779-783 (1992)).

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

Techniques for conjugating therapeutic agents to antibodies are well known (see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to an antibody. A "therapeutic agent" as referred to herein, is a composition useful in treating or preventing a disease such as cancer.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "ligand" refers to an agent, e.g., a polypeptide or other molecule, capable of binding to a receptor.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a pharmaceutical composition as provided herein and a cell or a pCREB detection agent as described herein and a pCREB antigen. In embodiments contacting includes, for example, allowing a pharmaceutical composition as described herein to interact with a cell or a patient. In further embodiments, contacting includes, for example, allowing a pCREB detection agent as described herein to interact with a pCREB antigen.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated," when applied to a protein, denotes that the protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term "purified" denotes that a protein gives rise to essentially one band in an electrophoretic gel. Particularly, it means that the protein is at least 85% pure, more preferably at least 95% pure, and most preferably at least 99% pure.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Typically a specific or selective reaction will be at least twice background signal or noise and more typically more than 10 to 100 times background.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells.

As defined herein, the term "inhibition", "inhibit", "inhibiting" and the like in reference to a protein-inhibitor (e.g., an A2A receptor antagonist or a PD-1 signaling pathway inhibitor) interaction means negatively affecting (e.g., decreasing) the activity or function of the protein (e.g., decreasing the activity of an A2A receptor or a PD-1 protein or PD-L1 protein) relative to the activity or function of the protein in the absence of the inhibitor (e.g., an A2A receptor antagonist or a PD-1 signaling pathway inhibitor). In some embodiments, inhibition refers to reduction of a disease or symptoms of disease (e.g., cancer). Thus, inhibition includes, at least in part, partially or totally blocking stimulation, decreasing, preventing, or delaying activation, or inactivating, desensitizing, or down-regulating signal transduction or enzymatic activity or the amount of a protein (e.g., an A2A receptor or a PD-1 protein or PD-L1 protein). Similarly an "inhibitor" is a compound or protein that inhibits an A2A receptor or a PD-1 protein or PD-L1 protein, e.g., by binding, partially or totally blocking, decreasing, preventing, delaying, inactivating, desensitizing, or down-regulating activity (e.g., an A2A receptor activity or a PD-1 protein activity or PD-L1 protein activity).

An "anti-cancer agent" is a therapeutic used in the treatment or prevention of cancer. An anti-cancer agent can be a large or small molecule. Example anti-cancer agents include antibodies, small molecules, and large molecules or combinations thereof.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5- azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-b enzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenyl acetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-azaepothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin A1 (i.e. BTO-956 and DIME), Fijianolide B, Laulimalide, Narcosine (also known as NSC-5366), Nascapine, Hemiasterlin, Vanadocene acetylacetonate, Monsatrol, lnanocine (i.e. NSC-698666), Eleutherobins (such as Desmethyleleutherobin, Desaetyleleutherobin, lsoeleutherobin A, and Z-Eleutherobin), Caribaeoside, Caribaeolin, Halichondrin B, Diazonamide A, Taccalonolide A, Diozostatin, (−)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., di ethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

"Analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound. In embodiments, an analog is an adenosine analog.

An example adenosine analog is 5'-N-ethylcarboxamidoadenosine (NECA), having the structure shown below:

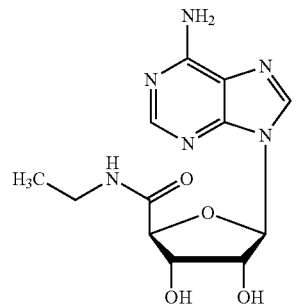

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

An "A2A receptor" or "adenosine A2A receptor" as referred to herein includes any of the recombinant or naturally-occurring forms of the adenosine A2A receptor also known as ADORA2A or variants or homologs thereof that maintain adenosine A2A receptor activity (e.g. within at least 50%, 80%, 90%, 95%, 96%, 97%, 98%, 99% or 100% activity compared to adenosine A2A receptor). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring adenosine A2A receptor. In embodiments, the adenosine A2A receptor is substantially identical to the protein identified by the UniProt reference number P29274 or a variant or homolog having substantial identity thereto. In embodiments, the adenosine A2A receptor is substantially identical to the protein identified by the UniProt reference number Q60613 or a variant or homolog having substantial identity thereto.

"A2B receptor" or "A2BR" or "Adenosine $A_{2B}$ receptor" are used interchangeably. A2B receptors are expressed in some mast cells, such as the BR line of canine mastocytoma cells, which appear to be responsible for triggering acute $Ca^{2+}$ mobilization and degranulation. (See Auchampach et al., *Mol. Pharmacol.* 1997, 52, 846-S60 and Forsyth et al., *Inflamm. Res.* 1999, 48, 301-307.) Adenosine $A_{2B}$ receptors also trigger $Ca^{2+}$ mobilization, and participate in a delayed IL8 release from human HMC-1 mast cells. Other functions associated with the $A_{2B}$ AR are the control of cell growth and gene expression, (See Neary et al., *Trends Neurosci.* 1996, 19, 13-18.) endothelial-dependent vasodilation (See Martin et al., *J Pharmacol. Exp. Ther.* 1993, 265, 248-2, 53.), and fluid secretion from intestinal epithelia. (See Strohmeier, et al., *J Biol. Chem.* 1995, 270, 2387-2394.) Adenosine acting through $A_{2B}$ receptor subtype has also been reported to stimulate chloride permeability in cells expressing the cystic fibrosis transport regulator. (See Clancy et al., *Am. J Physiol.* 1999, 276, C361-C369.) Example A2b receptor antagonists are described in WO 2008002902, included herein by reference in its entirety. In embodiments, the adenosine A2b receptor is substantially identical to the protein identified by the UniProt reference number P29275 or a variant or homolog having substantial identity thereto.

"Adenosine receptor agonist" refers to a molecule that activates adenosine receptors (e.g. A2a or A2b receptors). Adenosine receptors agonists can be small or large molecule agonists. Example adenosine receptors agonists include adenosine, NECA, or analogs thereof.

"Adenosine receptor antagonist" references to a molecule that inhibits activity of adenosine receptors (e.g. A2a or A2b receptors). Adenosine receptors antagonists can be small or large molecule antagonists. In embodiments, CPI-444 is an example A2A receptor antagonist.

A "PD-1 protein" or "PD-1" as referred to herein includes any of the recombinant or naturally-occurring forms of the Programmed cell death protein 1 (PD-1) also known as cluster of differentiation 279 (CD 279) or variants or homologs thereof that maintain PD-1 protein activity (e.g. within at least 50%, 80%, 90%, 95%, 96%, 97%, 98%, 99% or 100% activity compared to PD-1 protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-1 protein. In embodiments, the PD-1 protein is substantially identical to the protein identified by the UniProt reference number Q15116 or a variant or homolog having substantial identity thereto. In embodiments, the PD-1 protein is substantially identical to the protein identified by the UniProt reference number Q02242 or a variant or homolog having substantial identity thereto.

A "pCREB protein" or "pCREB" as referred to herein includes any of the recombinant or naturally-occurring forms of the cAMP response element-binding protein (pCREB) or variants or homologs thereof that maintain pCREB activity (e.g. within at least 50%, 80%, 90%, 95%, 96%, 97%, 98%, 99% or 100% activity compared to pCREB protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring pCREB protein. In embodiments, the pCREB protein is substantially identical to the protein identified by the UniProt reference number P16220 or a variant or homolog having substantial identity thereto.

A "PD-1 protein" or "PD-1" as referred to herein includes any of the recombinant or naturally-occurring forms of the Programmed cell death protein 1 (PD-1) also known as cluster of differentiation 279 (CD 279) or variants or homologs thereof that maintain PD-1 protein activity (e.g. within at least 50%, 80%, 90%, 95%, 96%, 97%, 98%, 99% or 100% activity compared to PD-1 protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-1 protein. In embodiments, the PD-1 protein is substantially identical to the protein identified by the UniProt reference number Q15116 or a variant or homolog having substantial identity thereto. In embodiments, the PD-1 protein is substantially identical to the protein identified by the UniProt reference number Q02242 or a variant or homolog having substantial identity thereto.

The term "atezolizumab" or "MPDL3280A" refers to a fully humanized, engineered monoclonal antibody of IgG1 isotype against the protein programmed cell death ligand 1 (PD-L1). In the customary sense, atezolizumab refers to CAS Registry number 1380723-44-3. Atezolizumab may be referred to as an anti-cancer agent. In embodiments, atezolizumab is referred to as with the tradename Tecentriq®.

Cyclic AMP (cAMP) response element binding protein (CREB) is a cellular transcription factor. CREB is activated by signaling cascades resultant from an array of extracellular signals. One such activating signal cascade is triggered by agonist binding to adenosine receptor (e.g. A2A and A2B receptors). Agonist activation of adenosine receptor results in activation of CREB by phosphorylation. Agonist activation of adenosine receptor also results in activation of protein kinase A (PKA) upstream of CREB. In embodiments, CREB is substantially identical to the protein identified by the UniProt reference number P16220 or a variant or homolog having substantial identity thereto. In embodiments, CREB is phosphorylated at Serine 133.

A "pCREB detection agent" refers to a chemical or molecular moiety capable of identifying phosphorylated CREB. A pCREB detection agent may comprise an antibody or other specific for the phosphorylated CREB. Antibodies specific to pCREB are commercially available, for example p-CREB Antibody (Ser133) (Cell Signaling Technology Cat. No.: 14001 or Santa Cruz Biotechnology Cat. No.: sc-7978).

The term "blood cell detection agent" refers to a chemical or molecular moiety capable of identifying blood cells. A blood cell detection agent can refer to, for example, a chemical stain or an antibody against cell surface markers. Example blood cell detection agents include B cell detection agents and T cell detection agents.

The term "B cell detection agent" refers to a chemical or molecular moiety capable of identifying B cells. In examples, a B cell detection agent can be an antibody to a B cell specific surface maker (e.g. an antibody against CD19, or an antibody against CD20). B cell detection agents can be used alone or in combination. B cell detection agents can further be detected by fluorescence activated cell sorting (FACS).

"B Cells" or "B lymphocytes" refer to their standard use in the art. B cells are lymphocytes, a type of white blood cell (leukocyte), that develops into a plasma cell (a "mature B cell"), which produces antibodies. An "immature B cell" is a cell that can develop into a mature B cell. Generally, pro-B cells undergo immunoglobulin heavy chain rearrangement to become pro B pre B cells, and further undergo immunoglobulin light chain rearrangement to become an immature B cells. Immature B cells include T1 and T2 B cells.

"T cell detection agents" refers to a chemical or molecular moiety capable of identifying T cells. In examples, a T cell detection agent can be an antibody to a T cell specific surface maker (e.g. an antibody against CD3, and antibody against C4, or an antibody against CD8). T cell detection agents can be used alone or in combination. T cell detection agents can further be detected by fluorescence activated cell sorting (FACS).

"T cells" or "T lymphocytes" as used herein are a type of lymphocyte (a subtype of white blood cell) that plays a central role in cell-mediated immunity. They can be distinguished from other lymphocytes, such as B cells and natural killer cells, by the presence of a T-cell receptor on the cell surface. T cells include, for example, natural killer T (NKT) cells, cytotoxic T lymphocytes (CTLs), regulatory T (Treg) cells, and T helper cells. Different types of T cells can be distinguished by use of T cell detection agents.

The term "cell subset detection agent" refers to a chemical or molecule detection agent that can be used to identify and distinguish a specific subset of cells (e.g. senescent cells, naïve cells, effector cells, memory cells etc). Example cell subset detection agents include "naïve cell detection agents", "memory cell detection agents", and "effector cell detection agent." Cell subset detection agents can include antibodies against distinguishing cell surface markers. In embodiments, cell subset detection agents include antibodies against CD27 or antibodies against CD45RA.

The term "apoptotic cells detection agent" refers to a chemical or molecule detection agent that can be used to identify and distinguish apoptotic cells. Apoptotic cell detection agents can include antibodies against distinguishing cell surface markers. An example apoptosis detection agent includes an antibody against cPARP. PARP is inactivated by caspase cleavage. Cleaved poly-ADP-ribose polymerase (PARP) (cPARP) is the cleavage product of PARP. cPARP can be used as a marker for apoptosis.

The term "CD" or "Cluster of Differentiation" refers to a nomenclature system for antigens found on lymphocytes, although CD antigens can be found on cells other than lymphocytes. This nomenclature is used to name antigens recognized by monoclonal antibodies that specifically bind an antigen on B cells, T cells or antigen presenting cells. Each numeric antigen is a specific protein that is recognized in the art by its CD designation.

The term "CD3" as referred to herein is a protein complex comprising four chains including a CD3γ chain, a CD3δ chain, and two CD3ε chains. An example sequences of CD3 complex chains include: Epsilon chain precursor (GENBANK® Accession No. NP_000724.1); Gamma chain precursor (GENBANK® Accession No. NP_000064.1); Delta chain precursor (GENBANK® Accession No. NP_000723.1) which are incorporated herein by reference. Multiple isoforms are possible for each of the chains of CD3.

The term "CD4" as referred to herein is a glycoprotein expressed on the surface of T helper cells, regulatory T cells, monocytes, macrophages, and dendritic cells. CD4 was originally known as leu-3 and T4 (after the OKT4 monoclonal antibody). CD4 as referred to herein has four immunoglobulin domains ($D_1$ to $D_4$) that are exposed on the extracellular surface of the cell, see ENTREZ No. 920, UNIPROT No. P01730, and GENBANK® Accession No. NP_000607, which are incorporated by reference.

A "CD4$^+$ T lymphocyte" or "CD4 T cell" as referred to herein is lymphocyte that expresses the CD4 glycoprotein on its surface. CD4 T cells include helper T cells, which are T cells that help orchestrate the immune response, including antibody responses and killer T cell responses. CD4 T cell precursors differentiate into one of several subtypes, including TH1 (type 1 helper T cell), TH2 (type 2 helper T cell), TH3 (T helper 3 cells), TH17 (T helper 17 cells) or TFH (Follicular B helper T cells). These subtypes of helper T cells are characterized by their secretion of different cytokines to facilitate different types of immune responses. In embodiments, a CD4 T cell is an effector T cell. An "effector T cell" as referred to herein is a T cell that has been activated by its cognate antigen, and is actively involved in eliminating a pathogen. Thus, an effector T cell actively responds to a stimulus (a pathogen or a co-stimulation) and carries out a cell-mediated immune response. Non-limiting examples of effector T cells as referred to herein include helper T cells, killer T cells (cytotoxic T cells) and regulatory T cells.

The term "CD8" as referred to herein is a transmembrane glycoprotein that serves as a co-receptor for the T cell receptor (TCR). Like the TCR, CD8 binds to a major histocompatibility complex (MHC) molecule, but is specific for the class I MHC protein, see ENTREZ No. 925 and UNIPROT No. P01732, which are incorporated by reference herein.

A "CD8$^+$ T lymphocyte" or "CD8 T cell" as referred to herein is a lymphocyte that expresses the CD8 glycoprotein on its surface. Examples of CD8 T cells include cytotoxic T cells and natural killer cells. In one embodiment, a CD8 T cell is a cytotoxic T cell. In embodiments, a CD8 T cell is a suppressor T cell.

CD20 is involved in regulating early steps in the activation and differentiation process of B cells (Tedder et al., *Eur. J. Immunol.* 16:881-887, 1986) and can function as a calcium ion channel (Tedder et al., *J. Cell. Biochem.* 14D:195, 1990). Exemplary amino acid sequences for CD19 are provided in GENBANK® Accession Nos. NP_068769.2 (human), NP_690605.1 (human), and NP_031667.1 (mouse), which are incorporated by reference herein.

CD27: A costimulatory immune checkpoint molecule. CD27 precursor (human)(GENBANK® Accession No. NP_001233.1). Multiple isoforms exist.

The term "CD45RA" as provided herein refers to the CD45 Receptor antigen also known as Protein tyrosine phosphatase, receptor type, C (PTPRC). Exemplary amino acid sequences for CD45RA include GENBANK® Accession Nos. NP_002829.3, NP_563578.2, NP_563578.2, and NP_002829.3, which are all incorporated herein by reference. CD45RA is expressed on naïve T cells, as well as on CD8- and CD4-expressing effector cells. After antigen interaction, T cells gain expression of CD45RO and lose expression of CD45RA. Thus, either CD45RA or CD45RO is used to generally differentiate the naïve from memory T cell populations. Thus, a "CD45RA-negative CD8 T cell" as provided herein is a CD8 T cell which lacks expression of detectable amounts of CD45RA. In embodiments, the CD45RA-negative CD8 T cell is a memory T cell. A "CD45RA-negative CD4 T cell" as provided herein is a CD4 T cell which lacks expression of detectable amounts of CD45RA. In embodiments, the CD45RA-negative CD4 T cell is a memory T cell. In embodiments, the CD45RA-negative CD8 T cell is a memory T cell.

A "memory T cell" is a T cell that has previously encountered and responded to its cognate antigen during prior infection, encounter with cancer or previous vaccination. At a second encounter with its cognate antigen memory T cells can reproduce (divide) to mount a faster and stronger immune response than the first time the immune system responded to the pathogen. In embodiments, the memory T cell is a CD45RA-negative CD4 T cell. In embodiments, the memory T cell is a CD45RA-negative CD8 T cell.

A "regulatory T cell" or "suppressor T cell" is a lymphocyte which modulates the immune system, maintains tolerance to self-antigens, and prevents autoimmune disease. Regulatory T cells express the CD4, FOXP3, and CD25 and are thought to be derived from the same lineage as naïve CD4 cells.

A "fixation agent" is a chemical or molecular agent capable of fixing a cell (e.g. of preserving a cell). A fixation agent can be used to prevent further biological process in preparation for cell staining, imaging or sorting. Fixation agents can be used alone or in combination. Non-limiting examples of fixation agents include formaldehyde, glutaraldehyde, ethanol, methanol, Potassium dichromate, chromic acid, and potassium permanganate, B-5, Zenker's fixative, picrates, and HOPE.

A "cell permeabilizing agent" can include chemical or molecular agent, or a mechanical means of permeabilizing a cell. Non-limiting examples of permeabilization agents include organic solvents, such as methanol and acetone, and detergents such as saponin, Triton X-100 and Tween-20. The organic solvents dissolve lipids from cell membranes making them permeable to antibodies.

A "refractory subject" as provided herein is a subject that has been or is being treated for a disease or condition and does not respond to attempted forms of treatment for said disease or condition. For example, a cancer is said to be refractory when it does not respond to (or is resistant to) cancer treatment. A refractory cancer is also known as resistant cancer. Thus, a refractory subject is a subject that does not respond or is resistant to treatment of a disease or condition the subject is suffering from. In embodiments, a refractory subject is a cancer patient unresponsive to anti-PD-1 therapy. Where the cancer patient is unresponsive to anti-PD-1 therapy the patient shows less than 20% reduction in tumor size or volume after administration of anti-PD-1 relative to a control. Thus, in embodiments, a refractory subject shows less than 20% reduction in tumor size or volume after administration of anti-PD-1 relative to a control. In embodiments, a refractory subject shows less than 10% reduction in tumor size or volume after administration of anti-PD-1 relative to a control. In embodiments, a refractory subject shows less than 5% reduction in tumor size or volume after administration of anti-PD-1 relative to a control. In embodiments, a refractory subject shows less than 1% reduction in tumor size or volume after administration of anti-PD-1 relative to a control. In embodiments, a refractory subject shows less than 0.5% reduction in tumor size or volume after administration of anti-PD-1 relative to a control. In embodiments, a refractory subject shows less than 0.1% reduction in tumor size or volume after administration of anti-PD-1 relative to a control.

The term "anti-tumor immune memory" as provided herein refers to the ability of the immune system of a subject to recognize (memorize) previously encountered tumor antigen. Once the tumor antigen has been recognized, the immune system reproduces (e.g., through T cell activation and proliferation) and can mount a faster and stronger immune response than the first time it responded to the same tumor antigen.

The term "global immune activation" as provided herein refers to the activation of immune cells of the adaptive immune system in a subject. Examples of immune cells activated during global immune activation are without limitation, antigen presenting cells (macrophages, dendritic cells), B cells and T cells. The activation may occur through recognition of a previously encountered antigen (tumor antigen) or it may occur through encounter of a novel (not previously encountered) antigen (tumor antigen).

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

A "control" sample or value refers to a sample that serves as a reference, usually a known reference, for comparison to a test sample. For example, a test sample can be taken from a patient suspected of having a given disease (cancer) and compared to samples from a known cancer patient, or a known normal (non-disease) individual. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters.

One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, aleukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tubular carcinoma, tuberous carcinoma, verrucous carcinoma, or carcinoma *villosum*.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A patient or subject for the purposes of the present invention includes both humans and other animals, particularly mammals. Thus, the methods are applicable to both human therapy and veterinary applications. In the preferred embodiment the patient is a mammal, preferably a primate, and in the most preferred embodiment the patient is human.
Methods of Treating Cancer The methods provided herein are, inter alia, useful for the treatment of cancer. Cancer treatment can include administration of an anti-cancer agent. In embodiments, an anti-cancer agent includes an adenosine receptor antagonist, alone or in combination. In embodiments, an adenosine receptor antagonist is an A2A receptor antagonist. Through administration of a therapeutically effective amount of an adenosine-A2A (A2A) receptor antagonist alone or in combination with a programmed cell death protein 1 (PD-1) signaling pathway inhibitor cancer may be treated in a subject in need thereof.

An "adenosine-A2A (A2A) receptor antagonist" as provided herein refers to a substance capable of detectably lowering expression or activity level of an adenosine-A2A (A2A) receptor compared to a control. The inhibited expression or activity of the A2A receptor can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "antagonist" is a compound or small molecule that inhibits an A2A receptor e.g., by binding, partially or totally blocking stimulation, decrease, prevent, or delay activation, or inactivate, desensitize, or down-regulate signal transduction, gene expression or enzymatic activity necessary for A2A activity. In embodiments, the A2A receptor antagonist is a compound or a small molecule. In embodiments, the A2A receptor antagonist is CPI-444. In embodiments, the programmed cell death protein 1 (PD-1) signaling pathway inhibitor is atezolizumab. In embodiments, the A2A receptor antagonist and the PD-1 signaling pathway inhibitor are administered simultaneously or sequentially.

Likewise, a "PD-1 signaling pathway inhibitor" as provided herein refers to a substance capable of detectably lowering expression of or activity level of the PD-1 signaling pathway compared to a control. The inhibited expression or activity of the PD-1 signaling pathway can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" is a compound or small molecule that inhibits the PD-1 signaling pathway e.g., by binding, partially or totally blocking stimulation of the PD-1 signaling pathway, decrease, prevent, or delay activation of the PD-1 signaling pathway, or inactivate, desensitize, or down-regulate signal transduction, gene expression or enzymatic activity of the PD-1 signaling pathway. In embodiments, the PD-1 signaling pathway inhibitor inhibits PD-1 activity or expression. In embodiments, the PD-1 signaling pathway inhibitor inhibits PD-L1 activity or expression. In embodiments, the PD-1 signaling pathway inhibitor is a compound or a small molecule. In embodiments, the PD-1 signaling pathway inhibitor is an antibody.

According to the methods provided herein, the subject is administered an effective amount of one or more of the agents (e.g., an A2A receptor antagonist and/or a PD-1 signaling pathway inhibitor) provided herein. An "effective amount" is an amount sufficient to accomplish a stated purpose (e.g. achieve the effect for which it is administered, treat a disease (e.g., cancer), reduce receptor signaling activity, reduce one or more symptoms of a disease or condition). An example of an "effective amount" is an amount sufficient to contribute to the treatment, prevention, or reduction of a symptom or symptoms of a disease (e.g., cancer), which could also be referred to as a "therapeutically effective amount." A "reduction" of a symptom or symptoms (and grammatical equivalents of this phrase) means decreasing of the severity or frequency of the symptom(s), or elimination of the symptom(s). Guidance can be found in the literature for appropriate dosages for given classes of pharmaceutical products. For example, for the given parameter, a therapeutically effective amount will show an increase or decrease of at least 5%, 10%, 15%, 20%, 25%, 40%, 50%, 60%, 75%, 80%, 90%, or at least 100%. In embodiments, this increase or decrease for a given parameter may vary throughout the day (e.g. a peak percentage increase or decrease may differ from a percentage increase or decrease when therapeutic concentrations in circulating blood are at their peak or trough concentrations dependent on daily dosing patterns and individual pharmacokinetics). Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

Thus, in one aspect, a method of treating cancer in a subject in need thereof is provided. The method includes administering to the subject a therapeutically effective amount of an adenosine-A2A (A2A) receptor antagonist and a programmed cell death protein 1 (PD-1) signaling pathway inhibitor.

In embodiments, the A2A receptor antagonist is a compound of formula:

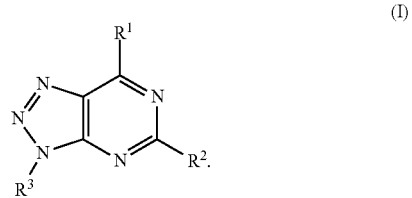

(I)

In formula (I), $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —N(O)$_{m1}$, —$NR^9R^{10}$, —NH—O—$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —N(O)$_{m2}$, —$NR^{11}R^{12}$, —NH—O—$R^{11}$, —C(O)$R^{11}$, —C(O)—$OR^{11}$, —C(O)$NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —N(O)$_{m3}$, —$NR^{13}R^{14}$, —NH—O—$R^{13}$, —C(O)$R^{13}$, —C(O)—$OR^{13}$, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$, $R^{10}$, $R^{11}$, $R^{12}$, $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or submitted or unsubstituted heteroaryl.

$X^a$, $X^b$ and $X^c$ are independently —F, —Cl, —Br, or —I.

The symbols $n_1$, $n_2$ and $n_3$ are independently an integer from 0 to 4. In embodiments, $n_1$ is 0. In embodiments, $n_1$ is 1. In embodiments, $n_1$ is 3. In embodiments, $n_1$ is 4. In embodiments, $n_2$ is 0. In embodiments, $n_2$ is 1. In embodiments, $n_2$ is 3. In embodiments, $n_2$ is 4. In embodiments, $n_3$ is 0. In embodiments, $n_3$ is 1. In embodiments, $n_3$ is 3. In embodiments, $n_3$ is 4.

The symbols $m_1$, $m_2$ and $m_3$ are independently an integer from 1 to 2. In embodiments, $m_1$ is 0. In embodiments, $m_1$ is 1. In embodiments, $m_1$ is 2. In embodiments, $m_2$ is 0. In embodiments, $m_2$ is 1. In embodiments, $m_2$ is 2. In embodiments, $m_3$ is 0. In embodiments, $m_3$ is 1. In embodiments, $m_2$ is 2.

The symbols $v_1$, $v_2$ and $v_3$ are independently an integer from 1 to 2. In embodiments, $v_1$ is 0. In embodiments, $v_1$ is 1. In embodiments, $v_1$ is 2. In embodiments, $v_2$ is 0. In embodiments, $v_2$ is 1. In embodiments, $v_2$ is 2. In embodiments, $v_3$ is 0. In embodiments, $v_3$ is 1. In embodiments, $v_3$ is 2.

In embodiments, $R^1$ is independently hydrogen, halogen, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{1A}$-substituted or unsubstituted alkyl, $R^{1A}$-substituted or unsubstituted heteroalkyl, $R^{1A}$-substituted or unsubstituted cycloalkyl, $R^{1A}$-substituted or unsubstituted heterocycloalkyl, $R^{1A}$-substituted or unsubstituted aryl, or $R^{1A}$-substituted or unsubstituted heteroaryl. $R^1$ may be $R^{1A}$-substituted or unsubstituted (e.g., $C_1$-$C_{20}$ or $C_1$-$C_6$) alkyl, $R^{1A}$-substituted or unsubstituted (e.g., 2 to 20 membered or 2 to 6 membered) heteroalkyl, $R^{1A}$-substituted or unsubstituted (e.g., $C_3$-$C_8$ or $C_5$-$C_7$) cycloalkyl, $R^{1A}$-substituted or unsubstituted (e.g., 3 to 8 membered or 3 to 6 membered) heterocycloalkyl, $R^{1A}$-substituted or unsubstituted (e.g., $C_5$-$C_{10}$ or $C_5$-$C_6$) aryl, or $R^{1A}$-substituted or unsubstituted (e.g., 5 to 10 membered or 5 to 6 membered) heteroaryl.

In embodiments, $R^{1A}$ is independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{1B}$-substituted or unsubstituted alkyl, $R^{1B}$-substituted or unsubstituted heteroalkyl, $R^{1B}$-substituted or unsubstituted cycloalkyl, $R^{1B}$-substituted or unsubstituted heterocycloalkyl, $R^{1B}$-substituted or unsubstituted aryl, or $R^{1B}$-substituted or unsubstituted heteroaryl. $R^{1A}$ may be $R^{1B}$-substituted or unsubstituted (e.g., $C_1$-$C_{20}$ or $C_1$-$C_6$) alkyl, $R^{1B}$-substituted or unsubstituted (e.g., 2 to 20 membered or 2 to 6 membered) heteroalkyl, $R^{1B}$-substituted or unsubstituted (e.g., $C_3$-$C_8$ or $C_5$-$C_7$) cycloalkyl, $R^{1B}$- substituted or unsubstituted (e.g., 3 to 8 membered or 3 to 6 membered) heterocycloalkyl, $R^{1B}$-substituted or unsubstituted (e.g., $C_5$-$C_{10}$ or $C_5$-$C_6$) aryl, or $R^{1B}$-substituted or unsubstituted (e.g., 5 to 10 membered or 5 to 6 membered) heteroaryl.

In embodiments, $R^{1B}$ is independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{1C}$-substituted or unsubstituted alkyl, $R^{1C}$-substituted or unsubstituted heteroalkyl, $R^{1C}$-substituted or unsubstituted cycloalkyl, $R^{1C}$-substituted or unsubstituted heterocycloalkyl, $R^{1C}$-substituted or unsubstituted aryl, or $R^{1C}$-substituted or unsubstituted heteroaryl. $R^{1B}$ may be $R^{1C}$-substituted or unsubstituted (e.g., $C_1$-$C_{20}$ or $C_1$-$C_6$) alkyl, $R^{1C}$-substituted or unsubstituted (e.g., 2 to 20 membered or 2 to 6 membered) heteroalkyl, $R^{1C}$-substituted or unsubstituted (e.g., $C_3$-$C_8$ or $C_5$-$C_7$) cycloalkyl, $R^{1C}$-substituted or unsubstituted (e.g., 3 to 8 membered or 3 to 6 membered) heterocycloalkyl, $R^{1C}$-substituted or unsubstituted (e.g., $C_5$-$C_{10}$ or $C_5$-$C_6$) aryl, or $R^{1C}$-substituted or unsubstituted (e.g., 5 to 10 membered or 5 to 6 membered) heteroaryl.

$R^{1C}$ is independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. $R^{1C}$ may be independently unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, $R^1$ is independently $R^{1A}$-substituted or unsubstituted alkyl, $R^{1A}$-substituted or unsubstituted heteroalkyl, $R^{1A}$-substituted or unsubstituted cycloalkyl, $R^{1A}$-substituted or unsubstituted heterocycloalkyl, $R^{1A}$-substituted or unsubstituted aryl, or s $R^{1A}$-substituted or unsubstituted heteroaryl. In embodiments, $R^1$ is $R^{1A}$-substituted or unsubstituted (e.g., 5 to 10 membered or 5 to 6 membered) heteroaryl. In embodiments, $R^1$ is unsubstituted 5 to 6 membered heteroaryl. In embodiments, $R^1$ is $R^{1A}$-substituted 5 to 6 membered heteroaryl. In embodiments, $R^1$ is unsubstituted 5 membered heteroaryl. In embodiments, $R^1$ is $R^{1A}$-substituted 5 membered heteroaryl. In embodiments, $R^1$ is $R^{1A}$-substituted furanyl.

In embodiments, $R^{1A}$ is $R^{1B}$-substituted or unsubstituted (e.g., $C_1$-$C_{20}$ or $C_1$-$C_6$) alkyl. In embodiments, $R^{1A}$ is $R^{1B}$-substituted $C_1$-$C_6$ alkyl. In embodiments, $R^{1A}$ is unsubstituted $C_1$-$C_6$ alkyl. In embodiments, $R^{1A}$ is $R^{1B}$-substituted $C_1$-$C_4$ alkyl. In embodiments, $R^{1A}$ is unsubstituted $C_1$-$C_4$ alkyl. In embodiments, $R^{1A}$ is $R^{1B}$-substituted $C_1$-$C_3$ alkyl. In embodiments, $R^{1A}$ is unsubstituted $C_1$-$C_3$ alkyl. In embodiments, $R^{1A}$ is methyl.

In embodiments, $R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$_{NR}{}^{11}R^{12}$, —NH—O—$R^{11}$, —C(O)$R^{11}$, —C(O)—$OR^{11}$, —C(O)$NR^{11}R^{12}$, or —$OR^{11}$. In embodiments of the methods provided herein, $R^2$ is independently hydrogen, halogen, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^2$ is —$NR^{11}R^{12}$. In embodiments, $R^{11}$ and $R^{12}$ are independently hydrogen or substituted or unsubstituted (e.g., $C_1$-$C_{20}$ or $C_1$-$C_6$) alkyl. In embodiments, $R^{11}$ and $R^{12}$ are independently substituted or unsubstituted $C_1$-$C_6$ alkyl. In embodiments, $R^{11}$ and $R^{12}$ are independently substituted or unsubstituted $C_1$-$C_4$ alkyl. In embodiments, $R^{11}$ and $R^{12}$ are independently substituted or unsubstituted $C_1$-$C_3$ alkyl. In embodiments, $R^{11}$ and $R^{12}$ are independently unsubstituted $C_1$-$C_6$ alkyl. In embodiments, $R^{11}$ and $R^{12}$ are independently substituted or unsubstituted $C_1$-$C_4$ alkyl. In embodiments, $R^{11}$ and $R^{12}$ are independently unsubstituted $C_1$-$C_3$ alkyl. In embodiments, $R^{11}$ and $R^{12}$ are independently hydrogen.

In embodiments, $R^3$ is independently hydrogen, halogen, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^4$-substituted or unsubstituted alkyl, $R^4$-substituted or unsubstituted heteroalkyl, $R^4$-substituted or unsubstituted cycloalkyl, $R^4$-substituted or unsubstituted heterocycloalkyl, $R^4$-substituted or unsubstituted aryl, or $R^4$-substituted or unsubstituted heteroaryl. $R^3$ may be $R^4$-substituted or unsubstituted (e.g., $C_1$-$C_{20}$ or $C_1$-$C_6$) alkyl, $R^4$-substituted or unsubstituted (e.g., 2 to 20 membered or 2 to 6 membered) heteroalkyl, $R^4$-substituted or unsubstituted (e.g., $C_3$-$C_8$ or $C_5$-$C_7$) cycloalkyl, $R^4$-substituted or unsubstituted (e.g., 3 to 8 membered or 3 to 6 membered) heterocycloalkyl, $R^4$-substituted or unsubstituted (e.g., $C_5$-$C_{10}$ or $C_5$-$C_6$) aryl, or $R^4$-substituted or unsubstituted (e.g., 5 to 10 membered or 5 to 6 membered) heteroaryl.

$R^4$ is independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^5$-substituted or unsubstituted alkyl, $R^5$-substituted or unsubstituted heteroalkyl, $R^5$-substituted or unsubstituted cycloalkyl, $R^5$-substituted or unsubstituted heterocycloalkyl, $R^5$-substituted or unsubstituted aryl, or $R^5$-substituted or unsubstituted heteroaryl. $R^4$ may be $R^5$-substituted or unsubstituted (e.g., $C_1$-$C_{20}$ or $C_1$-$C_6$) alkyl, $R^5$-substituted or unsubstituted (e.g., 2 to 20 membered or 2 to 6 membered) heteroalkyl, $R^5$-substituted or unsubstituted (e.g., $C_3$-$C_8$ or $C_5$-$C_7$) cycloalkyl, $R^5$-substituted or unsubstituted (e.g., 3 to 8 membered or 3 to 6 membered) heterocycloalkyl, $R^5$-substituted or unsubstituted (e.g., $C_5$-$C_{10}$ or $C_5$-$C_6$) aryl, or $R^5$-substituted or unsubstituted (e.g., 5 to 10 membered or 5 to 6 membered) heteroaryl.

$R^5$ is independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^6$-substituted or unsubstituted alkyl, $R^6$-substituted or unsubstituted heteroalkyl, $R^6$-substituted or unsubstituted cycloalkyl, $R^6$-substituted or unsubstituted heterocycloalkyl, $R^6$-substituted or unsubstituted aryl, or $R^6$-substituted or unsubstituted heteroaryl. $R^5$ may be $R^6$-substituted or unsubstituted (e.g., $C_1$-$C_{20}$ or $C_1$-$C_6$) alkyl, $R^6$-substituted or unsubstituted (e.g., 2 to 20 membered or 2 to 6 membered) heteroalkyl, $R^6$-substituted or unsubstituted (e.g., $C_3$-$C_8$ or $C_5$-$C_7$) cycloalkyl, $R^6$-substituted or unsubstituted (e.g., 3 to 8 membered or 3 to 6 membered) heterocycloalkyl, $R^6$-substituted or unsubstituted (e.g., $C_5$-$C_{10}$ or $C_5$-$C_6$) aryl, or $R^6$-substituted or unsubstituted (e.g., 5 to 10 membered or 5 to 6 membered) heteroaryl.

$R^6$ is independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —$NHC=(O)NHNH_2$, $R^7$-substituted or unsubstituted alkyl, $R^7$-substituted or unsubstituted heteroalkyl, $R^7$-substituted or unsubstituted cycloalkyl, R'-substituted or unsubstituted heterocycloalkyl, $R^7$-substituted or unsubstituted aryl, or $R^7$-substituted or unsubstituted heteroaryl. $R^6$ may be $R^7$-substituted or unsubstituted (e.g., $C_1$-$C_{20}$ or $C_1$-$C_6$) alkyl, $R^7$-substituted or unsubstituted (e.g., 2 to 20 membered or 2 to 6 membered) heteroalkyl, $R^7$-substituted or unsubstituted (e.g., $C_3$-$C_8$ or $C_5$-$C_7$) cycloalkyl, $R^7$-substituted or unsubstituted (e.g., 3 to 8 membered or 3 to 6 membered) heterocycloalkyl, $R^7$-substituted or unsubstituted (e.g., $C_5$-$C_{10}$ or $C_5$-$C_6$) aryl, or $R^7$-substituted or unsubstituted (e.g., 5 to 10 membered or 5 to 6 membered) heteroaryl.

In embodiments, $R^3$ is independently hydrogen, halogen, $R^4$-substituted or unsubstituted alkyl, $R^4$-substituted or unsubstituted heteroalkyl, $R^4$-substituted or unsubstituted cycloalkyl, $R^4$-substituted or unsubstituted heterocycloalkyl, $R^4$-substituted or unsubstituted aryl, or $R^4$-substituted or unsubstituted heteroaryl. In embodiments, $R^3$ is independently $R^4$-substituted or unsubstituted (e.g., $C_1$-$C_{20}$ or $C_1$-$C_6$) alkyl. In embodiments, $R^3$ is independently $R^4$-substituted or unsubstituted $C_1$-$C_6$ alkyl. In embodiments, $R^3$ is independently $R^4$-substituted or unsubstituted $C_1$-$C_5$ alkyl. In embodiments, $R^3$ is independently $R^4$-substituted or unsubstituted $C_1$-$C_4$ alkyl. In embodiments, $R^3$ is independently $R^4$-substituted or unsubstituted $C_1$-$C_3$ alkyl. In embodiments, $R^3$ is independently unsubstituted $C_1$-$C_6$ alkyl. In embodiments, $R^3$ is independently unsubstituted $C_1$-$C_5$ alkyl. In embodiments, $R^3$ is independently $R^4$-unsubstituted $C_1$-$C_4$ alkyl. In embodiments, $R^3$ is independently unsubstituted $C_1$-$C_3$ alkyl. In embodiments, $R^3$ is independently $R^4$-substituted $C_1$-$C_6$ alkyl. In embodiments, $R^3$ is independently $R^4$-substituted $C_1$-$C_5$ alkyl. In embodiments, $R^3$ is independently $R^4$-substituted $C_1$-$C_4$ alkyl. In embodiments, $R^3$ is independently $R^4$-substituted $C_1$-$C_3$ alkyl. In embodiments, $R^3$ is $R^4$-substituted $C_1$ alkyl.

In embodiments, $R^4$ is $R^5$-substituted or unsubstituted (e.g., $C_1$-$C_{20}$ or $C_1$-$C_6$) alkyl, $R^5$-substituted or unsubstituted (e.g., 2 to 20 membered or 2 to 6 membered) heteroalkyl, $R^5$-substituted or unsubstituted (e.g., $C_3$-$C_8$ or $C_5$-$C_7$) cycloalkyl, $R^5$-substituted or unsubstituted (e.g., 3 to 8 membered or 3 to 6 membered) heterocycloalkyl, $R^5$-substituted or unsubstituted (e.g., $C_5$-$C_{10}$ or $C_5$-$C_6$) aryl, or $R^5$-substituted or unsubstituted (e.g., 5 to 10 membered or 5 to 6 membered) heteroaryl. In embodiments, $R^4$ is $R^5$-substituted or unsubstituted 5 to 6 membered heteroaryl. In embodiments, $R^4$ is $R^5$-substituted or unsubstituted 6 membered heteroaryl. In embodiments, $R^4$ is unsubstituted 6 membered heteroaryl. In embodiments, $R^4$ is $R^5$-substituted 6 membered heteroaryl. In embodiments, $R^4$ is $R^5$-substituted pyridinyl.

In embodiments, $R^5$ is $R^6$-substituted or unsubstituted (e.g., $C_1$-$C_{20}$ or $C_1$-$C_6$) alkyl, $R^6$-substituted or unsubstituted (e.g., 2 to 20 membered or 2 to 6 membered) heteroalkyl, $R^6$-substituted or unsubstituted (e.g., $C_3$-$C_8$ or $C_5$-$C_7$) cycloalkyl, $R^6$-substituted or unsubstituted (e.g., 3 to 8 membered or 3 to 6 membered) heterocycloalkyl, $R^6$-substituted or unsubstituted (e.g., $C_5$-$C_{10}$ or $C_5$-$C_6$) aryl, or $R^6$-substituted or unsubstituted (e.g., 5 to 10 membered or 5 to 6 membered) heteroaryl. In embodiments, $R^5$ is $R^6$-substituted 2 to 6 membered heteroalkyl. In embodiments, $R^5$ is $R^6$-substituted or unsubstituted 2 to 5 membered heteroalkyl. In embodiments, $R^5$ is $R^6$-substituted or unsubstituted 2 to 4 membered heteroalkyl. In embodiments, $R^5$ is $R^6$-substituted or unsubstituted 2 to 3 membered heteroalkyl. In embodiments, $R^5$ is $R^6$-substituted or unsubstituted 2 membered heteroalkyl. In embodiments, $R^5$ is unsubstituted 2 to 6 membered heteroalkyl. In embodiments, $R^5$ is unsubstituted 2 to 5 membered heteroalkyl. In embodiments, $R^5$ is unsubstituted 2 to 4 membered heteroalkyl. In embodiments, $R^5$ unsubstituted 2 to 3 membered heteroalkyl. In embodiments, $R^5$ is unsubstituted 2 membered heteroalkyl. In embodiments, $R^5$ is $R^6$-substituted 2 to 6 membered heteroalkyl. In embodiments, $R^5$ is $R^6$-substituted 2 to 5 membered heteroalkyl. In embodiments, $R^5$ is $R^6$-substituted 2 to 4 membered heteroalkyl. In embodiments, $R^5$ is $R^6$-substituted 2 to 3 membered heteroalkyl. In embodiments, $R^5$ is $R^6$-substituted 2 membered heteroalkyl.

In embodiments, $R^6$ is $R^7$-substituted or unsubstituted (e.g., $C_1$-$C_{20}$ or $C_1$-$C_6$) alkyl, $R^7$-substituted or unsubstituted (e.g., 2 to 20 membered or 2 to 6 membered) heteroalkyl, $R^7$-substituted or unsubstituted (e.g., $C_3$-$C_8$ or $C_5$-$C_7$) cycloalkyl, $R^7$-substituted or unsubstituted (e.g., 3 to 8 membered or 3 to 6 membered) heterocycloalkyl, $R^7$-substituted or unsubstituted (e.g., $C_5$-$C_{10}$ or $C_5$-$C_6$) aryl, or $R^7$-substituted or unsubstituted (e.g., 5 to 10 membered or 5 to 6 membered) heteroaryl. In embodiments, $R^6$ is $R^7$-substituted or unsubstituted 3 to 6 membered heterocycloalkyl. In embodiments, $R^6$ is $R^7$-substituted or unsubstituted 5 membered heterocycloalkyl. In embodiments, $R^6$ is $R^7$-substituted 5 membered heterocycloalkyl. In embodiments, $R^6$ is unsubstituted 5 membered heterocycloalkyl. In embodiments, $R^6$ is unsubstituted tetrahydrofuranyl.

In embodiments of the methods provided herein, $R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —$NHC=(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^1$ is $R^{1A}$-substituted furanyl. In one further embodiment, $R^{1A}$ is methyl. In another further embodiment, $R^2$ is —$NR^{11}R^{12}$. In another further embodiment, $R^{11}$ and $R^{12}$ are independently hydrogen. In yet another further embodiment, $R^3$ is $R^4$-substituted $C_1$ alkyl. In another further embodiment, $R^4$ is $R^5$-substituted pyridinyl. In yet another further embodiment, $R^5$ is $R^6$-substituted 2 membered heteroalkyl. In another further embodiments, $R^6$ is unsubstituted tetrahydrofuranyl.

In embodiments, the A2A receptor antagonist is a compound of formula:

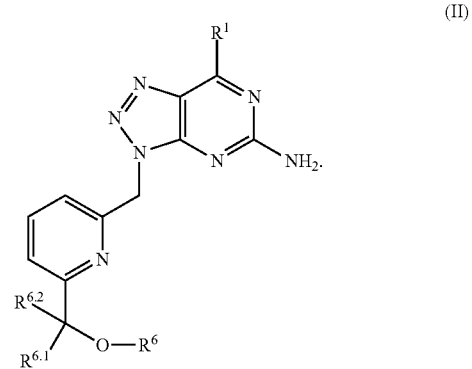

(II)

In formula (II), $R^6$, $R^{6.1}$ and $R^{6.2}$ are independently hydrogen, halogen, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$, $R^{6.1}$ and $R^{6.2}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{6.1}$ and $R^{6.2}$ are hydrogen and R6 is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{6.1}$ and $R^{6.2}$ are hydrogen and R6 is substituted or unsubstituted heterocycloalkyl. In embodiments, $R^{6.1}$ and $R^{6.2}$ are hydrogen and R6 is unsubstituted heterocycloalkyl. In embodiments, $R^1$ is substituted (e.g. with an unsubstituted $C_1$-$C_5$ alkyl) or unsubstituted heteroaryl. In embodiments, $R^1$ is substituted (e.g. with an unsubstituted $C_1$-$C_5$ alkyl) or unsubstituted furanyl. In embodiments, $R^1$ is methyl-substituted furanyl.

In formula (II), $R^1$ and $R^6$ are as described above (e.g., $R^6$ may be $R^7$-substituted or unsubstituted 3 to 6 membered heterocycloalkyl and $R^1$ may be $R^{1.4}$-substituted 5 to 6 membered heteroaryl). Thus, in embodiments, $R^6$ is unsubstituted tetrahydrofuranyl and $R^1$ is $R^{1.4}$-substituted furanyl.

In formula (II), $R^{6.1}$ may be independently hydrogen, halogen, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{7.1}$-substituted or unsubstituted alkyl, $R^{7.1}$-substituted or unsubstituted heteroalkyl, $R^{7.1}$-substituted or unsubstituted cycloalkyl, $R^{7.1}$-substituted or unsubstituted heterocycloalkyl, $R^{7.1}$-substituted or unsubstituted aryl, or $R^{7.1}$-substituted or unsubstituted heteroaryl. $R^{6.1}$ may be $R^{7.1}$-substituted or unsubstituted (e.g., $C_1$-$C_{20}$ or $C_1$-$C_6$) alkyl, $R^{7.1}$-substituted or unsubstituted (e.g., 2 to 20 membered or 2 to 6 membered) heteroalkyl, $R^{7.1}$-substituted or unsubstituted (e.g., $C_3$-$C_8$ or $C_5$-$C_7$) cycloalkyl, $R^{7.1}$-substituted or unsubstituted (e.g., 3 to 8 membered or 3 to 6 membered) heterocycloalkyl, $R^{7.1}$-substituted or unsubstituted (e.g., $C_5$-$C_{10}$ or $C_5$-$C_6$) aryl, or $R^{7.1}$-substituted or unsubstituted (e.g., 5 to 10 membered or 5 to 6 membered) heteroaryl. In embodiments, $R^{6.1}$ is $R^{7.1}$-substituted or unsubstituted $C_1$-$C_6$ alkyl. In embodiments, $R^{6.1}$ is $R^{7.1}$-substituted or unsubstituted $C_1$-$C_5$ alkyl. In embodiments, $R^{6.1}$ is $R^{7.1}$-substituted or unsubstituted $C_1$-$C_4$ alkyl. In embodiments, $R^{6.1}$ is $R^{7.1}$-substituted or unsubstituted $C_1$-$C_3$ alkyl. In embodiments, $R^{6.1}$ is $R^{7.1}$-substituted $C_1$-$C_6$ alkyl. In embodiments, $R^{6.1}$ is $R^{7.1}$-substituted $C_1$-$C_5$ alkyl. In embodiments, $R^{6.1}$ is $R^{7.1}$-substituted $C_1$-$C_4$ alkyl. In embodiments, $R^{6.1}$ is $R^{7.1}$-substituted $C_1$-$C_3$ alkyl. In embodiments, $R^{6.1}$ is unsubstituted $C_1$-$C_6$ alkyl. In embodiments, $R^{6.1}$ is unsubstituted $C_1$-$C_5$ alkyl. In embodiments, $R^{6.1}$ is unsubstituted $C_1$-$C_4$ alkyl. In embodiments, $R^{6.1}$ is unsubstituted $C_1$-$C_3$ alkyl. In embodiments, $R^{6.1}$ is unsubstituted methyl.

$R^{6.2}$ is independently hydrogen, halogen, =O, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{7.2}$-substituted or unsubstituted alkyl, $R^{7.2}$-substituted or unsubstituted heteroalkyl, $R^{7.2}$-substituted or unsubstituted cycloalkyl, $R^{7.2}$-substituted or unsubstituted heterocycloalkyl, $R^{7.2}$-substituted or unsubstituted aryl, or $R^{7.2}$-substituted or unsubstituted heteroaryl. $R^{6.2}$ may be $R^{7.2}$-substituted or unsubstituted (e.g., $C_1$-$C_{20}$ or $C_1$-$C_6$) alkyl, $R^{7.2}$-substituted or unsubstituted (e.g., 2 to 20 membered or 2 to 6 membered) heteroalkyl, $R^{7.2}$-substituted or unsubstituted (e.g., $C_3$-$C_8$ or $C_5$-$C_7$) cycloalkyl, $R^{7.2}$-substituted or unsubstituted (e.g., 3 to 8 membered or 3 to 6 membered) heterocycloalkyl, $R^{7.2}$-substituted or unsubstituted (e.g., $C_5$-$C_{10}$ or $C_5$-$C_6$) aryl, or $R^{7.2}$-substituted or unsubstituted (e.g., 5 to 10 membered or 5 to 6 membered) heteroaryl. In embodiments, $R^{6.2}$ is $R^{7.2}$-substituted or unsubstituted $C_1$-$C_6$ alkyl. In embodiments, $R^{6.2}$ is $R^{7.2}$-substituted or unsubstituted $C_1$-$C_5$ alkyl. In embodiments, $R^{6.2}$ is substituted or unsubstituted $C_1$-$C_4$ alkyl. In embodiments, $R^{6.2}$ is $R^{7.2}$-substituted or unsubstituted $C_1$-$C_3$ alkyl. In embodiments, $R^{6.2}$ is $R^{7.2}$-substituted $C_1$-$C_6$ alkyl. In embodiments, $R^{6.2}$ is substituted $C_1$-$C_5$ alkyl. In embodiments, $R^{6.2}$ is $R^{7.2}$-substituted $C_1$-$C_4$ alkyl. In embodiments, $R^{6.2}$ is $R^{7.2}$-substituted $C_1$-$C_3$ alkyl. In embodiments, $R^{6.2}$ is unsubstituted $C_1$-$C_6$ alkyl. In embodiments, $R^{6.2}$ is unsubstituted $C_1$-$C_5$ alkyl. In embodiments, $R^{6.2}$ is unsubstituted $C_1$-$C_4$ alkyl. In embodiments, $R^{6.2}$ is unsubstituted $C_1$-$C_3$ alkyl. In embodiments, $R^{6.2}$ is unsubstituted methyl.

$R^7$, $R^{7.1}$ and $R^{7.2}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. $R^7$, $R^{7.1}$ and $R^{7.2}$ may be independently unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, the A2A receptor antagonist is a compound of formula:

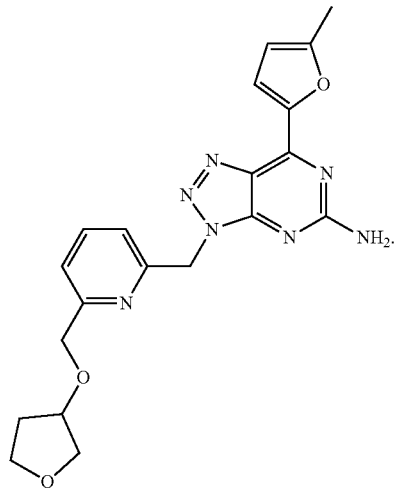 [SMILES: Cc1ccc(-c2nc(N)nc3c2nnn3Cc2cccc(COC3CCOC3)n2)o1]

In embodiments, the A2A receptor antagonist is a compound of formula:

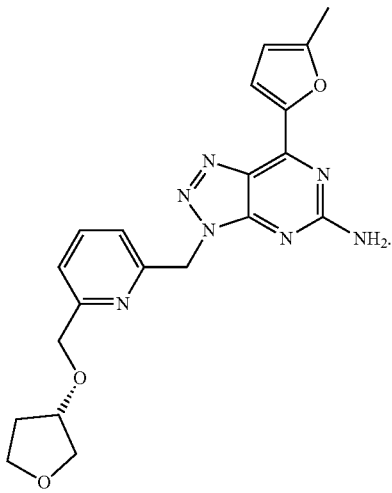

In embodiments, the A2A receptor antagonist is a compound of formula:

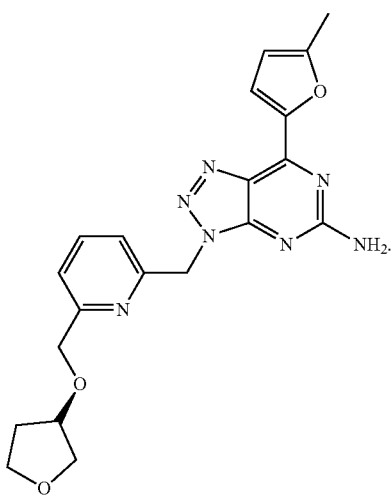

All compounds provided herein may optionally be provided as a pharmaceutically acceptable salt.

In embodiments, the PD-1 signaling pathway inhibitor is a programmed death-ligand 1 (PD-L1) antagonist or a PD-1 antagonist. A PD-L1 antagonist as provided herein is a substance that, at least in part, partially or totally blocks stimulation, decreases, prevents, or delays activation, or inactivates, desensitizes, or down-regulates signal transduction of PD-L1. Likewise, a PD-1 antagonist as provided herein is a substance that, at least in part, partially or totally blocks stimulation, decreases, prevents, or delays activation, or inactivates, desensitizes, or down-regulates signal transduction of PD-1. In embodiments, the programmed death-ligand 1 (PD-L1) antagonist is an antibody or a small molecule. In embodiments, the PD-L1 antagonist is an antibody. In embodiments, the antibody is atezolizumab. The term "atezolizumab" refers to a fully humanized, engineered monoclonal antibody of IgG1 isotype against the protein programmed cell death ligand 1 (PD-L1). Atezolizumab is also known as "MPDL3280A." In the customary sense, atezolizumab refers to CAS Registry number 1380723-44-3.

In embodiments, the PD-1 antagonist is an antibody or a small molecule.

In embodiments, an adenosine receptor antagonists is administration in conjunction with an additional anti-cancer agent. In embodiments, an adenosine receptor antagonist is administered in conjunction with an antibody anti-cancer agent. In embodiments, an adenosine receptor antagonist is administered with a PD-L1 antagonist. In embodiments, an A2A receptor antagonist is administered in conjunction with an antibody against PD-L1. In embodiments, CPI-444 is administered in conjunction with azetolizumab.

In embodiments, the A2A receptor antagonist and the PD-1 signaling pathway inhibitor are administered in a combined synergistic amount. A "combined synergistic amount" as used herein refers to the sum of a first amount (e.g., an amount of an A2A receptor antagonist) and a second amount (e.g., an amount of a PD-1 signaling pathway inhibitor) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of compounds administered in combination where the measured effect is greater than the sum of the individual effects of each of the compounds administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the A2A receptor antagonist when used separately from the PD-1 signaling pathway inhibitor. In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the PD-1 signaling pathway inhibitor when used separately from the A2A receptor antagonist.

The synergistic effect may be an A2A receptor activity decreasing effect and/or a PD-1 signaling pathway activity decreasing effect. In embodiments, synergy between the A2A receptor antagonist and the PD-1 signaling pathway inhibitor may result in about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater decrease (e.g., decrease of A2A receptor activity or decrease of PD-1 signaling pathway activity) than the sum of the decrease of the A2A receptor antagonist or the PD-1 signaling pathway when used individually and separately. In embodiments, synergy between the A2A receptor antagonist and the PD-1 signaling pathway inhibitor may result in 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater inhibition of the A2A receptor and/or the PD-1 signaling pathway than the sum of the inhibition of the A2A receptor antagonist or the PD-1 signaling pathway inhibitor when used individually and separately.

The synergistic effect may be a cancer-treating effect such as an lung cancer (i.e. a lung cancer-treating synergistic effect), bladder cancer (i.e. a bladder cancer-treating synergistic effect), melanoma (i.e. a melanoma-treating synergistic effect), renal cell carcinoma (i.e. a renal cell carcinoma-treating synergistic effect), colon cancer (i.e. a colon cancer-treating synergistic effect), ovarian cancer (i.e. an ovarian cancer-treating synergistic effect), gastric cancer (i.e. a gastric cancer-treating synergistic effect), breast cancer (i.e. a breast cancer-treating synergistic effect), head and neck carcinoma (i.e. a head and neck carcinoma-treating synergistic effect), prostate cancer (i.e. a prostate cancer-treating synergistic effect) and a hematologic malignancy (i.e. a hematologic malignancy-treating synergistic effect).

The A2A receptor antagonist and the PD-1 signaling pathway inhibitor may be administered in combination either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of the A2A receptor antagonist and the PD-1 signaling pathway inhibitor. In embodiments, where the A2A receptor antagonist and the PD-1 signaling pathway inhibitor are administered sequentially, the A2A receptor antagonist is administered at a first time point and the PD-1 signaling pathway inhibitor is administered at a second time point, wherein the first time point precedes the second time point. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly). Thus, in embodiments, the A2A receptor antagonist and the PD-1 signaling pathway inhibitor are administered simultaneously or sequentially.

In embodiments, the A2A receptor antagonist is administered at a first time point and the PD-1 signaling pathway inhibitor is administered at a second time point, wherein the first time point precedes the second time point. In embodiments, the second time point is within less than about 120, 90, 60, 50, 40, 30, 20, 19, 18, 17, 16, 15, 14, 13, 12, 10, 11, 9, 8, 7, 6, 5, 4, 3, 2 or 1 days from the first time point. In embodiments, the second time point is within less than about 120 days from the first time point. In embodiments, the second time point is within less than about 90 days from the first time point. In embodiments, the second time point is within less than about 60 days from the first time point. In embodiments, the second time point is within less than about 50 days from the first time point. In embodiments, the second time point is within less than about 40 days from the first time point. In embodiments, the second time point is within less than about 30 days from the first time point. In embodiments, the second time point is within less than about 20 days from the first time point.

In embodiments, the second time point is within less than about 19 days from the first time point. In embodiments, the second time point is within less than about 18 days from the first time point. In embodiments, the second time point is within less than about 17 days from the first time point. In embodiments, the second time point is within less than about 16 days from the first time point. In embodiments, the second time point is within less than about 15 days from the first time point. In embodiments, the second time point is within less than about 14 days from the first time point. In embodiments, the second time point is within less than about 13 days from the first time point. In embodiments, the second time point is within less than about 12 days from the first time point. In embodiments, the second time point is within less than about 11 days from the first time point. In embodiments, the second time point is within less than about 10 days from the first time point. In embodiments, the second time point is within less than about 9 days from the first time point. In embodiments, the second time point is within less than about 8 days from the first time point. In embodiments, the second time point is within less than about 7 days from the first time point. In embodiments, the second time point is within less than about 6 days from the first time point. In embodiments, the second time point is within less than about 5 days from the first time point. In embodiments, the second time point is within less than about 4 days from the first time point. In embodiments, the second time point is within less than about 3 days from the first time point. In embodiments, the second time point is within less than about 2 days from the first time point. In embodiments, the second time point is within less than about 1 day from the first time point.

In embodiments, the second time point is within about 8, 10 or 12 days from the first time point. In embodiments, the second time point is within about 8, days from the first time point. In embodiments, the second time point is within about 10 days from the first time point. In embodiments, the second time point is within about 12 days from the first time point. In embodiments, the PD-1 signaling pathway inhibitor and the A2A receptor antagonist are simultaneously administered at the second time point. In embodiments, the PD-1 signaling pathway inhibitor and the A2A receptor antagonist are concomitantly administered at the second time point. In embodiments, the PD-1 signaling pathway inhibitor is administered at the second time point and the A2A receptor antagonist is not administered at the second time point.

In embodiments, the PD-1 signaling pathway inhibitor is administered at a first time point and the A2A receptor antagonist is administered at a second time point, wherein the first time point precedes the second time point. In embodiments, the second time point is within less than about 120, 90, 60, 50, 40, 30, 20, 19, 18, 17, 16, 15, 14, 13, 12, 10, 11, 9, 8, 7, 6, 5, 4, 3, 2 or 1 days from the first time point. In embodiments, the second time point is within less than about 120 days from the first time point. In embodiments, the second time point is within less than about 90 days from the first time point. In embodiments, the second time point is within less than about 60 days from the first time point. In embodiments, the second time point is within less than about 50 days from the first time point. In embodiments, the second time point is within less than about 40 days from the first time point. In embodiments, the second time point is within less than about 30 days from the first time point. In embodiments, the second time point is within less than about 20 days from the first time point.

In embodiments, the second time point is within less than about 19 days from the first time point. In embodiments, the second time point is within less than about 18 days from the first time point. In embodiments, the second time point is within less than about 17 days from the first time point. In embodiments, the second time point is within less than about 16 days from the first time point. In embodiments, the second time point is within less than about 15 days from the first time point. In embodiments, the second time point is within less than about 14 days from the first time point. In embodiments, the second time point is within less than about 13 days from the first time point. In embodiments, the second time point is within less than about 12 days from the first time point. In embodiments, the second time point is within less than about 11 days from the first time point. In embodiments, the second time point is within less than about 10 days from the first time point. In embodiments, the second time point is within less than about 9 days from the first time point. In embodiments, the second time point is within less than about 8 days from the first time point. In embodiments, the second time point is within less than about 7 days from the first time point. In embodiments, the second time point is within less than about 6 days from the first time point. In embodiments, the second time point is within less than about 5 days from the first time point. In embodiments, the second time point is within less than about 4 days from the first time point. In embodiments, the second time point is within less than about 3 days from the first time point. In embodiments, the second time point is within less than about 2 days from the first time point. In embodiments, the second time point is within less than about 1 day from the first time point.

In embodiments, the second time point is within about 8, 10 or 12 days from the first time point. In embodiments, the second time point is within about 8, days from the first time point. In embodiments, the second time point is within about 10 days from the first time point. In embodiments, the second time point is within about 12 days from the first time point. In embodiments, the PD-1 signaling pathway inhibitor and the A2A receptor antagonist are simultaneously administered at the second time point. In embodiments, the PD-1 signaling pathway inhibitor and the A2A receptor antagonist are concomitantly administered at the second time point. In embodiments, the A2A receptor antagonist is administered at the second time point and the PD-1 signaling pathway inhibitor is not administered at the second time point.

According to the methods provided herein, the subject is administered an effective amount of one or more of the agents (e.g., an A2A receptor antagonist and/or a PD-1 signaling pathway inhibitor) provided herein. An "effective amount" is an amount sufficient to accomplish a stated purpose (e.g. achieve the effect for which it is administered, treat a disease (e.g., cancer), reduce receptor signalling activity, reduce one or more symptoms of a disease or condition). An example of an "effective amount" is an amount sufficient to contribute to the treatment, prevention, or reduction of a symptom or symptoms of a disease (e.g., cancer), which could also be referred to as a "therapeutically effective amount." A "reduction" of a symptom or symptoms (and grammatical equivalents of this phrase) means decreasing of the severity or frequency of the symptom(s), or elimination of the symptom(s). Guidance can be found in the literature for appropriate dosages for given classes of pharmaceutical products. For example, for the given parameter, a therapeutically effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

In embodiments, the A2A receptor antagonist is administered at an amount of about 0.5 mg/kg, 1 mg/kg, 2 mg/kg, 3 mg/kg, 4 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg or 300 mg/kg. In embodiments, the A2A receptor antagonist is administered at an amount of about 0.5 mg/kg. In embodiments, the A2A receptor antagonist is administered at an amount of about 1 mg/kg. In embodiments, the A2A receptor antagonist is administered at an amount of about 5 mg/kg. In embodiments, the A2A receptor antagonist is administered at an amount of about 10 mg/kg. In embodiments, the A2A receptor antagonist is administered at an amount of about 20 mg/kg. In embodiments, the A2A receptor antagonist is administered at an amount of about 30 mg/kg. In embodiments, the A2A receptor antagonist is administered at an amount of about 40 mg/kg. In embodiments, the A2A receptor antagonist is administered at an amount of about 50 mg/kg. In embodiments, the A2A receptor antagonist is administered at an amount of about 60 mg/kg. In embodiments, the A2A receptor antagonist is administered at an amount of about 70 mg/kg. In embodiments, the A2A receptor antagonist is administered at an amount of about 80 mg/kg. In embodiments, the A2A receptor antagonist is administered at an amount of about 90 mg/kg. In embodiments, the A2A receptor antagonist is administered at an amount of about 100 mg/kg. In embodiments, the A2A receptor antagonist is administered at an amount of about 200 mg/kg. In embodiments, the A2A receptor antagonist is administered at an amount of about 300 mg/kg. It is understood that where the amount is referred to as "mg/kg", the amount is milligram per kilogram body weight of the subject being administered with the A2A receptor antagonist.

In embodiments, the A2A receptor antagonist is administered at an amount of about 0.5 mg/kg, 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg or 300 mg/kg. In embodiments, the A2A receptor antagonist is administered at an amount of about 1 mg/kg. In embodiments, the A2A receptor antagonist is administered at an amount of about 1 mg/kg to 2 mg/kg. In embodiments, the A2A receptor antagonist is administered at an amount of about 1 mg/kg to 3 mg/kg. In embodiments, the A2A receptor antagonist is administered at an amount of about 1 mg/kg to 4 mg/kg. In embodiments, the A2A receptor antagonist is administered at an amount of about 1 mg/kg to 5 mg/kg.

In embodiments, the A2A receptor antagonist is administered at an amount of about 10 mg BID, 20 mg BID, 30 mg BID, 40 mg BID, 50 mg BID, 60 mg BID, 70 mg BID, 80 mg BID, 90 mg BID, 100 mg BID, 110 mg BID, 120 mg BID, 130 mg BID, 140 mg BID, 150 mg BID, 160 mg BID, 170 mg BID, 180 mg BID, 190 mg BID, 200 mg BID, 210 mg BID, 220 mg BID, 230 mg BID, 240 mg BID, 250 mg BID, 260 mg BID, 270 mg BID, 280 mg BID, 290 mg BID, or 300 mg BID. In embodiments, the A2A receptor antagonist is administered at an amount of about 10 mg BID. In embodiments, the A2A receptor antagonist is administered at an amount of about 20 mg BID. In embodiments, the A2A receptor antagonist is administered at an amount of about 30 mg BID. In embodiments, the A2A receptor antagonist is administered at an amount of about 40 mg BID. In embodiments, the A2A receptor antagonist is administered at an amount of about 50 mg BID. In embodiments, the A2A receptor antagonist is administered at an amount of about 60 mg BID. In embodiments, the A2A receptor antagonist is administered at an amount of about 70 mg BID. In embodiments, the A2A receptor antagonist is administered at an amount of about 80 mg BID. In embodiments, the A2A receptor antagonist is administered at an amount of about 90 mg BID. In embodiments, the A2A receptor antagonist is administered at an amount of about 100 mg BID. It is understood that where the amount is referred to as "BID" which stands for "bis in die", the amount is administered twice a day.

In embodiments, the A2A receptor antagonist is administered at an amount of about 110 mg BID. In embodiments, the A2A receptor antagonist is administered at an amount of about 120 mg BID. In embodiments, the A2A receptor antagonist is administered at an amount of about 130 mg BID. In embodiments, the A2A receptor antagonist is administered at an amount of about 140 mg BID. In embodiments, the A2A receptor antagonist is administered at an amount of about 150 mg BID. In embodiments, the A2A receptor antagonist is administered at an amount of about 160 mg BID. In embodiments, the A2A receptor antagonist is administered at an amount of about 170 mg BID. In embodiments, the A2A receptor antagonist is administered at an amount of about 180 mg BID. In embodiments, the A2A receptor antagonist is administered at an amount of about 190 mg BID. In embodiments, the A2A receptor antagonist is administered at an amount of about 200 mg BID. It is understood that where the amount is referred to as "BID" which stands for "bis in die", the amount is administered twice a day.

In embodiments, the A2A receptor antagonist is administered at an amount of about 210 mg BID. In embodiments, the A2A receptor antagonist is administered at an amount of about 220 mg BID. In embodiments, the A2A receptor antagonist is administered at an amount of about 230 mg BID. In embodiments, the A2A receptor antagonist is administered at an amount of about 240 mg BID. In embodiments, the A2A receptor antagonist is administered at an amount of about 250 mg BID. In embodiments, the A2A receptor antagonist is administered at an amount of about 260 mg BID. In embodiments, the A2A receptor antagonist is administered at an amount of about 270 mg BID. In embodiments, the A2A receptor antagonist is administered at an amount of about 280 mg BID. In embodiments, the A2A receptor antagonist is administered at an amount of about 290 mg BID. In embodiments, the A2A receptor antagonist is administered at an amount of about 300 mg BID. It is understood that where the amount is referred to as "BID" which stands for "bis in die", the amount is administered twice a day.

In embodiments, the A2A receptor antagonist is administered at an amount of about 10 mg QD, 20 mg QD, 30 mg QD, 40 mg QD, 50 mg QD, 60 mg QD, 70 mg QD, 80 mg QD, 90 mg QD, 100 mg QD, 110 mg QD, 120 mg QD, 130 mg QD, 140 mg QD, 150 mg QD, 160 mg QD, 170 mg QD, 180 mg QD, 190 mg QD, 200 mg QD, 210 mg QD, 220 mg QD, 230 mg QD, 240 mg QD, 250 mg QD, 260 mg QD, 270 mg QD, 280 mg QD, 290 mg QD, or 300 mg QD. In embodiments, the A2A receptor antagonist is administered at an amount of about 10 mg QD. In embodiments, the A2A receptor antagonist is administered at an amount of about 20 mg QD. In embodiments, the A2A receptor antagonist is administered at an amount of about 30 mg QD. In embodiments, the A2A receptor antagonist is administered at an amount of about 40 mg QD. In embodiments, the A2A receptor antagonist is administered at an amount of about 50 mg QD. In embodiments, the A2A receptor antagonist is administered at an amount of about 60 mg QD. In embodiments, the A2A receptor antagonist is administered at an amount of about 70 mg QD. In embodiments, the A2A receptor antagonist is administered at an amount of about 80 mg QD. In embodiments, the A2A receptor antagonist is administered at an amount of about 90 mg QD. In embodiments, the A2A receptor antagonist is administered at an amount of about 100 mg QD. It is understood that where the amount is referred to as "QD" which stands for "quaque die", the amount is administered once a day.

In embodiments, the A2A receptor antagonist is administered at an amount of about 110 mg QD. In embodiments, the A2A receptor antagonist is administered at an amount of about 120 mg QD. In embodiments, the A2A receptor antagonist is administered at an amount of about 130 mg QD. In embodiments, the A2A receptor antagonist is administered at an amount of about 140 mg QD. In embodiments, the A2A receptor antagonist is administered at an amount of about 150 mg QD. In embodiments, the A2A receptor antagonist is administered at an amount of about 160 mg QD. In embodiments, the A2A receptor antagonist is administered at an amount of about 170 mg QD. In embodiments, the A2A receptor antagonist is administered at an amount of about 180 mg QD. In embodiments, the A2A receptor antagonist is administered at an amount of about 190 mg QD. In embodiments, the A2A receptor antagonist is administered at an amount of about 200 mg QD. It is understood that where the amount is referred to as "QD" which stands for "quaque die", the amount is administered once a day.

In embodiments, the A2A receptor antagonist is administered at an amount of about 210 mg QD. In embodiments, the A2A receptor antagonist is administered at an amount of about 220 mg QD. In embodiments, the A2A receptor antagonist is administered at an amount of about 230 mg QD. In embodiments, the A2A receptor antagonist is administered at an amount of about 240 mg QD. In embodiments, the A2A receptor antagonist is administered at an amount of about 250 mg QD. In embodiments, the A2A receptor antagonist is administered at an amount of about 260 mg QD. In embodiments, the A2A receptor antagonist is administered at an amount of about 270 mg QD. In embodiments, the A2A receptor antagonist is administered at an amount of about 280 mg QD. In embodiments, the A2A receptor antagonist is administered at an amount of about 290 mg QD. In embodiments, the A2A receptor antagonist is administered at an amount of about 300 mg QD. It is understood that where the amount is referred to as "QD" which stands for "quaque die", the amount is administered once a day.

The A2A receptor antagonist may be administered at an amount as provided herein on 28 consecutive days. The A2A receptor antagonist may be administered at an amount as provided herein on 14 consecutive days. In embodiments, the A2A receptor antagonist is administered at 50 mg BID, 100 mg BID or 200 mg QD. In embodiments, the A2A receptor antagonist is administered at 50 mg BID. In embodiments, the A2A receptor antagonist is administered at 100 mg BID. In embodiments, the A2A receptor antagonist is administered at 200 mg QD. In embodiments, the A2A receptor antagonist is administered at 100 mg BID and the PD-1 signaling pathway inhibitor is administered at an amount of 840 mg. In further embodiments, the A2A receptor antagonist and the PD-1 signaling pathway inhibitor are administered simultaneously on 28 consecutive days. In other further embodiments, the A2A receptor antagonist and the PD-1 signaling pathway inhibitor are administered simultaneously on 14 consecutive days.

In embodiments, the PD-1 signaling pathway inhibitor is administered at an amount of less than about 1,300 mg. In embodiments, the PD-1 signaling pathway inhibitor is administered at an amount of less than about 1,200 mg. In embodiments, the PD-1 signaling pathway inhibitor is administered at an amount of less than about 1,100 mg. In embodiments, the PD-1 signaling pathway inhibitor is administered at an amount of less than about 1,000 mg. In embodiments, the PD-1 signaling pathway inhibitor is administered at an amount of less than about 900 mg. In embodiments, the PD-1 signaling pathway inhibitor is administered at an amount of less than about 800 mg. In embodiments, the PD-1 signaling pathway inhibitor is administered at an amount of less than about 700 mg. In embodiments, the PD-1 signaling pathway inhibitor is administered at an amount of less than about 600 mg. In embodiments, the PD-1 signaling pathway inhibitor is administered at an amount of less than about 500 mg. In embodiments, the PD-1 signaling pathway inhibitor is administered at an amount of less than about 400 mg. In embodiments, the PD-1 signaling pathway inhibitor is administered at an amount of less than about 300 mg. In embodiments, the PD-1 signaling pathway inhibitor is administered at an amount of less than about 200 mg. In embodiments, the PD-1 signaling pathway inhibitor is administered at an amount of less than about 100 mg. In embodiments, the PD-1 signaling pathway inhibitor is administered at an amount of about 100 mg, 200 mg, 300 mg, 400 mg, 500 mg, 600 mg, 700 mg, 800 mg, 900 mg, 1.00 mg, 1,100 mg, 1,200 mg, or 1,300 mg. It is understood that where the amount is referred to as "mg" that the amount is the total amount in milligram of PD-1 signaling pathway inhibitor administered to the subject.

In embodiments, the PD-1 signaling pathway inhibitor is administered at an amount of about 700 mg. In embodiments, the PD-1 signaling pathway inhibitor is administered at an amount of about 720 mg. In embodiments, the PD-1 signaling pathway inhibitor is administered at an amount of about 740 mg. In embodiments, the PD-1 signaling pathway inhibitor is administered at an amount of about 760 mg. In embodiments, the PD-1 signaling pathway inhibitor is administered at an amount of about 780 mg. In embodiments, the PD-1 signaling pathway inhibitor is administered at an amount of about 800 mg. In embodiments, the PD-1 signaling pathway inhibitor is administered at an amount of about 820 mg. In embodiments, the PD-1 signaling pathway inhibitor is administered at an amount of about 840 mg. In embodiments, the PD-1 signaling pathway inhibitor is administered at an amount of about 860 mg. In embodiments, the PD-1 signaling pathway inhibitor is administered at an amount of about 880 mg. In embodiments, the PD-1 signaling pathway inhibitor is administered at an amount of about 900 mg. It is understood that where the amount is referred to as "mg" that the amount is the total amount in milligram of PD-1 signaling pathway inhibitor administered to the subject.

The methods provided herein are, inter alia, useful for the treatment of cancer. In embodiments, the cancer is selected from lung cancer, bladder cancer, melanoma, renal cell carcinoma, colon cancer, ovarian cancer, gastric cancer, breast cancer, head and neck carcinoma, prostate cancer and a hematologic malignancy. In embodiments, the cancer is lung cancer. In embodiments, the cancer is bladder cancer. In embodiments, the cancer is melanoma. In embodiments, the cancer is renal cell carcinoma. In embodiments, the cancer is colon cancer. In embodiments, the cancer is ovarian cancer. In embodiments, the cancer is gastric cancer. In embodiments, the cancer is breast cancer. In embodiments, the cancer is head and neck carcinoma. In embodiments, the cancer is prostate cancer. In embodiments, the cancer is a hematologic malignancy.

In another aspect, a method of treating cancer in a subject in need thereof is provided. The method includes administering to the subject a therapeutically effective amount of an adenosine-A2A (A2A) receptor antagonist of formula:

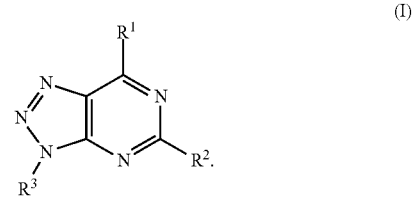

(I)

In formula (I), $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —N(O)$_{m1}$, —$NR^9R^{10}$, —NH—O—$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)

$NR^{11}R^{12}$, —$N(O)_{m2}$, —$NR^{11}R^{12}$, —NH—O—$R^{11}$, —C(O)$R^{11}$, —C(O)—O$R^{11}$, —C(O)$NR^{11}R^{12}$, —O$R^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —$N(O)_{m3}$, —$NR^{13}R^{14}$, —NH—O—$R^{13}$, —C(O)$R^{13}$, —C(O)—O$R^{13}$, —C(O)$NR^{13}R^{14}$, —O$R^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$X^a$, $X^b$ and $X^c$ are independently —F, —Cl, —Br, or —I.

$n_1$, $n_2$ and $n_3$ are independently an integer from 0 to 4.

$m_1$, $m_2$ and $m_3$ are independently an integer from 1 to 2.

And $v_1$, $v_2$ and $v_3$ are independently an integer from 1 to 2.

The A2A receptor antagonist provided herein is the same A2A receptor antagonist as described above for aspects of treating cancer using an A2A receptor antagonist and a PD-1 signaling pathway inhibitor. Therefore, the definitions for substituents and variables of formula (I) and (II) are the same as described above (e.g., $R^1$ is $R^{1.4}$-substituted furanyl; $R^{1.4}$ is methyl; $R^2$ is —$NR^{11}R^{12}$; $R^{11}$ and $R^{12}$ are independently hydrogen; $R^3$ is $R^4$-substituted $C_1$ alkyl; $R^4$ is $R^5$-substituted pyridinyl; $R^5$ is $R^6$-substituted 2 membered heteroalkyl; $R^6$ is unsubstituted tetrahydrofuranyl and are incorporated herewith.

Thus, in embodiments, the A2A receptor antagonist is a compound of formula:

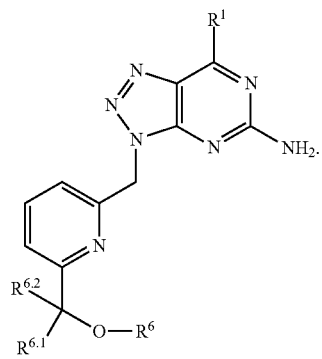

In formula (II), $R^6$, $R^{6.1}$ and $R^{6.2}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the A2A receptor antagonist is a compound of formula:

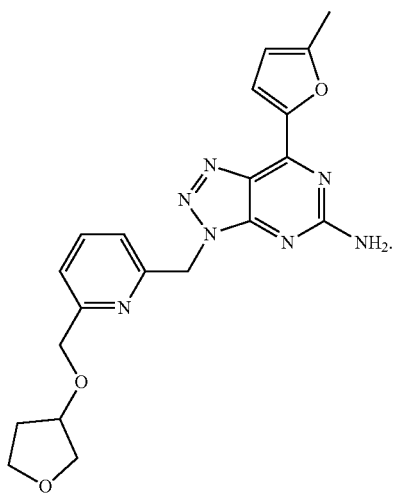

In embodiments, the A2A receptor antagonist is a compound of formula:

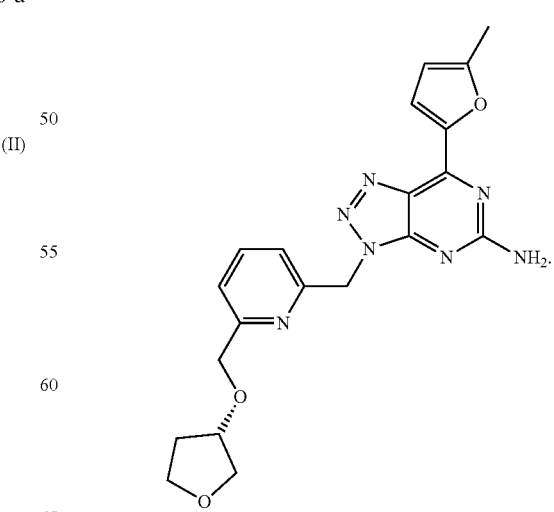

In embodiments, the A2A receptor antagonist is a compound of formula:

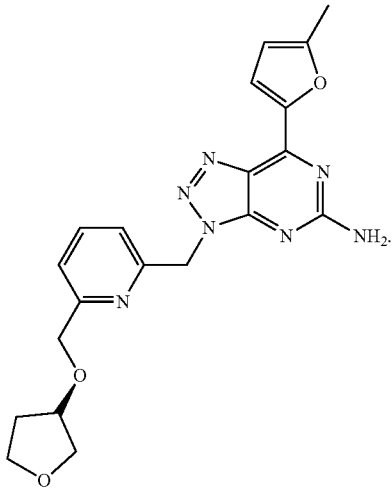

In embodiments, the method further includes administering a therapeutically effective amount of a PD-1 signaling pathway inhibitor. In embodiments, the A2A receptor antagonist and the PD-1 signaling pathway inhibitor are administered in a combined synergistic amount. In embodiments, the A2A receptor antagonist and the PD-1 signaling pathway inhibitor are administered simultaneously or sequentially. In embodiments, the A2A receptor antagonist is administered at a first time point and the PD-1 signaling pathway inhibitor is administered at a second time point, wherein the first time point precedes the second time point. In embodiments, the second time point is within less than about 120, 90, 60, 50, 40, 30, 20, 19, 18, 17, 16, 15, 14, 13, 12, 10, 11, 9, 8, 7, 6, 5, 4, 3, 2, or 1 days from the first time point. In embodiments, the second time point is within about 8, 10 or 12 days from the first time point. In embodiments, the PD-1 signaling pathway inhibitor is administered at a first time point and the A2A receptor antagonist is administered at a second time point, wherein the first time point precedes the second time point. In embodiments, the second time point is within less than about 120, 90, 60, 50, 40, 30, 20, 19, 18, 17, 16, 15, 14, 13, 12, 10, 11, 9, 8, 7, 6, 5, 4, 3, 2, or 1 days from the first time point. In embodiments, the second time point is within about 8, 10 or 12 days from the first time point.

In embodiments, the A2A receptor antagonist is administered at an amount of about 0.5 mg/kg, 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg or 300 mg/kg. In embodiments, the A2A receptor antagonist is administered at an amount of about 1 mg/kg. In embodiments, the PD-1 signaling pathway inhibitor is administered at an amount of less than about 1,300 mg. In embodiments, the PD-1 signaling pathway inhibitor is administered at an amount of less than about 1,200 mg. In embodiments, the cancer is selected from lung cancer, bladder cancer, melanoma, renal cell carcinoma, colon cancer, ovarian cancer, gastric cancer, breast cancer, head and neck carcinoma, prostate cancer and a hematologic malignancy.

Methods of Activating T Cells

In one aspect, a method of activating a T cell is provided. The method includes contacting the T cell with an A2A receptor antagonist, wherein the A2A receptor antagonist is a compound of formula:

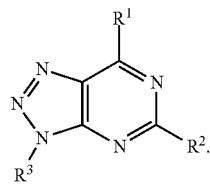

In formula (I), $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —N(O)$_{m1}$, —$NR^9R^{10}$, —NH—O—$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —N(O)$_{m2}$, —$NR^{11}R^{12}$, —NH—O—$R^{11}$, —C(O)$R^{11}$, —C(O)—$OR^{11}$, —C(O)$NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —N(O)$_{m3}$, —$NR^{13}R^{14}$, —NH—O—$R^{13}$, —C(O)$R^{13}$, —C(O)—$OR^{13}$, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently —F, —Cl, —Br, or —I. $n_1$, $n_2$ and $n_3$ are independently an integer from 0 to 4. $m_1$, $m_2$ and $m_3$ are independently an integer from 1 to 2. And $v_1$, $v_2$ and $v_3$ are independently an integer from 1 to 2.

The A2A receptor antagonist provided herein is the same A2A receptor antagonist as described above for aspects of treating cancer using an A2A receptor antagonist and a PD-1 signaling pathway inhibitor. Therefore, the definitions for substituents and variables of formula (I) and (II) are the same as described above (e.g., $R^1$ is $R^{1A}$-substituted furanyl; $R^{1A}$ is methyl; $R^2$ is —$NR^{11}R^{12}$; $R^{11}$ and $R^{12}$ are independently hydrogen; $R^3$ is $R^4$-substituted $C_1$ alkyl; $R^4$ is $R^5$-substituted pyridinyl; $R^5$ is $R^6$-substituted 2 membered heteroalkyl; $R^6$ is unsubstituted tetrahydrofuranyl) and are incorporated herewith.

Thus, in embodiments, the A2A receptor antagonist is a compound of formula:

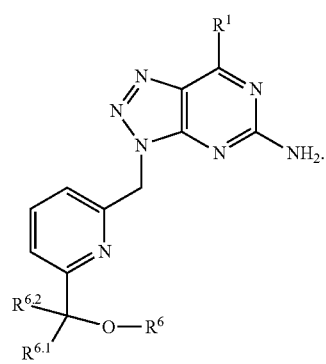

(II)

In formula (II), $R^6$, $R^{6.1}$ and $R^{6.2}$ are independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the A2A receptor antagonist is a compound of formula:

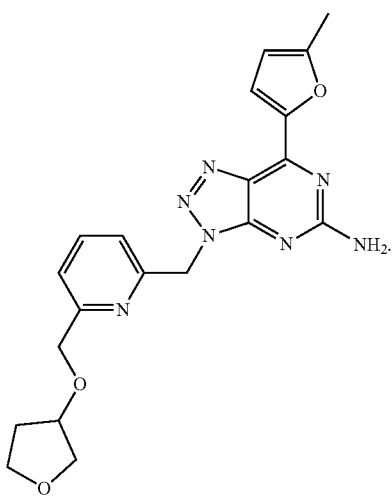 [SMILES: Cc1ccc(-c2nc(N)nc3c2nnn3Cc2cccc(COC3CCOC3)n2)o1]

In embodiments, the A2A receptor antagonist is a compound of formula:

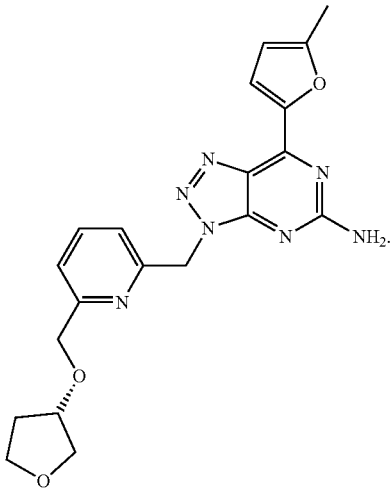

In embodiments, the A2A receptor antagonist is a compound of formula:

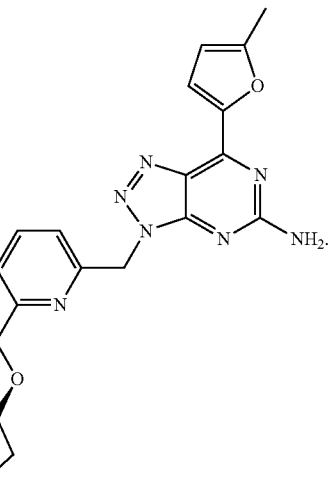

In embodiments, the method includes contacting the T cell with a PD-1 signaling pathway inhibitor. In embodiments, the PD-1 signaling pathway inhibitor is an antibody or a small molecule. In embodiments, the T cell is an effector T cell or a natural killer cell. In embodiments, the T cell is an adenosine-suppressed T cell. "An adenosine-suppressed T cell" is an effector T cell or a natural killer cell bound to adenosine through its A2A receptor, wherein the adenosine is bound in an amount sufficient to inhibit expression and/or secretion of immune response activating cytokines (e.g., expression of IL-2, IFN-γ or TNF). In embodiments, the T cell is a CD8 T cell. In embodiments, the CD8 T cell is a CD45RA-negative CD8 T cell. In embodiments, the T cell is a CD4 T cell. In embodiments, the CD4 T cell is a CD45RA-negative CD4 T cell. In embodiments, the T cell is within a subject. In embodiments, the subject is a cancer subject. In embodiments, the cancer subject is an anti-PD-1 refractory subject.

Methods of Inhibiting A2A Receptor Activity

In one aspect, a method of inhibiting A2A receptor activity of a cell is provided. The method includes contacting the cell with an A2A receptor antagonist, wherein the A2A receptor antagonist is a compound of formula:

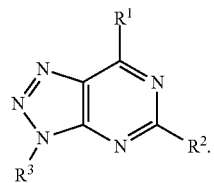

(I)

In formula (I), $R^1$ is independently hydrogen, halogen, $-CX^a_3$, $-CN$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$, $-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, $-CX^b_3$, $-CN$, $-SO_2Cl$, $-SO_{n2}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-NH-O-R^{11}$, $-C(O)R^{11}$, $-C(O)-OR^{11}$, $-C(O)NR^{11}R^{12}$, $-OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, $-CX^c_3$, $-CN$, $-SO_2Cl$, $-SO_{n3}R^{13}$, $-SO_{v3}NR^{13}R^{14}$, $-NHNH_2$, $-ONR^{13}R^{14}$, $-NHC=(O)NHNH_2$, $-NHC=(O)NR^{13}R^{14}$, $-N(O)_{m3}$, $-NR^{13}R^{14}$, $-NH-O-R^{13}$, $-C(O)R^{13}$, $-C(O)-OR^{13}$, $-C(O)NR^{13}R^{14}$, $-OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently $-F$, $-Cl$, $-Br$, or $-I$. $n_1$, $n_2$ and $n_3$ are independently an integer from 0 to 4. $m_1$, $m_2$ and $m_3$ are independently an integer from 1 to 2. And $v_1$, $v_2$ and $v_3$ are independently an integer from 1 to 2.

The A2A receptor antagonist provided herein is the same A2A receptor antagonist as described above for aspects of treating cancer using an A2A receptor antagonist and a PD-1 signaling pathway inhibitor. Therefore, the definitions for substituents and variables of formula (I) and (II) are the same as described above (e.g., $R^1$ is $R^{1.A}$-substituted furanyl; $R^{1.A}$ is methyl; $R^2$ is $-NR^{11}R^{12}$; $R^{11}$ and $R^{12}$ are independently hydrogen; $R^3$ is $R^4$-substituted $C_1$ alkyl; $R^4$ is $R^5$-substituted pyridinyl; $R^5$ is $R^6$-substituted 2 membered heteroalkyl; $R^6$ is unsubstituted tetrahydrofuranyl) and are incorporated herewith.

Thus, in embodiments, the A2A receptor antagonist is a compound of formula:

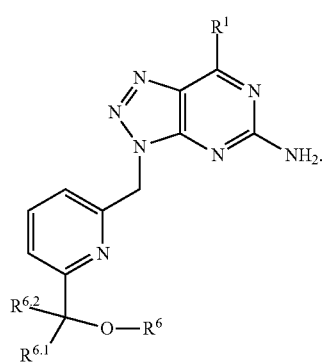

(II)

In formula (II), $R^6$, $R^{6.1}$ and $R^{6.2}$ are independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the A2A receptor antagonist is a compound of formula:

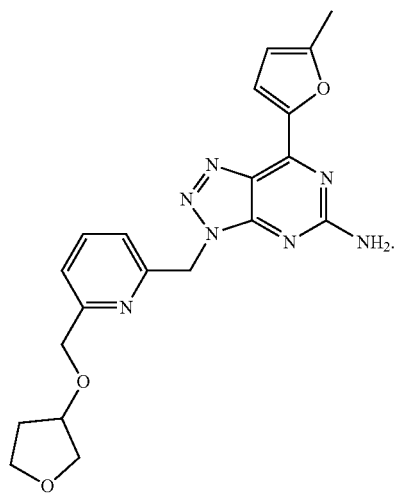

In embodiments, the A2A receptor antagonist is a compound of formula:

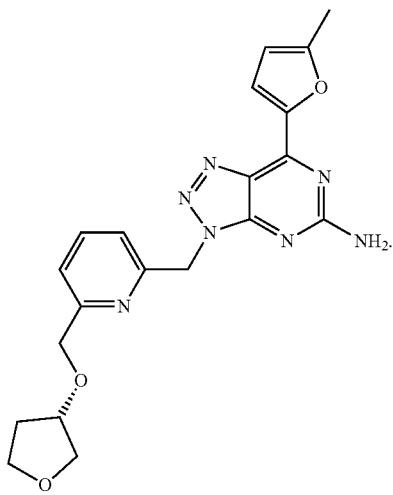

In embodiments, the A2A receptor antagonist is a compound of formula:

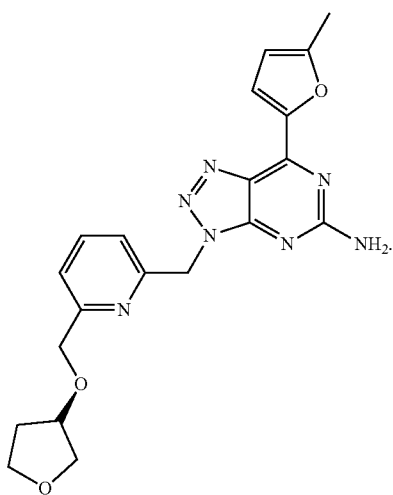

In embodiments, the contacting includes binding the A2A receptor antagonist to an A2A receptor of the cell. In embodiments, the cell is a T cell. In embodiments, the T cell is an effector T cell or a natural killer cell. In embodiments, T cell is a CD8 T cell. In embodiments, the CD8 T cell is a CD45RA-negative CD8 Tcell. In embodiments, the T cell is a CD4 Tcell. In embodiments, the CD4 T cell is a CD45RA-negative CD4 Tcell. In embodiments, the T cell is within a subject. In embodiments, the subject is a cancer subject. In embodiments, the cancer subject is an anti-PD-1 refractory subject.

Methods of Increasing Anti-Tumor Response

In one aspect, a method of increasing an anti-tumor immune response in a subject in need thereof is provided. The method includes administering to the subject a therapeutically effective amount of an adenosine-A2A (A2A) receptor antagonist and a programmed cell death protein 1 (PD-1) signaling pathway inhibitor.

In another aspect, a method of increasing an anti-tumor immune response in a subject in need thereof is provided. The method includes administering to the subject a therapeutically effective amount of an adenosine-A2A (A2A) receptor antagonist, wherein the A2A receptor antagonist is a compound of formula:

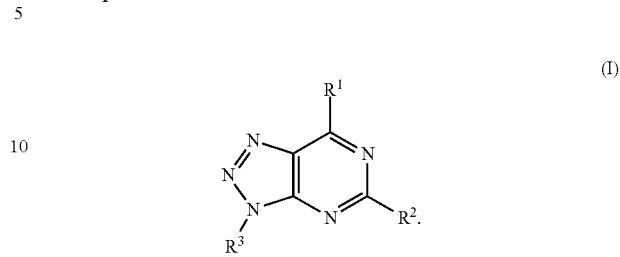

(I)

In formula (I), $R^1$ is independently hydrogen, halogen, $-CX^a_3$, $-CN$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$, $-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, $-CX^b_3$, $-CN$, $-SO_2Cl$, $-SO_{n2}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-NH-O-R^{11}$, $-C(O)R^{11}$, $-C(O)-OR^{11}$, $-C(O)NR^{11}R^{12}$, $-OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, $-CX^c_3$, $-CN$, $-SO_2Cl$, $-SO_{n3}R^{13}$, $-SO_{v3}NR^{13}R^{14}$, $-NHNH_2$, $-ONR^{13}R^{14}$, $-NHC=(O)NHNH_2$, $-NHC=(O)NR^{13}R^{14}$, $-N(O)_{m3}$, $-NR^{13}R^{14}$, $-NH-O-R^{13}$, $-C(O)R^{13}$, $-C(O)-OR^{13}$, $-C(O)NR^{13}R^{14}$, $-OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently $-F$, $-Cl$, $-Br$, or $-I$. $n_1$, $n_2$ and $n_3$ are independently an integer from 0 to 4. $m_1$, $m_2$ and $m_3$ are independently an integer from 1 to 2. And $v_1$, $v_2$ and $v_3$ are independently an integer from 1 to 2.

The A2A receptor antagonist and the PD-1 signaling pathway inhibitor provided herein are the same as described above for aspects of treating cancer using an A2A receptor antagonist and a PD-1 signaling pathway inhibitor. Therefore, the definitions for substituents and variables of formula (I) and (II) are the same as described above (e.g., $R^1$ is $R^{1A}$-substituted furanyl; $R^{1A}$ is methyl; $R^2$ is $-NR^{11}R^{12}$; $R^{11}$ and $R^{12}$ are independently hydrogen; $R^3$ is $R^4$-substituted $C_1$ alkyl; $R^4$ is $R^5$-substituted pyridinyl; $R^5$ is $R^6$-substituted 2 membered heteroalkyl; $R^6$ is unsubstituted tetrahydrofuranyl) and are incorporated herewith.

In embodiments, the A2A receptor antagonist is a compound of formula:

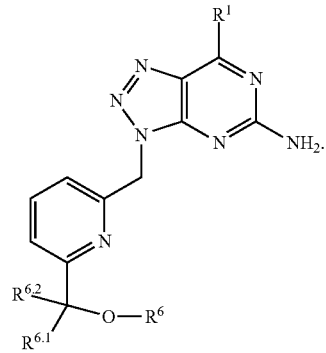

(II)

In formula (II), $R^6$, $R^{6.1}$ and $R^{6.2}$ are independently hydrogen, halogen, =O, =S, —$CF_3$, —CN, —$CCl_3$, —COOH, —$CH_2$COOH, —$CONH_2$, —OH, —SH, —$SO_2$Cl, —$SO_3$H, —$SO_4$H, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the A2A receptor antagonist is a compound of formula:

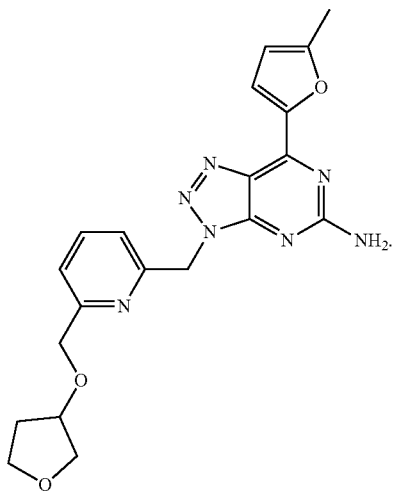

In embodiments, the A2A receptor antagonist is a compound of formula:

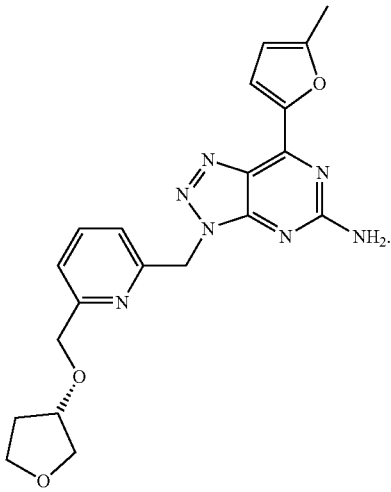

In embodiments, the A2A receptor antagonist is a compound of formula:

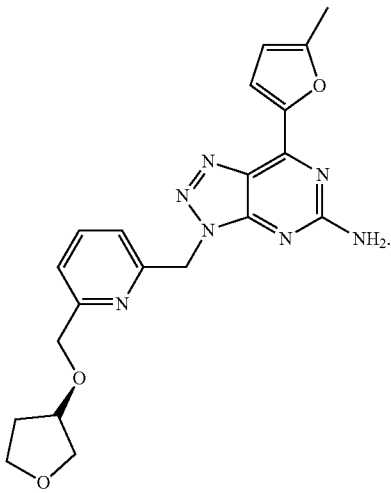

In embodiments, the method includes administering a therapeutically effective amount of a PD-1 signaling pathway inhibitor. In embodiments, the PD-1 signaling pathway inhibitor is a PD-L1 antagonist. In embodiments, the PD-L1 antagonist is a small molecule or an antibody.

Methods of Increasing CD8-Positive Cell Numbers

In one aspect, a method of increasing the amount of CD8-positive cells relative to the amount of regulatory T cells in a subject in need thereof is provided. The method includes administering to the subject a therapeutically effective amount of an adenosine-A2A (A2A) receptor antagonist and a programmed cell death protein 1 (PD-1) signaling pathway inhibitor.

In one aspect, a method of increasing the amount of CD8-positive cells relative to the amount of regulatory T cells in a subject in need thereof is provided. The method includes administering to the subject a therapeutically effective amount of an adenosine-A2A (A2A) receptor antagonist, wherein the A2A receptor antagonist is a compound of formula:

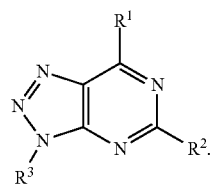

(I)

In formula (I), $R^1$ is independently hydrogen, halogen, $-CX^a_3$, $-CN$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$, $-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, $-CX^b_3$, $-CN$, $-SO_2Cl$, $-SO_{n2}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-NH-O-R^{11}$, $-C(O)R^{11}$, $-C(O)-OR^{11}$, $-C(O)NR^{11}R^{12}$, $-OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, $-CX^c_3$, $-CN$, $-SO_2Cl$, $-SO_{n3}R^{13}$, $-SO_{v3}NR^{13}R^{14}$, $-NHNH_2$, $-ONR^{13}R^{14}$, $-NHC=(O)NHNH_2$, $-NHC=(O)NR^{13}R^{14}$, $-N(O)_{m3}$, $-NR^{13}R^{14}$, $-NH-O-R^{13}$, $-C(O)R^{13}$, $-C(O)-OR^{13}$, $-C(O)NR^{13}R^{14}$, $-OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently $-F$, $-Cl$, $-Br$, or $-I$. $n_1$, $n_2$ and $n_3$ are independently an integer from 0 to 4. $m_1$, $m_2$ and $m_3$ are independently an integer from 1 to 2. And $v_1$, $v_2$ and $v_3$ are independently an integer from 1 to 2.

The A2A receptor antagonist and the PD-1 signaling pathway inhibitor provided herein are the same as described above for aspects of treating cancer using an A2A receptor antagonist and a PD-1 signaling pathway inhibitor. Therefore, the definitions for substituents and variables of formula (I) and (II) are the same as described above (e.g., $R^1$ is $R^{1.4}$-substituted furanyl; $R^{1.4}$ is methyl; $R^2$ is $-NR^{11}R^{12}$; $R^{11}$ and $R^{12}$ are independently hydrogen; $R^3$ is $R^4$-substituted $C_1$ alkyl; $R^4$ is $R^5$-substituted pyridinyl; $R^5$ is $R^6$-substituted 2 membered heteroalkyl; $R^6$ is unsubstituted tetrahydrofuranyl) and are incorporated herewith.

In embodiments, the A2A receptor antagonist is a compound of formula:

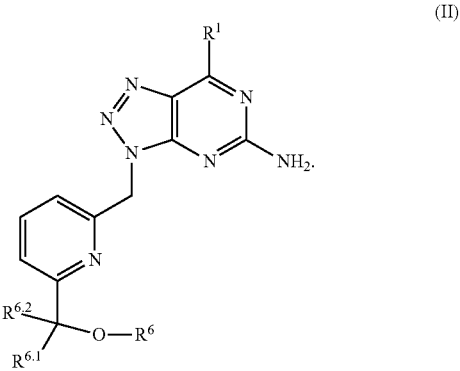

(II)

In formula (II), $R^6$, $R^{6.1}$ and $R^{6.2}$ are independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the A2A receptor antagonist is a compound of formula:

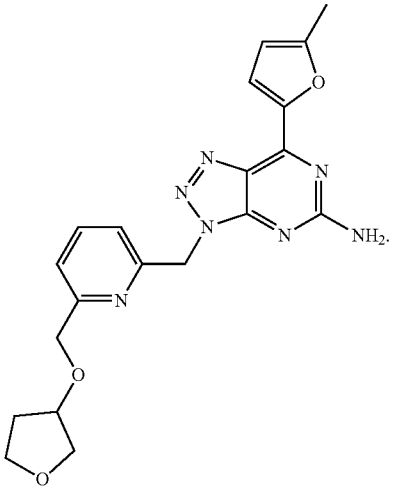

In embodiments, the A2A receptor antagonist is a compound of formula:

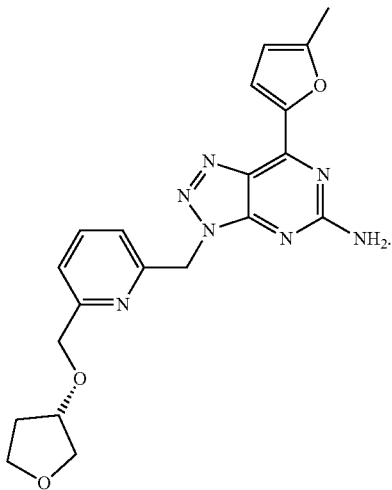

In embodiments, the A2A receptor antagonist is a compound of formula:

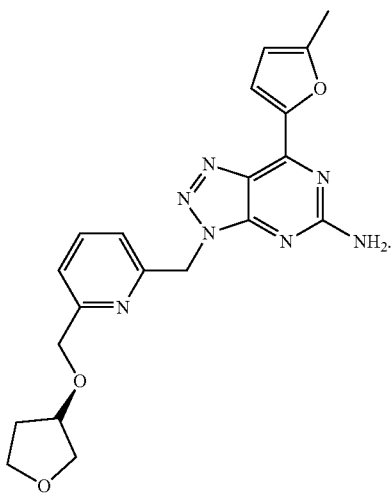

In embodiments, the method includes administering a therapeutically effective amount of a PD-1 signaling pathway inhibitor. In embodiments, the PD-1 signaling pathway inhibitor is a PD-L1 antagonist. In embodiments, the PD-L1 antagonist is a small molecule or an antibody.

Methods of Decreasing Tumor Volume

In one aspect, a method of decreasing tumor volume in a subject in need thereof is provided. The method includes administering to the subject a therapeutically effective amount of an adenosine-A2A (A2A) receptor antagonist and a programmed cell death protein 1 (PD-1) signaling pathway inhibitor.

In one aspect, a method of decreasing tumor volume in a subject in need thereof is provided. The method includes administering to the subject a therapeutically effective amount of an adenosine-A2A (A2A) receptor antagonist, wherein the A2A receptor antagonist is a compound of formula:

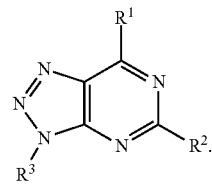 (I)

In formula (I), $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —$N(O)_{m1}$, —$NR^9R^{10}$, —NH—O—$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$NR^{11}R^{12}$, —NH—O—$R^{11}$, —C(O)$R^{11}$, —C(O)—$OR^{11}$, —C(O)$NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —$N(O)_{m3}$, —$NR^{13}R^{14}$, —NH—O—$R^{13}$, —C(O)$R^{13}$, —C(O)—$OR^{13}$, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently —F, —Cl, —Br, or —I. $n_1$, $n_2$ and $n_3$ are independently an integer from 0 to 4. $m_1$, $m_2$ and $m_3$ are independently an integer from 1 to 2. And $v_1$, $v_2$ and $v_3$ are independently an integer from 1 to 2.

The A2A receptor antagonist and the PD-1 signaling pathway inhibitor provided herein are the same as described above for aspects of treating cancer using an A2A receptor antagonist and a PD-1 signaling pathway inhibitor. Therefore, the definitions for substituents and variables of formula (I) and (II) are the same as described above (e.g., $R^1$ is $R^{14}$-substituted furanyl; $R^{14}$ is methyl; $R^2$ is —$NR^{11}R^{12}$; $R^{11}$ and $R^{12}$ are independently hydrogen; $R^3$ is $R^4$-substituted $C_1$ alkyl; $R^4$ is $R^5$-substituted pyridinyl; $R^5$ is $R^6$-substituted 2 membered heteroalkyl; $R^6$ is unsubstituted tetrahydrofuranyl) and are incorporated herewith.

In embodiments, the A2A receptor antagonist is a compound of formula:

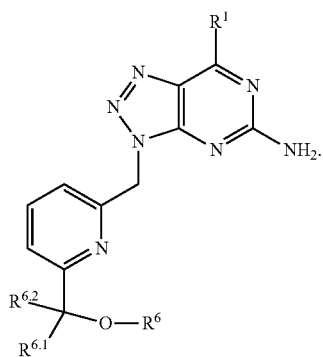

In formula (II), $R^6$, $R^{6.1}$ and $R^{6.2}$ are independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the A2A receptor antagonist is a compound of formula:

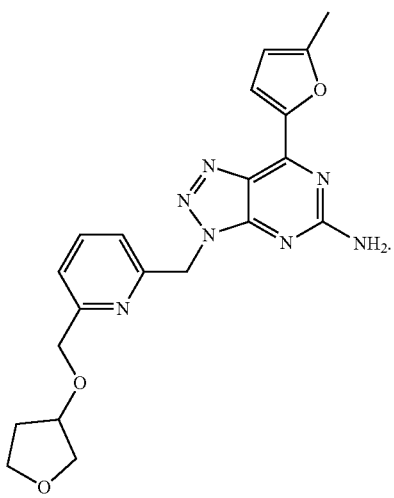

In embodiments, the A2A receptor antagonist is a compound of formula:

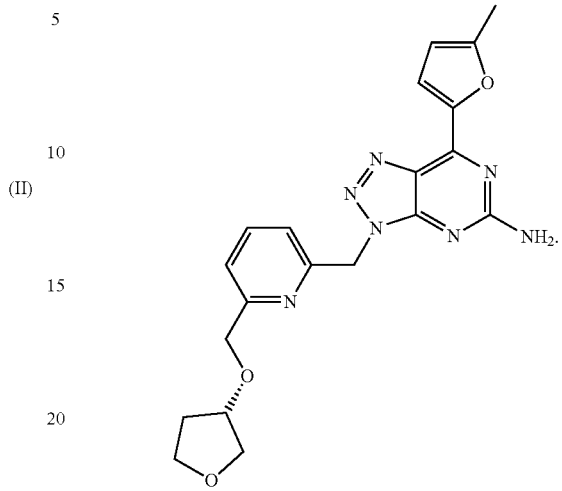

In embodiments, the A2A receptor antagonist is a compound of formula:

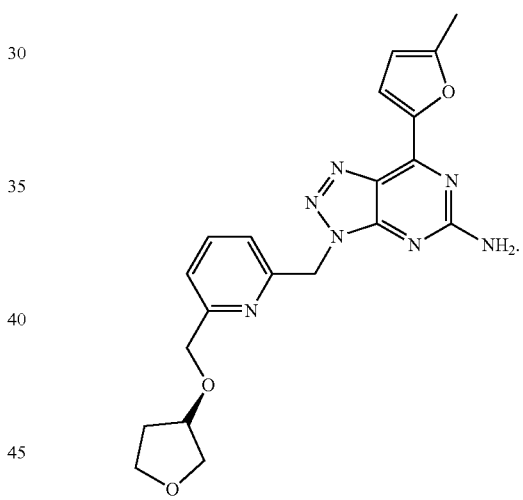

In embodiments, the method includes administering a therapeutically effective amount of a PD-1 signaling pathway inhibitor. In embodiments, the PD-1 signaling pathway inhibitor is a PD-L1 antagonist. In embodiments, the PD-L1 antagonist is a small molecule or an antibody.

Methods of Enhancing Anti-Tumor Memory

In one aspect, a method of enhancing anti-tumor immune memory in a subject in need thereof is provided. The method includes administering to the subject a therapeutically effective amount of an adenosine-A2A (A2A) receptor antagonist and a programmed cell death protein 1 (PD-1) signaling pathway inhibitor.

In one aspect, a method of enhancing anti-tumor immune memory in a subject in need thereof is provided. The method includes administering to the subject a therapeutically effective amount of an adenosine-A2A (A2A) receptor antagonist, wherein the A2A receptor antagonist is a compound of formula:

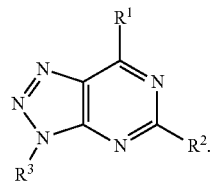

(I)

In formula (I), $R^1$ is independently hydrogen, halogen, $-CX^a_3$, $-CN$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$, $-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, $-CX^b_3$, $-CN$, $-SO_2Cl$, $-SO_{n2}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-NH-O-R^{11}$, $-C(O)R^{11}$, $-C(O)-OR^{11}$, $-C(O)NR^{11}R^{12}$, $-OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, $-CX^c_3$, $-CN$, $-SO_2Cl$, $-SO_{n3}R^{13}$, $-SO_{v3}NR^{13}R^{14}$, $-NHNH_2$, $-ONR^{13}R^{14}$, $-NHC=(O)NHNH_2$, $-NHC=(O)NR^{13}R^{14}$, $-N(O)_{m3}$, $-NR^{13}R^{14}$, $-NH-O-R^{13}$, $-C(O)R^{13}$, $-C(O)-OR^{13}$, $-C(O)NR^{13}R^{14}$, $-OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently $-F$, $-Cl$, $-Br$, or $-I$. $n_1$, $n_2$ and $n_3$ are independently an integer from 0 to 4. $m_1$, $m_2$ and $m_3$ are independently an integer from 1 to 2. And $v_1$, $v_2$ and $v_3$ are independently an integer from 1 to 2.

The A2A receptor antagonist and the PD-1 signaling pathway inhibitor provided herein are the same as described above for aspects of treating cancer using an A2A receptor antagonist and a PD-1 signaling pathway inhibitor. Therefore, the definitions for substituents and variables of formula (I) and (II) are the same as described above (e.g., $R^1$ is $R^{14}$-substituted furanyl; $R^{14}$ is methyl; $R^2$ is $-NR^{11}R^{12}$; $R^{11}$ and $R^{12}$ are independently hydrogen; $R^3$ is $R^4$-substituted $C_1$ alkyl; $R^4$ is $R^5$-substituted pyridinyl; $R^5$ is $R^6$-substituted 2 membered heteroalkyl; $R^6$ is unsubstituted tetrahydrofuranyl) and are incorporated herewith.

In embodiments, the A2A receptor antagonist is a compound of formula:

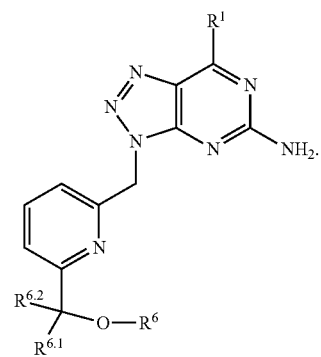

(II)

In formula (II), $R^6$, $R^{6.1}$ and $R^{6.2}$ are independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the A2A receptor antagonist is a compound of formula:

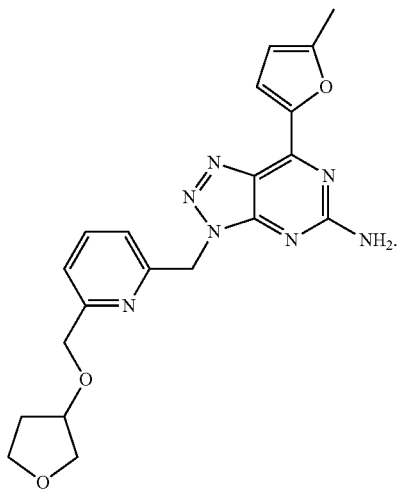 [SMILES: Cc1ccc(-c2nc(N)nc3c2nnn3Cc2cccc(COC3CCOC3)n2)o1]

In embodiments, the A2A receptor antagonist is a compound of formula:

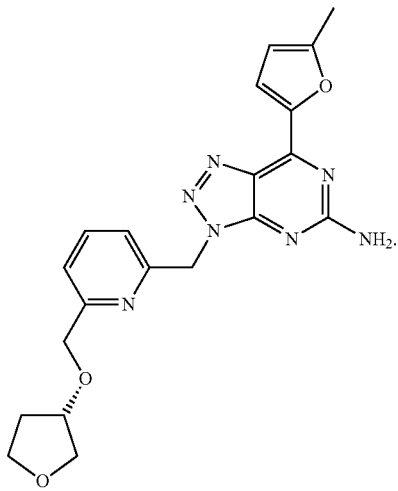

In embodiments, the A2A receptor antagonist is a compound of formula:

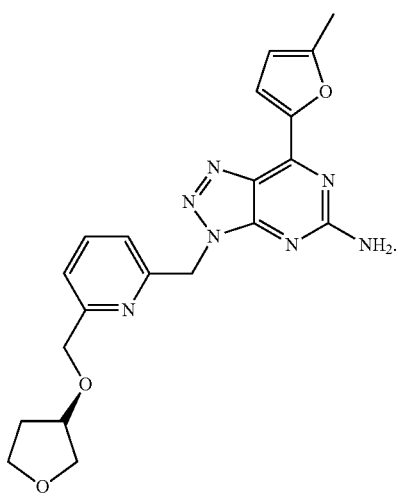

In embodiments, the method includes administering a therapeutically effective amount of a PD-1 signaling pathway inhibitor. In embodiments, the PD-1 signaling pathway inhibitor is a PD-L1 antagonist. In embodiments, the PD-L1 antagonist is a small molecule or an antibody.

In one aspect, a method of increasing global immune activation in a subject in need thereof is provided. The method includes administering to said subject a therapeutically effective amount of an adenosine-A2A (A2A) receptor antagonist, wherein the A2A receptor antagonist is a compound of formula:

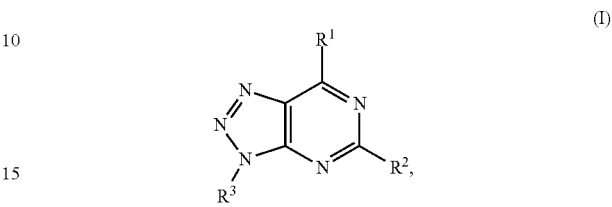

(I)

In formula (I), $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —N(O)$_{m1}$, —$NR^9R^{10}$, —NH—O—$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —N(O)$_{m2}$, —$NR^{11}R^{12}$, —NH—O—$R^{11}$, —C(O)$R^{11}$, —C(O)—$OR^{11}$, —C(O)$NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —N(O)$_{m3}$, —$NR^{13}R^{14}$, —NH—O—$R^{13}$, —C(O)$R^{13}$, —C(O)—$OR^{13}$, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)NHNH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently —F, —Cl, —Br, or —I. $n_1$, $n_2$ and $n_3$ are independently an integer from 0 to 4. $m_1$, $m_2$ and $m_3$ are independently an integer from 1 to 2. And $v_1$, $v_2$ and $v_3$ are independently an integer from 1 to 2.

In embodiments, the A2A receptor antagonist is a compound of formula:

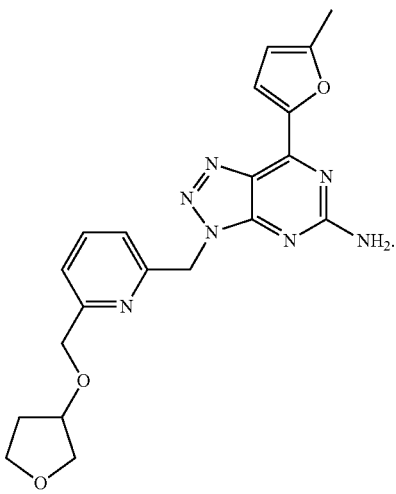

In embodiments, the A2A receptor antagonist is a compound of formula:

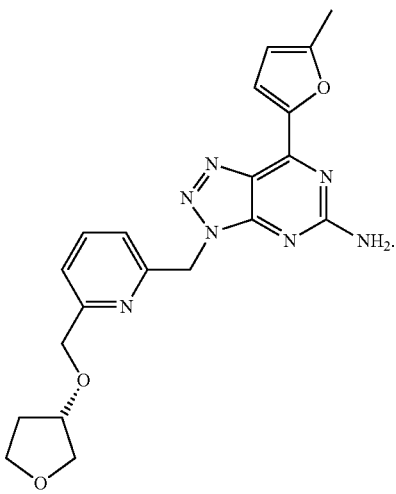

In embodiments, the A2A receptor antagonist is a compound of formula:

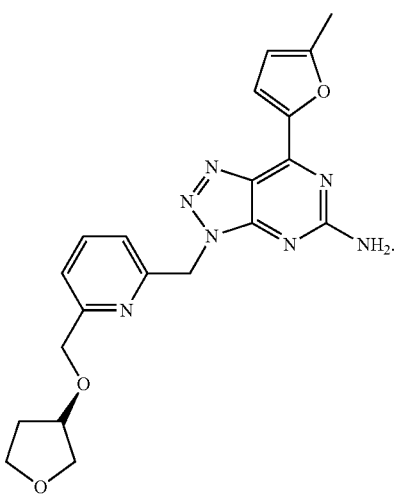

In embodiments, the method further includes administering a therapeutically effective amount of a PD-1 signaling pathway inhibitor. In embodiments, the PD-1 signaling pathway inhibitor is a PD-L1 antagonist. In embodiments, the PD-L1 antagonist is a small molecule or an antibody. In embodiments, the method includes activating a CD4 T cell in the subject. In embodiments, the CD4 T cell is a memory T cell. In embodiments, CD4 T cell is an effector T cell.

In embodiments, the relative amount of CD45RA-negative CD4 T cells in the subject is increased. In embodiments, the relative amount of CD4 T cells in the subject is increased. Where the relative amount of CD4 T cells in the subject is increased the amount of CD4 T cells in the subject can be 10%, 20%, 30%, 40%, 50%, 60%, 70%, 80%, 90% or more than that in a control. In certain instances, the increase is 1.5-fold, 2-fold, 3-fold, 4-fold, 5-fold, 10-fold, or more in comparison to a control. In embodiments, the relative amount of memory T cells in the subject is increased. Where the relative amount of memory T cells in the subject is increased the amount of memory T cells in the subject can be 10%, 20%, 30%, 40%, 50%, 60%, 70%, 80%, 90% or more than that in a control. In certain instances, the increase is 1.5-fold, 2-fold, 3-fold, 4-fold, 5-fold, 10-fold, or more in comparison to a control. In embodiments, the relative amount of effector T cells in the subject is increased. Where the relative amount of effector T cells in the subject is increased the amount of effector T cells in the subject can be 10%, 20%, 30%, 40%, 50%, 60%, 70%, 80%, 90% or more than that in a control. In certain instances, the increase is 1.5-fold, 2-fold, 3-fold, 4-fold, 5-fold, 10-fold, or more in comparison to a control. In embodiments, the method includes increasing the number of PD-1 positive cells in the subject. Where the number of PD-1 positive cells in the subject is increased the amount of PD-1 positive cells in the subject can be 10%, 20%, 30%, 40%, 50%, 60%, 70%, 80%, 90% or more than that in a control. In certain instances, the increase is 1.5-fold, 2-fold, 3-fold, 4-fold, 5-fold, 10-fold, or more in comparison to a control.

In embodiments, the method includes activating a CD8 T cell in the subject. In embodiments, the relative amount of CD8 T cells in the subject is increased. In embodiments, the relative frequency of TCR recombination is increased. Where the relative frequency of TCR recombination is increased the amounts of TCR recombination events can be 10%, 20%, 30%, 40%, 50%, 60%, 70%, 80%, 90% or more than that in a control. In certain instances, the increase is 1.5-fold, 2-fold, 3-fold, 4-fold, 5-fold, 10-fold, or more in comparison to a control. Where the frequency of TCR recombination is increased, the T cell receptor repertoire (the number of T cells recognizing antigens that are chemically different from each other) is increased. Thus, the methods provided herein may increase the diversity of T cell clones in the subject.

In embodiments, the subject is an anti-PD-1 refractory subject.

For the methods provided herein the A2A receptor antagonist may be administered at an amount of about 100 mg BID. In embodiments, the A2A receptor antagonist is administered for 28 consecutive days. In embodiments, the A2A receptor antagonist is administered for 14 consecutive days. In embodiments, the PD-1 signaling pathway inhibitor is administered at an amount of about 840 mg. In embodiments, the PD-1 signaling pathway inhibitor is administered for 28 consecutive days. In embodiments, the PD-1 signaling pathway inhibitor is administered for 14 consecutive days. In further embodiments, the A2A receptor antagonist and the PD-1 signaling pathway inhibitor are administered on the same day.

In embodiments, the A2A receptor antagonist is administered at a first time point and the PD-1 signaling pathway inhibitor is administered at a second time point, wherein the first time point precedes the second time point. In embodiments, the second time point is within less than about 120, 90, 60, 50, 40, 30, 28, 20, 19, 18, 17, 16, 15, 14, 13, 12, 11, 10, 9, 8, 7, 6, 5, 4, 3, 2 or 1 days from said first time point. In embodiments, the second time point is within less than about 120 days. In embodiments, the second time point is within less than about 90 days. In embodiments, the second time point is within less than about 60 days. In embodiments, the second time point is within less than about 50 days. In embodiments, the second time point is within less than about 40 days. In embodiments, the second time point is within less than about 30 days. In embodiments, the second time point is within less than about 28 days. In embodiments, the second time point is within less than about 20 days. In embodiments, the second time point is within less than about 19 days. In embodiments, the second time point is within less than about 18 days. In embodiments, the second time point is within less than about 17 days. In embodiments, the second time point is within less than about 16 days. In embodiments, the second time point is within less than about 15 days. In embodiments, the second time point is within less than about 14 days. In embodiments, the second time point is within less than about 13 days. In embodiments, the second time point is within less than about 12 days. In embodiments, the second time point is within less than about 11 days. In embodiments, the second time point is within less than about 10 days. In embodiments, the second time point is within less than about 9 days. In embodiments, the second time point is within less than about 8 days. In embodiments, the second time point is within less than about 7 days. In embodiments, the second time point is within less than about 6 days. In embodiments, the second time point is within less than about 5 days. In embodiments, the second time point is within less than about 4 days. In embodiments, the second time point is within less than about 3 days. In embodiments, the second time point is within less than about 2 days. In embodiments, the second time point is within less than about 2 days. In embodiments, the second time point is within less than about 1 day.

In embodiments, the second time point is within about 14 or 28 days from the first time point. In embodiments, the second time point is within about 14 days from the first time point. In embodiments, the second time point is within about 28 days from the first time point.

The methods provided herein including embodiments thereof may include activating a T cell in the subject. The methods provided herein including embodiments thereof may include activating a CD4 T cell in the subject. In embodiments, the CD4 T cell is a memory T cell. In embodiments, the CD4 T cell is an effector T cell. In embodiments, the CD4 T cell is a CD45RA-negative CD4 T cell. In embodiments, the relative amount of a CD4 T cell is increased in the subject. In embodiments, the relative amount of an effector T cell is increased in the subject. In embodiments, the relative amount of a CD45RA-negative CD4 T cell is increased in the subject.

The methods provided herein including embodiments thereof may include inhibiting A2A receptor activity of a cell in the subject. The methods provided herein including embodiments thereof may include increasing an anti-tumor immune response in a subject. The methods provided herein including embodiments thereof may include increasing the amount of CD8-positive cells relative to the amount of regulatory T cells in the subject. The methods provided herein including embodiments thereof may include enhancing anti-tumor immune memory in the subject. The methods provided herein including embodiments thereof may include enhancing anti-tumor immune memory in the subject. The methods provided herein including embodiments thereof may include increasing global immune activation in the subject.

Pharmaceutical Compositions

Provided herein are pharmaceutical compositions including an A2A receptor antagonist, a PD-1 signaling pathway inhibitor and a pharmaceutically acceptable excipient. The provided compositions are, inter alia, suitable for formulation and administration in vitro or in vivo. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

Compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient.

Pharmaceutical compositions provided by the present invention include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, the compounds and antibodies described herein will contain an amount of active ingredient effective to achieve the desired result, e.g., modulating the activity of a target molecule, and/or reducing, eliminating, or slowing the progression of disease symptoms. Determination of a therapeutically effective amount of a compound of the invention is well within the capabilities of those skilled in the art, especially in light of the detailed disclosure herein.

Provided compositions can include a single agent or more than one agent. The compositions for administration will commonly include an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any composition (e.g., the compounds and antibodies provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred "Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

In one aspect, a pharmaceutical composition including an A2A receptor antagonist, a PD-1 signaling pathway inhibitor and a pharmaceutically acceptable excipient is provided.

In embodiments, the A2A receptor antagonist is a compound of formula:

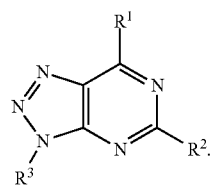

(I)

In formula (I), $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —N(O)$_{m1}$, —$NR^9R^{10}$, —NH—O—$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —N(O)$_{m2}$, —$NR^{11}R^{12}$, —NH—O—$R^{11}$, —C(O)$R^{11}$, —C(O)—$OR^{11}$, —C(O)$NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —N(O)$_{m3}$, —$NR^{13}R^{14}$, —NH—O—$R^{13}$, —C(O)$R^{13}$, —C(O)—$OR^{13}$, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently —F, —Cl, —Br, or —I. $n_1$, $n_2$ and $n_3$ are independently an integer from 0 to 4. $m_1$, $m_2$ and $m_3$ are independently an integer from 1 to 2. And $v_1$, $v_2$ and $v_3$ are independently an integer from 1 to 2.

The A2A receptor antagonist and the PD-1 signaling pathway inhibitor provided herein are the same as described above for aspects of treating cancer using an A2A receptor antagonist and a PD-1 signaling pathway inhibitor. Therefore, the definitions for substituents and variables of formula (I) and (II) are the same as described above (e.g., $R^1$ is $R^{1A}$-substituted furanyl; $R^{1A}$ is methyl; $R^2$ is —$NR^{11}R^{12}$; $R^{11}$ and $R^{12}$ are independently hydrogen; $R^3$ is $R^4$-substituted $C_1$ alkyl; $R^4$ is $R^5$-substituted pyridinyl; $R^5$ is $R^6$-substituted 2 membered heteroalkyl; $R^6$ is unsubstituted tetrahydrofuranyl) and are incorporated herewith.

In embodiments, the A2A receptor antagonist is a compound of formula:

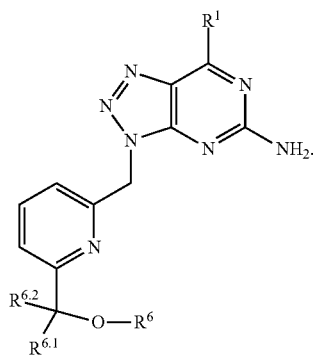

(II)

In formula (II), $R^6$, $R^{6.1}$ and $R^{6.2}$ are independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the A2A receptor antagonist is a compound of formula:

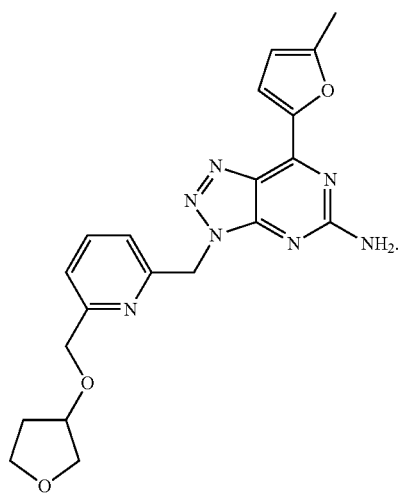 [SMILES: Cc1ccc(-c2nc(N)nc3c2nnn3Cc2cccc(COC3CCOC3)n2)o1]

In embodiments, the A2A receptor antagonist is a compound of formula:

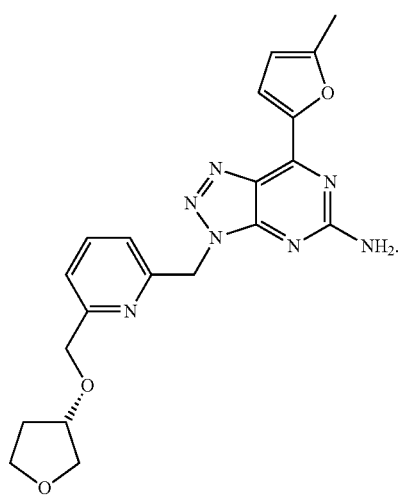

In embodiments, the A2A receptor antagonist is a compound of formula:

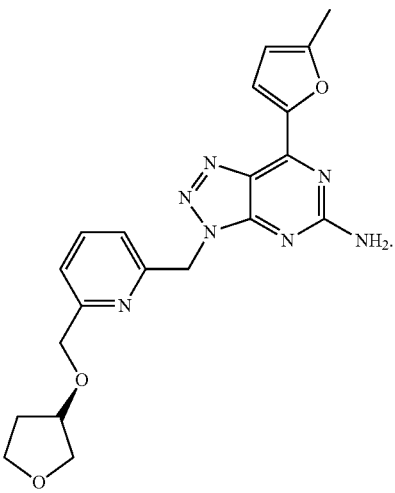

In embodiments, the PD-1 signaling pathway inhibitor is a programmed death-ligand 1 (PD-L1) antagonist or a PD-1 antagonist. In embodiments, the programmed death-ligand 1 (PD-L1) antagonist is an antibody or a small molecule. In embodiments, the PD-L1 antagonist is an antibody. In embodiments, the antibody is atezolizumab. In embodiments, the PD-1 antagonist is an antibody or a small molecule. In embodiments, the A2A receptor antagonist and the PD-1 signaling pathway inhibitor are present in a combined synergistic amount, wherein the combined synergistic amount is effective to treat cancer in a subject in need thereof.

In embodiments, the pharmaceutical composition is in oral dosage form. In embodiments, the adenosine-A2A (A2A) receptor antagonist (e.g, CPI-444) is presented as size 0-elongated hydroxypropyl methylcellulose (HPMC) capsules containing adenosine-A2A (A2A) receptor antagonist compound (e.g, CPI-444) at 10 mg, 25 mg or 100 mg, as a dry powder mixture of adenosine-A2A (A2A) receptor antagonist compound (e.g, CPI-444) resinate with common excipients and packaged in high density polyethylene (HDPE) bottles fitted with a polypropylene tamper evident child-resistant cap with an integrated desiccant. The adenosine-A2A (A2A) receptor antagonist (e.g, CPI-444) resinate is a complex of the adenosine-A2A (A2A) receptor antagonist and a cation exchange resin (Amberlite IRP69™). The ingredients are listed in Table A.

TABLE A

| CPI-444 Capsules Table of Ingredients | |
|---|---|
| Ingredient | Function |
| CPI-444 (adenosine-A2A (A2A) receptor antagonist) | Active ingredient |
| Sodium polystyrene sulfonate (Amberlite IRP69) resin | Ion-exchange resin, release modifying agent |
| Mannitol, spray-dried | Diluent |
| Croscarmellose sodium | Disintegrant |
| Colloidal silicon dioxide | Glidant |
| Sodium stearylfumarate | Lubricant |
| Size 0-elongated HPMC capsule | Capsule shell: 10 mg - opaque, Swedish orange 25 mg - opaque white 100 mg - opaque, Swedish orange |

Detecting Adenosine Receptor Activation

Cyclic AMP (cAMP) response element binding protein (CREB) is a cellular transcription factor. CREB is activated by signaling cascades resultant from an array of extracellular signals. One such activating signal cascade is triggered by agonist binding to adenosine receptor (e.g. A2A and A2B receptors). Agonist activation of adenosine receptor results in activation of CREB by phosphorylation. Agonist activation of adenosine receptor also results in activation of protein kinase A (PKA) upstream of CREB.

Figure 24:
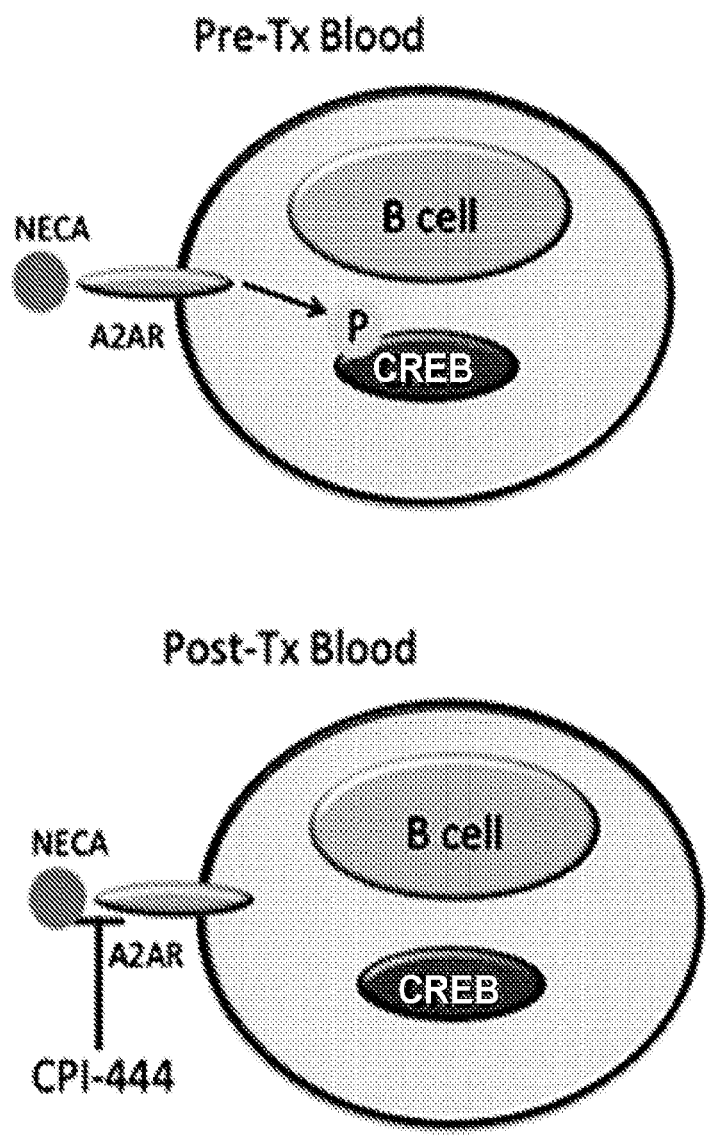
FIG. 24: A schematic showing the role of CPI-444 in CREB phosphorylation.

Cancer therapies described above which include adenosine receptor antagonists, alone or in combination, alter signaling cascades that result in CREB activation (see FIG. 24). Detection of downstream effects of treatment with adenosine receptor antagonists can be assayed to determine cellular response to treatment. Activation of CREB activation can be detected by detection of phosphorylated CREB.

In embodiments, pCREB is detected by a pCREB detection agent. In embodiments, pCREB is detected by an antibody (e.g. a commercially available antibody). In embodiments, a pCREB detection agent is detected by Fluorescence-activated cell sorting (FACS). In embodiments, pCREB is detected in a subpopulation of cells (e.g. T cells and/or B cells). In embodiments, pCREB is detected using an antibody in an ELISA format. In embodiments, ELISA detection can be from bulk cell lysate or sorted B cells and/or T cells.

In embodiments, cells for detection of pCREB can be harvested from blood (e.g. from circulating blood). In embodiments, cells for detection of pCREB can be harvested from a tumor site. In embodiments, cells for the detection of pCREB are isolated, stained and fixed. In embodiments, cell staining is with antibodies against pCREB, CD3, CD4, CD8, CD27, CD20, CD45RA, cPARP. In embodiments, cells for the detection of pCREB are sorted by FACs. In embodiments, FACS detection of an antibody against CD19 and an antibody against CD20 indicate a B cell. In embodiment, FACS detection of antibodies against CD3, CD4 and CD8 indicates a T cell. In embodiments, FACS detection of antibodies against cPARP indicates an apoptotic cell. In embodiments, detection of pCREB induction is from an isolated cell population (e.g. B cells or T cells).

In embodiments, detection of activated PKA is used in addition to, or as a proxy for, detection of pCREB.

CREB activation can be induced by activation of adenosine receptor agonists including adenosine, NECA, or analogs thereof. NECA is a synthetic adenosine analog. In embodiments, NECA is administered to cells in a concentration of about 0.1 µM, 0.2 µM, 0.3 µM, 0.4 µM, 0.5 µM, 1.0 µM, 2 µM, 3 µM, 4 µM, 5 µM, 6 µM, 10 µM, 15 µM, 20 µM, 30 µM or more to activate adenosine receptors.

In embodiments, inhibition of pCREB induction by an adenosine receptor agonist can be used as an in vitro screening or evaluation assay to identify and characterize adenosine receptor antagonists.

Patient Selection and Dosage Adjustment

In patients treated with adenosine receptor antagonists, alone or in combination, effects on downstream effectors (e.g. CREB) can be used to determine treatment or dosage efficacy of the adenosine receptor antagonist therapy. Furthermore, assessment of CREB activation can be used to determine the diurnal timing of therapy administration.

An individual patient reaction to treatment with an adenosine receptor antagonist (e.g. an A2A receptor or A2B receptor antagonist) can be detected by measuring of cellular effects. In embodiments, cellular effects of treatment can be monitored in a patient sample (e.g. a blood or tumor sample). In embodiments, a blood sample is used to assay CREB activation. As described above adenosine receptor agonists result in CREB activation, conversely adenosine receptor antagonists can inhibit the activation of CREB. In embodiments, monitoring inhibition of activation of CREB via the adenosine receptor pathway can indicate efficacy of an adenosine receptor antagonist.

In embodiments, cells are isolated from a patient sample (e.g. a blood or tumor sample). In embodiments, CREB activation following treatment with an adenosine receptor agonist (e.g. NECA) is monitored prior to treatment with an adenosine receptor antagonist (e.g. detection of induction of pCREB prior to treatment with CPI-444). In embodiments, pCREB induction by an adenosine receptor agonist is assayed relative to a control sample (e.g. cells treated with PMA). In embodiments, an additional sample is collected following treatment with an adenosine receptor antagonist, alone or in combination (e.g. CPI-444, or CPI-444 combination therapy with azetolizumab). In embodiments, a sample is collected after about 7 days, 8 days, 9 days, 10 days, 11 days, 12 days, 13 days, 2 weeks, 3 weeks, 4 weeks, 8 weeks, 12 weeks or more following treatment with an adenosine receptor antagonist. A comparison can be made between pCREB induction by an adenosine receptor agonist prior to and following treatment with an adenosine receptor antagonist to determine the degree to which treatment has reduced downstream effects of adenosine receptor activation (e.g. pCREB induction).

In embodiments, subjects who display attenuated induction of pCREB by an adenosine receptor agonist following treatment with an adenosine receptor antagonist are selected as responsive to treatment with adenosine receptor antagonists. In embodiments, where attenuation or inhibition of pCREB induction by NECA by an adenosine receptor antagonist is incomplete a dosage of the adenosine receptor antagonist can be increased. In embodiments, a patient sample is taken prior to adenosine pathway blockade (e.g. with an adenosine receptor antagonist) and treated with an adenosine receptor agonist to determine the level of induced pCREB signaling which may guide patient selection for treatment by adenosine pathway blockade (e.g. with an adenosine receptor antagonist).

Furthermore, diurnal variations in concentration of an adenosine receptor antagonist in the circulation result from one or twice daily administration. This variation in concentration throughout the course of the day can impact treatment efficacy. Using methods and compositions of the present invention variations of the efficacy of treatment can be monitored by detecting pCREB induction by an adenosine receptor agonist at different time points following administration of an adenosine receptor antagonist. In embodiments, pCREB induction by an adenosine receptor agonist can be monitored at about 0 hours, 0.5 hours, 1 hours, 2 hours 3 hours, 4 hours, 5 hours, 8 hours, 9 hours, 10 hours, 12 hours, 14 hours, 16 hours, 20 hours, or 24 hours following administration of an adenosine receptor antagonist. In embodiments, timing of administration of an adenosine receptor antagonist can be altered for maximal inhibition of pCREB induction by an adenosine receptor agonist.

EXAMPLES

Example 1

Binding Affinity for Human Adenosine Receptors (V81444-07-076)

The ability of CPI-444 to displace radioligand binding for the four identified adenosine receptor subtypes (A1, A2A, A2B, and A3) was tested in human recombinant receptors expressed in mammalian cell lines. Results are shown in Table 1.

TABLE 1

Displacement of radioligand binding by CPI-444

| Receptor | pKi Mean | Ki nM | Selectivity against $A_{2A}$ |
|---|---|---|---|
| Adenosine $A_1$ | 6.72 | 192 | ×54 |
| Adenosine $A_{2A}$ | 8.45 | 3.54 | |
| Adenosine $A_{2B}$ | 5.82 | 1,528 | ×431 |
| Adenosine $A_3$ | 5.61 | 2,455 | ×693 |

CPI-444 bound A2A receptors with an affinity (Ki) value of 3.54 nM (the negative logarithm of Ki [pKi]=8.45). CPI-444 showed greater than 50 fold selectivity for the A2A receptor over other adenosine receptor subtypes.

Functional Activity on Human Adenosine Receptors (V81444-07-078)

CPI-444 was evaluated in experimental paradigms designed to quantify antagonist interactions with the four identified human adenosine receptor subtypes expressed in Chinese hamster ovary (CHO-K1) cells. At all concentrations tested, CPI-444 caused a right-shift in the agonist concentration-response curve without decreasing the maximum agonist response, indicating a competitive mode of action. Antagonist pA2 (negative logarithm of the antagonist concentration causing a 2-fold shift in the agonist concentration response curve [equivalent to 50% occupancy]) values were estimated from the extent of this rightshift and showed V81444 to be a potent A2A receptor antagonist with a pA2 value of 8.49 (3.2 nM) at the A2A receptor (Table 2).

TABLE 2

CPI-444 adenosine receptor antagonist activity.

| Receptor | $pA_2$ mean | $pA_2$ expressed as chemical concentration nM | Selectivity against $A_{2A}$ |
|---|---|---|---|
| Adenosine $A_1$ | 6.53 | 295 | ×92 |
| Adenosine $A_{2A}$ | 8.49 | 3.2 | |
| Adenosine $A_{2B}$ | 6.36 | 436 | ×136 |
| Adenosine $A_3$ | 5.65 | 2,240 | ×700 |

CPI-444 was more than 90-fold selective for the A2A receptor relative to the other adenosine receptors.

Effect of CPI-444 on cAMP Production (CPI-RSR-003)
Adenosine signaling through A2AR leads to increases in the levels of cAMP. This study evaluated the ability of CPI-444 to prevent cAMP production in primary human T cells stimulated with NECA, a stable analog of adenosine (CPI-RSR-003).

Figure 6:
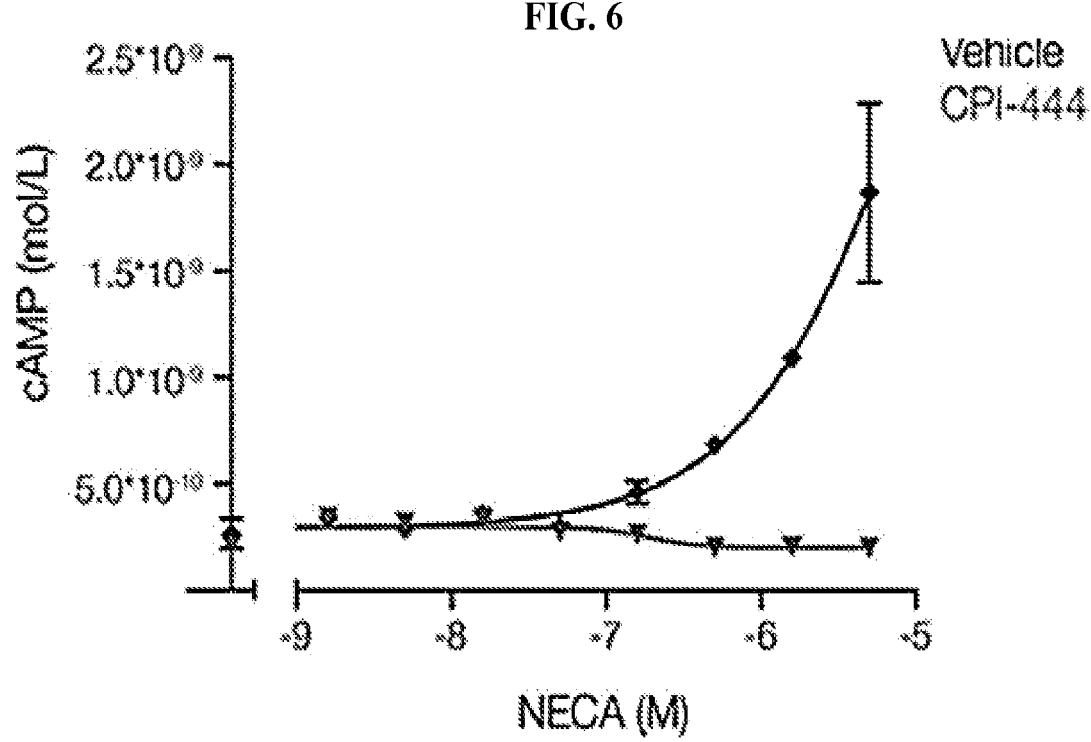
FIG. 6: CPI-444 Inhibits cAMP Production in T cells
Figure 6:
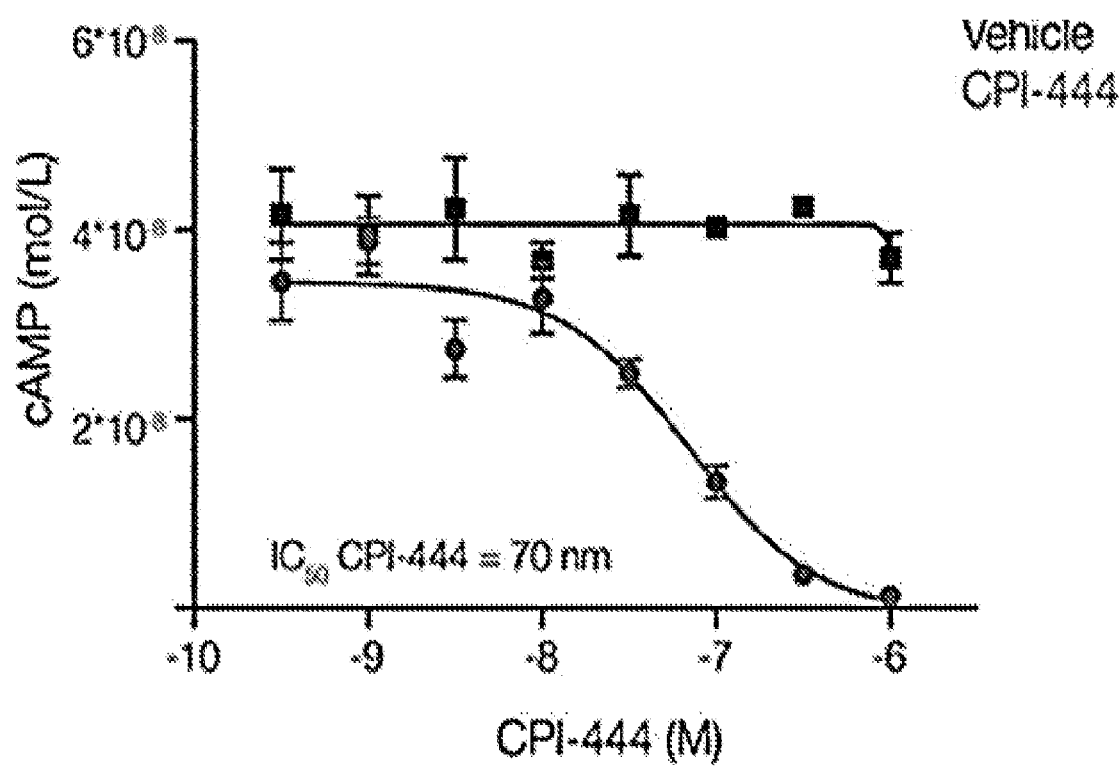

T cells were isolated from human PBMC by negative selection and activated via CD3/CD28 stimulation for 48 hours to induce A2AR expression. Stimulated T cells were then "rested" for 24 hours by removal of CD3/CD28 stimulation in order to minimize background levels of cAMP. Rested T cells were incubated in the presence of NECA and CPI-444 or vehicle control for 10 minutes prior to measurement of cAMP using the LANCE Ultra cAMP FRET-based assay (Perkin Elmer). CPI-444 completely blocked the production of cAMP upon NECA treatment at all levels of NECA tested (10-5 to 10-9 M). CPI-444 also prevented cAMP production upon NECA stimulation in a dose-dependent manner (FIG. 6). These results confirm that CPI-444 is an A2AR antagonist capable of inhibiting cAMP induced by adenosine signaling.

Effect of CPI-444 on IL-2 and IFNγ Secretion (CPI-RSR-002)

Figure 7:
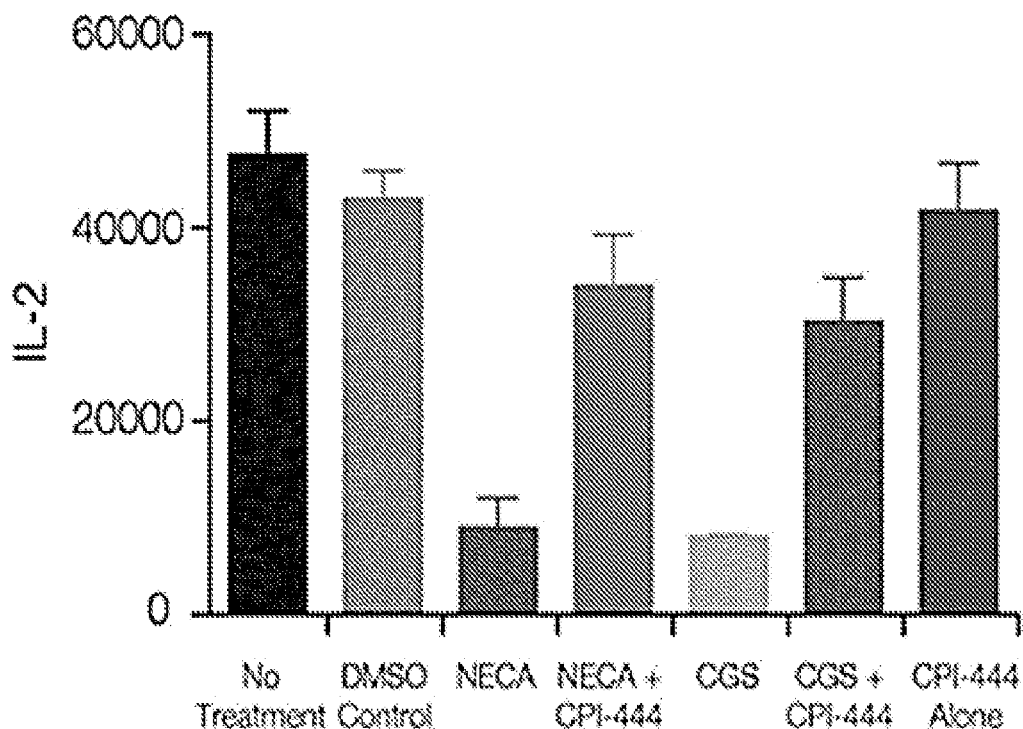
FIG. 7: CPI-444 Restores IL-2 and IFNγ From Activated T Cells. Primary human PBMCs were cultured for 1 hour in the presence of an A2Ar agonist (NECA or CGS21680, 1 μm) to stimulate the effects of adenosine on immune cell function. Purified anti-CD3 and anti-CD28 monoclonal antibodies (1 ug/ml) were then added to activate T cells for 48 hours. NECA and CGS21680 suppressed release of the Th1 cytokines IL-1 and IFNγ, mimicking the immunosuppressive effects of adenosine signaling. Blockade of A2AR with CPI-444 (1 μM) neutralized the immunosuppressive effects of NECA and CGS21680 and restored IL-2 and IFNγ secretion back to levels observed in the absence of exogenous adenosine signaling (DMSO control).
Figure 7:
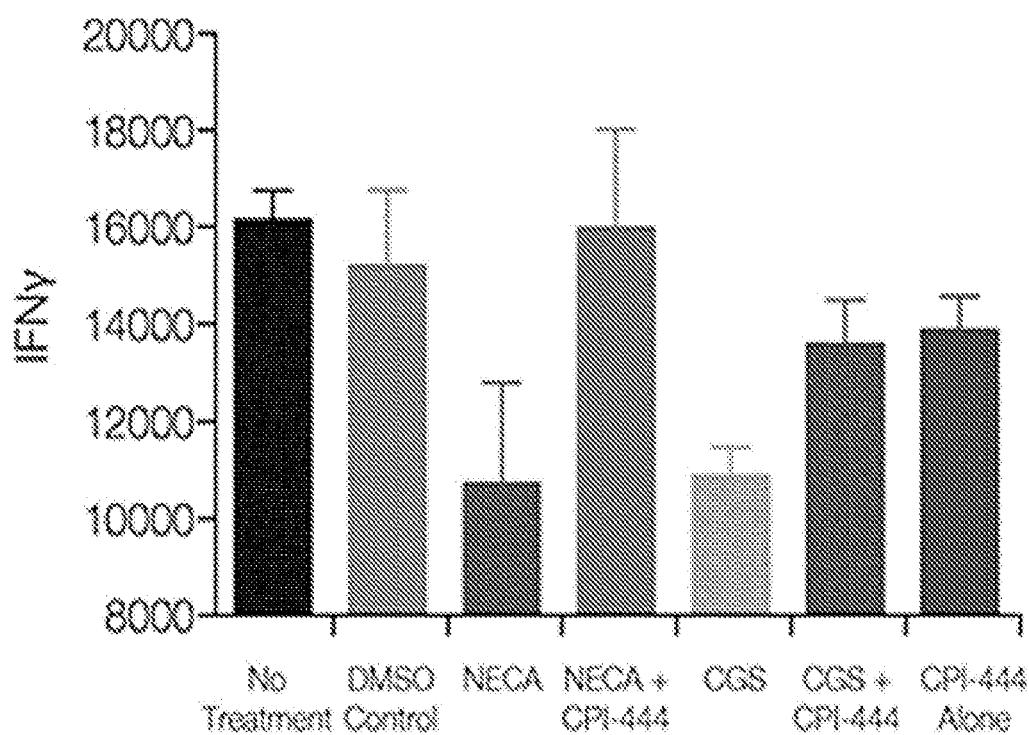

The objective of this study was to determine if CPI-444 abrogates the immunosuppressive effects of adenosine on T cell activation and Th1 cytokine release in vitro (CPI-RSR-002). Primary human PBMCs were cultured for 1 hour in the presence of an A2AR agonist (NECA or CGS21680, 1 µM) to simulate the effects of adenosine on immune cell function. Purified anti-CD3 and anti-CD28 monoclonal antibodies (1 ug/ml) were then added to activate T cells for 48 hours. In this study, AlphaLISA assays (PerkinElmer) analyzed on an EnVision MultiLabel Reader were used to measure cytokine release according to the manufacturer's instructions. NECA and CGS21680 suppressed release of the Th1 cytokines IL-2 and IFNγ, mimicking the immunosuppressive effects of adenosine signaling (FIG. 7).

Blockade of A2AR with CPI-444 (1 µM) prior to T cell activation neutralized the immunosuppressive effects of NECA and CGS21680 and restored IL-2 and IFNγ secretion back to levels observed in the absence of exogenous adenosine signaling (DMSO control). These results show that restoration of T cell function is an important mechanism by which CPI-444 enables an anti-tumor response in vivo.

CPI-444 does not Inhibit Tumor Cell Proliferation In Vitro (CPI444-RSR-006)

Figure 8:
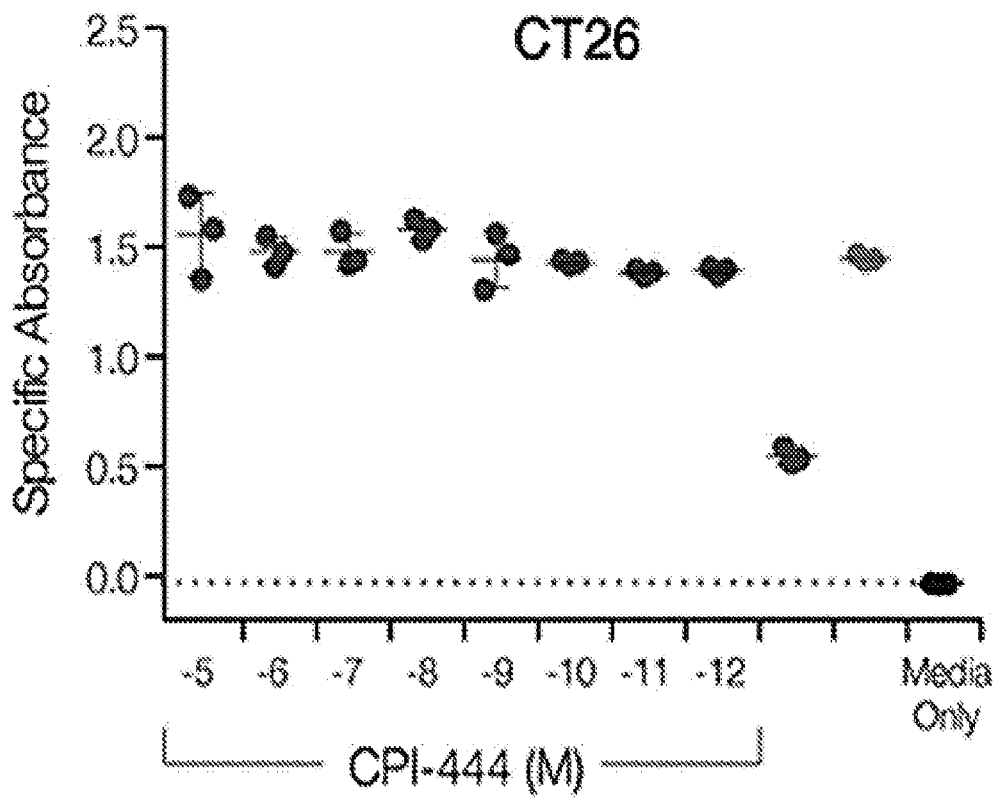
FIG. 8: CPI-444 Does Not Affect Tumor Cell Proliferation In Vitro
Figure 8:
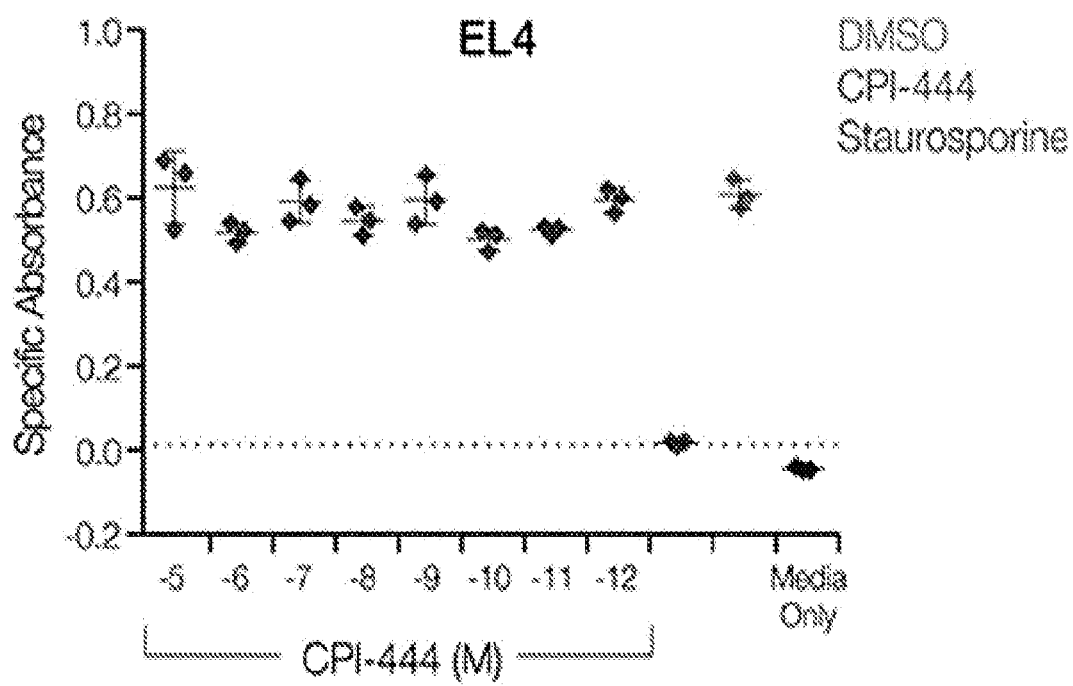

CPI-444 inhibits the growth of MC38, CT26, and EL4 tumors at either primary (MC38, CT26) or metastatic (EL4) sites in syngeneic mouse tumor models. This study evaluated the effects of CPI-444 on mouse tumor cell proliferation and viability. MC38, CT26, and EL4 cells were cultured in the presence of CPI-444 at a concentrations ranging from 10 □M to 1 pM for 24 hours. Staurosporine, a well-characterized inducer of apoptosis, was included as a positive control for cell death. Cell viability/proliferation was measured by XTT. In this assay, XTT salts are cleaved by metabolically active (viable) cells, thereby producing a colorimetric change in the culture media that can be quantified by measuring absorbance at 405 nm and 620 nm on a spectrophotometer. No significant decrease in the Specific Absorbance (A450Test—A450Blank—A620Test) was observed in MC38, CT26, or EL4 cultures at any concentration of CPI-444 tested (representative results, FIG. 8). These results indicate that CPI-444 efficacy observed in vivo is likely not due to a direct effect on tumor cell proliferation.

Effect of CPI-444 on pERK Levels in Human CD4+ Cells (CPI-RSR-008)

Figure 9:
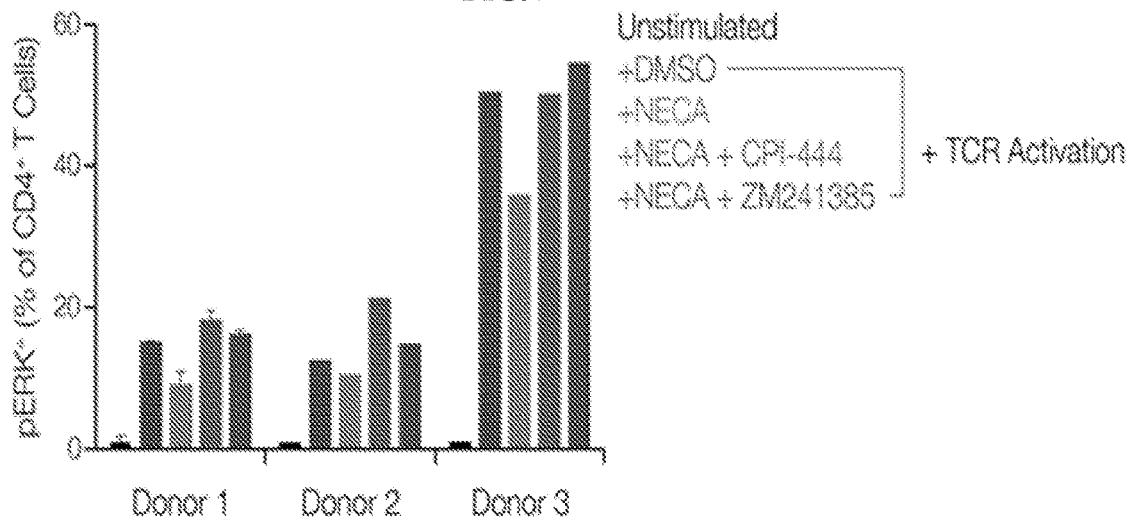
FIG. 9: CPI-444 Restores pERK In CD4$^+$ T Cells

This study shows that stimulation of A2AR with an adenosine analog (NECA) dampens ERK activation in human PBMCs following TCR cross-linking (CPI-RSR-008). Both CPI-444 and the A2AR specific antagonist ZM 241385 restore ERK signaling in the presence of NECA. The percentage of CD4+ T cells showing TCR-mediated ERK phosphorylation was reduced in the presence of NECA (1 µM). Addition of CPI-444 restored pERK levels in a dose-dependent manner (FIG. 9). This finding supports a role for CPI-444 in restoring T cell activation in the presence of otherwise immunosuppressive levels of adenosine.

Effect of CPI-444 on Phosphorylation of cAMP Response Element Binding Protein (pCREB; CPI-RSR-007)

Figure 10:
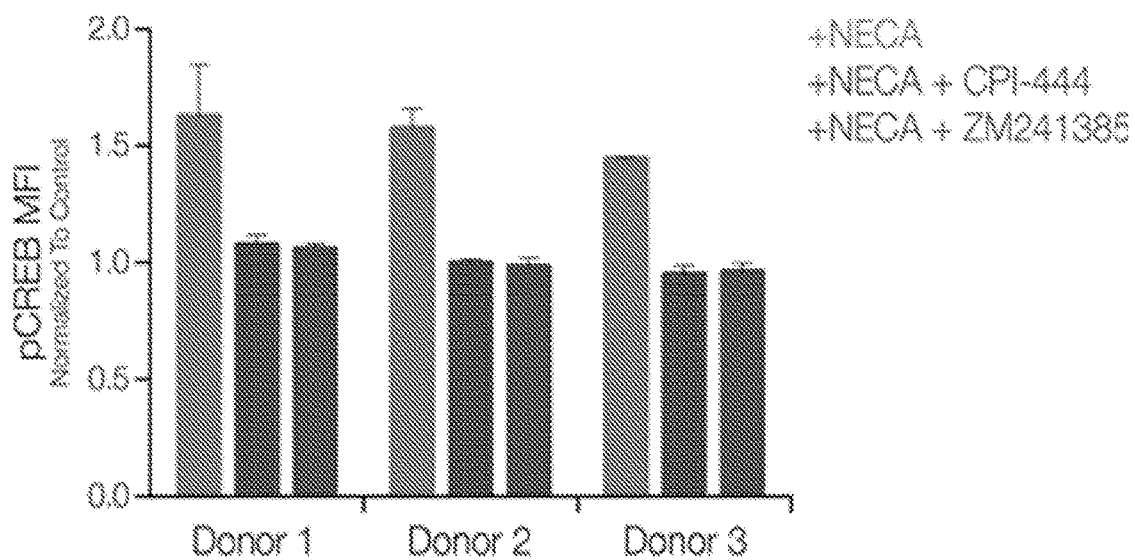
FIG. 10: CPI-444 Prevents pCREB Induction in B Cells

Adenosine signaling via A2AR leads to an increase in intracellular cAMP and subsequent phosphorylation of CREB. This study demonstrates that the adenosine analog NECA activates phospho-CREB in fresh PBMCs, primarily in the B cell population (CPI-RSR-007). Furthermore, this phosphorylation event is completely inhibited by CPI-444, as well as by the known A2AR antagonist ZM 241385 (FIG. 10). This finding demonstrates that CPI-444 inhibits NECA-mediated cell signaling through A2AR and provides a functional assay for CPI-444 activity.

In Vivo Studies

Oral administration of CPI-444 at 100 mg/kg or 10 mg/kg significantly inhibits the growth of MC38 colon tumors compared to the vehicle control in syngeneic hosts.

Oral administration of CPI-444 at 10, 30 or 100 mg/kg produced a therapeutic response on established primary tumors in the EL4 syngeneic mouse lymphoma model. A significant dose-dependent inhibition of tumor growth within regional lymph nodes was observed in mice treated with CPI-444.

CPI-444 (100 mg/kg) or anti-PD-1 antibody monotherapy inhibits the growth of CT26 colon tumors in syngeneic hosts. CPI-444+anti-PD-1 combination therapy eliminated CT26 tumors in nearly all mice. Combination therapy also produced a significant increase in long-term survival compared to either agent administered alone.

Syngeneic EL4 Mouse Lymphoma Model (CPI-RSR-001)

This study evaluated the anti-tumor effect of CPI-444 on tumor growth and metastasis in a transplanted CD4+ mouse T cell lymphoma model (CPI-RSR-001). Syngeneic C57BL/6 female mice (8-10 weeks old) were injected (via subcutaneous route) with EL4 cells. Tumor-bearing mice were administered control vehicle (40% Hydroxypropyl Beta-Cyclodextrin) or CPI-444 solution daily by oral gavage upon formation of measurable tumors (140±55 mm3). CPI-444 doses of 10, 30, and 100 mg/kg were evaluated. CPI-444 treatment produced a minimal therapeutic response on established primary tumors. A dose response was observed, yet all dose levels failed to produce a significant inhibition of tumor growth. In contrast, a significant, dose-dependent decrease in the number and size of enlarged regional lymph nodes was observed (FIG. 11), indicating that CPI-444 inhibited or eliminated tumor metastases in this model.

Syngeneic MC38 Mouse Colon Carcinoma Model (CPI-RSR-004)

Figure 12:
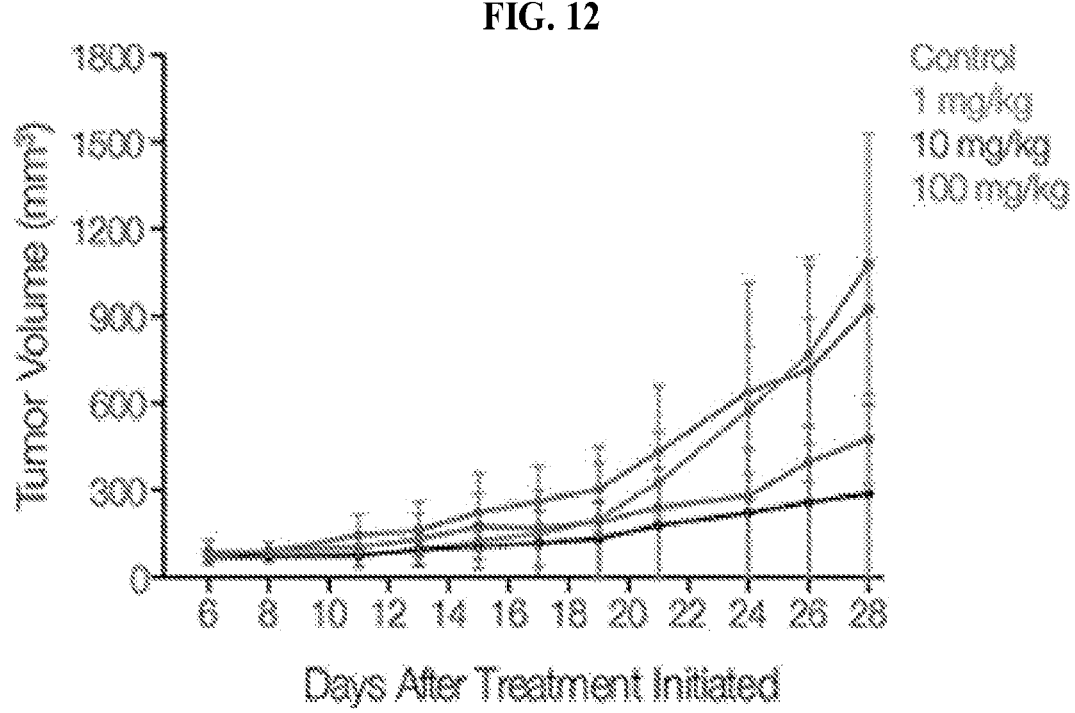
FIG. 12: CPI-444 Inhibits Growth of MC38 Tumors
Figure 12:
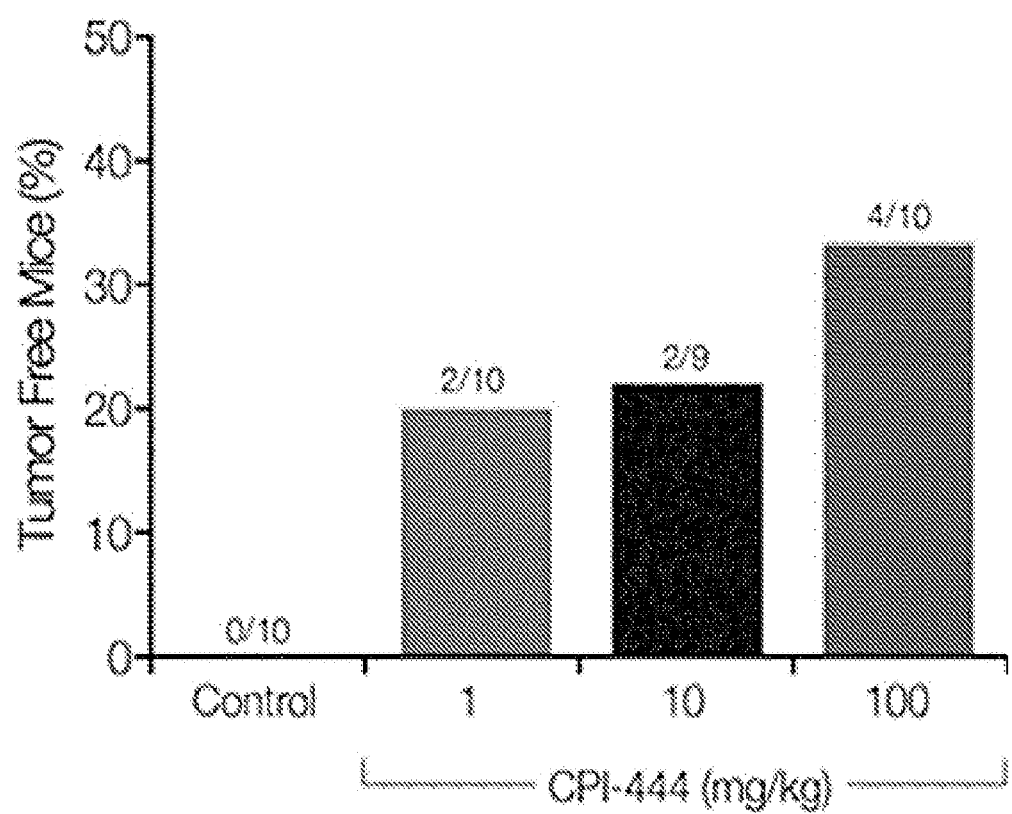

The objective of this study was to evaluate the anti-tumor activity of CPI-444 in a mouse colon carcinoma model (CPI-RSR-004). MC38 colon cancer cells were subcutaneously injected onto the backs of syngeneic C57BL/6 mice. One day after tumor cell engraftment, vehicle control (40% Hydroxypropyl Beta-Cyclodextrin) or CPI-444 was administered daily via oral gavage for 28 days. Administration of CPI-444 at 1 mg/kg did not inhibit tumor growth, however doses of 10 mg/kg and 100 mg/kg resulted in a significant inhibition of tumor growth (FIG. 12). Notably, complete tumor regression was observed in a subset of mice within all cohorts treated with CPI-444 (FIG. 12). It is possible that full tumor eradication could be achieved in additional mice with longer administration of CPI-444. These results demonstrate that MC38 is responsive to CPI-444 treatment.

Syngeneic CT26 Mouse Colon Cancer Model with CPI-444 in Combination with anti-PD1 (CPI-RSR-005)

Figure 13:
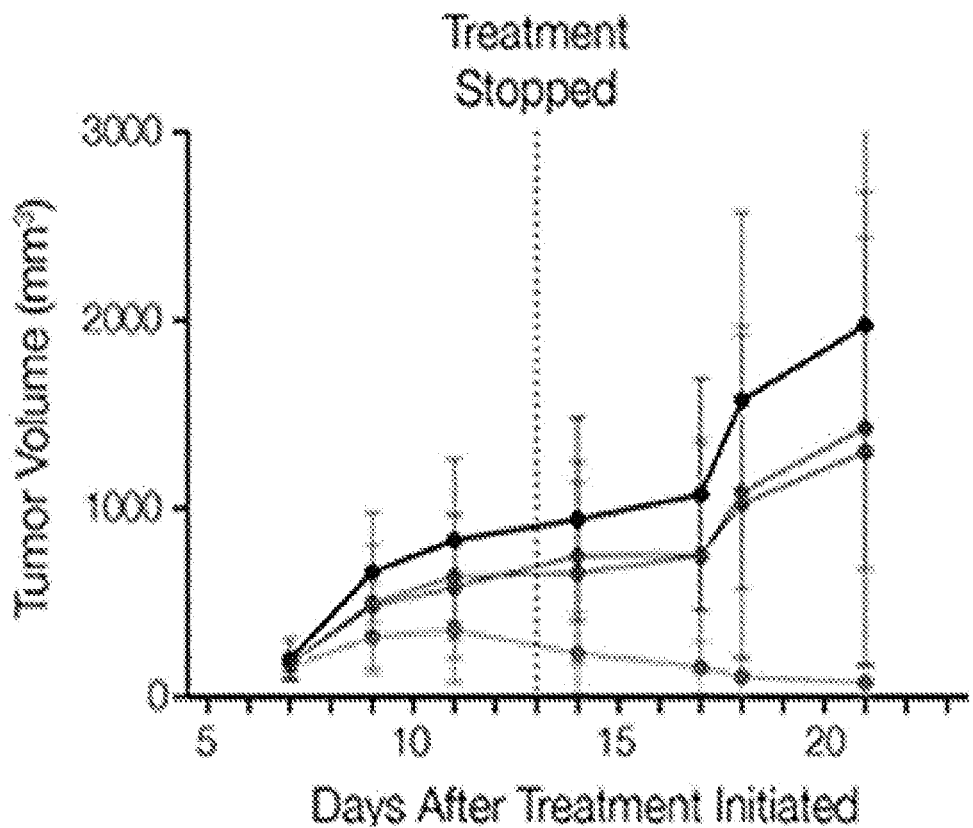
FIG. 13: CT26 Model: Combo extends long-term survival in 80% mice. Oral administration of control vehicle (40% solution of hydroxypropyl-beta-cyclodextrin) or CPI-444 (100 mg/kg) was initiated the same day tumors were engrafted (Day 0). Treatment continued for 12 days. Half of the mice in the vehicle control group as well as half the mice in the CPI-444 treatment group received anti-PD-1 mAb (RMP1-14, 100 ug/mouse, i.p.) on days 7, 9, 11, and 13. Administration of anti-PD-1 or CPI-444 resulted in an inhibition of tumor growth, however, tumors were not completely eradicated by either treatment. Administration of CPI-444 in combination with anti-PD-1 stabilized or eliminated tumors in 8/9 mice, resulting in improved overall survival for more than 3 weeks following the last dose of CPI-44 or anti PD-1 antibody.
Figure 13:
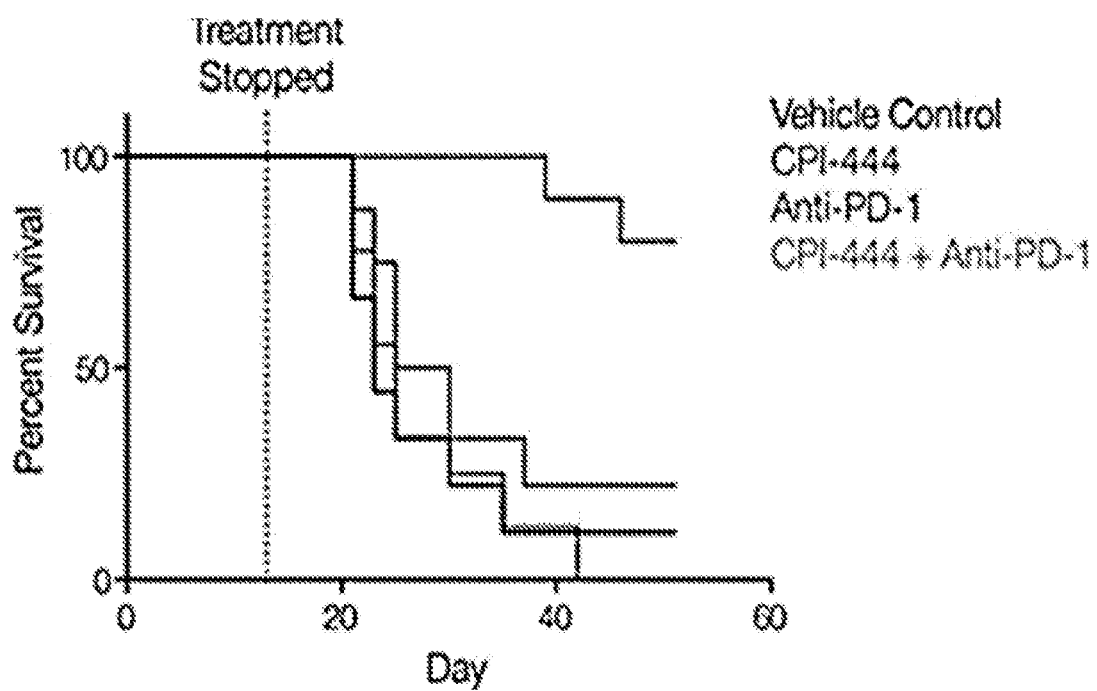
Figure 14A:
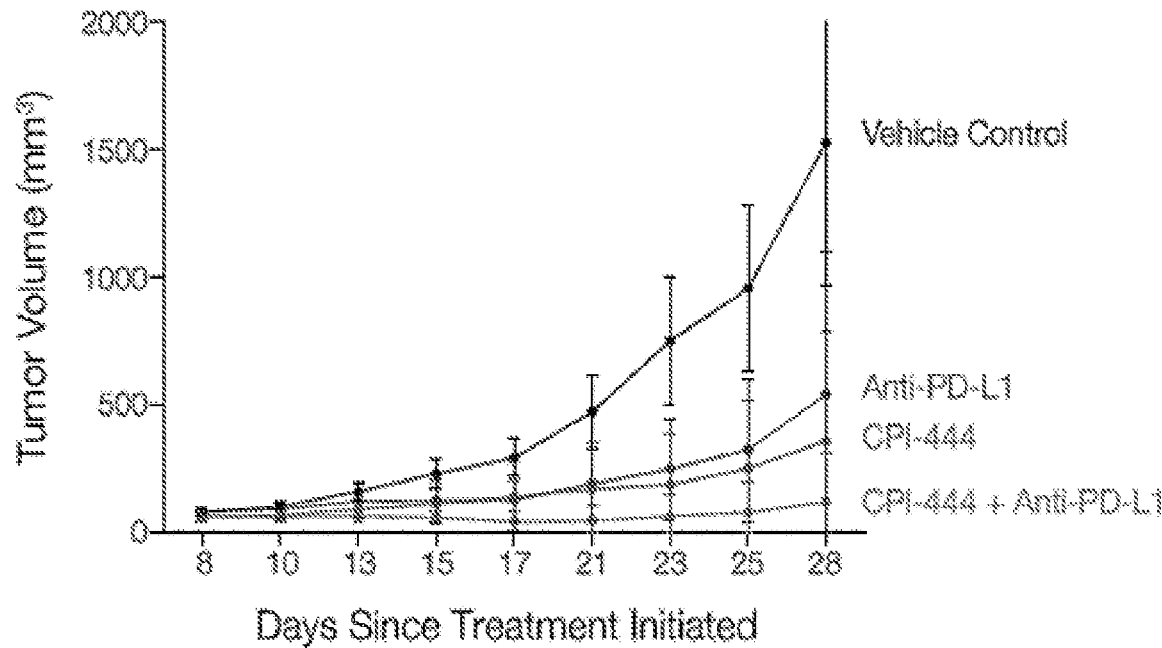
FIGS. 14A and 14B: MC38 Model: CPI-444 eliminates tumors in 30% of mice. Combo eliminates tumors in 50% of mice. MC 38 mouse colon cancer cells were engrafted onto the back of syngeneic C57Bl/6 mice. Oral administration of control vehicle or CPI-444 (100 mg/kg) was initiated the same day tumors were engrafted (Day 0). Treatment continued for 12 days. Half of the mice in the vehicle control group as well as half the mice in the CPI-444 treatment group received anti-PD-L1 mAb (10F.9G2, 200 ug/mouse, i.p.) on days 7, 10, 13, and 16. Administration of anti-PD-L1 or CPI-444 resulted in an inhibition of tumor growth, however, tumors were not completely eradicated by either treatment. In contrast, administration of CPI-444 in combination with anti-PD-L1 stabilized or eliminated tumors in 5/10 mice.
Figure 14B:
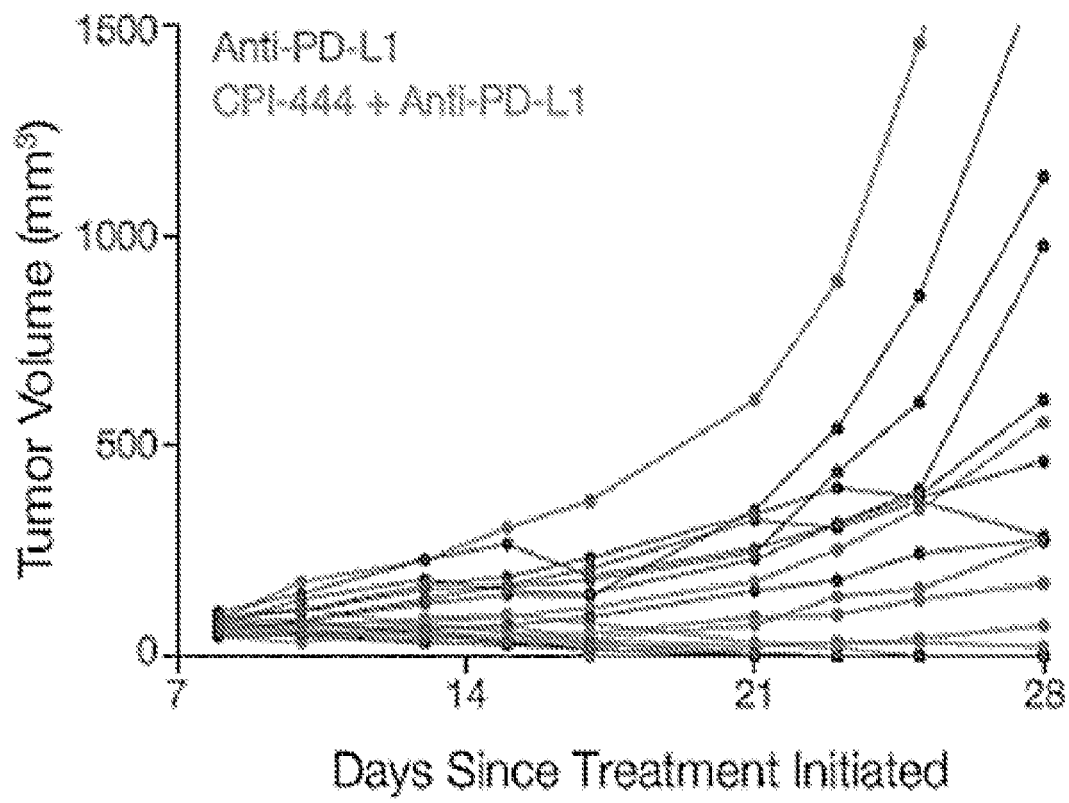
Figure 15A:
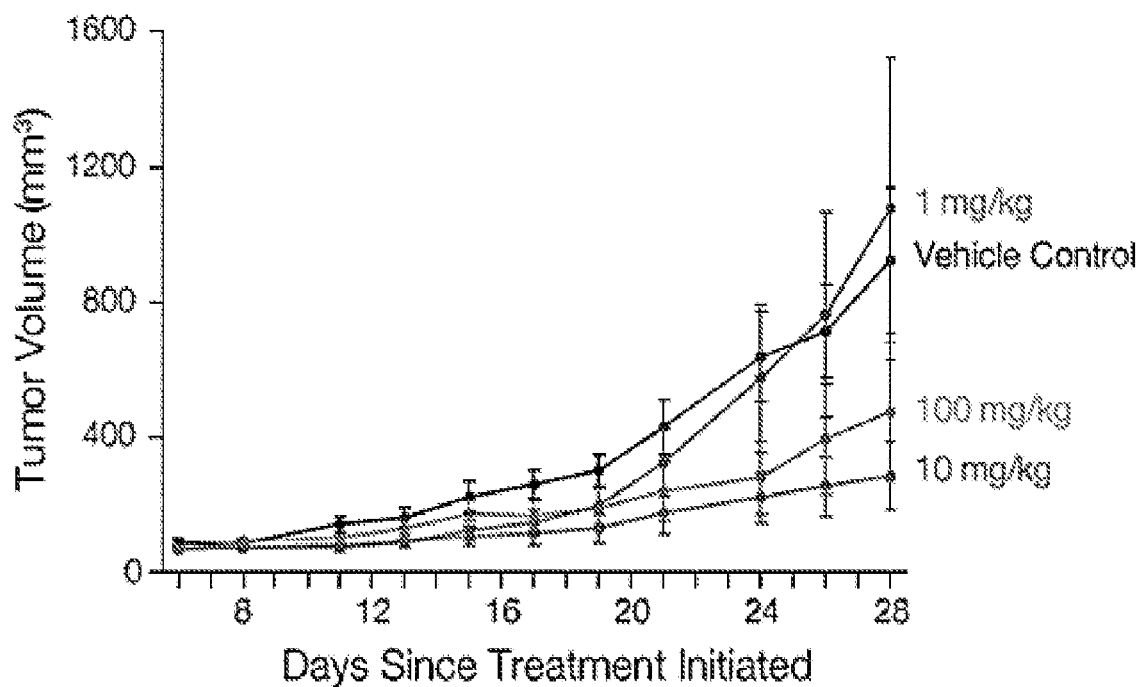
FIGS. 15A and 15B: MC38 Model: CPI-444 eliminated tumors in 30% of mice. 100% protected from rechallenge. Nine mice that achieved complete tumor growth inhibition at the end of the CPI-444 dose response study (FIG. 15A) were monitored for signs of reoccurrence for an additional 6 weeks. No tumor growth was observed, indicating that the tumor had been fully eliminated. These mice were challenged with the new engraftment of MC38 tumor cells. Modest tumor growth was observed in the first 5 days after rechallenge, however the tumors were fully rejected in all 9 mice over the following 15 days (FIG. 15B). Notably, tumor elimination occurred in the absence of any additional CPI-444 treatment. These results clearly demonstrate that CPI-444 treatment can elicit durable systemic anti-tumor immune memory.
Figure 15B:
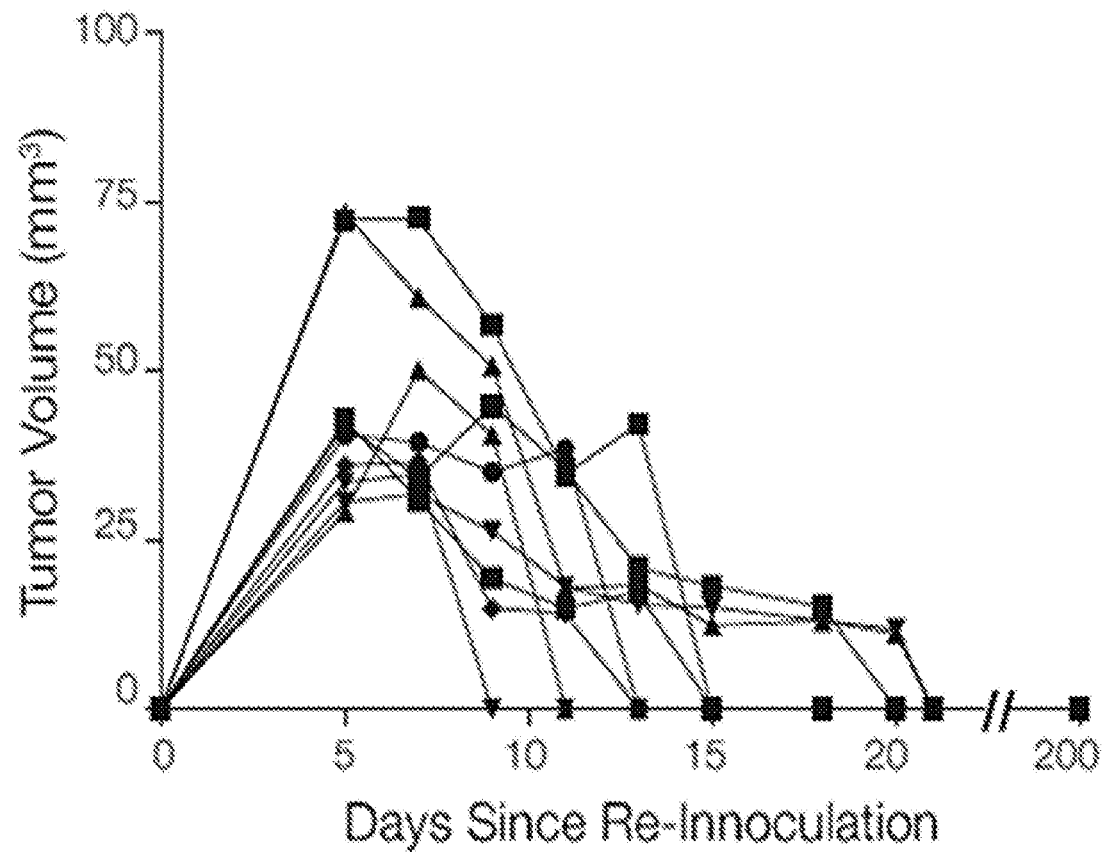
Figure 16A:
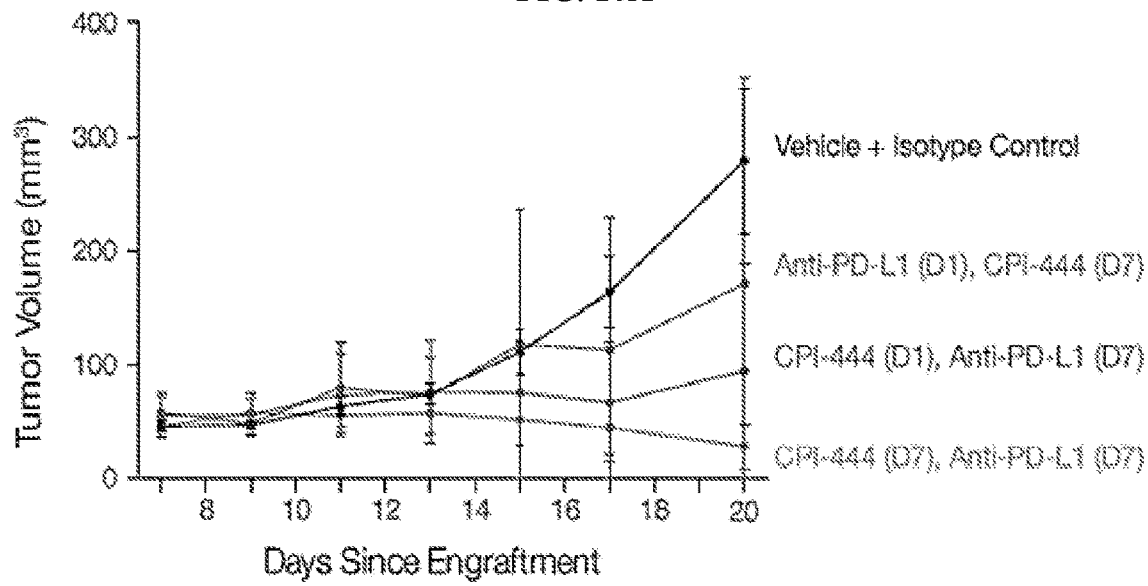
FIGS. 16A and 16B: MC38 Model: Established tumors eliminated in 8/9 mice.
Figure 16B:
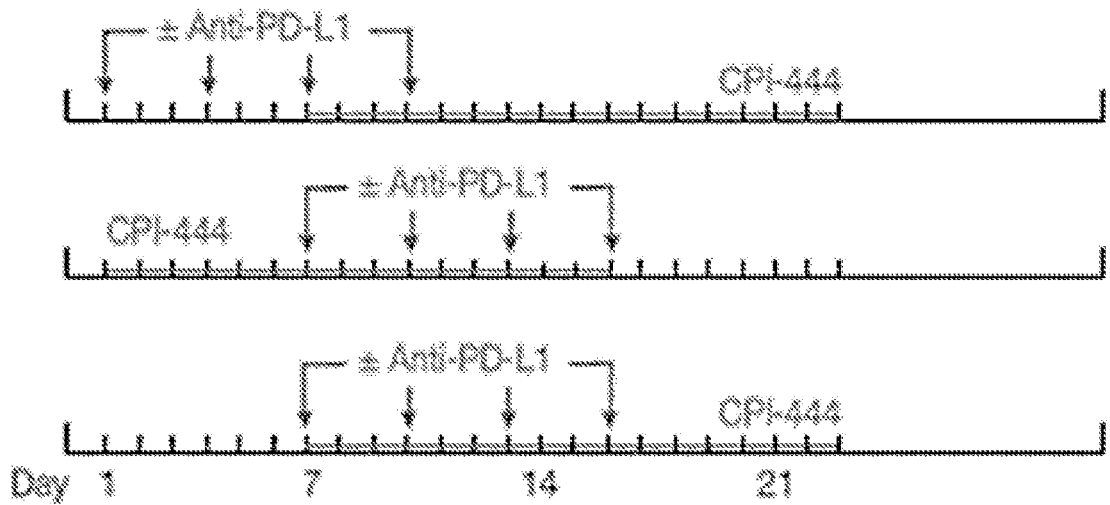
Figure 17:
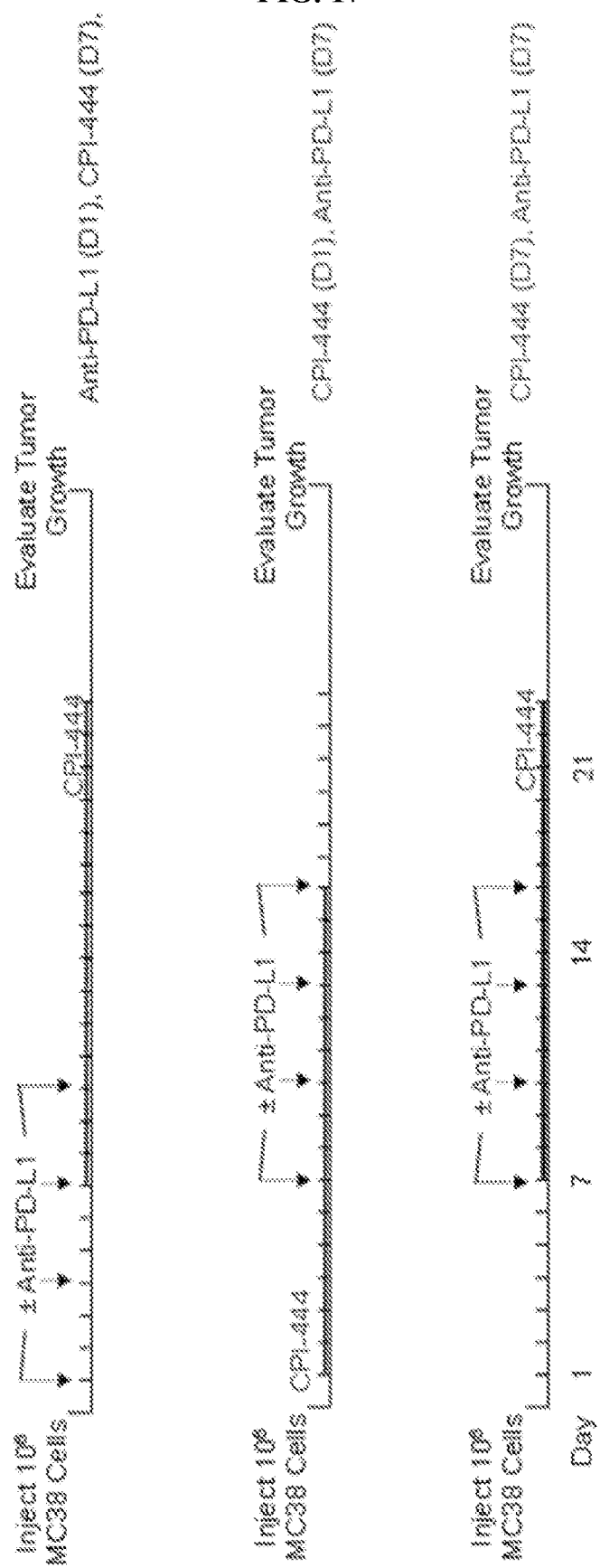
FIG. 17: MC38 Colon Cancer: Cartoon of Dosing Strategies: Determine optimal order of CPI-444 and anti-PD-L1.
Figure 18A:
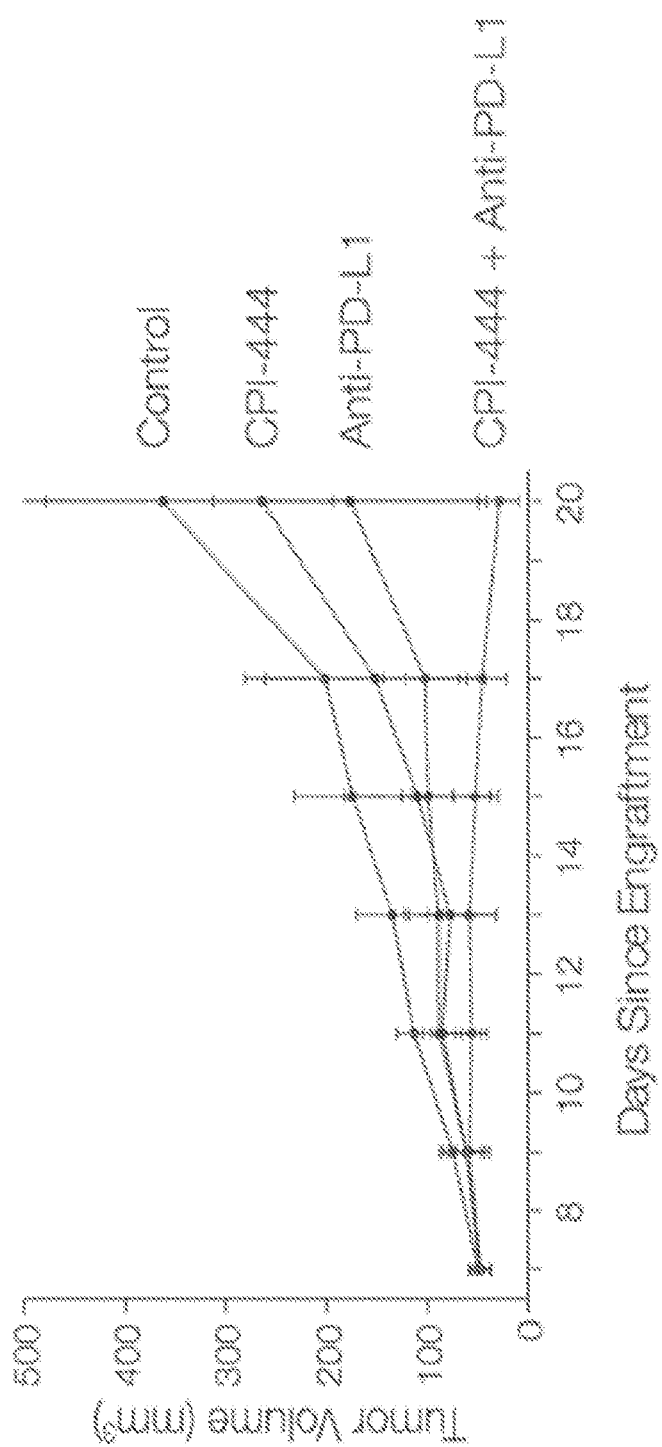
FIGS. 18A and 18B: MC38 Colon Cancer: All treatments started on Day 7 (established tumors). Size of tumor volume (FIG. 18A). Cartoon of dosing strategies (FIG. 18B).
Figure 18B:
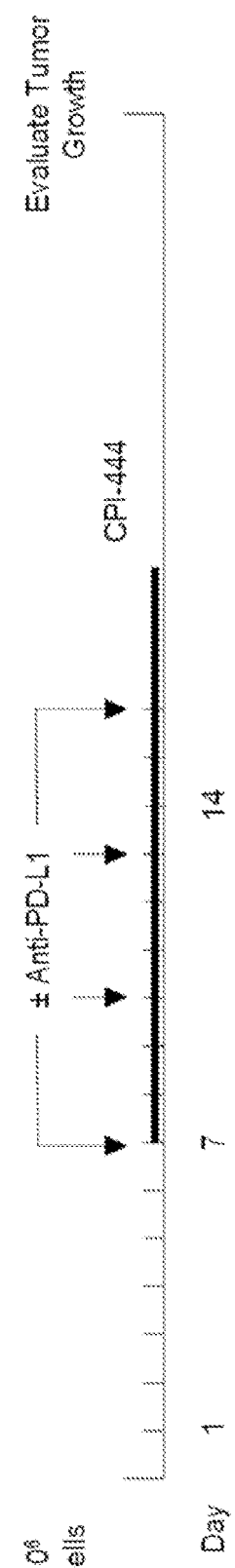

The objective of this study was to evaluate the effects of CPI-444 in a transplanted mouse colon cancer model in combination with a blocking anti-PD-1 monoclonal antibody (CPI-RSR-005). CT26 mouse colon cancer cells were engrafted onto the back of syngeneic male Balb/c mice. Oral administration of control vehicle (40% solution of hydroxypropyl-beta-cyclodextrin) or CPI-444 (100 mg/kg) was initiated the same day tumors were engrafted (Day 0). Treatment continued for 12 days. Half of the mice in the vehicle control group as well as half the mice in the CPI-444 treatment group received anti-PD-1 mAb (RMP1-14, 100 ug/mouse, i.p.) on days 7, 9, 11, and 13. Administration of anti-PD-1 or CPI-444 resulted in an inhibition of tumor growth, however tumors were not completely eradicated by either treatment (FIG. 13). Administration of CPI-444 in combination with anti-PD-1 stabilized or eliminated tumors in 8/9 mice, resulting in improved overall survival for more than 3 weeks following the last dose of CPI-444 or anti-PD-1 antibody (FIG. 13).

Example 2

Biomarker and Clinical Activity of CPI-444, a Novel Small Molecule Inhibitor of A2A Receptor (A2AR), in a Ph1b Study in Advanced Cancers Adenosine is immunosuppressive and is produced at high concentrations in tumors by both CD73 and direct release from tumor cells. Adenosine activates A2AR, an immune checkpoint that leads to direct suppression of effector T cells and stimulation of regulatory T cells. CPI-444 is an oral, selective A2AR inhibitor that has been well tolerated in Phase (Ph) 1 and 2 studies in non-oncology indications. CPI-444 shows activity in multiple preclinical tumor models as a single agent and synergistic efficacy when given in combination with other checkpoint inhibitors, including anti-PD-L1.

CPI-444, with or without the investigational agent atezolizumab (anti-PD-L1), is being studied in an ongoing Ph1b trial in solid tumor patients (pts). Pts with either lung, melanoma, triple negative breast, bladder, colorectal, renal, or head and neck cancers are treated at various doses of either single agent CPI-444 or combined with atezolizumab. After a dose selection stage, pts are treated in 10 disease specific cohorts (5 single agent and 5 combination). Cohorts may be expanded based on response criteria: complete response, partial response or stable disease (SD). Biomarkers are evaluated including immune cells by flow cytometry in peripheral blood and pre/post treatment tumor biopsies as well as adenosine pathway modulation by immunohistochemistry and gene expression.

In 7 pts treated to date, CPI-444 has been well tolerated with no Grade 3 or 4 treatment related adverse events. 2 pts (1 combination and 1 single agent) have reached the first efficacy assessment by CT and both demonstrated SD (unconfirmed at 2 months); these 2 pts, and 4 others who have not yet reached efficacy evaluation, remain on treatment.

In the two pts with SD, peripheral blood showed increases in PD-1+CD8+ cells (1.7 and 2.4 fold compared to baseline). This is consistent with preclinical models and reflects effector T cell activation, similar to reports by others in patients treated with anti-PD-L1.

CPI-444 is well tolerated and demonstrates biological activity indicating activation of T cell immunity. This is the first demonstration of treatment-associated immune modulation in cancer patients receiving an adenosine antagonist.

Example 3

Adenosine A2A Receptor Antagonist, CPI-444, Blocks Adenosine-Aediated T Cell Suppression and Exhibits Anti-Tumor Activity Alone and in Combination with Anti-PD-1 and Anti-PD-L1

Elevated extracellular adenosine in the tumor microenvironment generates an immunosuppressive niche that promotes tumor growth and metastasis. Adenosine signaling via A2A receptor (A2AR) on immune cells suppresses anti-tumor immunity and may also limit efficacy of immunotherapies such as anti-PD-L1 and anti-PD-1 antibodies.

CPI-444 is a potent, oral, selective A2AR antagonist that has been well tolerated in Ph 1 and 2 studies in non-oncology indications. Efficacy of CPI-444 was evaluated in MC38 and CT26 syngeneic mouse tumor models. In MC38, daily treatment of mice with CPI-444 (1, 10, 100 mg/kg) led to dose-dependent inhibition of tumor growth, leading to tumor elimination in 9/30 mice. Combining CPI-444 with anti-PD-L1 treatment in MC38 synergistically inhibited tumor growth and eliminated tumors in 90% of treated mice. In an additional model, CT26, CPI-444 alone or anti-PD-1 alone led to non-significant reductions in tumor growth; however, the combination of CPI-444 and anti-PD-1 led to a synergistic inhibition of tumor growth and prolonged survival compared to either agent alone.

When cured mice were later re-challenged with MC38 cells, tumor growth was fully inhibited, indicating that CPI-444 induced systemic anti-tumor immune memory. CD8$^+$ T cell depletion abrogated the efficacy of CPI-444±anti-PD-L1 treatment, demonstrating a role for CD8$^+$ T cells in mediating primary and secondary immune responses.

Anti-tumor efficacy of CPI-444±anti-PD-L1 was associated with increased CD8$^+$ cell infiltration and activation in MC38 tumor tissues. Additionally, levels of immune checkpoints were modulated by treatment with CPI-444, including GITR, OX40, and LAG3 on tumor infiltrating lymphocytes and circulating T cells, suggesting a broad role for adenosine mediated immunosuppression.

Based on these results and others, Applicants have initiated a Phase 1b clinical trial to examine safety, tolerability, biomarkers, and preliminary efficacy of CPI-444 as a single agent and in combination the investigational anti-PD-L1 antibody, Atezolizumab, in patients with solid tumors.

Example 4

CPI-444: A Potent and Selective Inhibitor of Adenosine 2A Receptor (A2AR) Induces Anti-Tumor Responses Alone and in Combination with Anti-PD-L1.

Adenosine is immune-suppressive, acting through adenosine 2A receptor (A2AR) which is expressed on cytotoxic, helper and regulatory T cells, as well as NK, dendritic and myeloid derive suppressor cells. CPI-444 is an oral, selective inhibitor of A2AR that is active as a single agent in multiple syngeneic mouse models and is synergistic when combined with anti-PD-1 or anti-PD-L1 antibodies in these models. 75 subjects were previously dosed with CPI-444 in non-oncology trials, and CPI-444 well was well tolerated with no significant adverse events noted. A Phase 1/1b study was initiated that explores safety and efficacy of CPI-444 as a single agent as well as in combination with the anti-PD-L1 antibody TECENTRIQ® (atezolizumab) in selected histologies.

Figure 19B:
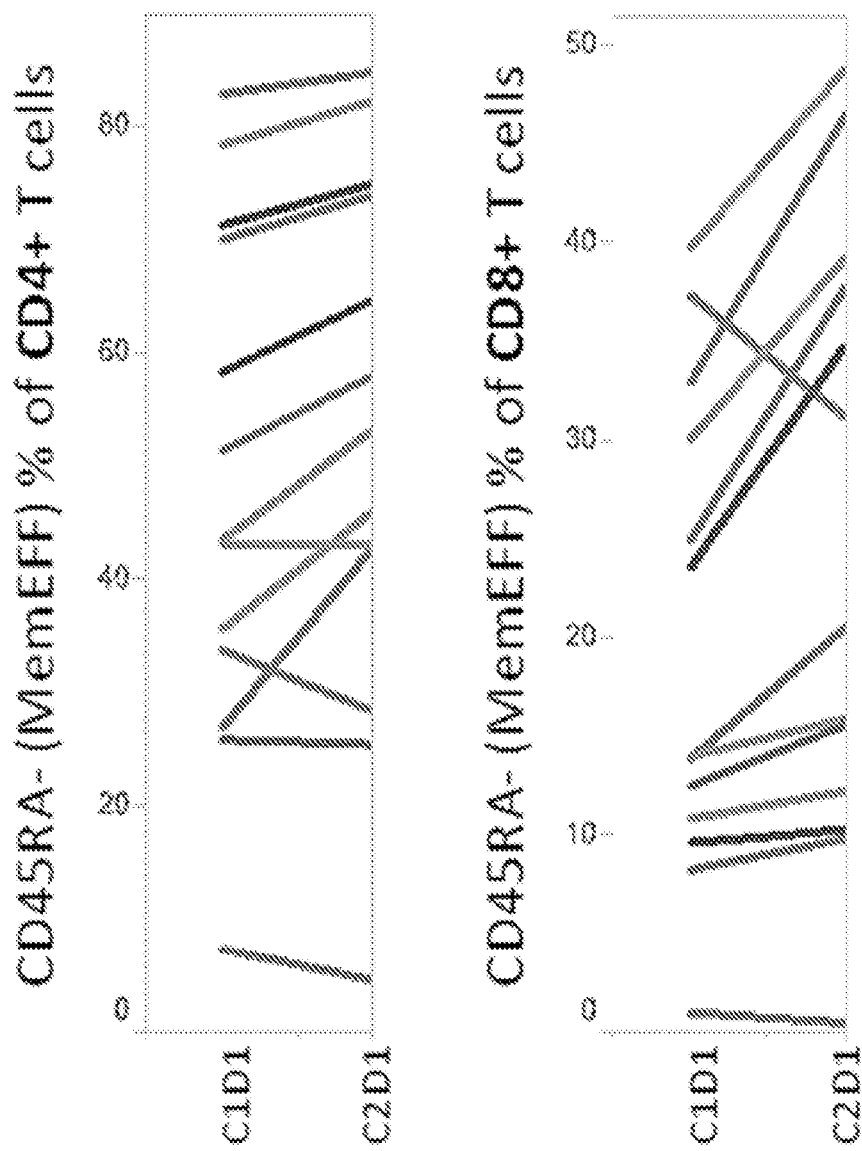
Figure 20A:
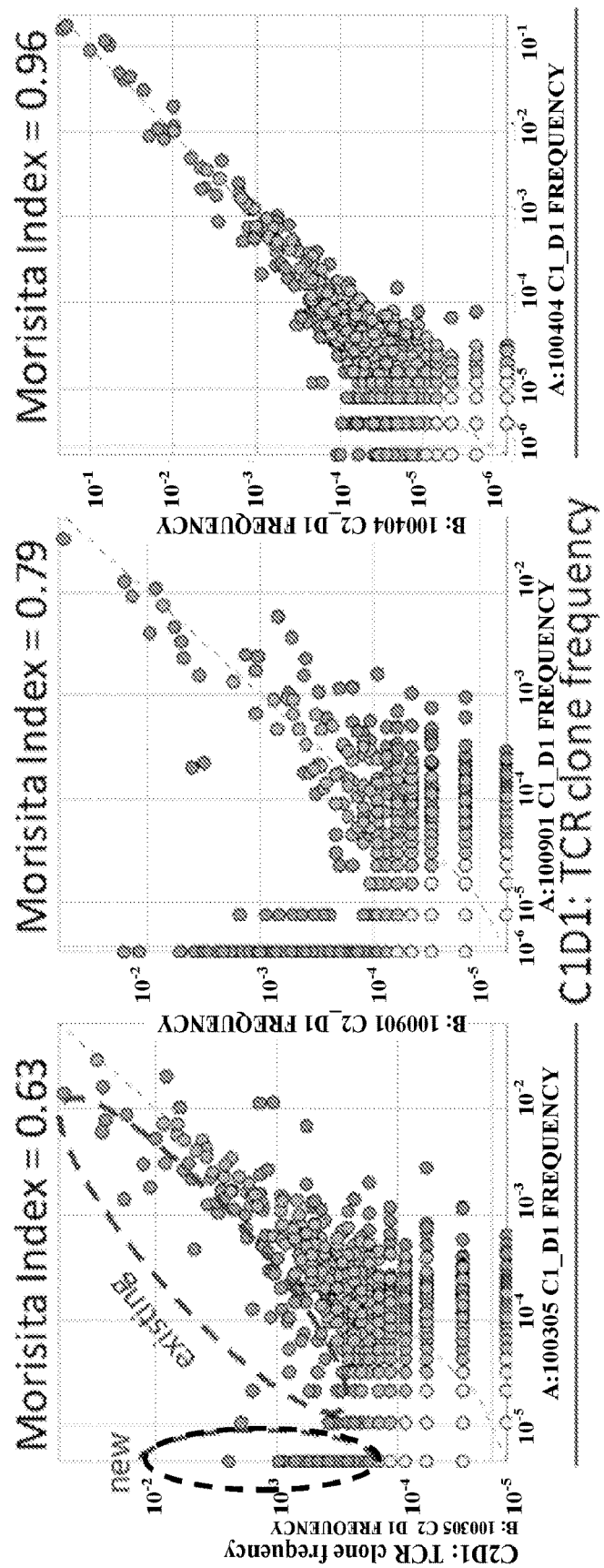
FIGS. 20A-20C: CPI-444 is associated with changes in T cell repertoire. Whole blood was collected on Day 1 of Cycles 1 and 2 and PBMCs were prepared. DNA was extracted from PBMCs and sequenced for TCRβ repertoire by Adaptive Biotechnologies. Expansion of pre-existing and new T cell clones is observed in response to treatment with single agent CPI-444 (FIG. 20A). Morisita Index measures T cell repertoir similarity comparing pre- and post-dose PBMCs. A Morisita Index of 1 is equal to identity, indicating no longitudinal change. Morisita Index distribution in single agent and combination cohorts (FIG. 20B). Graph showing Morisita Index by cohort (FIG. 20C). CPI-444 induces robust changes in TCR repertoire in some patients treated with single agent CPI-444 and in combination with Tecentriq®. Changes were driven predominantly by TCR clone expansion (clonality).
Figure 20B:
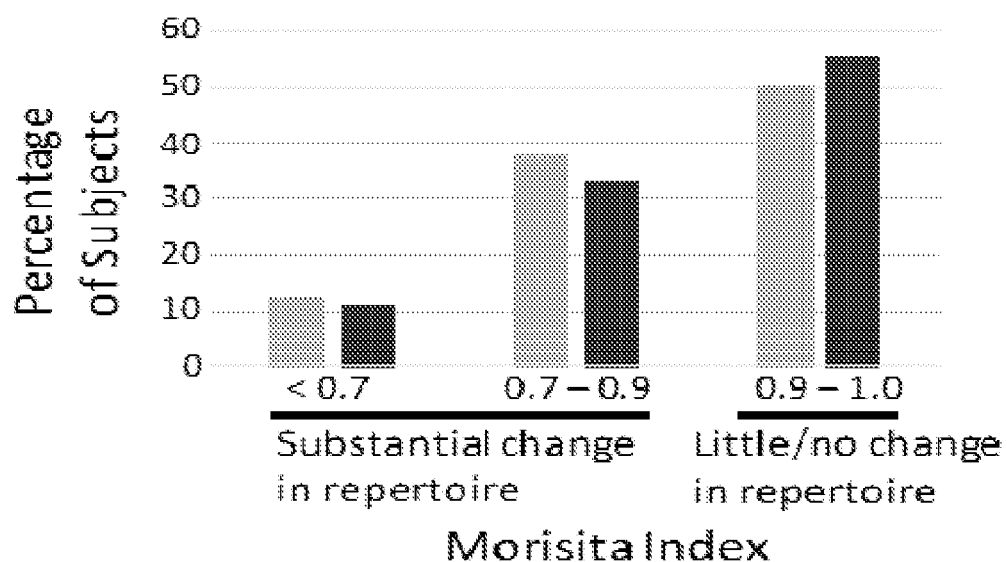
Figure 20C:
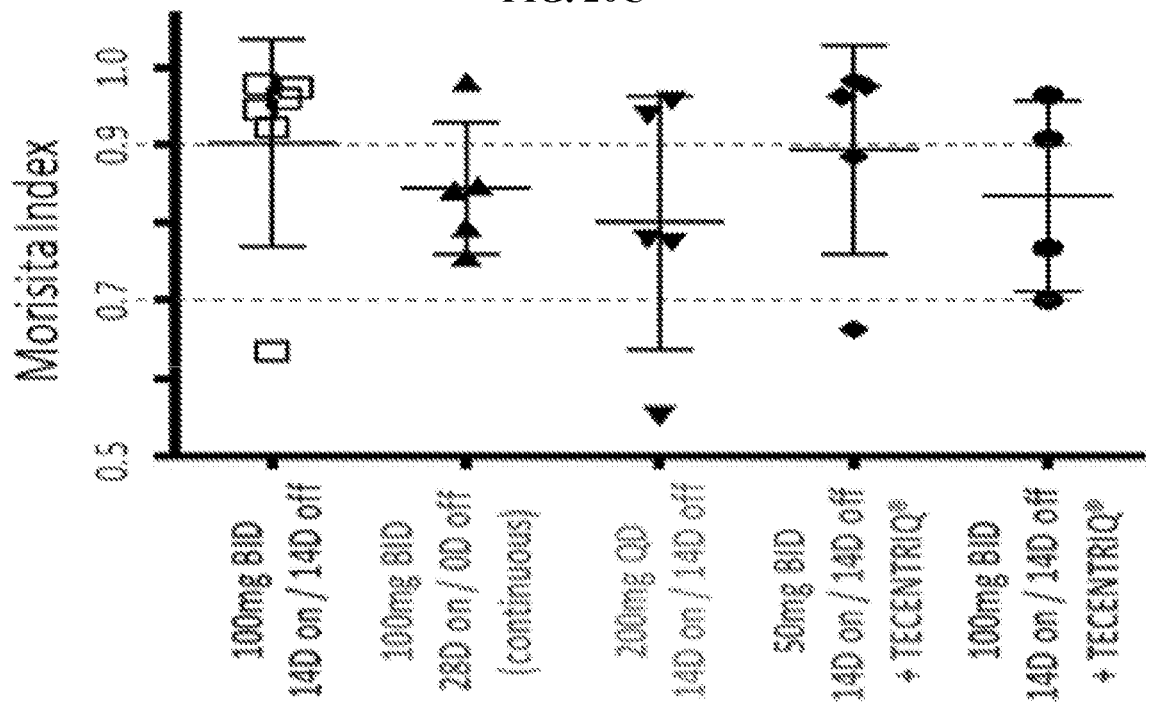

In step 1 of the trial, patients were dosed with either 100 mg BID for 14 days out of a 28 day cycle, 100 mg BID for 28 days, 200 mg QD for 14 days or 50 mg or 100 mg BID for 14 days in combination with TECENTRIQ® (840 mg Q2W). Pharmacodynamic analysis was conducted on peripheral blood cells to inform dose selection. Step 1 of Phase1/1b was fully enrolled (n=48) and dose was selected (100 mg BID) based on pharmacodynamic analysis of A2AR pathway. Complete inhibition observed at 100 mg BID dose that is sustained in 28 day continuous dosing cohort. Increases in activated CD8 cell frequencies were observed in patients treated with single agent CPI-444 and combined with TECENTRIQ®, suggesting immune activation in response to treatment (FIG. 19A). TCR repertoire changes were induced in peripheral blood by single agent CPI-444 in patient subsets, including patients refractory to prior anti-PD-1 therapy (FIGS. 20A-20C).

Figure 21B:
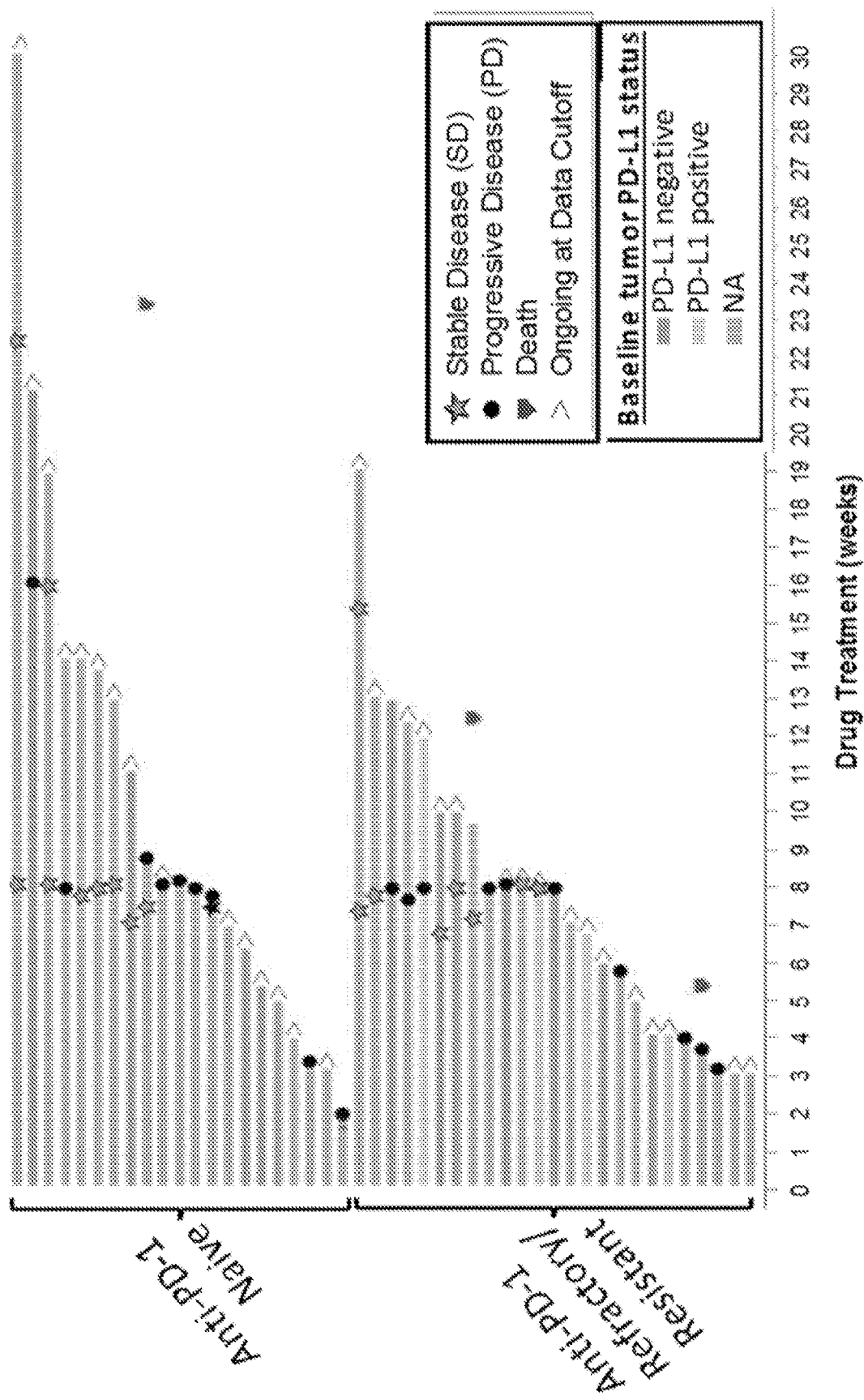
Figure 21C:
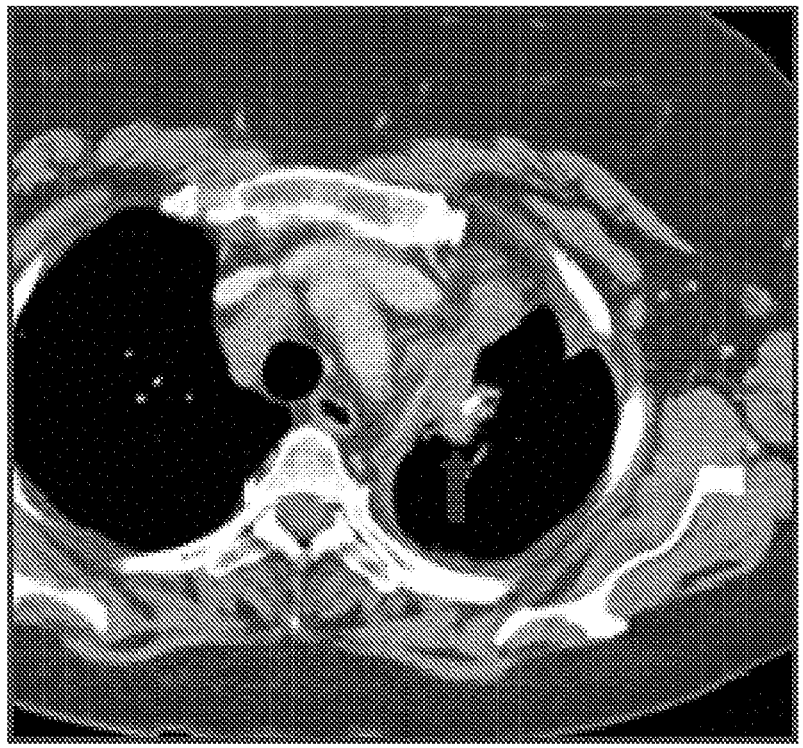
Figure 21C:
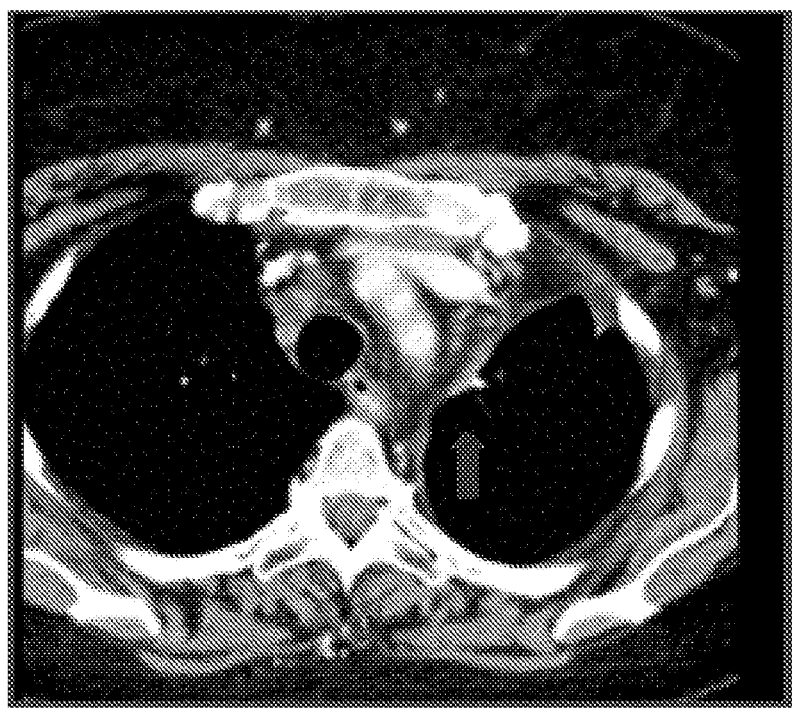
Figure 22A:
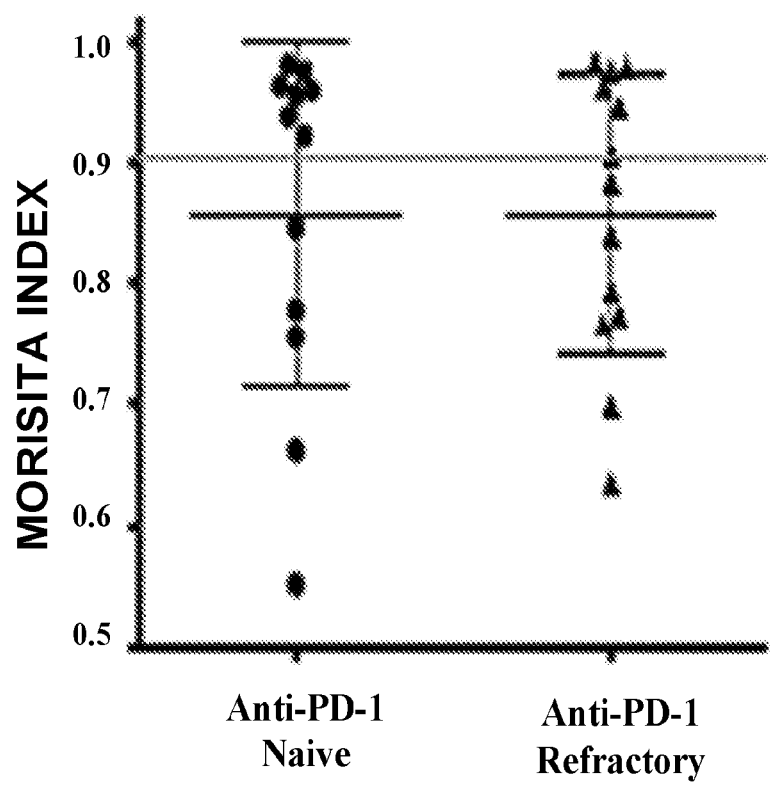
FIGS. 22A-22C: Relationship between TCR repertoire and efficacy. TCR repertoire changes are similar between patients that are naïve and refractory to prior anti-PD-1 therapy and may associate with efficacy (FIG. 22A).
Figure 22B:
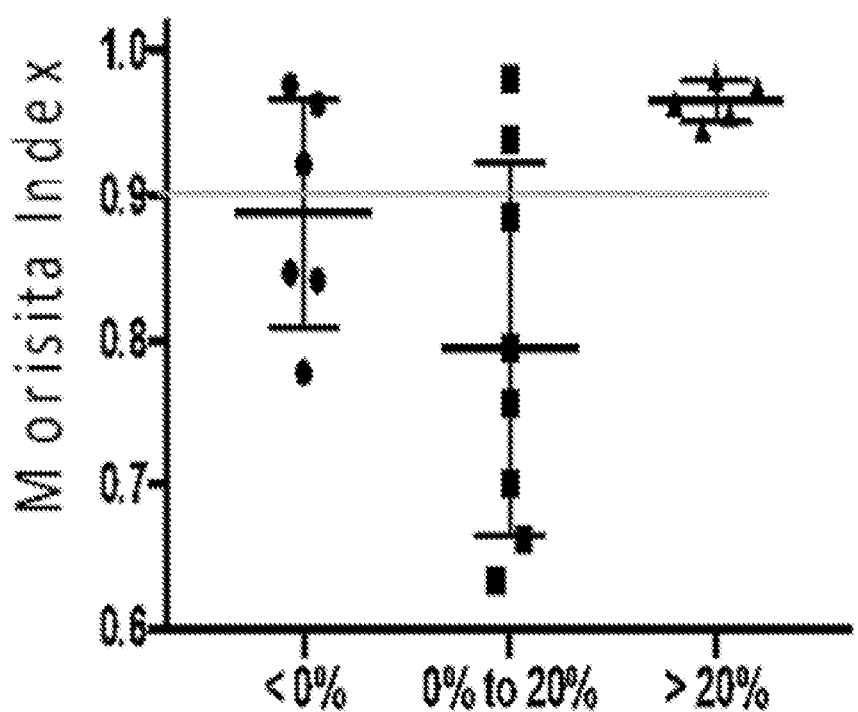
Figure 22C:
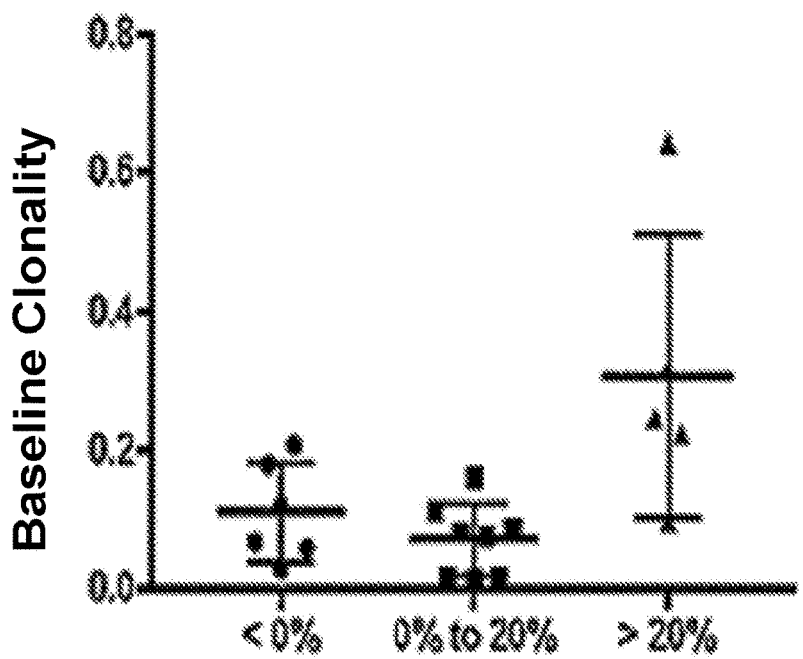

High TCR diversity (low clonality) at baseline and changes in TCR repertoire following treatment show association with early efficacy data in anti-PD-1 naïve and refractory patients. A similar rate of stable disease was observed in anti-PD-1 refractory patients and in both PD-L1 positive and negative patient subsets (FIGS. 21A and 21B). This is the first demonstration of immune cell activation and anti-tumor activity in patients receiving an adenosine antagonist.

Example 5

Figure 23A:
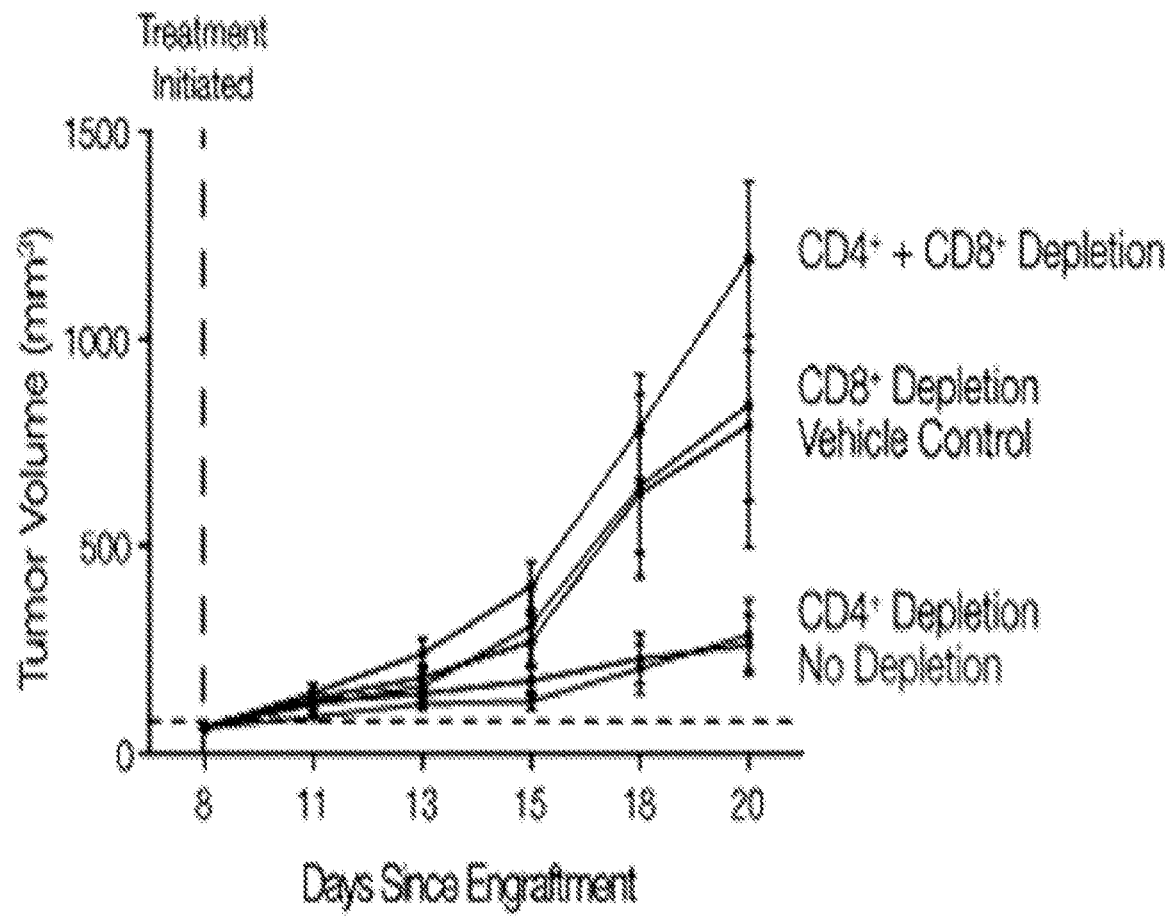
FIGS. 23A-23C: CPI-444 efficacy requires CD8+ T cells. MC38 mouse colon cancer cells were engrafted onto the back of syngeneic C57BL/6 mice. Oral administration of control vehicle or CPI-444 (100 mg/kg) was initiated 7 days after tumors were engrafted (Day 0) (FIG. 23C). Treatment continued for more than 9 days (FIG. 23C). Half of the mice in the vehicle control group as well as half the mice in the CPI-444 treatment group received anti-PD-L1 mAb (10F.9G2, 200 ug/mouse, i.p.) on days 7, 10, 13, and 16 (FIG. 23C). 100 ug of Anti-mCD4 (Clone GK1.5) and/or 500 ug of Anti-mCD8 (Clone 53-6.72) was administered on day 6. T cell depletion was verified by flow analysis.
Figure 23B:
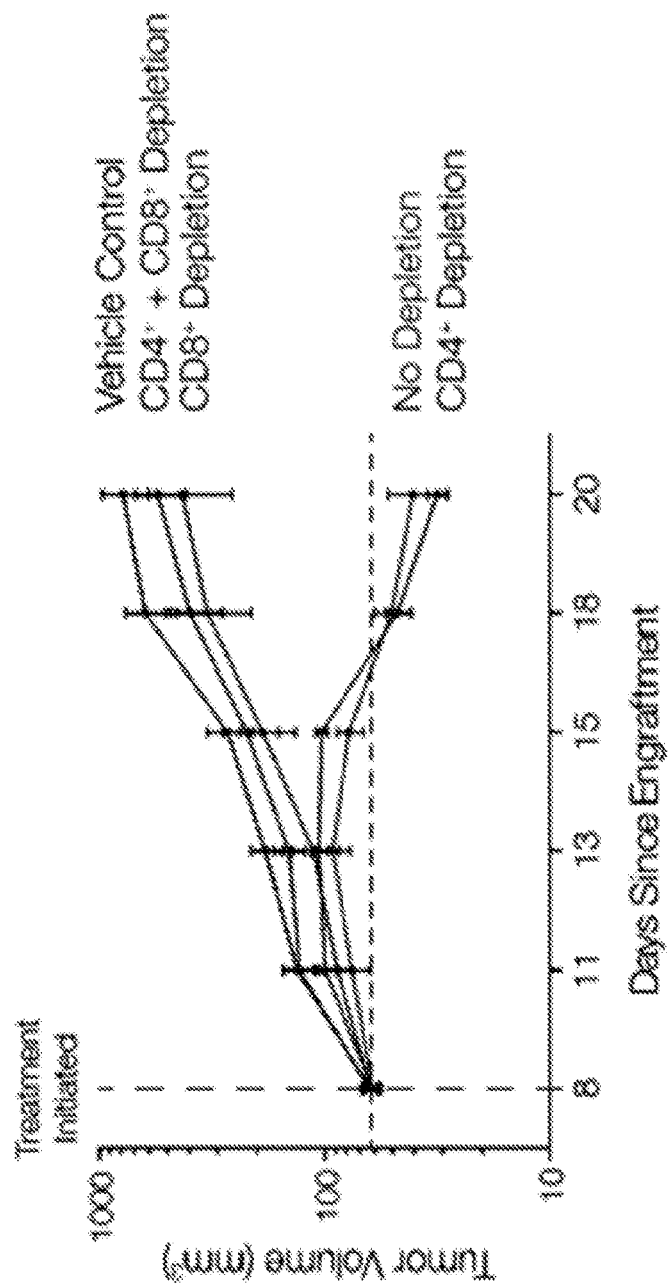

MC38 mouse colon cancer cells were engrafted onto the back of syngeneic C57BL/6 mice. Oral administration of control vehicle or CPI-444 (100 mg/kg) was initiated 9 days after tumors were engrafted (Day 0). Treatment continued for 12 days. Half of the mice in the vehicle control group as well as half the mice in the CPI-444 treatment group received anti-PD-L1 mAb (10F.9G2, 200 ug/mouse, i.p.) on days 9, 12, 15, and 18. 100 ug of Anti-mCD4 (Clone GK1.5) was administered on days 8, 11, 14, and 17, and 500 ug of Anti-mCD8 (Clone 53-6.72) was administered on days 8 and 15. T cell depletion was verified by flow analysis. FIGS. 23A and 23B show tumor volume at different time points since engraftment for the dosing cohorts. These results suggest CD8+ T cells are required for the efficacy of CPI-444 alone or in combination with Anti-PD-L1.

Example 6

Figure 23C:
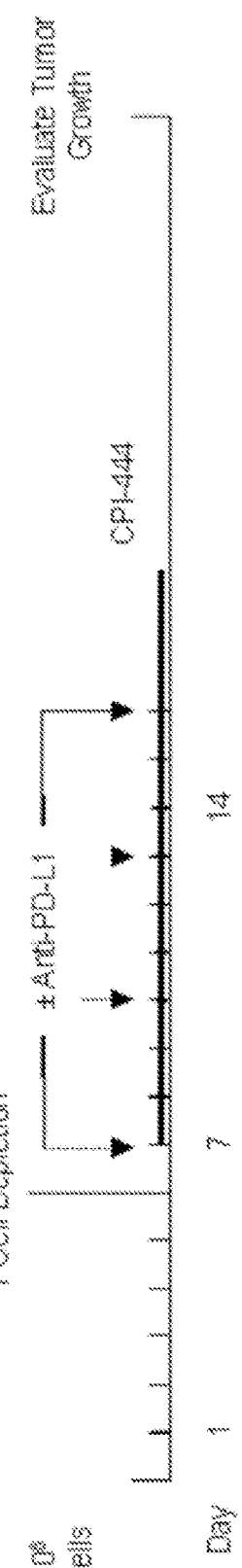

MC38 mouse colon cancer cells were engrafted onto the back of syngeneic C57BL/6 mice. Oral administration of control vehicle or CPI-444 (100 mg/kg) was initiated 7 days after tumors were engrafted (Day 0) (FIG. 23C). Treatment continued for more than 9 days. Half of the mice in the vehicle control group as well as half the mice in the CPI-444 treatment group received anti-PD-L1 mAb (10F.9G2, 200 ug/mouse, i.p.) on days 7, 10, 13, and 16. 100 ug of Anti-mCD4 (Clone GK1.5) and/or 500 ug of Anti-mCD8 (Clone 53-6.72) was administered on day 6. T cell depletion was verified by flow analysis. FIGS. 23A and 23B show tumor volume at different time points since engraftment for the dosing cohorts. These results suggest CD8+ T cells are required for the efficacy of CPI-444 alone or in combination with Anti-PD-L1.

Example 7

Materials and Methods
Whole Blood Processing
  Blood samples were derived from patients and processed using the following protocol:
    Whole blood in heparin delivered overnight and assay begins the next morning
    Aliquot 67.5 uL blood per well and recover at 37 C for 1 hr
    Add 7.5 uL of NECA or PMA per well for 15 minutes at 37 C
    NECA at 1, 3 or 10 uM
    Fix cells with 1.5 mL of BD Lyse/Fix buffer according to manufacturer
    Spin and resuspend in 1 mL cold MeOH and store −80 C.
Antibody Staining
  Fix cells derived from patient blood were stained using the following protocol:
    Spin out of MeOH
    Wash 2× with FACS buffer (phosphate buffered saline containing 1% bovine serum albumin and 0.1% sodium azide)
    Stain 1 hour
      Antibody cocktail:
        pCREB Alexa Flour647 (Cell Signaling Technology Cat. No. 14001S)
        CD3 Horizon V500 (BD Cat. No. 561416)
        CD4 Brilliant Violet 421 (BD Cat. No. 562424)
        CD8 PerCP-Cy5.5 (BD Cat. No. 560662)
        CD27 FITC (BD Cat. No. 340424)
        CD20 PE (BD Cat. No. 561174)
        CD45RA PE-Cy7 (BD Cat. No. 649457)
        cPARP Alexa Flour700 (BD Cat. No. 560640)
    Wash 2× with FACS buffer
    Fix cells with 1.6% paraformaldehyde (PFA) for 5 minutes at ambient temperature
    Spin, aspirate, and bring cells to acquisition volume in 1.6% PFA
    Acquire cells on flow cytometer.

Example 8

Induction of pCREB by NECA in B cells harvested from whole blood and stained as described above was monitored. Two subjects were assayed, one treated with 200QD CPI-444 (FIG. 27) and a subject treated with 50BID CPI-444+Atezolizumab (atezo) (FIG. 28) prior to treatment and at 2 time points after 14 days of treatment. NECA was used to stimulate CREB activation via the adenosine receptor pathway in concentrations of 1 uM NECA, (sub-saturation, where inhibition is expected), and 10 uM NECA (saturation, where NECA may out-compete CPI-444 resulting in inhibition). Control samples were treated with phorbol myristate acetate (PMA).

Baseline induction of pCREB following NECA treatment is shown at C1D1 prior to treatment. NECA induction of pCREB was then monitored at C1D14 at 0 hr (trough) prior to CPI-444 or CPI-444+atezo treatment, when CPI-444 concentration in circulating blood is at its lowest (see FIG. 26). The second time point is C1D14, 1.5 hours after administration of CPI-444 or CPI-444+atezo treatment.

Figure 27:
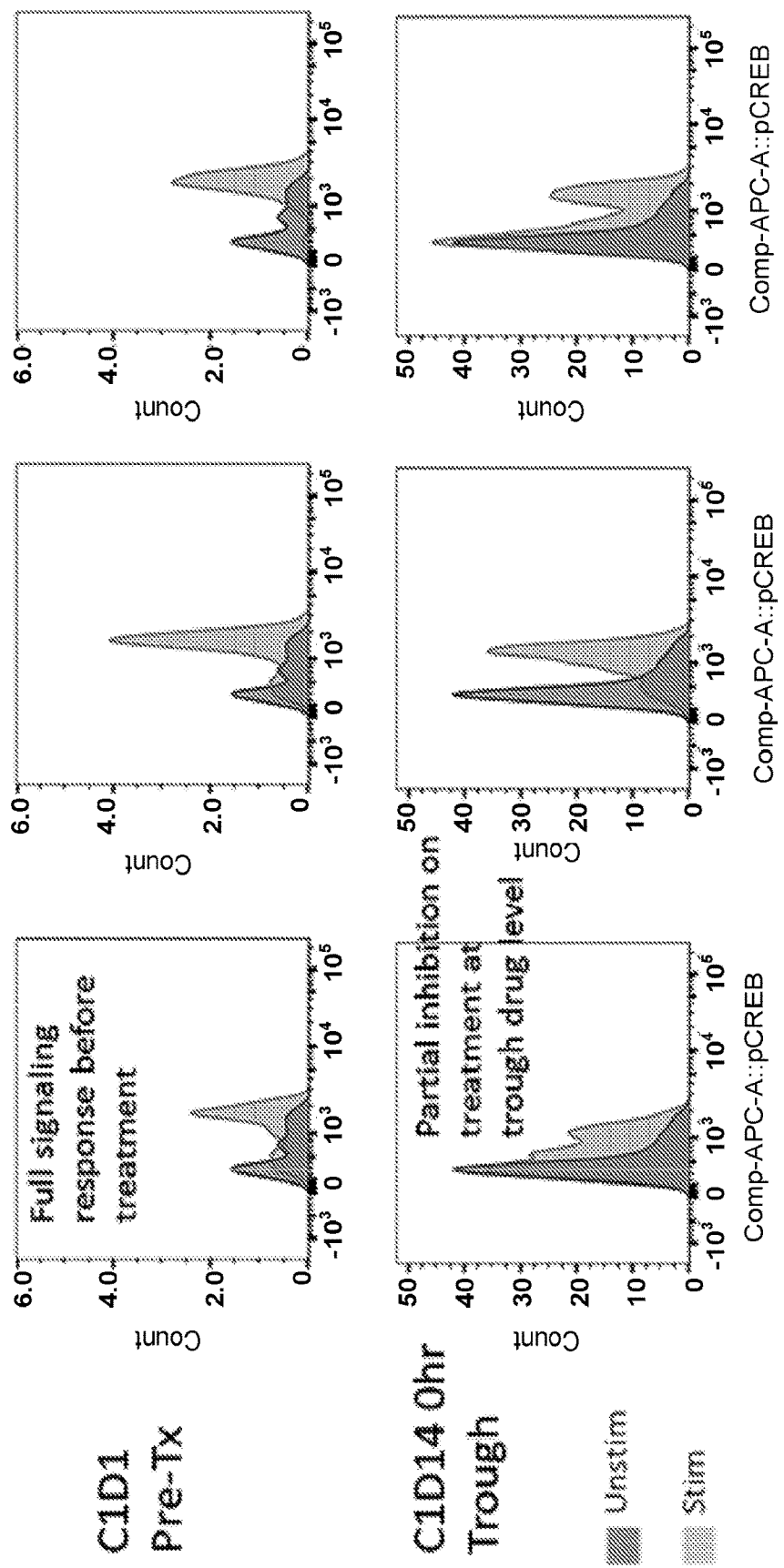
FIG. 27: A series of graphs charting pCREB induction in B cells in a subject receiving 200QD CPI-444 for 14 days. Trough refers to pharmacokinetic troughs as seen in FIG. 26.
Figure 28:
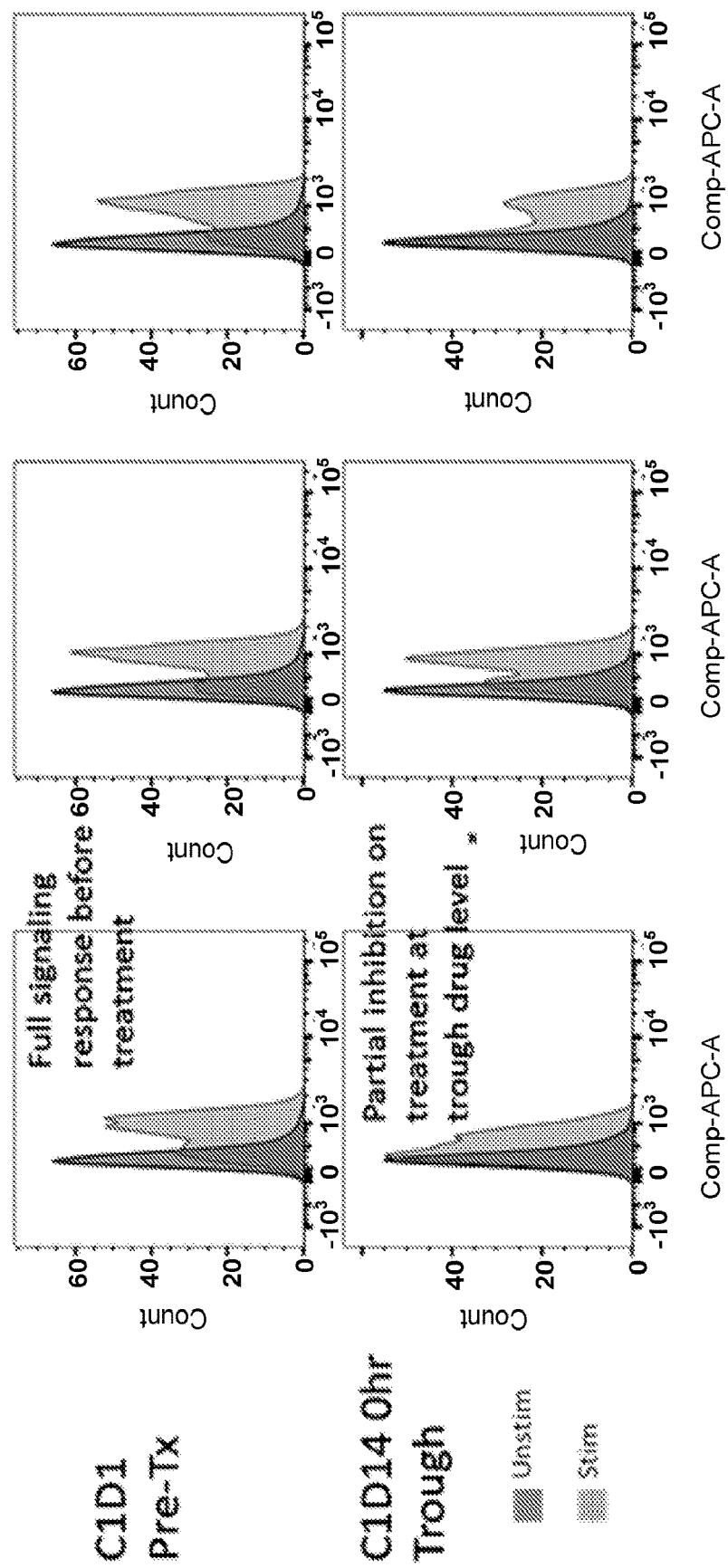
FIG. 28: A series of graphs charting pCREB induction in B cells in a subject receiving 50 mg BID CPI-444+Atezolizumab for 14 days. Trough refers to pharmacokinetic troughs as seen in FIG. 26.

In FIG. 27, partial inhibition of the adenosine receptor activation by CPI-444 is seen by the inhibition of the NECA induced increase of pCREB in B cells treated with 1 μM NECA. In FIG. 28, near complete inhibition of adenosine receptor activation by CPI-444+atezo is seen by the inhibition of the NECA induced increase of pCREB in B cells treated with 1 μM NECA.

Example 9

Figure 29:
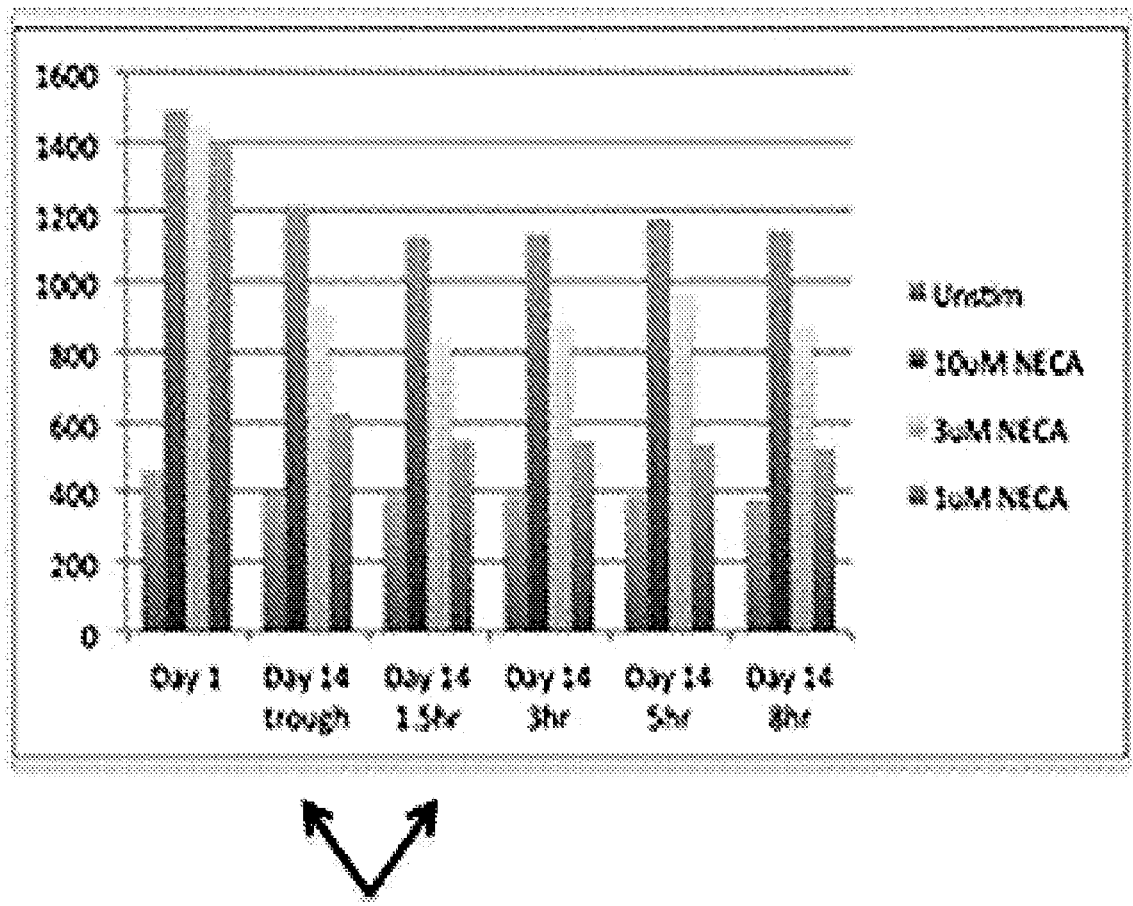
FIG. 29: A graph showing CREB phosphorylation in B cells at different concentrations of NECA prior to adenosine receptor antagonist treatment and after 14 days of treatment at trough, 1.5 hour, 3 hour, 5 hour and 8 hour time points for a subject receiving CPI-444 alone and a subject receiving combination therapy of CPI-444 and atezolizumab.'
Figure 29:
Figure 30:
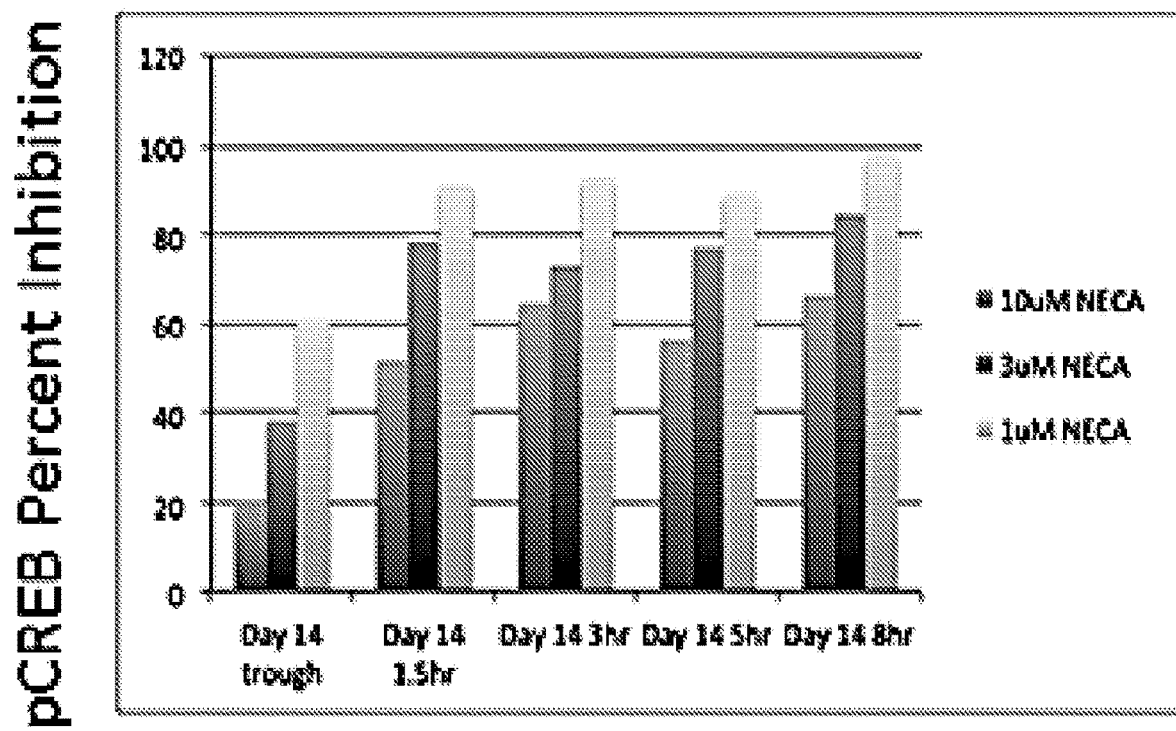
FIG. 30: A graph showing inhibition of CREB phosphorylation in B cells relative to baseline signaling at different concentrations of NECA after 14 days of adenosine receptor antagonist treatment at trough, 1.5 hour, 3 hour, 5 hour and 8 hour time points for subjects receiving CPI-444 alone (subject 100301: 200 mg QD CPI-444; and subject 100303: 100 mg BID CPI-444) and subjects receiving combination therapy of CPI-444 and atezolizumab (subject 100302: 50 mg BID CPI-444+atezo; and subject 100402: 50 mg BID CPI-444+atezo).
Figure 31:
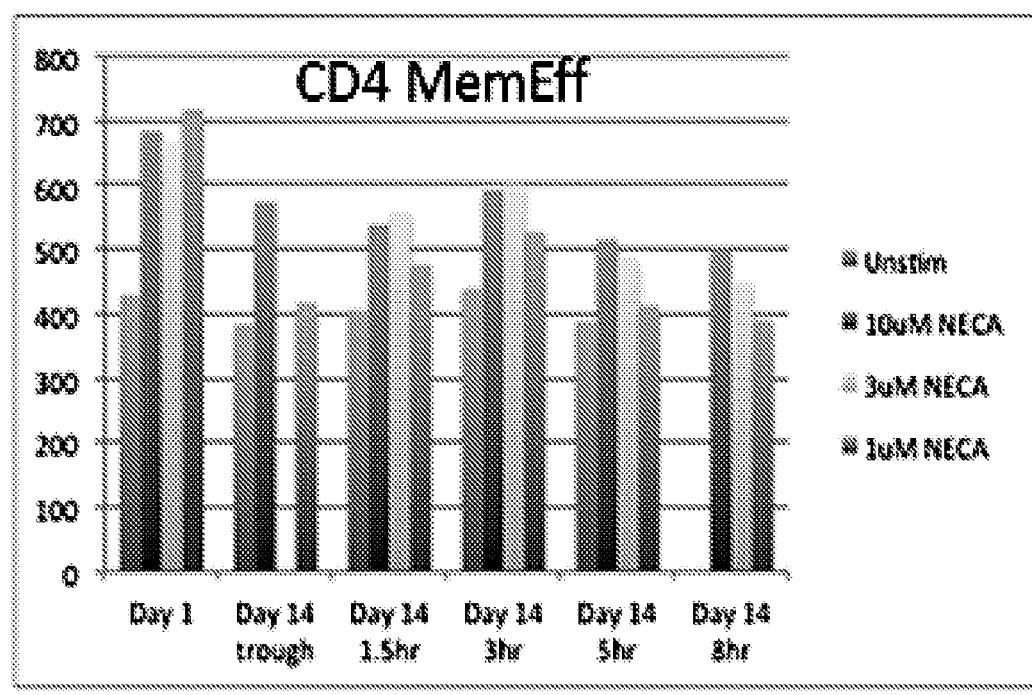
FIG. 31: A graph showing CREB phosphorylation in T cells at different concentrations of NECA at trough, 1.5 hour, 3 hour, 5 hour and 8 hour time points for a subject receiving CPI-444 alone (200QD CPI-444 for 14 days) and a subject receiving combination therapy of CPI-444 and atezolizumab (50BID CPI-444+atezolizumab for 14 days).
Figure 32:
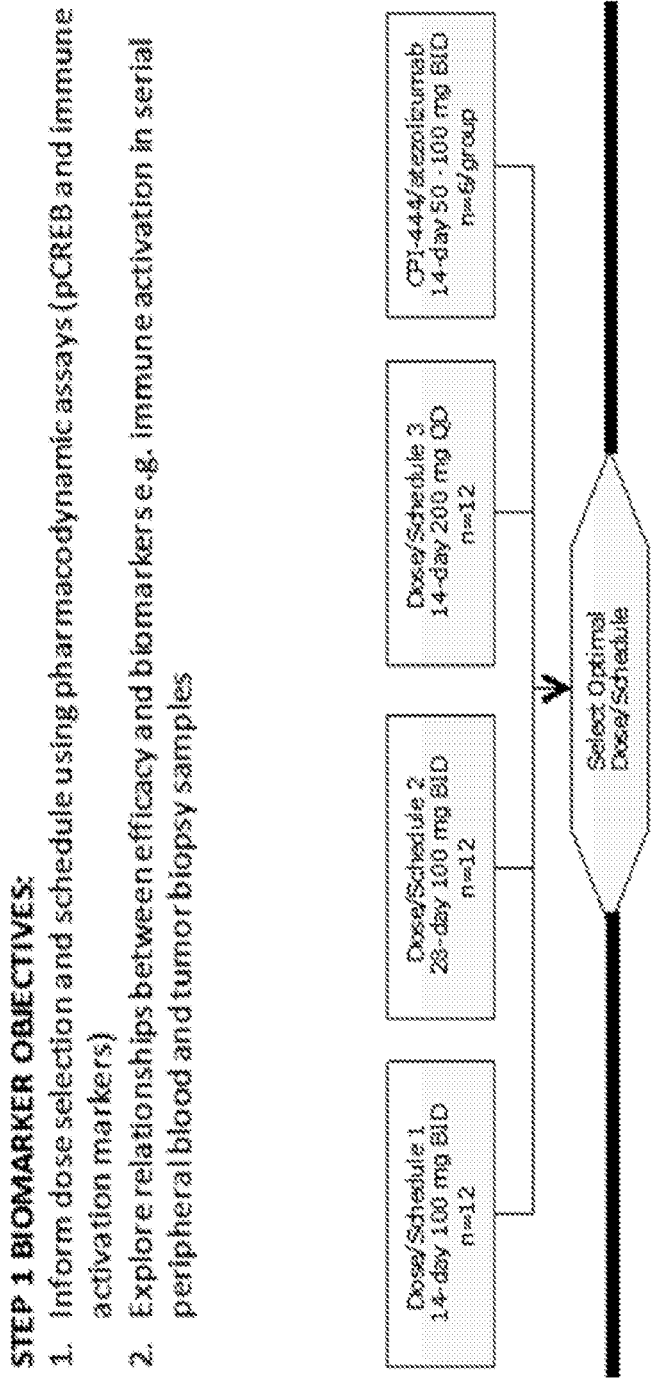
FIG. 32: Phase 1/1B clinical trial design. Step 1 shows the biomarker objectives to 1) inform dose selection and schedule using pharamacodynamics assays (pCREB and immune activation markers) and 2) explore relationships between efficacy and biomarkers, e.g., immune activation in serial peripheral blood and tumor biopsy samples. Step 2 shows the trial design.
Figure 33A:
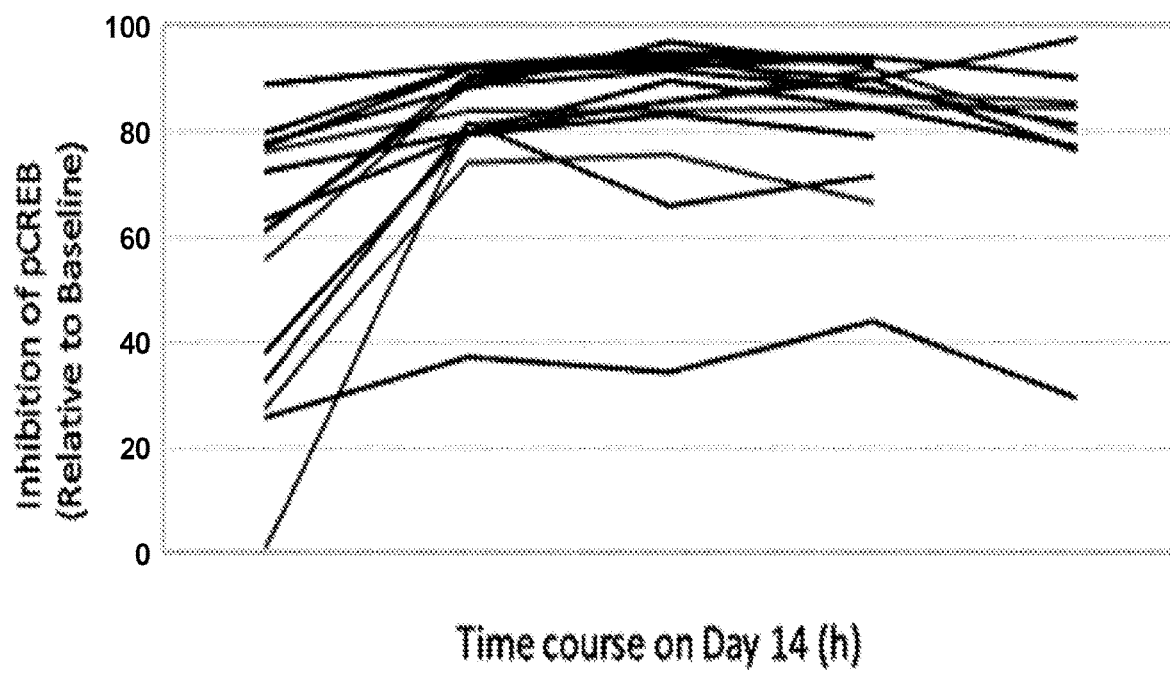
FIGS. 33A-33B: CPI-444 blocks A2AR in treated subjects. Whole blood was collected on Day 1 pre-treatment and on Day 14 at pre-dose and post dose at 1.5 hr, 3 hr, 5.5 hr and 8 hr time points. Blood was activated with an adenosine analog (NECA) and subsequently stained for intracellular phospho-CREB (pCREB) and cell lineage markers for flow cytometry. For each Day 14 time point, the percent inhibition of NECA-induced pCREB is relative to baseline.
Figure 33B:
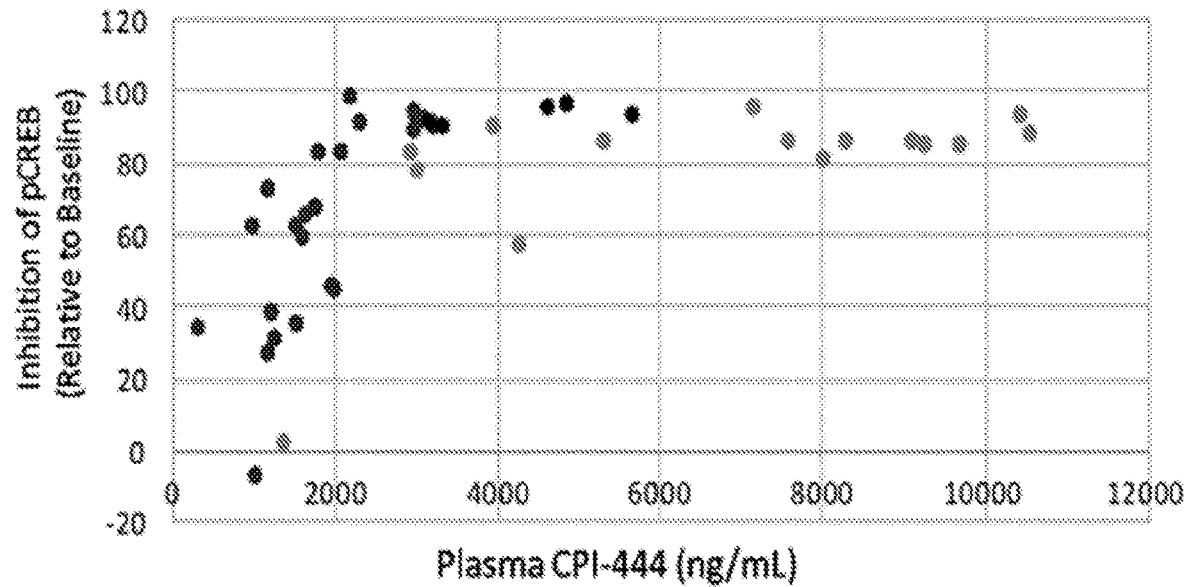

Induction of pCREB by NECA in B cells (FIG. 29 and FIG. 30) and T cells (FIG. 31) harvested from whole blood and stained as described above was monitored. Two subjects were assayed, one treated with 200QD CPI-444 and a subject treated with 50BID CPI-444+Atezolizumab (atezo) prior to treatment and at multiple time points after 14 days of treatment. NECA was used to stimulate CREB activation via the adenosine receptor pathway in concentrations of 1 uM, 3 uM, and 10 uM. Unstimulated control samples were treated with phorbol myristate acetate (PMA).

pCREB induction was measured at day 1 pre-treatment and a day 14 of treatment at trough (prior to treatment administration), 1.5 hours, 3 hours, 5 hours, and 8 hours following administration of CPI-444 or CPI-444+atezo.

pCREB induction by NECA is attenuated following 14 days of treatment of CPI-444 and CPI-444+atezo. This attenuation is clearest with treatment of sub-saturation NECA (1 uM, and 3 uM) in B cells. The 14 day time points show the maximal inhibition at 1.5 hr 3 hr and the minimal inhibition at trough and thus reveal the degree of inhibition across time (e.g. whether maximal inhibition is maintained over time).

Example 10

Biomarkers were analyzed in archival tumor tissue and serial biopsies as well as in peripheral blood to determine whether CPI-444 affects peripheral and intra-tumoral immune activation and T cell repertoires and to identify markers that are associated with efficacy.

Example 11

Figure 25:
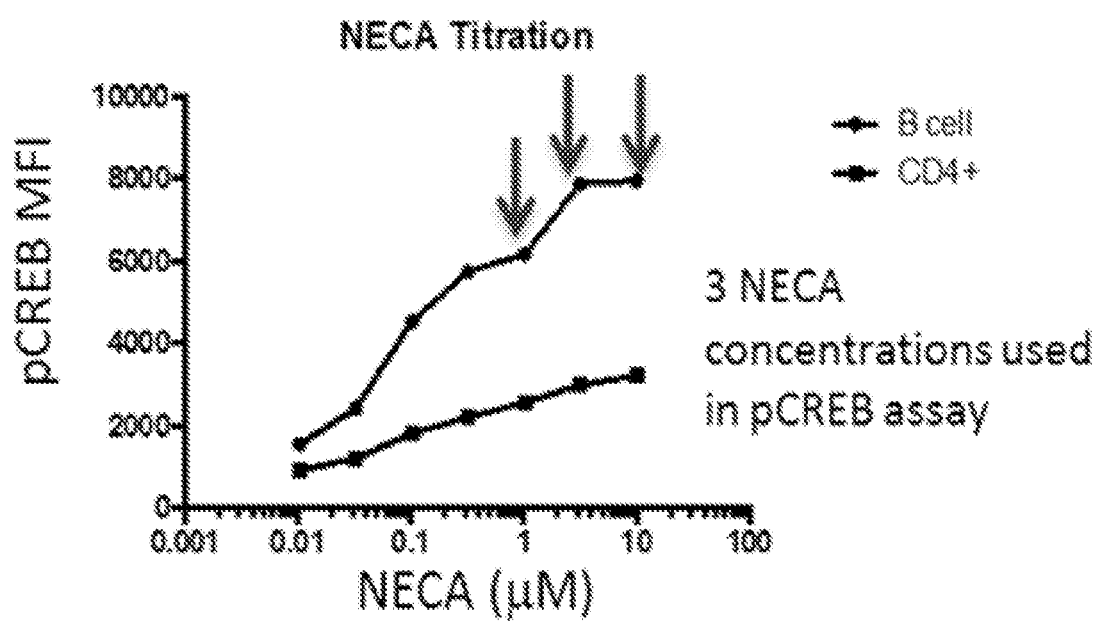
FIG. 25: A Graph indicating that 5'N-ethylcarboxamidoadenosine (NECA), NECA, a synthetic adenosine analog, activates CREB in whole blood.
Figure 26:
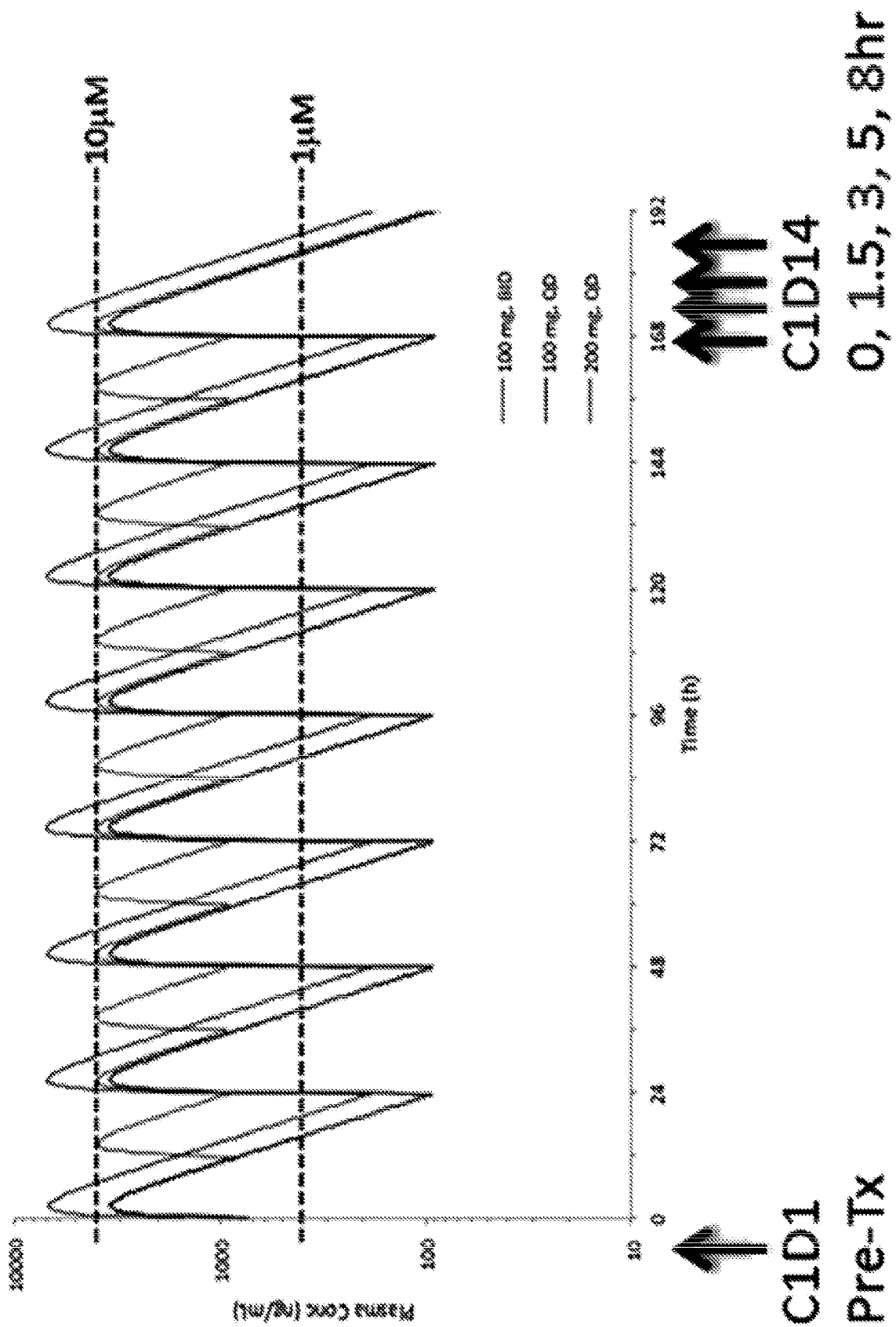
FIG. 26: A schematic showing a pharmacokinetic time course of pCREB induction in CPI-444 dosing. The pCREB assay is performed at: Day 1 before dosing; Day 14 with PK time course. Concentrations used are: 50 mg BID, 100 mg BID, and 200 mg QD.

On day 1, prior to drug therapy, blood was collected and stimulated with NECA to induce CREB phosphorylation (pCREB) (FIGS. 24 and 25) and the level of uninhibited signaling in B cells and T cells was determined (FIGS. 26-28). On day 14, blood was collected prior to dosing (0 hr, trough) and for a time course post-dose (1.5, 3, 5.5, 8 hr) (FIGS. 26-28). The level of signaling was determined and the percent inhibition on Day 14 compared to Day 1 pre-treatment was calculated.

Figure 34A:
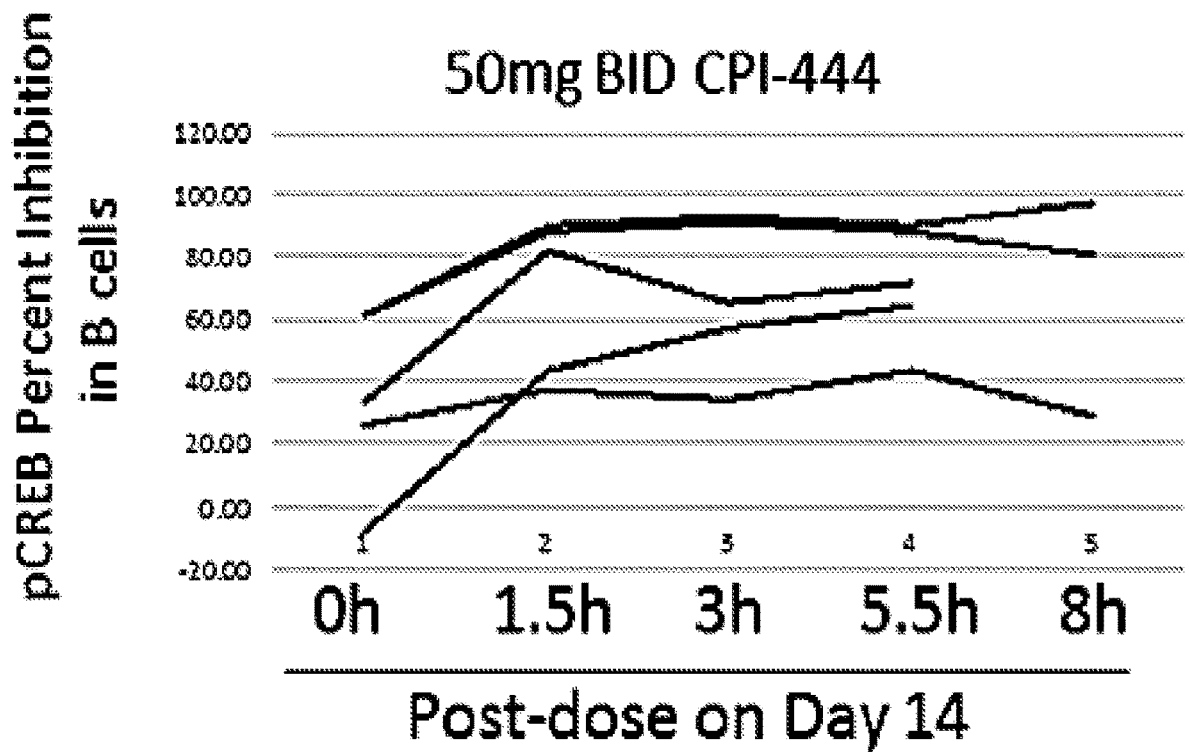
FIGS. 34A-34D: Graphs showing pCREB percent inhibition in B cells across the 8 hr time course of Day 14. Each line represents a single patient and each graph represents a different does used in step 1 of the clinical trial.
Figure 34B:
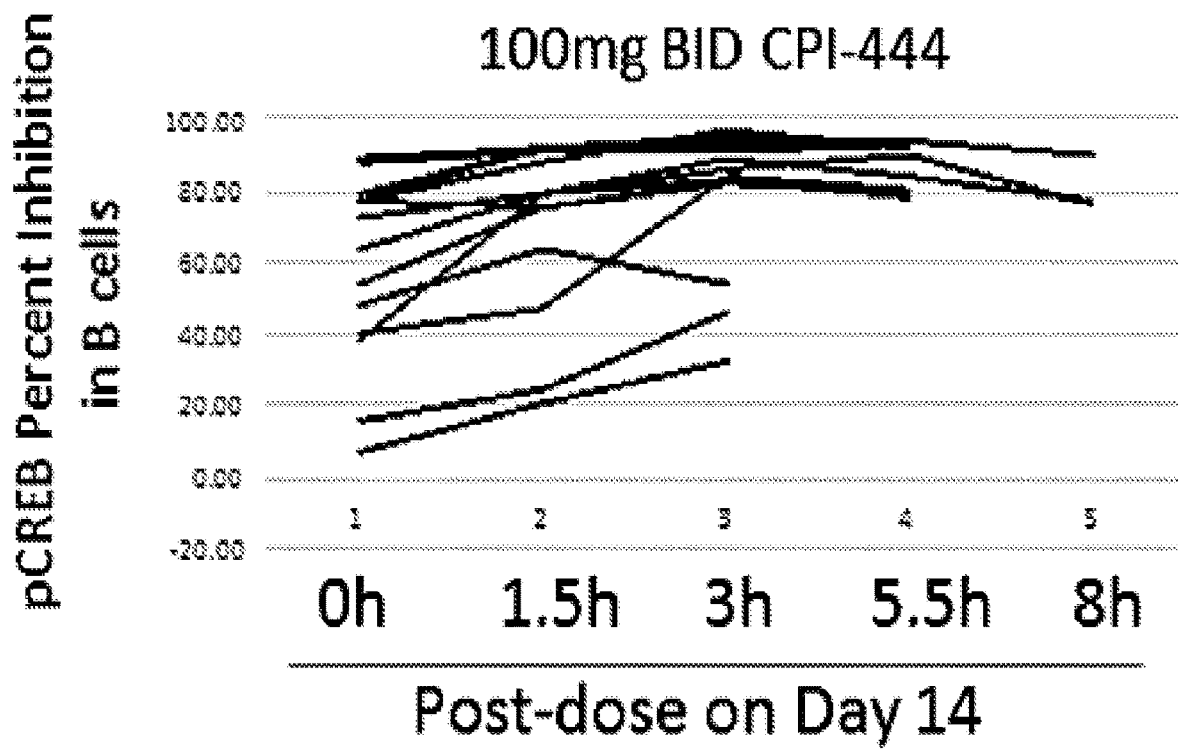
Figure 34C:
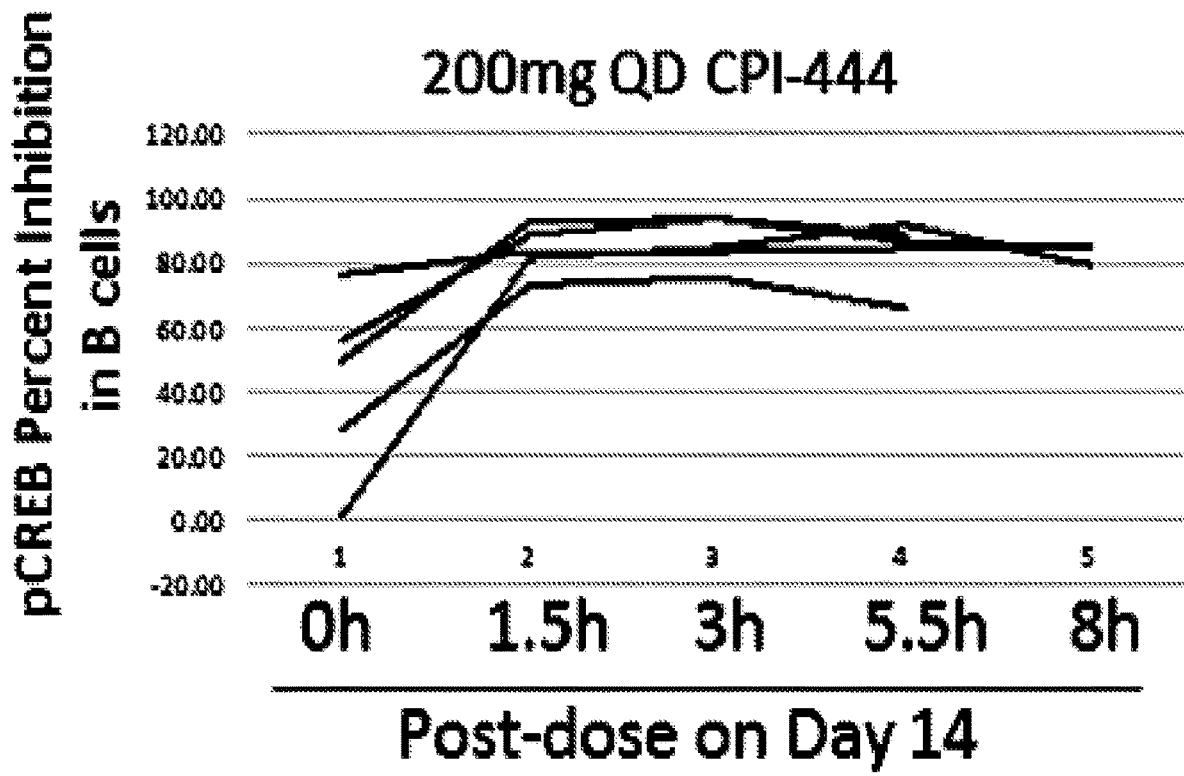
Figure 34D:
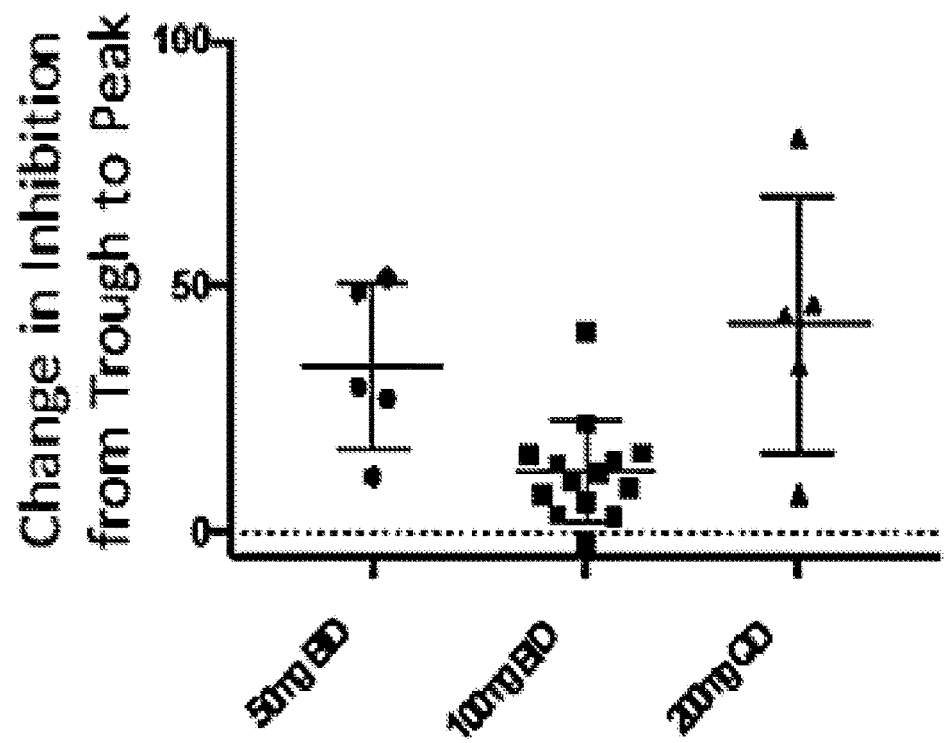

The relative amount of pCREB inhibition was assessed for each dosing cohort. The majority of patients in the 100 mg BID cohort had the highest pCREB inhibition at trough and near complete inhibition after taking their morning dose (FIG. 34B). Little fluctuation from trough to peak in the 100 mg BID dosing group was observed, demonstrating that peak inhibition (at the 3 hr time of peak plasma drug levels) is maintained through drug trough and therefore 100 mg BID is an appropriate dose for continuous functional inhibition (FIG. 34D). The 50 mg BID is not high enough for sustained inhibition (FIG. 34A), and the 200 mg QD dose achieves high peak levels but is not maintained at trough as CPI-444 is administered only once per day (FIG. 34C).

Figure 35A:
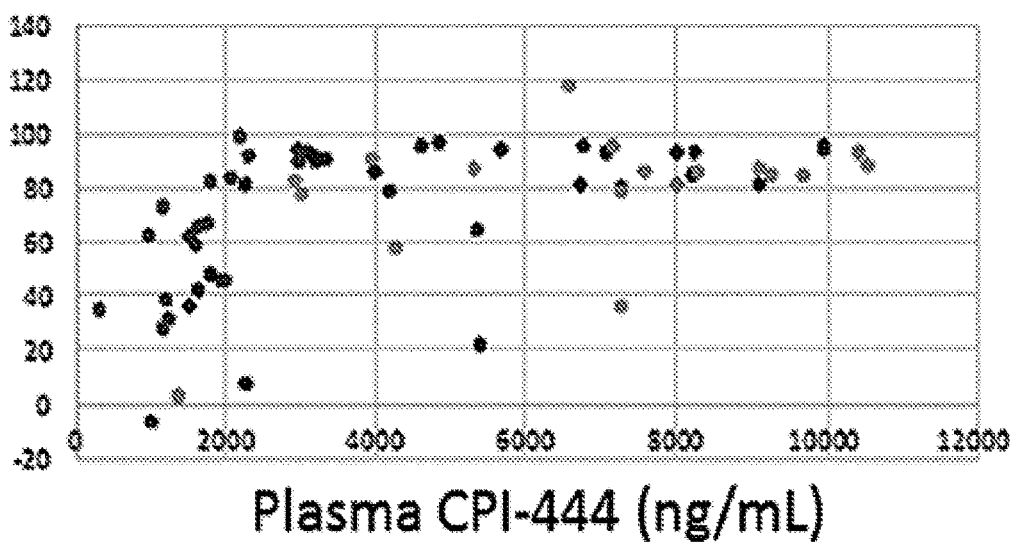
FIGS. 35A-35B: Percent inhibition of CREB phosphorylation by plasma levels of CPI-444. Each dot in FIG. 35A
Figure 35B:
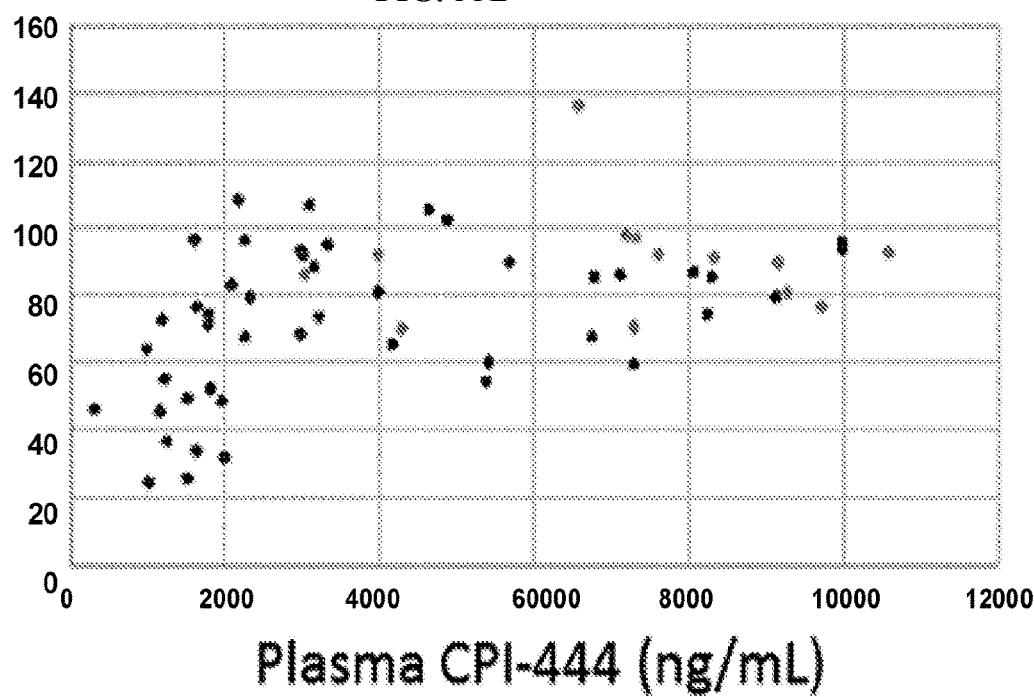

Assessing pharmacokinetics and pharmacodynamics revealed a relationship between pCREB percent inhibition and plasma levels of CPI-444. For CPI-444 plasma levels greater than 2,000 ng/mL, near complete inhibition of pCREB was observed in both B cells (FIG. 35A) and T cells (FIG. 35B).

Figure 36:
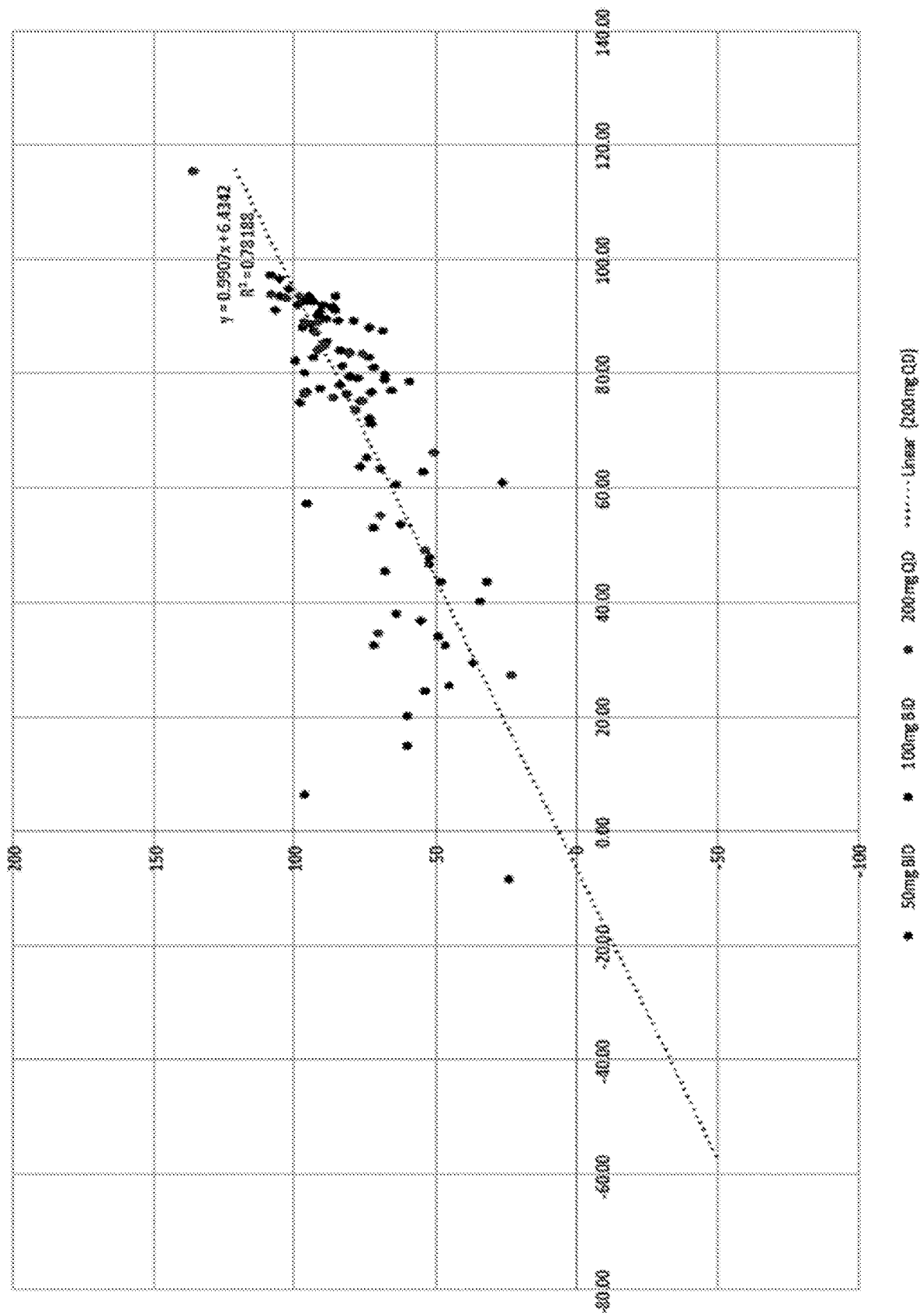
FIG. 36: pCREB inhibition is correlated between B cells and CD4+ T cells. Each dot represents a single time point for a single subject. The x-axis shows pCREB percent inhibition in B cells and the y-axis shows pCREB percent inhibition in CD4+ Tcells. There is a strong correlation between inhibition in B cells and CD4+ T cells.

Applicants observed a strong correlation between inhibition of pCREB in B cells and inhibition of pCREB in CD4+ T cells (FIG. 36). In this assay, the pCREB signal is stronger in B cells than CD4+ T cells, thus the signal-to-noise is better in B cells. This shows that at the population level, pCREB inhibition in B cells is an appropriate surrogate for directly measuring pCREB in T cells, a cell type of interest for CPI-444 activity.

REFERENCES

Antonioli L, Blandizzi C, Pacher P, Hasko G. Immunity, inflammation and cancer: a leading role for adenosine. Nat Rev Cancer. 2013 December; 13(12):842-57.

Blank C, Gajewski T F, Mackensen A. Interaction of PD-L1 on tumor cells with PD 1 on tumor-specific T cells as a mechanism of immune evasion: implications for tumor immunotherapy. Cancer Immunol Immunother 2005; 54:307-14.

Blank C, Mackensen A. Contribution of the PD-L1/PD-1 pathway to T-cell exhaustion: an update on implications for chronic infections and tumor evasion. Cancer Immunol Immunother 2007; 56:739-45.

Chalmin F, Mignot G, Bruchard M, Chevriaux A, Vegran F, Hichami A, et al. Stat3 and Gfi-1 transcription factors control Th17 cell immunosuppressive activity via the regulation of ectonucleotidase expression. Immunity. 2012; 36(3):362-73.

Csoka B, Himer L, Selmeczy Z, Vizi E S, Pacher P, Ledent C, et al. Adenosine A2A receptor activation inhibits T helper 1 and T helper 2 cell development and effector function. FASEB J. 2008; 22(10):3491-9.

D'Addio F, Riella L V, Mfarrej B G, et al. The link between the PDL1 costimulatory pathway and Th17 in fetomaternal tolerance. J Immunol 2011; 187:4530-41.

Gao Z W, Dong K, Zhang H Z. The roles of CD73 in cancer. Biomed Res Int. 2014; 2014:4606-54.

Guleria I, Khosroshahi A, Ansari M J, et al. A critical role for the programmed death ligand 1 in fetomaternal tolerance. J Exp Med 2005; 202:231-7.

Habicht A, Dada S, Jurewicz M, et al. A link between PDL1 and T regulatory cells in fetomaternal tolerance. J Immunol 2007; 179:5211-9.

Hasko G, Linden J, Cronstein B, Pacher P. Adenosine receptors: therapeutic aspects for inflammatory and immune diseases. Nat Rev Drug Discov. 2008; 7(9):759-70.

Herbst R S, Soria J C, Kowanetz M, et al. Predictive correlates of response to the anti PD-L1 antibody MPDL3280A in cancer patients. Nature 2014; 515:563-7.

Hodi F S, O'Day S J, McDermott D F, et al. Improved survival with ipilimumab in patients with metastatic melanoma. N Engl J Med 2010; 363:711-23.

Iwai Y, Ishida M, Tanaka Y, et al. Involvement of PD-L1 on tumor cells in the escape from host immune system and tumor immunotherapy by PD-L1 blockade. Proc Natl Acad Sci USA 2002; 99:12293-7.

Keir M E, Butte M J, Freeman G J, et al. PD-1 and its ligands in tolerance and immunity. Annual Rev Immunol 2008; 26:677-704.

Loi S, Pommey S, Haibe-Kains B, Beavis P A, Darcy P K, Smyth M J, et al. CD73 promotes anthracycline resistance and poor prognosis in triple negative breast cancer. Proc Natl Acad Sci USA. 2013; 110(27):11091-6.

Marzec M, Zhang Q, Goradia A, et al. Oncogenic kinase NPM/ALK induces through STAT3 expression of immunosuppressive protein CD274 (PD-L1, B7-H1). Proc Natl Acad Sci USA. 2008 December 30; 105(52):20852-7.

Mittal D, Young A, Stannard K, Yong M, Teng M W, Allard B, et al. Antimetastatic effects of blocking PD-1 and the adenosine A2A receptor. Cancer Research. 2014; 74(14): 3652-8.

Ohta A, Gorelik E, Prasad S J, Ronchese F, Lukashev D, Wong M K, et al. A2A adenosine receptor protects tumors from antitumor T cells. Proc Natl Acad Sci USA. 2006; 103(35):13132 7.

Raskovalova T, Huang X, Sitkovsky M, Zacharia L C, Jackson E K, Gorelik E. Gs protein-coupled adenosine receptor signaling and lytic function of activated NK cells. J Immunol. 2005; 175(7):4383-91.

Schadendorf D, Hodi F S, Robert C, et al. Pooled analysis of long-term survival data from phase II and phase III trials of ipilimumab in metastatic or locally advanced, unresectable melanoma [abstract]. Eur Cancer Congress 2013 LBA24.

Sica A. Role of tumour-associated macrophages in cancer-related inflammation. Exp Oncol. 2010; 32(3):153-8.

Stagg J, Divisekera U, McLaughlin N, Sharkey J, Pommey S, Denoyer D, et al. Anti-CD73 antibody therapy inhibits breast tumor growth and metastasis. Proc Natl Acad Sci USA. 2010; 107(4):1547-52.

Stagg J, Loi S, Divisekera U, et al. Anti-ErbB-2 mAb therapy requires type I and II interferons and synergizes with anti-PD-1 or anti-CD137 mAb therapy. Proc Natl Acad Sci USA 2011; 108:7142-7.

Strome S E, Dong H, Tamura H, et al. B7-H1 blockade augments adoptive T-cell immunotherapy for squamous cell carcinoma. Cancer Res 2003; 63:6501-5.

Waickman A T, Alme A, Senaldi L, Zarek P E, Horton M, Powell J D. Enhancement of tumor immunotherapy by deletion of the A2A adenosine receptor. Cancer Immunol Immunother. 2012; 61(6):917-26.

Embodiments I

Embodiment 1

A method of treating cancer in a subject in need thereof, said method comprising administering to said subject a therapeutically effective amount of an adenosine-A2A (A2A) receptor antagonist and a programmed cell death protein 1 (PD-1) signaling pathway inhibitor.

Embodiment 2

The method of embodiment 1, wherein said A2A receptor antagonist is a compound of formula:

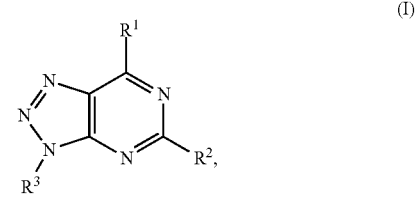

(I)

wherein, $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —N(O)$_{m1}$, —$NR^9R^{10}$, —NH—O—$R^9$, —C(O)R⁹, —C(O)—OR⁹, —C(O)NR⁹R¹⁰, —OR⁹, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R² is independently hydrogen, halogen, —CX$^b_3$, —CN, —SO₂Cl, —SO$_{n2}$R¹¹, —SO$_{v2}$NR¹¹R¹², —NHNH₂, —ONR¹¹R¹², —NHC═(O)NHNH₂, —NHC═(O)NR¹¹R¹², —N(O)$_{m2}$, —NR¹¹R¹², —NH—O—R¹¹, —C(O)R¹¹, —C(O)—OR¹¹, —C(O)NR¹¹R¹², —OR¹¹, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R³ is independently hydrogen, halogen, —CX$^c_3$, —CN, —SO₂Cl, —SO$_{n3}$R¹³, —SO$_{v3}$NR¹³R¹⁴, —NHNH₂, —ONR¹³R¹⁴, —NHC═(O)NHNH₂, —NHC═(O)NR¹³R¹⁴, —N(O)$_{m3}$, —NR¹³R¹⁴, —NH—O—R¹³, —C(O)R¹³, —C(O)—OR¹³, —C(O)NR¹³R¹⁴, —OR¹³, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁹, R¹⁰, R¹¹, R¹², R¹³ and R¹⁴ are independently hydrogen, halogen, ═O, ═S, —CF₃, —CN, —CCl₃, —COOH, —CH₂COOH, —CONH₂, —OH, —SH, —SO₂Cl, —SO₃H, —SO₄H, —SO₂NH₂, —NO₂, —NH₂, —NHNH₂, —ONH₂, —NHC═(O)NHNH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X$^a$, X$^b$ and X$^c$ are independently —F, —Cl, —Br, or —I;

$n_1$, $n_2$ and $n_3$ are independently an integer from 0 to 4;

$m_1$, $m_2$ and $m_3$ are independently an integer from 1 to 2; and $v_1$, $v_2$ and $v_3$ are independently an integer from 1 to 2.

Embodiment 3

The method of embodiment 2, wherein said A2A receptor antagonist is a compound of formula:

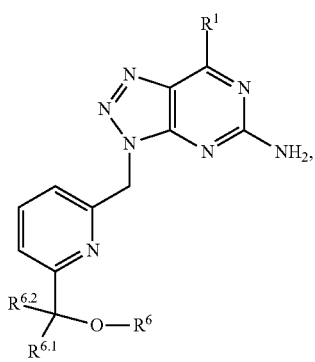

(II)

wherein
R⁶, R$^{6.1}$ and R$^{6.2}$ are independently hydrogen, halogen, ═O, ═S, —CF₃, —CN, —CCl₃, —COOH, —CH₂COOH, —CONH₂, —OH, —SH, —SO₂Cl, —SO₃H, —SO₄H, —SO₂NH₂, —NO₂, —NH₂, —NHNH₂, —ONH₂, —NHC═(O)NHNH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 4

The method of one of embodiments 1-3, wherein said A2A receptor antagonist is a compound of formula:

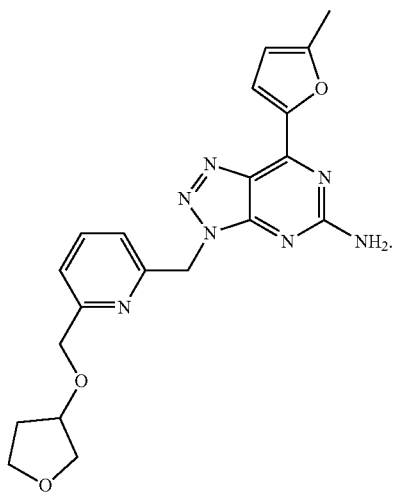

Embodiment 5

The method of one of embodiments 1-4, wherein said PD-1 signaling pathway inhibitor is a programmed death-ligand 1 (PD-L1) antagonist or a PD-1 antagonist.

Embodiment 6

The method of embodiment 5, wherein said programmed death-ligand 1 (PD-L1) antagonist is an antibody or a small molecule.

Embodiment 7

The method of embodiment 6, wherein said PD-L1 antagonist is an antibody.

Embodiment 8

The method of embodiment 7, wherein said antibody is atezolizumab.

Embodiment 9

The method of embodiment 5, wherein said PD-1 antagonist is an antibody or a small molecule.

Embodiment 10

The method of any one of embodiments 1-9, wherein said A2A receptor antagonist and said PD-1 signaling pathway inhibitor are administered in a combined synergistic amount.

Embodiment 11

The method of one of embodiments 1-10, wherein said A2A receptor antagonist and said PD-1 signaling pathway inhibitor are administered simultaneously or sequentially.

Embodiment 12

The method of one of embodiments 1-11, wherein said A2A receptor antagonist is administered at a first time point and said PD-1 signaling pathway inhibitor is administered at a second time point, wherein said first time point precedes said second time point.

Embodiment 13

The method of embodiment 12, wherein said second time point is within less than about 120, 90, 60, 50, 40, 30, 20, 19, 18, 17, 16, 15, 14, 13, 12, 10, 11, 9, 8, 7, 6, 5, 4, 3, 2 or 1 days from said first time point.

Embodiment 14

The method of embodiment 12 or 13, wherein said second time point is within about 8, 10 or 12 days from said first time point.

Embodiment 15

The method of one of embodiments 1-11, wherein said PD-1 signaling pathway inhibitor is administered at a first time point and said A2A receptor antagonist is administered at a second time point, wherein said first time point precedes said second time point.

Embodiment 16

The method of embodiment 15, wherein said second time point is within less than about 120, 90, 60, 50, 40, 30, 20, 19, 18, 17, 16, 15, 14, 13, 12, 10, 11, 9, 8, 7, 6, 5, 4, 3, 2 or 1 days from said first time point.

Embodiment 17

The method of embodiment 15 or 16, wherein said second time point is within about 8, 10 or 12 days from said first time point.

Embodiment 18

The method of one of embodiments 1-17, wherein said A2A receptor antagonist is administered at an amount of about 0.5 mg/kg, 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg or 300 mg/kg.

Embodiment 19

The method of one of embodiments 1-18, wherein said A2A receptor antagonist is administered at an amount of about 1 mg/kg.

Embodiment 20

The method of one of embodiments 1-18, wherein said PD-1 signaling pathway inhibitor is administered at an amount of less than about 1,300 mg.

Embodiment 21

The method of one of embodiments 1-20, wherein said PD-1 signaling pathway inhibitor is administered at an amount of about 1,200 mg.

Embodiment 22

The method of one of embodiments 1-21, wherein said cancer is selected from lung cancer, bladder cancer, melanoma, renal cell carcinoma, colon cancer, ovarian cancer, gastric cancer, breast cancer, head and neck carcinoma, prostate cancer and a hematologic malignancy.

Embodiment 23

A method of treating cancer in a subject in need thereof, said method comprising administering to said subject a therapeutically effective amount of an adenosine-A2A (A2A) receptor antagonist, wherein said A2A receptor antagonist is a compound of formula:

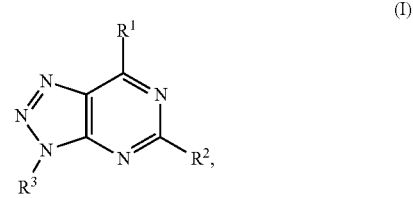

wherein, $R^1$ is independently hydrogen, halogen, $-CX^a_3$, $-CN$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$, $-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, $-CX^b_3$, $-CN$, $-SO_2Cl$, $-SO_{n2}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-NH-O-R^{11}$, $-C(O)R^{11}$, $-C(O)-OR^{11}$, $-C(O)NR^{11}R^{12}$, $-OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R³ is independently hydrogen, halogen, —CX$^c_3$, —CN, —SO$_2$Cl, —SO$_{n3}$R$^{13}$, —SO$_{v3}$NR$^{13}$R$^{14}$, —NHNH$_2$, —ONR$^{13}$R$^{14}$, —NHC=(O)NHNH$_2$, —NHC=(O)NR$^{13}$R$^{14}$, —N(O)$_{m3}$, —NR$^{13}$R$^{14}$, —NH—O—R$^{13}$, —C(O)R$^{13}$, —C(O)—OR$^{13}$, —C(O)NR$^{13}$R$^{14}$, —OR$^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$, R$^{10}$, R$^{11}$, R$^{12}$, R$^{13}$ and R$^{14}$ are independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X$^a$, X$^b$ and X$^c$ are independently —F, —Cl, —Br, or —I;

n$_1$, n$_2$ and n$_3$ are independently an integer from 0 to 4;

m$_1$, m$_2$ and m$_3$ are independently an integer from 1 to 2; and v$_1$, v$_2$ and v$_3$ are independently an integer from 1 to 2.

Embodiment 24

The method of embodiment 23, wherein said A2A receptor antagonist is a compound of formula:

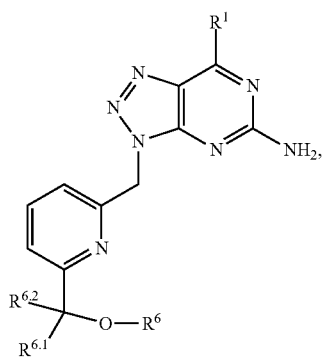

(II)

wherein

R$^6$, R$^{6.1}$ and R$^{6.2}$ are independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 25

The method of embodiment 23 or 24, wherein said A2A receptor antagonist is a compound of formula:

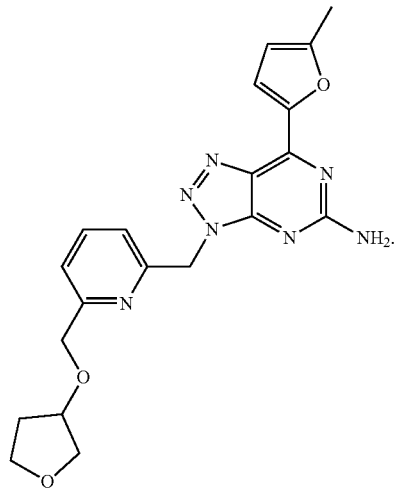

Embodiment 26

The method of one of embodiments 23-25, further comprising administering a therapeutically effective amount of a PD-1 signaling pathway inhibitor.

Embodiment 27

The method of embodiment 26, wherein said A2A receptor antagonist and said PD-1 signaling pathway inhibitor are administered in a combined synergistic amount.

Embodiment 28

The method of one of embodiments 26-27, wherein said A2A receptor antagonist and said PD-1 signaling pathway inhibitor are administered simultaneously or sequentially.

Embodiment 29

The method of one of embodiments 26-28, wherein said A2A receptor antagonist is administered at a first time point and said PD-1 signaling pathway inhibitor is administered at a second time point, wherein said first time point precedes said second time point.

Embodiment 30

The method of embodiment 29, wherein said second time point is within less than about 120, 90, 60, 50, 40, 30, 20, 19, 18, 17, 16, 15, 14, 13, 12, 10, 11, 9, 8, 7, 6, 5, 4, 3, 2, or 1 days from said first time point.

Embodiment 31

The method of embodiment 29 or 30, wherein said second time point is within about 8, 10 or 12 days from said first time point.

Embodiment 32

The method of one of embodiments 26-28, wherein said PD-1 signaling pathway inhibitor is administered at a first time point and said A2A receptor antagonist is administered at a second time point, wherein said first time point precedes said second time point.

Embodiment 33

The method of embodiment 32, wherein said second time point is within less than about 120, 90, 60, 50, 40, 30, 20, 19, 18, 17, 16, 15, 14, 13, 12, 10, 11, 9, 8, 7, 6, 5, 4, 3, 2, or 1 days from said first time point.

Embodiment 34

The method of embodiment 32 or 33, wherein said second time point is within about 8, 10 or 12 days from said first time point.

Embodiment 35

The method of one of embodiments 23-34, wherein said A2A receptor antagonist is administered at an amount of about 0.5 mg/kg, 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg or 300 mg/kg.

Embodiment 36

The method of one of embodiments 23-35, wherein said A2A receptor antagonist is administered at an amount of about 1 mg/kg.

Embodiment 37

The method of one of embodiments 23-35, wherein said PD-1 signaling pathway inhibitor is administered at an amount of less than about 1,300 mg.

Embodiment 38

The method of one of embodiments 23-37, wherein said PD-1 signaling pathway inhibitor is administered at an amount of less than about 1,200 mg.

Embodiment 39

The method of one of embodiments 23-38, wherein said cancer is selected from lung cancer, bladder cancer, melanoma, renal cell carcinoma, colon cancer, ovarian cancer, gastric cancer, breast cancer, head and neck carcinoma, prostate cancer and a hematologic malignancy.

Embodiment 40

A method of activating a T cell, said method comprising contacting said T cell with an A2A receptor antagonist, wherein said A2A receptor antagonist is a compound of formula:

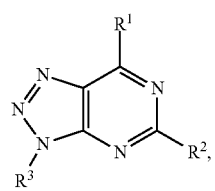

(I)

wherein, $R^1$ is independently hydrogen, halogen, $-CX^a_3$, $-CN$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$, $-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, $-CX^b_3$, $-CN$, $-SO_2Cl$, $-SO_{n2}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-NH-O-R^{11}$, $-C(O)R^{11}$, $-C(O)-OR^{11}$, $-C(O)NR^{11}R^{12}$, $-OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, $-CX^c_3$, $-CN$, $-SO_2Cl$, $-SO_{n3}R^{13}$, $-SO_{v3}NR^{13}R^{14}$, $-NHNH_2$, $-ONR^{13}R^{14}$, $-NHC=(O)NHNH_2$, $-NHC=(O)NR^{13}R^{14}$, $-N(O)_{m3}$, $-NR^{13}R^{14}$, $-NH-O-R^{13}$, $-C(O)R^{13}$, $-C(O)-OR^{13}$, $-C(O)NR^{13}R^{14}$, $-OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$, $R^{11}$, $R^{12}$, $R^{13}$ and $R^{14}$ are independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$X^a$, $X^b$ and $X^c$ are independently $-F$, $-Cl$, $-Br$, or $-I$;

$n_1$, $n_2$ and $n_3$ are independently an integer from 0 to 4;

$m_1$, $m_2$ and $m_3$ are independently an integer from 1 to 2; and $v_1$, $v_2$ and $v_3$ are independently an integer from 1 to 2.

Embodiment 41

The method of embodiment 40, further comprising contacting said T cell with a PD-1 signaling pathway inhibitor.

Embodiment 42

The method of embodiment 41, wherein said PD-1 signaling pathway inhibitor is an antibody or a small molecule.

Embodiment 43

The method of one of embodiments 40-42, wherein said T cell is an effector T cell or a natural killer cell.

Embodiment 44

The method of one of embodiments 40-43, wherein said T cell is an adenosine-suppressed T cell.

Embodiment 45

The method of one of embodiments 40-44, wherein said T cell is a CD8 T cell.

Embodiment 46

The method of embodiment 45, wherein said CD8 T cell is a CD45RA-negative CD8 Tcell.

Embodiment 47

The method of one of embodiments 40-42, wherein said T cell is a CD4 T cell.

Embodiment 48

The method of embodiment 47, wherein said CD4 T cell is a CD45RA-negative CD4 Tcell.

Embodiment 49

The method of one of embodiments 40-48, wherein said T cell is within a subject.

Embodiment 50

The method of embodiment 49, wherein said subject is a cancer subject.

Embodiment 51

The method of embodiment 50, wherein said cancer subject is an anti-PD-1 refractory subject.

Embodiment 52

A method of inhibiting A2A receptor activity of a cell, said method comprising contacting said cell with an A2A receptor antagonist, wherein said A2A receptor antagonist is a compound of formula:

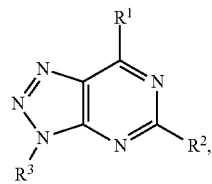

(I)

wherein,

R$^1$ is independently hydrogen, halogen, —CX$^a$$_3$, —CN, —SO$_2$Cl, —SO$_{n1}$R$^9$, —SO$_{v1}$NR$^9$R$^{10}$, —NHNH$_2$, —ONR$^9$R$^{10}$, —NHC=(O)NHNH$_2$, —NHC=(O)NR$^9$R$^{10}$, —N(O)$_{m1}$, —NR$^9$R$^{10}$, —NH—O—R$^9$, —C(O)R$^9$, —C(O)—OR$^9$, —C(O)NR$^9$R$^{10}$, —OR$^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ is independently hydrogen, halogen, —CX$^b$$_3$, —CN, —SO$_2$Cl, —SO$_{n2}$R$^{11}$, —SO$_{v2}$NR$^{11}$R$^{12}$, —NHNH$_2$, —ONR$^{11}$R$^{12}$, —NHC=(O)NHNH$_2$, —NHC=(O)NR$^{11}$R$^{12}$, —N(O)$_{m2}$, —NR$^{11}$R$^{12}$, —NH—O—R$^{11}$, —C(O)R$^{11}$, —C(O)—OR$^{11}$, —C(O)NR$^{11}$R$^{12}$, —OR$^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is independently hydrogen, halogen, —CX$^c$$_3$, —CN, —SO$_2$Cl, —SO$_{n3}$R$^{13}$, —SO$_{v3}$NR$^{13}$R$^{14}$, —NHNH$_2$, —ONR$^{13}$R$^{14}$, —NHC=(O)NHNH$_2$, —NHC=(O)NR$^{13}$R$^{14}$, —N(O)$_{m3}$, —NR$^{13}$R$^{14}$, —NH—O—R$^{13}$, —C(O)R$^{13}$, —C(O)—OR$^{13}$, —C(O)NR$^{13}$R$^{14}$, —OR$^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$, R$^{10}$, R$^{11}$, R$^{12}$, R$^{13}$ and R$^{14}$ are independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X$^a$, X$^b$ and X$^c$ are independently —F, —Cl, —Br, or —I;

n$_1$, n$_2$ and n$_3$ are independently an integer from 0 to 4;

m$_1$, m$_2$ and m$_3$ are independently an integer from 1 to 2; and v$_1$, v$_2$ and v$_3$ are independently an integer from 1 to 2.

Embodiment 53

The method of embodiment 52, wherein said A2A receptor antagonist is a compound of formula:

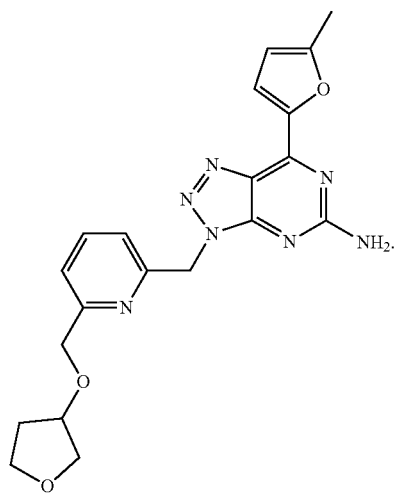

Embodiment 54

The method of embodiment 52 or 53, wherein said contacting comprises binding said A2A receptor antagonist to an A2A receptor of said cell.

125

Embodiment 55

The method of any one of embodiments 52-54, wherein said cell is a T cell.

Embodiment 56

The method of embodiment 55, wherein said T cell is an effector T cell or a natural killer cell.

Embodiment 57

The method of embodiment 55, wherein said T cell is a CD8 T cell.

Embodiment 58

The method of embodiment 57, wherein said CD8 T cell is a CD45RA-negative CD8 Tcell.

Embodiment 59

The method of embodiment 55, wherein said T cell is a CD4 Tcell.

Embodiment 60

The method of embodiment 59, wherein said CD4 T cell is a CD45RA-negative CD4 Tcell.

Embodiment 61

The method of one of embodiments 55-60, wherein said T cell is within a subject.

Embodiment 62

The method of embodiment 61, wherein said subject is a cancer subject.

Embodiment 63

The method of embodiment 62, wherein said cancer subject is an anti-PD-1 refractory subject.

Embodiment 64

A method of increasing an anti-tumor immune response in a subject in need thereof, said method comprising administering to said subject a therapeutically effective amount of an adenosine-A2A (A2A) receptor antagonist and a programmed cell death protein 1 (PD-1) signaling pathway inhibitor.

Embodiment 65

A method of increasing an anti-tumor immune response in a subject in need thereof, said method comprising administering to said subject a therapeutically effective amount of an adenosine-A2A (A2A) receptor antagonist, wherein said A2A receptor antagonist is a compound of formula:

126

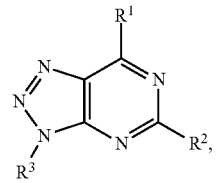

(I)

wherein, $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —$NHC=(O)NHNH_2$, —$NHC=(O)NR^9R^{10}$, —$N(O)_{m1}$, —$NR^9R^{10}$, —NH—O—$R^9$, —$C(O)R^9$, —$C(O)$—$OR^9$, —$C(O)NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —$NHC=(O)NHNH_2$, —$NHC=(O)NR^{11}R^{12}$, —$N(O)_{m2}$, —$NR^{11}R^{12}$, —NH—O—$R^{11}$, —$C(O)R^{11}$, —$C(O)$—$OR^{11}$, —$C(O)NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —$NHC=(O)NHNH_2$, —$NHC=(O)NR^{13}R^{14}$, —$N(O)_{m3}$, —$NR^{13}R^{14}$, —NH—O—$R^{13}$, —$C(O)R^{13}$, —$C(O)$—$OR^{13}$, —$C(O)NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —$NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$X^a$, $X^b$ and $X^c$ are independently —F, —Cl, —Br, or —I;

$n_1$, $n_2$ and $n_3$ are independently an integer from 0 to 4;

$m_1$, $m_2$ and $m_3$ are independently an integer from 1 to 2; and $v_1$, $v_2$ and $v_3$ are independently an integer from 1 to 2.

Embodiment 66

The method of embodiment 65, wherein said A2A receptor antagonist is a compound of formula:

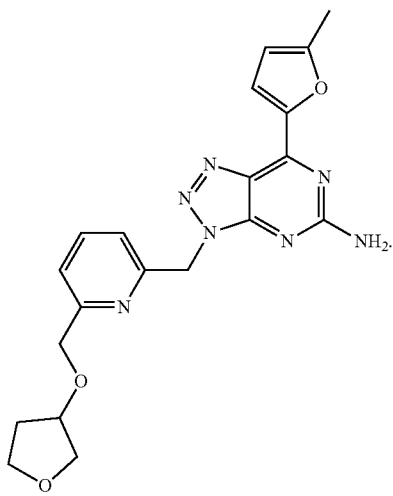 [SMILES: Cc1ccc(-c2nc(N)nc3c2nnn3Cc2cccc(COC3CCOC3)n2)o1]

Embodiment 67

The method of embodiment 65 or 66, further comprising administering a therapeutically effective amount of a PD-1 signaling pathway inhibitor.

Embodiment 68

The method of embodiment 67, wherein said PD-1 signaling pathway inhibitor is a PD-L1 antagonist.

Embodiment 69

The method of embodiment 68, wherein said PD-L1 antagonist is a small molecule or an antibody.

Embodiment 70

A method of increasing the amount of CD8-positive cells relative to the amount of regulatory T cells in a subject in need thereof, said method comprising administering to said subject a therapeutically effective amount of an adenosine-A2A (A2A) receptor antagonist and a programmed cell death protein 1 (PD-1) signaling pathway inhibitor.

Embodiment 71

A method of increasing the amount of CD8-positive cells relative to the amount of regulatory T cells in a subject in need thereof, said method comprising administering to said subject a therapeutically effective amount of an adenosine-A2A (A2A) receptor antagonist, wherein said A2A receptor antagonist is a compound of formula:

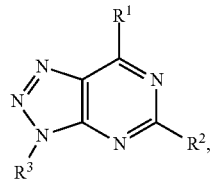

(I)

wherein, $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —$N(O)_{m1}$, —$NR^9R^{10}$, —NH—O—$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$NR^{11}R^{12}$, —NH—O—$R^{11}$, —C(O)$R^{11}$, —C(O)—$OR^{11}$, —C(O)$NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —$N(O)_{m3}$, —$NR^{13}R^{14}$, —NH—O—$R^{13}$, —C(O)$R^{13}$, —C(O)—$OR^{13}$, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$X^a$, $X^b$ and $X^c$ are independently —F, —Cl, —Br, or —I;

$n_1$, $n_2$ and $n_3$ are independently an integer from 0 to 4;

$m_1$, $m_2$ and $m_3$ are independently an integer from 1 to 2; and $v_1$, $v_2$ and $v_3$ are independently an integer from 1 to 2.

Embodiment 72

The method of embodiment 71, wherein said A2A receptor antagonist is a compound of formula:

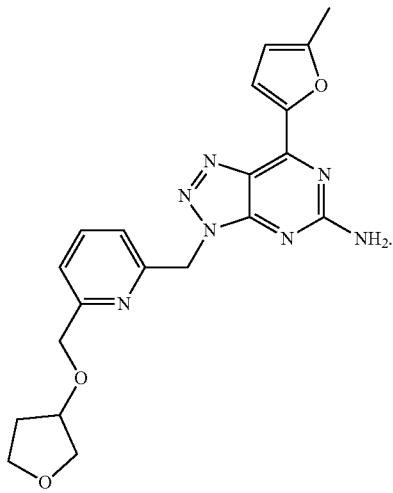 [SMILES: Cc1ccc(-c2nc(N)nc3c2nnn3Cc2cccc(COC3CCOC3)n2)o1]

Embodiment 73

The method of embodiment 71 or 72, further comprising administering a therapeutically effective amount of a PD-1 signaling pathway inhibitor.

Embodiment 74

The method of embodiment 73, wherein said PD-1 signaling pathway inhibitor is a PD-L1 antagonist.

Embodiment 75

The method of embodiment 74, wherein said PD-L1 antagonist is a small molecule or an antibody.

Embodiment 76

A method of decreasing tumor volume in a subject in need thereof, said method comprising administering to said subject a therapeutically effective amount of an adenosine-A2A (A2A) receptor antagonist and a programmed cell death protein 1 (PD-1) signaling pathway inhibitor.

Embodiment 77

A method of decreasing tumor volume in a subject in need thereof, said method comprising administering to said subject a therapeutically effective amount of an adenosine-A2A (A2A) receptor antagonist, wherein said A2A receptor antagonist is a compound of formula:

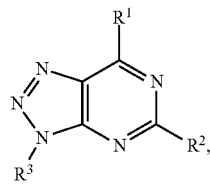

(I)

wherein, $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —$N(O)_{m1}$, —$NR^9R^{10}$, —NH—O—$R^9$, —$C(O)R^9$, —C(O)—$OR^9$, —$C(O)NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$NR^{11}R^{12}$, —NH—O—$R^{11}$, —$C(O)R^{11}$, —C(O)—$OR^{11}$, —$C(O)NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —$N(O)_{m3}$, —$NR^{13}R^{14}$, —NH—O—$R^{13}$, —$C(O)R^{13}$, —C(O)—$OR^{13}$, —$C(O)NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$X^a$, $X^b$ and $X^c$ are independently —F, —Cl, —Br, or —I;

$n_1$, $n_2$ and $n_3$ are independently an integer from 0 to 4;

$m_1$, $m_2$ and $m_3$ are independently an integer from 1 to 2; and $v_1$, $v_2$ and $v_3$ are independently an integer from 1 to 2.

Embodiment 78

The method of embodiment 77, wherein said A2A receptor antagonist is a compound of formula:

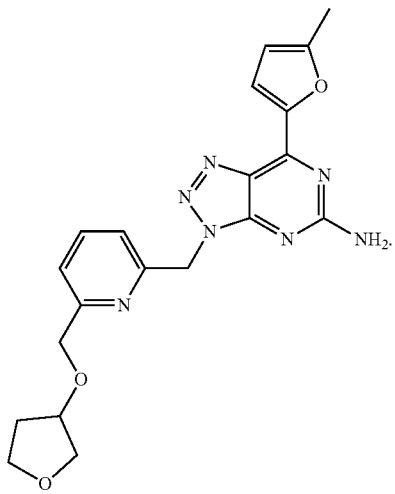 [SMILES: Cc1ccc(-c2nc(N)nc3c2nnn3Cc2cccc(COC3CCOC3)n2)o1]

Embodiment 79

The method of embodiment 77 or 78, further comprising administering a therapeutically effective amount of a PD-1 signaling pathway inhibitor.

Embodiment 80

The method of embodiment 79, wherein said PD-1 signaling pathway inhibitor is a PD-L1 antagonist.

Embodiment 81

The method of embodiment 80, wherein said PD-L1 antagonist is a small molecule or an antibody.

Embodiment 82

A method of enhancing anti-tumor immune memory in a subject in need thereof, said method comprising administering to said subject a therapeutically effective amount of an adenosine-A2A (A2A) receptor antagonist and a programmed cell death protein 1 (PD-1) signaling pathway inhibitor.

Embodiment 83

A method of enhancing anti-tumor immune memory in a subject in need thereof, said method comprising administering to said subject a therapeutically effective amount of an adenosine-A2A (A2A) receptor antagonist, wherein said A2A receptor antagonist is a compound of formula:

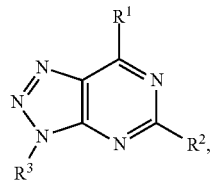

(I)

wherein, $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —$NHC$=(O)$NHNH_2$, —$NHC$=(O)$NR^9R^{10}$, —$N(O)_{m1}$, —$NR^9R^{10}$, —NH—O—$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —$NHC$=(O)$NHNH_2$, —$NHC$=(O)$NR^{11}R^{12}$, —$N(O)_{m2}$, —$NR^{11}R^{12}$, —NH—O—$R^{11}$, —C(O)$R^{11}$, —C(O)—$OR^{11}$, —C(O)$NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —$NHC$=(O)$NHNH_2$, —$NHC$=(O)$NR^{13}R^{14}$, —$N(O)_{m3}$, —$NR^{13}R^{14}$, —NH—O—$R^{13}$, —C(O)$R^{13}$, —C(O)—$OR^{13}$, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —$NHC$=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$X^a$, $X^b$ and $X^c$ are independently —F, —Cl, —Br, or —I;

$n_1$, $n_2$ and $n_3$ are independently an integer from 0 to 4;

$m_1$ $m_2$ and $m_3$ are independently an integer from 1 to 2; and $v_1$, $v_2$ and $v_3$ are independently an integer from 1 to 2.

133

Embodiment 84

The method of embodiment 83, wherein said A2A receptor antagonist is a compound of formula:

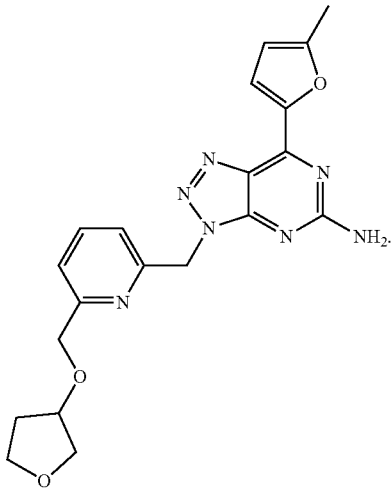 [SMILES: Cc1ccc(-c2nc(N)nc3c2nnn3Cc2cccc(COC3CCOC3)n2)o1]

Embodiment 85

The method of embodiment 83 or 84, further comprising administering a therapeutically effective amount of a PD-1 signaling pathway inhibitor.

Embodiment 86

The method of embodiment 85, wherein said PD-1 signaling pathway inhibitor is a PD-L1 antagonist.

Embodiment 87

The method of embodiment 86, wherein said PD-L1 antagonist is a small molecule or an antibody.

Embodiment 88

A method of increasing global immune activation in a subject in need thereof, said method comprising administering to said subject a therapeutically effective amount of an adenosine-A2A (A2A) receptor antagonist, wherein said A2A receptor antagonist is a compound of formula:

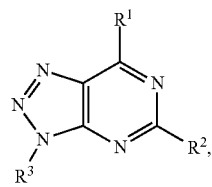

(I)

wherein,
R$^1$ is independently hydrogen, halogen, —CX$^a_3$, —CN, —SO$_2$Cl, —SO$_{n1}$R$^9$, —SO$_{v1}$NR$^9$R$^{10}$, —NHNH$_2$, —ONR$^9$R$^{10}$, —NHC=(O)NHNH$_2$, —NHC=(O)NR$^9$R$^{10}$, —N(O)$_{m1}$, —NR$^9$R$^{10}$, —NH—O—R$^9$, —C(O)R$^9$, —C(O)—OR$^9$, —C(O)NR$^9$R$^{10}$, —OR$^9$,

134 substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ is independently hydrogen, halogen, —CX$^b_3$, —CN, —SO$_2$Cl, —SO$_{n2}$R$^{11}$, —SO$_{v2}$NR$^{11}$R$^{12}$, —NHNH$_2$, —ONR$^{11}$R$^{12}$, —NHC=(O)NHNH$_2$, —NHC=(O)NR$^{11}$R$^{12}$, —N(O)$_{m2}$, —NR$^{11}$R$^{12}$, —NH—O—R$^{11}$, —C(O)R$^{11}$, —C(O)—OR$^{11}$, —C(O)NR$^{11}$R$^{12}$, —OR$^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is independently hydrogen, halogen, —CX$^c_3$, —CN, —SO$_2$Cl, —SO$_{n3}$R$^{13}$, —SO$_{v3}$NR$^{13}$R$^{14}$, —NHNH$_2$, —ONR$^{13}$R$^{14}$, —NHC=(O)NHNH$_2$, —NHC=(O)NR$^{13}$R$^{14}$, —N(O)$_{m3}$, —NR$^{13}$R$^{14}$, —NH—O—R$^{13}$, —C(O)R$^{13}$, —C(O)—OR$^{13}$, —C(O)NR$^{13}$R$^{14}$, —OR$^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$, R$^{10}$, R$^{11}$, R$^{12}$, R$^{13}$ and R$^{14}$ are independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X$^a$, X$^b$ and X$^c$ are independently —F, —Cl, —Br, or —I;
n$_1$, n$_2$ and n$_3$ are independently an integer from 0 to 4;
m$_1$, m$_2$ and m$_3$ are independently an integer from 1 to 2; and
v$_1$, v$_2$ and v$_3$ are independently an integer from 1 to 2.

Embodiment 89

The method of embodiment 88, wherein said A2A receptor antagonist is a compound of formula:

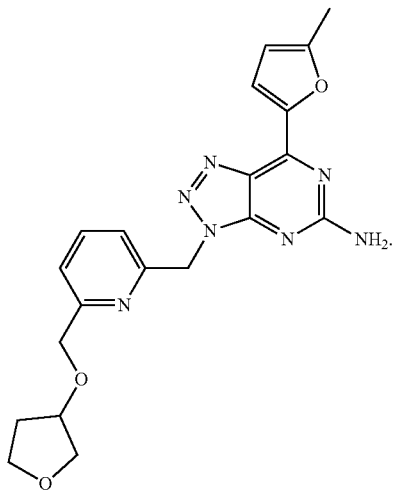

Embodiment 90

The method of embodiment 88 or 89, further comprising administering a therapeutically effective amount of a PD-1 signaling pathway inhibitor.

Embodiment 91

The method of embodiment 90, wherein said PD-1 signaling pathway inhibitor is a PD-L1 antagonist.

Embodiment 92

The method of embodiment 91, wherein said PD-L1 antagonist is a small molecule or an antibody.

Embodiment 93

The method of one of embodiments 88-92, wherein said method comprises activating a CD4 T cell in said subject.

Embodiment 94

The method of embodiment 93, wherein said CD4 T cell is a memory T cell.

Embodiment 95

The method of embodiment 93, wherein said CD4 T cell is an effector T cell.

Embodiment 96

The method of one of embodiments 88-95, wherein the relative amount of CD45RA-negative CD4 T cells in said subject is increased.

Embodiment 97

The method of one of embodiments 88-95, wherein the relative amount of CD4 T cells in said subject is increased.

Embodiment 98

The method of one of embodiments 88-95, wherein the relative amount of memory T cells in said subject is increased.

Embodiment 99

The method of one of embodiments 88-95, wherein the relative amount of effector T cells in said subject is increased.

Embodiment 100

The method of one of embodiments 88-95, wherein said method comprises increasing the number of PD-1 positive cells in said subject.

Embodiment 101

The method of one of embodiments 88-92, wherein said method comprises activating a CD8 T cell in said subject.

Embodiment 102

The method of embodiment 101, wherein the relative amount of CD8 T cells in said subject is increased.

Embodiment 103

The method of one of embodiments 88-102, wherein the relative frequency of TCR recombination is increased.

Embodiment 104

The methods of one of embodiments 1, 23, 64, 65, 70, 71, 76, 77, 82, 83 or 88 wherein said subject is an anti-PD-1 refractory subject.

Embodiment 105

The method of one of embodiments 1, 26, 64, 67, 76 or 79, wherein said A2A receptor antagonist is administered at an amount of about 100 mg BID.

Embodiment 106

The method of embodiment 105, wherein said A2A receptor antagonist is administered for 28 consecutive days.

Embodiment 107

The method of one of embodiments 1, 26, 64, 67, 76, 79, 105 or 106, wherein said PD-1 signaling pathway inhibitor is administered at an amount of about 840 mg.

Embodiment 108

The method of any one of embodiments 105-107, wherein said A2A receptor antagonist is administered at a first time point and said PD-1 signaling pathway inhibitor is administered at a second time point, wherein said first time point precedes said second time point.

Embodiment 109

The method of embodiment 108, wherein said second time point is within less than about 120, 90, 60, 50, 40, 30, 28, 20, 19, 18, 17, 16, 15, 14, 13, 12, 10, 11, 9, 8, 7, 6, 5, 4, 3, 2 or 1 days from said first time point.

Embodiment 110

The method of embodiment 108 or 109, wherein said second time point is within about 14 or 28 days from said first time point.

Embodiment 111

The method of one of embodiments 1, 23, 64 or 65, said method comprising activating a T cell in said subject.

Embodiment 112

The method of one of embodiments 1, 23, 64 or 65, said method comprising inhibiting A2A receptor activity of a cell in said subject.

Embodiment 113

The method of one of embodiments 1, 23, 64 or 65, said method comprising increasing an anti-tumor immune response in a subject.

Embodiment 114

The method of one of embodiments 1, 23, 64 or 65, said method comprising increasing the amount of CD8-positive cells relative to the amount of regulatory T cells in said subject.

Embodiment 115

The method of one of embodiments 1, 23, 64 or 65, said method comprising enhancing anti-tumor immune memory in said subject.

Embodiment 116

The method of one of embodiments 1, 23, 64 or 65, said method comprising increasing global immune activation in said subject.

Embodiment 117

A pharmaceutical composition comprising an A2A receptor antagonist, a PD-1 signaling pathway inhibitor and a pharmaceutically acceptable excipient.

Embodiment 118

The pharmaceutical composition of embodiment 117, wherein said A2A receptor antagonist is a compound of formula:

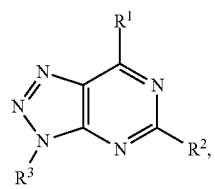

(I)

wherein,
- $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —$N(O)_{m1}$, —$NR^9R^{10}$, —NH—O—$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$NR^{11}R^{12}$, —NH—O—$R^{11}$, —C(O)$R^{11}$, —C(O)—$OR^{11}$, —C(O)$NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —$N(O)_{m3}$, —$NR^{13}R^{14}$, —NH—O—$R^{13}$, —C(O)$R^{13}$, —C(O)—$OR^{13}$, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $X^a$, $X^b$ and $X^c$ are independently —F, —Cl, —Br, or —I;
- $n_1$, $n_2$ and $n_3$ are independently an integer from 0 to 4;
- $m_1$, $m_2$ and $m_3$ are independently an integer from 1 to 2; and
- $v_1$, $v_2$ and $v_3$ are independently an integer from 1 to 2.

Embodiment 119

The pharmaceutical composition of embodiment 118, wherein said A2A receptor antagonist is a compound of formula:

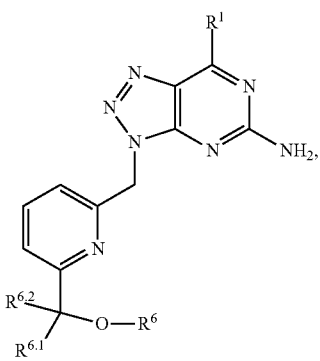

(II)

wherein
$R^6$, $R^{6.1}$ and $R^{6.2}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 120

The pharmaceutical composition of one of embodiments 117-119, wherein said A2A receptor antagonist is a compound of formula:

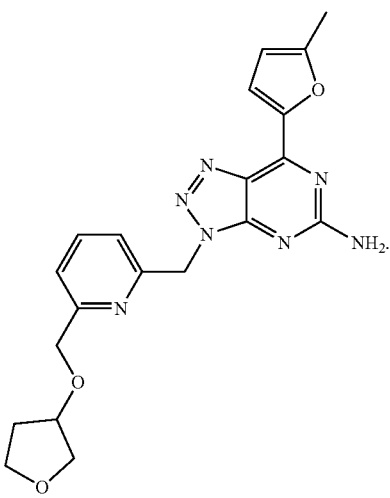 [SMILES: Cc1ccc(-c2nc(N)nc3c2nnn3Cc2cccc(COC3CCOC3)n2)o1]

Embodiment 121

The pharmaceutical composition of one of embodiments 117-120, wherein said PD-1 signaling pathway inhibitor is a programmed death-ligand 1 (PD-L1) antagonist or a PD-1 antagonist.

Embodiment 122

The pharmaceutical composition of embodiment 121, wherein said programmed death-ligand 1 (PD-L1) antagonist is an antibody or a small molecule.

Embodiment 123

The pharmaceutical composition of embodiment 121, wherein said PD-L1 antagonist is an antibody.

Embodiment 124

The pharmaceutical composition of embodiment 122 or 123, wherein said antibody is atezolizumab.

Embodiment 125

The pharmaceutical composition of one of embodiments 121-124, wherein said PD-1 antagonist is an antibody or a small molecule.

Embodiment 126

The pharmaceutical composition of one of embodiments 117-125, wherein said A2A receptor antagonist and said PD-1 signaling pathway inhibitor are present in a combined synergistic amount, wherein said combined synergistic amount is effective to treat cancer in a subject in need thereof.

Embodiments II

Embodiment 1

A method of detecting a phosphorylated cAMP response element-binding protein (pCREB) in a B-cell or T-cell of a mammalian subject, said method comprising:

(i) obtaining a blood sample from a mammalian subject;
(ii) contacting said blood sample with an adenosine receptor agonist;
(iii) contacting said blood sample with a pCREB detection agent and a blood cell detection agent, wherein said blood cell detection agent comprises a B-cell detection agent or T-cell detection agent, thereby forming a T-cell-detection agent complex or a B-cell-detection agent complex; and
(iv) detecting said T-cell detection agent complex or said B-cell detection complex thereby detecting said pCREB in a T-cell or B-cell.

Embodiment 2

The method of embodiment 1, wherein the adenosine receptor agonist comprises adenosine, 5'-N-Ethylcarboxamidoadenosine (NECA), or an analog thereof.

Embodiment 3

The method of any of embodiments 1 or 2, wherein the pCREB detection agent comprises an antibody against pCREB.

Embodiment 4

The method of any of embodiments 1-3, wherein the B cell detection agent comprises an antibody against CD19 and/or an antibody against CD20.

Embodiment 5

The method of any of embodiments 1-4, wherein the T cell detection agent comprises an antibody against CD3, CD4 and/or an antibody against CD8.

Embodiment 6

The method of any of embodiments 1-5, further comprising contacting said blood sample with a fixation agent and cell permeabilizing agent after contacting the blood sample with an adenonsine receptor agonist and prior to contacting said blood sample with a pCREB detection agent.

Embodiment 7

The method of any of embodiments 1-6, further comprising contacting said blood sample with an apoptotic cell detection agent.

Embodiment 8

The method of embodiment 7, wherein the apoptotic cell detection agent comprises an antibody against cPARP.

Embodiment 9

The method of any of embodiments 1-8, further comprising, prior to obtaining said blood sample, administering to said mammalian subject an adenosine receptor antagonist

Embodiment 10

The method of embodiment 9, wherein said adenosine receptor antagonist comprises an A2a receptor antagonist or an A2b receptor antagonist.

Embodiment 11

The method of embodiments 1-10, further comprising, prior to obtaining said blood sample, administering to said mammalian subject an anti-cancer agent.

Embodiment 12

The method of embodiment 11, wherein said anti-cancer agent comprises a PD-L1 antagonist.

Embodiment 13

The method of embodiment 12, wherein said PD-L1 antagonist comprises atezolizumab.

Embodiment 14

The method of any of embodiments 1-13, further comprising contacting said blood sample with a cell subset detection agent.

Embodiment 15

The method of embodiment 14, wherein the cell subset detection agent comprises a naïve cell detection agent, a memory cell detection agent, or an effector cell detection agent.

Embodiment 16

The method of embodiment 14, wherein said cell subset detection agent comprises an antibody against CD27 or an antibody against CD45RA.

Embodiment 17

The method of any one of embodiments 1-16, wherein said blood sample is collected from circulating blood.

Embodiment 18

The method of any one of embodiments 1-16, wherein said blood sample comprises an intratumoral sample.

Embodiment 19

A method of treating a subject with cancer, said method comprising:
(i) obtaining a blood sample from a subject with cancer;
(ii) detecting a level of pCREB induced by an adenosine receptor agonist in said sample;
(iii) administering an effective amount of an adenosine receptor antagonist to said subject.

Embodiment 20

The method of embodiment 19, wherein said detecting of said level of pCREB induced in said sample comprises:
(a) contacting said blood sample with an adenosine receptor agonist; and
(b) contacting said blood sample with a pCREB detection agent and a blood cell detection agent, wherein said blood cell detection agent comprises a B-cell detection agent or T-cell detection agent.

Embodiment 21

The method of embodiment 20, wherein the pCREB detection agent comprises an antibody against pCREB.

Embodiment 22

The method of embodiment 20, wherein the B cell detection agent comprises an antibody against CD19 and/or against CD20.

Embodiment 23

The method of embodiment 20, wherein the T cell detection agent comprises an antibody against CD3, CD4 and/or an antibody against CD8.

Embodiment 24

The method of embodiments 20-23, wherein said detecting said level of pCREB induced in said subject comprises measuring a level of pCREB in B cells or T cells prior to said administering of the effective amount of an adenosine receptor antagonist to said subject.

Embodiment 25

The method of embodiment 24, further comprising:
(iv) detecting a level of pCREB induced in said sample following said administering of the effective amount of adenosine receptor antagonist to said subject.

Embodiment 26

The method of embodiment 25, wherein said detecting of the level of pCREB induce in said sample comprises measuring a level of pCREB induced in B cells or T cells following said administering of the effective amount of adenosine receptor antagonist to said subject.

Embodiment 27

The method of embodiment 26, further comprising increasing a dose of an adenosine receptor antagonist based on the level of pCREB induced in said B cells.

Embodiment 28

A permeabilized blood cell comprising a pCREB detection agent and a blood cell detection agent, wherein said blood cell detection agent comprises a B-cell detection agent or T-cell detection agent and said permeabilized blood cell comprises a permeabilized B-cell or permeabilized T-cell.

Embodiment 29

The permeabilized blood cell of embodiment 28, further comprising an apoptotic cell detection agent.

Embodiment 30

The permeabilized blood cell of embodiment 29, wherein said apoptotic cell detection agent comprises an antibody against cPARP.

Embodiment 31

The permeabilized blood cell of embodiment 28, further comprising a mature cell detection agent.

Embodiment 32

The permeabilized blood cell embodiment 31, wherein said mature cell detection agent comprises antibody against CD27 or an antibody against CD45RA.

Embodiment 33

A container comprising an adenosine receptor agonist in combination with the permeabilized cell of embodiment 28.

Embodiment 34

A flow cytometer comprising the permeabilized blood cell of embodiment 28.

Embodiments III

Embodiment 1

A method of treating cancer in a subject in need thereof, said method comprising administering to said subject a therapeutically effective amount of an adenosine-A2A (A2A) receptor antagonist of formula:

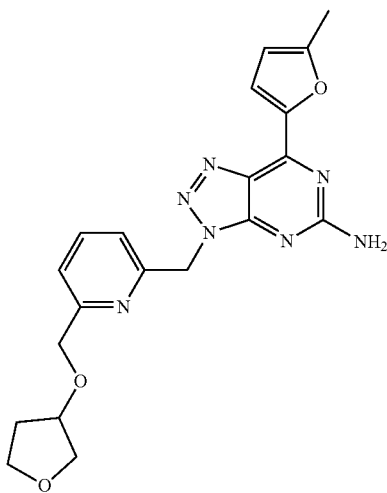 [SMILES: Cc1ccc(-c2nc(N)nc3c2nnn3Cc2cccc(COC3CCOC3)n2)o1]

and a therapeutically effective amount of atezolizumab.

Embodiment 2

The method of embodiment 1, wherein said A2A receptor antagonist and said atezolizumab are administered in a combined synergistic amount.

Embodiment 3

The method of embodiment 1 or 2, wherein said adenosine-A2A (A2A) receptor antagonist is administered at 100 mg.

Embodiment 4

The method of one of embodiments 1-3, wherein said adenosine-A2A (A2A) receptor antagonist is administered twice a day (BID).

Embodiment 5

The method of one of embodiments 1-4, wherein said atezolizumab is administered at 840 mg.

Embodiment 6

The method of one of embodiments 1-5, wherein said atezolizumab is administered once every two weeks (Q2W).

Embodiment 7

The method of one of embodiments 1-4 or 6, wherein said atezolizumab is administered at 1200 mg.

Embodiment 8

The method of one of embodiments 1-7, wherein said atezolizumab is administered once every three weeks (Q3W).

Embodiment 9

The method of one of embodiments 1-8, wherein said cancer is colon cancer, lung cancer, triple negative breast cancer, melanoma, head and neck cancer, prostate cancer, bladder cancer or renal cancer.

Embodiment 10

The method of one of embodiments 1-9, wherein said cancer is colon cancer.

Embodiment 11

The method of one of embodiments 1-9, wherein said cancer is lung cancer.

Embodiment 12

A pharmaceutical composition comprising an adenosine-A2A (A2A) receptor antagonist of formula:

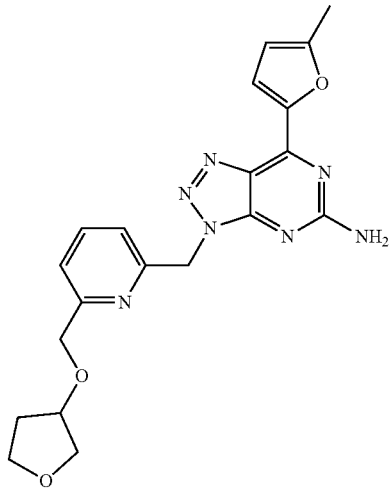 [SMILES: Cc1ccc(-c2nc(N)nc3c2nnn3Cc2cccc(COC3CCOC3)n2)o1]

and a pharmaceutically acceptable excipient, wherein said adenosine-A2A (A2A) receptor antagonist is present at 100 mg.

Embodiment 13

The pharmaceutical composition of embodiment 12, further comprising atezolizumab.

Embodiment 14

The pharmaceutical composition of embodiment 13, wherein said A2A receptor antagonist and said atezolizumab are present at a combined synergistic amount.

Embodiment 15

The pharmaceutical composition of one of embodiments 13-14, wherein said atezolizumab is present at 840 mg.

Embodiment 16

The pharmaceutical composition of one of embodiments 13-14, wherein said atezolizumab is present at 1200 mg.

Embodiment 17

The pharmaceutical composition of one of embodiments 12-16, wherein said pharmaceutical composition is an oral dosage form.

Embodiment 18

A pharmaceutical composition comprising an adenosine-A2A (A2A) receptor antagonist of formula:

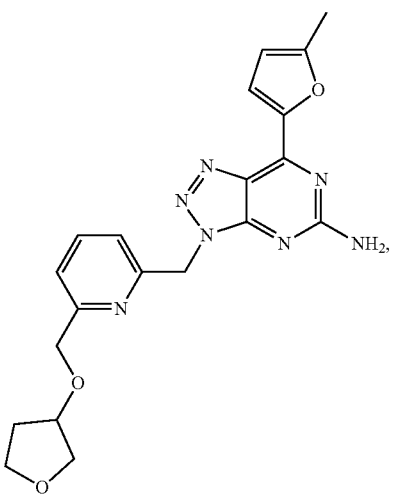

atezolizumab and a pharmaceutically acceptable excipient.

Embodiment 19

The pharmaceutical composition of embodiment 18, wherein said A2A receptor antagonist and said atezolizumab are present at a combined synergistic amount.

Embodiment 20

The pharmaceutical composition of embodiment 18 or 19, wherein said A2A receptor antagonist is present at 100 mg.

Embodiment 21

The pharmaceutical composition of any one of embodiments 18-20, wherein said atezolizumab is present at 840 mg.

Embodiment 22

The pharmaceutical composition of any one of embodiments 18-20, wherein said atezolizumab is present at 1200 mg.

Embodiment 23

The pharmaceutical composition of any one of embodiments 18-22, wherein said pharmaceutical composition is an oral dosage form.

Embodiment 24

A method of treating cancer in a subject in need thereof, said method comprising administering to said subject a therapeutically effective amount of an adenosine-A2A (A2A) receptor antagonist of formula:

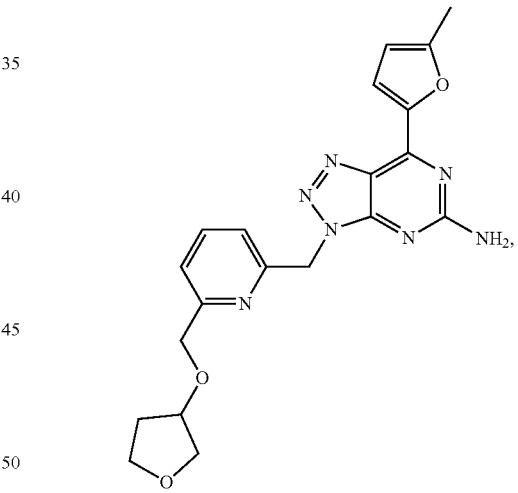

wherein said adenosine-A2A (A2A) receptor antagonist is administered at 100 mg twice a day (BID).

Embodiment 25

The method of embodiment 24, wherein said cancer is colon cancer, lung cancer, triple negative breast cancer, melanoma, head and neck cancer, prostate cancer, bladder cancer or renal cancer.

Embodiment 26

The method of embodiment 24 or 25, wherein said cancer is colon cancer.

147

Embodiment 27

The method of embodiment 24 or 25, wherein said cancer is lung cancer.

Embodiment 28

The method of one of embodiments 24-27, wherein said method further comprises administering to said subject a therapeutically effective amount of atezolizumab.

Embodiment 29

The method of embodiment 28, wherein said A2A receptor antagonist and said atezolizumab are administered in a combined synergistic amount.

Embodiment 30

The method of embodiment 28 or 29, wherein said atezolizumab is administered at 840 mg.

Embodiment 31

The method of one of embodiments 28-30, wherein said atezolizumab is administered once every two weeks (Q2W).

Embodiment 32

The method of embodiment 28 or 31, wherein said atezolizumab is administered at 1200 mg.

Embodiment 33

The method of one of embodiments 28-32, wherein said atezolizumab is administered once every three weeks (Q3W).

Embodiment 34

A method of activating a T cell, said method comprising contacting said T cell with an A2A receptor antagonist, wherein said adenosine-A2A (A2A) receptor antagonist is a compound of formula:

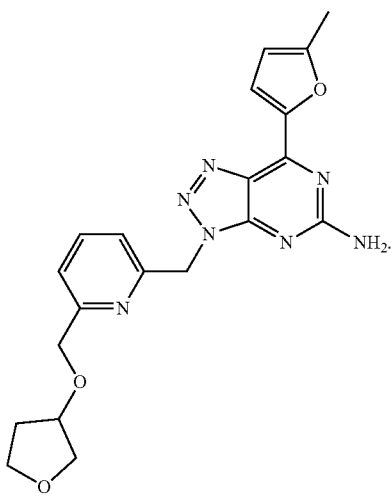

148

Embodiment 35

The method of embodiment 34, wherein said T cell is an effector T cell or a natural killer cell.

Embodiment 36

The method of embodiment 34 or 35, wherein said T cell is an adenosine-suppressed T cell.

Embodiment 37

The method of embodiment 34 or 35, wherein said T cell is a CD8 T cell.

Embodiment 38

The method of embodiment 37, wherein said CD8 T cell is a CD45RA-negative CD8 Tcell.

Embodiment 39

The method of any one of embodiments 34-38, wherein said T cell is within a subject.

Embodiment 40

A method of inhibiting A2A receptor activity of a cell, said method comprising contacting said cell with an A2A receptor antagonist, wherein said A2A receptor antagonist is a compound of formula:

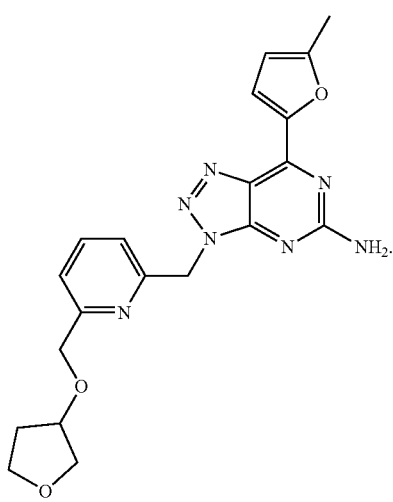

Embodiment 41

The method of embodiment 40, wherein said contacting comprises binding said A2A receptor antagonist to an A2A receptor of said cell.

Embodiment 42

The method of any one of embodiments 40-41, wherein said cell is a T cell.

Embodiment 43

The method of embodiment 42, wherein said T cell is an effector T cell or a natural killer cell.

Embodiment 44

The method of embodiment 42, wherein said T cell is a CD45RA-negative CD8 Tcell.

Embodiment 45

The method of one of embodiments 42-44, wherein said T cell is within a subject.

Embodiment 46

The method of embodiment 45, wherein said subject is a cancer subject.

Embodiment 47

The method of embodiment 46, wherein said cancer subject is an anti-PD-1 refractory subject.

Embodiment 48

A method of increasing an anti-tumor immune response in a subject in need thereof, said method comprising administering to said subject a therapeutically effective amount of an adenosine-A2A (A2A) receptor antagonist, wherein said adenosine-A2A (A2A) receptor antagonist is a compound of formula:

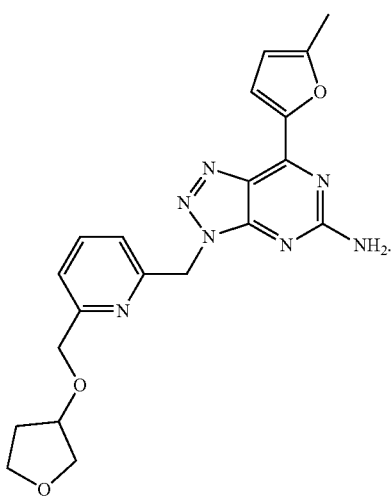 [SMILES: Cc1ccc(-c2nc(N)nc3c2nnn3Cc2cccc(COC3CCOC3)n2)o1]

Embodiment 49

The method of embodiment 48, further comprising administering a therapeutically effective amount of atezolizumab.

Embodiment 50

The method of embodiment 48 or 49, wherein said adenosine-A2A (A2A) receptor antagonist is administered at 100 mg twice a day (BID).

Embodiment 51

The method of any one of embodiments 48-50, wherein said atezolizumab is administered at 840 mg once every two weeks (Q2W).

Embodiment 52

The method of any one of embodiments 48-50, wherein said atezolizumab is administered at 1200 mg once every three weeks (Q3W).

Embodiment 53

A method of increasing the amount of CD8-positive cells relative to the amount of regulatory T cells in a subject in need thereof, said method comprising administering to said subject a therapeutically effective amount of an adenosine-A2A (A2A) receptor antagonist, wherein said adenosine-A2A (A2A) receptor antagonist is a compound of formula:

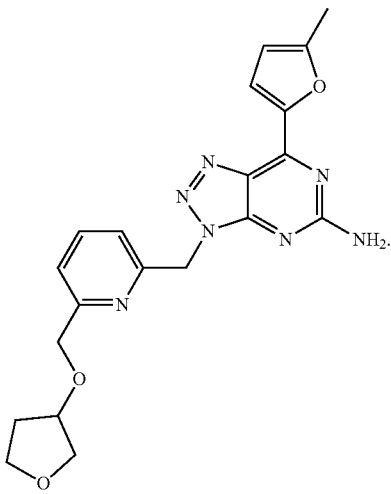

Embodiment 54

The method of embodiment 53, further comprising administering a therapeutically effective amount of atezolizumab.

Embodiment 55

The method of embodiment 53 or 54, wherein said adenosine-A2A (A2A) receptor antagonist is administered at 100 mg twice a day (BID).

Embodiment 56

The method of any one of embodiments 53-55, wherein said atezolizumab is administered at 840 mg once every two weeks (Q2W).

Embodiment 57

The method of any one of embodiments 53-55, wherein said atezolizumab is administered at 1200 mg once every three weeks (Q3W).

Embodiment 58

A method of decreasing tumor volume in a subject in need thereof, said method comprising administering to said subject a therapeutically effective amount of an adenosine-A2A (A2A) receptor antagonist, wherein said adenosine-A2A (A2A) receptor antagonist is a compound of formula:

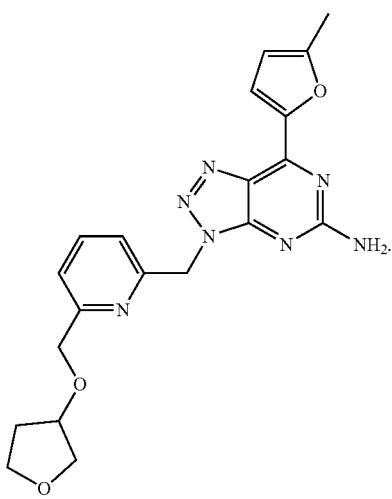 [SMILES: Cc1ccc(-c2nc(N)nc3c2nnn3Cc2cccc(COC3CCOC3)n2)o1]

Embodiment 59

The method of embodiment 58, further comprising administering a therapeutically effective amount of atezolizumab.

Embodiment 60

The method of embodiment 58 or 59, wherein said adenosine-A2A (A2A) receptor antagonist is administered at 100 mg twice a day (BID).

Embodiment 61

The method of any one of embodiments 58-60, wherein said atezolizumab is administered at 840 mg once every two weeks (Q2W).

Embodiment 62

The method of any one of embodiments 58-60, wherein said atezolizumab is administered at 1200 mg once every three weeks (Q3W).

Embodiment 63

A method of enhancing anti-tumor immune memory in a subject in need thereof, said method comprising administering to said subject a therapeutically effective amount of an adenosine-A2A (A2A) receptor antagonist, wherein said adenosine-A2A (A2A) receptor antagonist is a compound of formula:

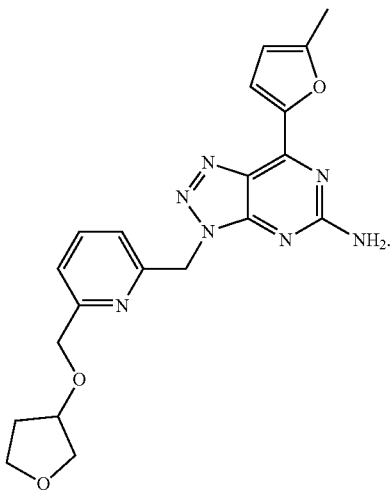

Embodiment 64

The method of embodiment 63, further comprising administering a therapeutically effective amount of atezolizumab.

Embodiment 65

The method of embodiment 63 or 64, wherein said adenosine-A2A (A2A) receptor antagonist is administered at 100 mg twice a day (BID).

Embodiment 66

The method of any one of embodiments 63-65, wherein said atezolizumab is administered at 840 mg once every two weeks (Q2W).

Embodiment 67

The method of any one of embodiments 63-65, wherein said atezolizumab is administered at 1200 mg once every three weeks (Q3W).

What is claimed is:

1. A method of treating cancer in a subject in need thereof, said method comprising administering to said subject a therapeutically effective amount of an adenosine-A2A receptor antagonist of formula:

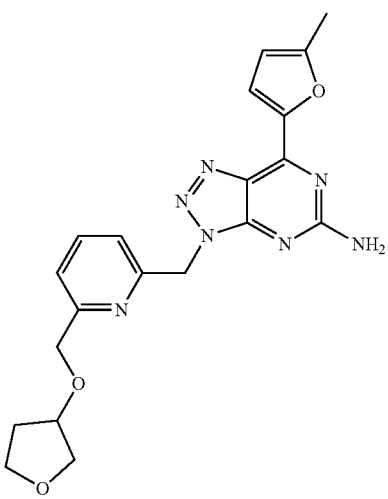

and a therapeutically effective amount of atezolizumab;
wherein the cancer is lymphoma, colon cancer, non-small cell lung cancer, triple negative breast cancer, melanoma, head and neck cancer, prostate cancer, bladder cancer, colorectal cancer, or renal cancer.

2. The method of claim 1, wherein said adenosine-A2A receptor antagonist and said atezolizumab are administered in a combined synergistic amount.

3. The method of claim 1, wherein said adenosine-A2A receptor antagonist is administered at 100 mg.

4. The method of claim 1, wherein said adenosine-A2A receptor antagonist is administered twice a day.

5. The method of claim 1, wherein said atezolizumab is administered at 840 mg.

6. The method of claim 1, wherein said atezolizumab is administered once every two weeks.

7. The method of claim 1, wherein said atezolizumab is administered at 1200 mg.

8. The method of claim 1, wherein said atezolizumab is administered once every three weeks.

9. The method of claim 1, wherein said cancer is colon cancer, non-small cell lung cancer, triple negative breast cancer, melanoma, prostate cancer, or renal cancer.

10. The method of claim 1, wherein the cancer is renal cancer.

11. The method of claim 1, wherein the cancer is renal cancer or non-small cell lung cancer.

12. The method of claim 1, wherein the cancer is renal cancer, non-small cell lung cancer, or prostate cancer.

\* \* \* \* \*